US009962511B2

(12) United States Patent
Ng et al.

(10) Patent No.: US 9,962,511 B2
(45) Date of Patent: *May 8, 2018

(54) MASK SYSTEM WITH SNAP-FIT SHROUD

(71) Applicant: ResMed Limited, Bella Vista, New South Wales (AU)

(72) Inventors: Eva Ng, Sydney (AU); David James Lockwood, Gosford (AU); Jamie Graeme Wehbeh, Sydney (AU); Zoran Valcic, Sydney (AU); Errol Savio Alex D'Souza, Sydney (AU); Matthew Eves, Sydney (AU); Mahsita Sari, Sydney (AU)

(73) Assignee: RESMED LIMITED, Bella Vista (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/724,732

(22) Filed: Oct. 4, 2017

(65) Prior Publication Data

US 2018/0021536 A1 Jan. 25, 2018

Related U.S. Application Data

(63) Continuation of application No. 15/682,117, filed on Aug. 21, 2017, which is a continuation of application
(Continued)

(51) Int. Cl.
*A61M 16/06* (2006.01)
*A61M 16/08* (2006.01)
(Continued)

(52) U.S. Cl.
CPC .... *A61M 16/0622* (2014.02); *A61M 16/0057* (2013.01); *A61M 16/0066* (2013.01);
(Continued)

(58) Field of Classification Search
CPC .............. A61M 16/06; A61M 16/0605; A61M 16/0633; A61M 16/0683; A61M 16/0816; A61M 16/0875; A61M 16/20
See application file for complete search history.

(56) References Cited

U.S. PATENT DOCUMENTS

| 364,394 A | 6/1887 | Bright |
| 428,592 A | 5/1890 | Chapman |

(Continued)

FOREIGN PATENT DOCUMENTS

| AU | 91/77110 | 11/1991 |
| AU | 94/64816 | 12/1994 |

(Continued)

OTHER PUBLICATIONS

Second Statutory Declaration of Daniel Anthony Hearn signed Oct. 27, 2017 and filed in New Zealand Application Nos. NZ 607032, NZ 622666, and NZ 622670, including Exhibits DH-20 and DH-21 (4 pages).

(Continued)

Primary Examiner — Kathryn E Ditmer
(74) Attorney, Agent, or Firm — Nixon & Vanderhye, P.C.

(57) ABSTRACT

A shroud (1020) for a mask system includes a retaining portion structured to retain a frame (1040), a pair of upper headgear connectors (1024) each including an elongated arm (1026) and a slot (1027) at the free end of the arm adapted to receive a headgear strap, and a pair of lower headgear connectors (1025) each adapted to attach to a headgear strap. The retaining portion, the upper headgear connectors, and the lower headgear connectors are integrally formed as a one piece structure.

30 Claims, 81 Drawing Sheets

Related U.S. Application Data

No. 15/440,972, filed on Feb. 23, 2017, now Pat. No. 9,770,568, which is a continuation of application No. 13/964,280, filed on Aug. 12, 2013, now Pat. No. 9,757,533, which is a continuation of application No. 13/745,077, filed on Jan. 18, 2013, now Pat. No. 8,528,561, which is a continuation of application No. 12/736,024, filed as application No. PCT/AU2009/000241 on Feb. 27, 2009, now Pat. No. 8,550,084.

(60) Provisional application No. 61/064,406, filed on Mar. 4, 2008, provisional application No. 61/071,893, filed on May 23, 2008, provisional application No. 61/136,617, filed on Sep. 19, 2008.

(51) Int. Cl.
*A61M 16/20* (2006.01)
*A61M 16/00* (2006.01)

(52) U.S. Cl.
CPC ........ *A61M 16/06* (2013.01); *A61M 16/0611* (2014.02); *A61M 16/0616* (2014.02); *A61M 16/0683* (2013.01); *A61M 16/0694* (2014.02); *A61M 16/0816* (2013.01); *A61M 16/0858* (2014.02); *A61M 16/0875* (2013.01); *A61M 16/20* (2013.01); *A61M 16/0633* (2014.02); *A61M 16/0825* (2014.02); *A61M 16/0841* (2014.02); *A61M 2016/0661* (2013.01)

(56) References Cited

U.S. PATENT DOCUMENTS

| | | |
|---|---|---|
| 443,191 A | 12/1890 | Illing |
| 781,516 A | 1/1905 | Guthrie, Jr. |
| 812,706 A | 2/1906 | Warbasse |
| 1,081,745 A | 12/1913 | Johnston et al. |
| 1,125,542 A | 1/1915 | Humphries |
| 1,176,886 A | 3/1916 | Ermold |
| 1,192,186 A | 7/1916 | Greene |
| 1,206,045 A | 11/1916 | Smith |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,502,450 A | 7/1924 | Wood |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,837,591 A | 12/1931 | Shindel |
| 1,873,160 A | 8/1932 | Sturtevant |
| 1,926,027 A | 9/1933 | Biggs |
| 2,011,733 A | 8/1935 | Shindel |
| 2,104,016 A | 1/1938 | Biggs |
| 2,123,353 A | 7/1938 | Catt |
| 2,127,136 A | 8/1938 | Pobirs |
| 2,130,555 A | 9/1938 | Malcom |
| 2,133,699 A | 10/1938 | Heidbrink |
| 2,149,067 A | 2/1939 | Otero |
| 2,166,164 A | 7/1939 | Lehmberg |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,625,155 A | 1/1953 | Engelder |
| 2,641,253 A | 6/1953 | Engelder |
| 2,693,178 A | 11/1954 | Gilroy |
| 2,706,983 A | 4/1955 | Matheson et al. |
| 2,749,910 A | 6/1956 | Faulconer, Jr. |
| RE24,193 E | 8/1956 | Emerson |
| 2,820,651 A | 1/1958 | Phillips |
| 2,827,900 A | 3/1958 | Marietta |
| 2,837,090 A | 6/1958 | Bloom et al. |
| 2,868,196 A | 1/1959 | Stampe |
| 2,875,757 A | 3/1959 | Galleher, Jr. |
| 2,875,759 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,917,045 A | 12/1959 | Schildknecht et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher, Jr. |
| 3,042,035 A | 7/1962 | Coanda |
| 3,117,574 A | 1/1964 | Replogle |
| 3,182,659 A | 5/1965 | Blount |
| 3,189,027 A | 6/1965 | Bartlett, Jr. |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 3/1972 | Mahon et al. |
| 3,682,171 A | 8/1972 | Dali et al. |
| 3,700,000 A | 10/1972 | Hesse et al. |
| 3,720,235 A | 3/1973 | Schrock |
| 3,725,953 A | 4/1973 | Johnson et al. |
| 3,739,774 A | 6/1973 | Gregory |
| 3,750,333 A | 8/1973 | Vance |
| 3,752,157 A | 8/1973 | Malmin |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 3,978,854 A | 9/1976 | Mills, Jr. |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D248,497 S | 7/1978 | Slosek |
| D250,131 S | 10/1978 | Lewis et al. |
| 4,120,302 A | 10/1978 | Ziegler |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,239,038 A | 12/1980 | Holmes |
| 4,245,632 A | 1/1981 | Houston |

(56) References Cited

U.S. PATENT DOCUMENTS

| | | |
|---|---|---|
| 4,248,218 A | 2/1981 | Fischer |
| 4,263,908 A | 4/1981 | Mizerak |
| 4,264,743 A | 4/1981 | Maruyama et al. |
| 4,265,239 A | 5/1981 | Fischer, Jr. et al. |
| 4,266,540 A | 5/1981 | Panzik et al. |
| 4,267,845 A | 5/1981 | Robertson, Jr. et al. |
| 4,273,124 A | 6/1981 | Zimmerman |
| 4,274,406 A | 6/1981 | Bartholomew |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,369,284 A | 1/1983 | Chen |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,417,575 A | 11/1983 | Hilton et al. |
| 4,422,456 A | 12/1983 | Teip |
| 4,446,576 A | 5/1984 | Hisataka |
| 4,449,526 A | 5/1984 | Elam |
| 4,454,880 A | 6/1984 | Muto et al. |
| 4,454,881 A | 6/1984 | Huber et al. |
| 4,455,675 A | 6/1984 | Bose et al. |
| 4,458,679 A | 7/1984 | Ward |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 11/1985 | Chein |
| 4,558,710 A | 12/1985 | Eichler |
| 4,572,323 A | 2/1986 | Randall |
| 4,579,113 A | 4/1986 | McCreadie et al. |
| 4,587,967 A | 5/1986 | Chu et al. |
| 4,593,688 A | 6/1986 | Payton |
| 4,601,465 A | 7/1986 | Roy |
| 4,603,692 A | 8/1986 | Montesi |
| D285,496 S | 9/1986 | Berman |
| 4,616,647 A | 10/1986 | McCreadie |
| 4,617,637 A | 11/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,657,010 A | 4/1987 | Wright |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,699,139 A | 10/1987 | Marshall et al. |
| 4,706,664 A | 11/1987 | Snook et al. |
| 4,707,863 A | 11/1987 | McNeal |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | While et al. |
| 4,753,233 A | 6/1988 | Grimes |
| 4,767,411 A | 8/1988 | Edmunds |
| 4,770,169 A | 9/1988 | Schmoegner et al. |
| 4,772,760 A | 9/1988 | Graham |
| 4,774,941 A | 10/1988 | Cook |
| 4,774,946 A | 11/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,830,138 A | 5/1989 | Palmaer et al. |
| 4,832,017 A | 5/1989 | Schnoor |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,886,058 A | 12/1989 | Brostrom et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,915,106 A | 4/1990 | Aulgur et al. |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| D313,277 S | 12/1990 | Haining |
| 4,976,698 A | 12/1990 | Stokley |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,996,983 A | 3/1991 | Amrhein |
| 5,000,173 A | 3/1991 | Zalkin et al. |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,027,809 A | 7/1991 | Robinson |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,123,677 A | 6/1992 | Kreczko et al. |

(56) References Cited

U.S. PATENT DOCUMENTS

| | | |
|---|---|---|
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,199,424 A | 4/1993 | Sullivan et al. |
| D335,322 S | 5/1993 | Jones |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,291,880 A | 3/1994 | Almovist et al. |
| 5,299,448 A | 4/1994 | Maryyanek |
| 5,299,579 A | 4/1994 | Gedeon et al. |
| 5,299,599 A | 4/1994 | Farmer et al. |
| 5,301,689 A | 4/1994 | Wennerholm |
| 5,304,146 A | 4/1994 | Johnson et al. |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| D349,586 S | 8/1994 | Handke |
| 5,334,646 A | 8/1994 | Chen |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,945 A | 10/1994 | Messina |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,390,373 A | 2/1995 | Flory |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,400,781 A | 3/1995 | Davenport |
| 5,404,871 A | 4/1995 | Goodman et al. |
| 5,419,317 A | 5/1995 | Blasdell et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,511,541 A | 4/1996 | Dearstine |
| 5,513,634 A | 5/1996 | Jackson |
| 5,513,635 A | 5/1996 | Bedi |
| 5,517,986 A | 5/1996 | Starr et al. |
| 5,522,382 A | 6/1996 | Sullivan et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,568,946 A | 10/1996 | Jackowski |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,623,923 A | 4/1997 | Bertheau et al. |
| 5,642,726 A | 7/1997 | Owens et al. |
| 5,642,730 A | 7/1997 | Baran |
| 5,645,054 A | 7/1997 | Cotner et al. |
| 5,647,355 A | 7/1997 | Starr et al. |
| 5,647,356 A | 7/1997 | Barnett et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,682,881 A | 11/1997 | Winthrop et al. |
| 5,685,296 A | 11/1997 | Zdrojkowski et al. |
| 5,687,715 A | 11/1997 | Landis et al. |
| D389,238 S | 1/1998 | Kirk, III et al. |
| 5,704,345 A | 1/1998 | Berthon-Jones |
| 5,707,342 A | 1/1998 | Tanaka |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,732,695 A | 3/1998 | Metzger |
| 5,735,272 A | 4/1998 | Dillon et al. |
| 5,740,799 A | 4/1998 | Nielson |
| 5,746,201 A | 5/1998 | Kidd |
| 5,752,509 A | 5/1998 | Lachmann et al. |
| 5,752,511 A | 5/1998 | Simmons et al. |
| 5,771,886 A | 6/1998 | Maire et al. |
| 5,778,872 A | 7/1998 | Fukunaga et al. |
| 5,782,774 A | 7/1998 | Shmulewitz |
| 5,794,615 A | 8/1998 | Estes |

(56) References Cited

U.S. PATENT DOCUMENTS

| | | | |
|---|---|---|---|
| 5,794,617 A | 8/1998 | Brunell et al. |
| 5,794,619 A | 8/1998 | Edeiman et al. |
| D398,987 S | 9/1998 | Cotner et al. |
| 5,807,341 A | 9/1998 | Heim |
| 5,813,423 A | 9/1998 | Kirchgeorg |
| 5,832,918 A | 11/1998 | Pantino |
| D402,755 S | 12/1998 | Kwok |
| 5,842,469 A | 12/1998 | Rapp et al. |
| RE36,165 E | 3/1999 | Behr |
| 5,884,624 A | 3/1999 | Barnett et al. |
| 5,887,587 A | 3/1999 | Groenke |
| 5,896,857 A | 4/1999 | Hely et al. |
| 5,906,203 A | 5/1999 | Klockseth et al. |
| 5,909,732 A | 6/1999 | Diesel et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,964,485 A | 10/1999 | Hame et al. |
| 5,966,745 A | 10/1999 | Schwartz et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,026,811 A | 2/2000 | Settle |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |
| 6,062,221 A | 5/2000 | Brostrom |
| 6,082,360 A | 7/2000 | Rudolph et al. |
| 6,086,118 A | 7/2000 | McNaughton et al. |
| 6,091,973 A | 7/2000 | Colla et al. |
| D428,987 S | 8/2000 | Kwok |
| 6,095,996 A | 8/2000 | Steer et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| D439,326 S | 3/2001 | Hecker et al. |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| D443,355 S | 6/2001 | Gunaratnam et al. |
| 6,241,930 B1 | 6/2001 | Harrison |
| 6,257,237 B1 | 7/2001 | Suzuki |
| 6,257,626 B1 | 7/2001 | Campau |
| 6,258,066 B1 | 7/2001 | Urich |
| 6,279,573 B1 | 8/2001 | Johnson et al. |
| 6,295,366 B1 | 9/2001 | Baller et al. |
| 6,298,849 B1 | 10/2001 | Scholey et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,435,181 B1 | 8/2002 | Jones, Jr. et al. |
| 6,439,230 B1 | 8/2002 | Gunaratnam et al. |
| 6,439,234 B1 | 8/2002 | Curti et al. |
| 6,448,303 B1 | 9/2002 | Paul |
| 6,457,473 B1 | 10/2002 | Brostrom et al. |
| 6,463,931 B1 | 10/2002 | Kwok et al. |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| D468,823 S | 1/2003 | Smart |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,188 B1 | 5/2003 | Ellis |
| 6,561,190 B1 | 5/2003 | Kwok |
| 6,561,191 B1 | 5/2003 | Kwok |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,594 B1 | 6/2003 | Drew |
| 6,581,601 B2 | 6/2003 | Ziaee |
| 6,581,602 B2 | 7/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,830 B1 | 9/2003 | Serowski et al. |
| 6,615,832 B1 | 9/2003 | Chen |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,261 B2 | 1/2004 | Lithgow |
| 6,679,265 B2 | 1/2004 | Strickland et al. |
| 6,691,707 B1 * | 2/2004 | Gunaratnam ......... A61M 16/06 128/206.21 |
| 6,691,708 B2 | 2/2004 | Kwok et al. |
| 6,701,535 B2 | 3/2004 | Dobbie et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,712,072 B1 | 3/2004 | Lang |
| 6,729,333 B2 | 5/2004 | Barnett et al. |
| 6,732,733 B1 * | 5/2004 | Brostrom ......... A41D 13/1146 128/206.27 |
| D492,992 S | 7/2004 | Guney et al. |

(56) References Cited

U.S. PATENT DOCUMENTS

| | | |
|---|---|---|
| D493,521 S | 7/2004 | Guney |
| 6,766,800 B2 | 7/2004 | da Silva |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,425 B2 | 2/2005 | Jaffre |
| 6,851,428 B2 | 2/2005 | Dennis |
| 6,851,429 B2 | 2/2005 | Bishop |
| 6,860,269 B2 | 3/2005 | Kwok et al. |
| 6,860,270 B2 | 3/2005 | Sniadich |
| 6,871,649 B2 | 3/2005 | Kwok et al. |
| 6,892,729 B2 | 5/2005 | Smith et al. |
| 6,895,965 B2 | 5/2005 | Scarberry et al. |
| 6,907,882 B2 | 6/2005 | Ging |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,951,218 B2 | 10/2005 | Gradon et al. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,040,321 B2 | 5/2006 | Goebel |
| 7,052,127 B2 | 5/2006 | Harrison |
| 7,059,326 B2 | 6/2006 | Heidmann et al. |
| 7,066,586 B2 | 6/2006 | da Silva |
| 7,069,932 B2 | 7/2006 | Eaton et al. |
| 7,076,282 B2 | 7/2006 | Munro et al. |
| 7,076,822 B2 | 7/2006 | Pearce |
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,114,497 B2 | 10/2006 | Aylsworth et al. |
| 7,121,279 B2 | 10/2006 | Dennis |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,185,652 B2 | 3/2007 | Gunaratnam et al. |
| 7,191,781 B2 | 3/2007 | Wood |
| 7,207,328 B1 | 4/2007 | Altemus |
| 7,207,335 B2 | 4/2007 | Kwok et al. |
| 7,210,481 B1 | 5/2007 | Lovell et al. |
| 7,216,647 B2 | 5/2007 | Lang et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,308,895 B2 | 12/2007 | Wixey et al. |
| 7,318,437 B2 | 1/2008 | Gunaratnam |
| 7,318,439 B2 | 1/2008 | Raje et al. |
| 7,320,323 B2 | 1/2008 | Lang et al. |
| 7,341,060 B2 | 3/2008 | Ging et al. |
| 7,353,826 B2 | 4/2008 | Sleeper et al. |
| 7,353,827 B2 | 4/2008 | Geist |
| 7,441,618 B2 | 10/2008 | Sorg |
| 7,461,656 B2 | 12/2008 | Gunaratnam et al. |
| 7,470,256 B2 | 12/2008 | Lampropoulos et al. |
| 7,481,220 B2 | 1/2009 | Meyer et al. |
| 7,487,772 B2 | 2/2009 | Ging et al. |
| 7,503,327 B2 | 3/2009 | Gunaratnam |
| 7,509,958 B2 | 3/2009 | Amarasinghe et al. |
| 7,520,869 B2 | 4/2009 | Lampropoulos et al. |
| 7,523,754 B2 | 4/2009 | Lithgow |
| 7,562,658 B2 | 7/2009 | Madaus et al. |
| 7,614,400 B2 | 11/2009 | Lithgow et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,640,934 B2 | 1/2010 | Zollinger et al. |
| 7,654,263 B2 | 2/2010 | Lang et al. |
| 7,658,189 B2 | 2/2010 | Davidson et al. |
| 7,665,464 B2 | 2/2010 | Kopacko et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,819,119 B2 | 10/2010 | Ho |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,900,631 B2 | 3/2011 | Persson |
| 7,900,635 B2 | 3/2011 | Gunaratnam et al. |
| 7,931,024 B2 | 4/2011 | Ho et al. |
| 7,958,893 B2 | 6/2011 | Lithgow et al. |
| 7,967,013 B2 | 6/2011 | Ging et al. |
| 7,967,014 B2 | 6/2011 | Heidmann et al. |
| 7,971,590 B2 | 7/2011 | Frater et al. |
| 7,992,559 B2 | 8/2011 | Lang et al. |
| 7,997,267 B2 | 8/2011 | Ging et al. |
| 8,042,538 B2 | 10/2011 | Ging et al. |
| 8,042,541 B2 | 10/2011 | Amarasinghe et al. |
| 8,042,542 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,096,301 B2 | 1/2012 | Smith et al. |
| 8,136,524 B2 | 3/2012 | Ging et al. |
| 8,136,525 B2 | 3/2012 | Lubke et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,297,283 B2 | 10/2012 | Hitchcock et al. |
| 8,397,728 B2 | 3/2013 | D'Souza et al. |
| 8,528,561 B2 | 9/2013 | Ng et al. |
| 8,944,061 B2 | 2/2015 | D'Souza et al. |
| 9,027,556 B2 | 5/2015 | Ng et al. |
| 9,119,931 B2 | 9/2015 | D'Souza et al. |
| 2001/0020474 A1 | 9/2001 | Hecker et al. |
| 2002/0020416 A1 | 2/2002 | Namey |
| 2002/0023649 A1 | 2/2002 | Gunaratnam et al. |
| 2002/0029780 A1 | 3/2002 | Frater et al. |
| 2002/0046755 A1 | 4/2002 | Devoss |
| 2002/0066452 A1 | 6/2002 | Kessler et al. |
| 2002/0069872 A1 | 6/2002 | Gradon et al. |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2003/0019495 A1 | 3/2003 | Palkon et al. |
| 2003/0062048 A1 | 4/2003 | Gradon et al. |
| 2003/0089373 A1 | 5/2003 | Gradon et al. |
| 2003/0154984 A1 | 8/2003 | Fernandes |
| 2003/0168063 A1 | 9/2003 | Gambone et al. |
| 2003/0196656 A1 | 10/2003 | Moore et al. |

(56) References Cited

U.S. PATENT DOCUMENTS

| | | |
|---|---|---|
| 2003/0196658 A1 | 10/2003 | Ging et al. |
| 2004/0025882 A1 | 2/2004 | Madaus et al. |
| 2004/0025883 A1 | 2/2004 | Eaton et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0118406 A1 | 6/2004 | Lithgow et al. |
| 2004/0127856 A1 | 7/2004 | Johnson |
| 2004/0177850 A1 | 9/2004 | Gradon et al. |
| 2004/0182396 A1 | 9/2004 | Dennis |
| 2004/0182398 A1 | 9/2004 | Sprinkle et al. |
| 2004/0211428 A1 | 10/2004 | Jones |
| 2004/0226566 A1 | 11/2004 | Gunaratnam et al. |
| 2004/0255949 A1 | 12/2004 | Lang |
| 2005/0005940 A1 | 1/2005 | Gunaratnam |
| 2005/0011521 A1 | 1/2005 | Sprinkle et al. |
| 2005/0011524 A1 | 1/2005 | Thomlinson et al. |
| 2005/0022820 A1 | 2/2005 | Kwok et al. |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0072428 A1 | 4/2005 | Ho et al. |
| 2005/0098183 A1 | 5/2005 | Nash et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2006/0000476 A1 | 1/2006 | Salem |
| 2006/0042629 A1 | 3/2006 | Geist |
| 2006/0060200 A1 | 3/2006 | Ho et al. |
| 2006/0076017 A1 | 4/2006 | Walker et al. |
| 2006/0076018 A1 | 4/2006 | Barnett et al. |
| 2006/0076019 A1 | 4/2006 | Ho |
| 2006/0107960 A1 | 5/2006 | Smart |
| 2006/0118117 A1 | 6/2006 | Berthon-Jones et al. |
| 2006/0124131 A1 | 6/2006 | Chandran et al. |
| 2006/0130844 A1 | 6/2006 | Ho |
| 2006/0137690 A1 | 6/2006 | Gunaratnam et al. |
| 2006/0174887 A1 | 8/2006 | Chandran et al. |
| 2006/0201514 A1 | 9/2006 | Jones |
| 2006/0207597 A1 | 9/2006 | Wright |
| 2006/0213520 A1 | 9/2006 | Frater et al. |
| 2006/0237018 A1 | 12/2006 | McAuley et al. |
| 2006/0272646 A1 | 12/2006 | Ho et al. |
| 2006/0283456 A1 | 12/2006 | Geiselhart |
| 2006/0283461 A1 | 12/2006 | Lubke et al. |
| 2007/0023044 A1 | 2/2007 | Kwok |
| 2007/0044804 A1 | 3/2007 | Matula, Jr. et al. |
| 2007/0137653 A1 | 6/2007 | Wood |
| 2007/0144525 A1 | 6/2007 | Davidson et al. |
| 2007/0163600 A1 | 7/2007 | Hoffman |
| 2007/0193583 A1 | 8/2007 | Reed |
| 2007/0215161 A1 | 9/2007 | Frater et al. |
| 2007/0221226 A1 | 9/2007 | Hansen et al. |
| 2007/0267017 A1 | 11/2007 | McAuley et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0066761 A1 | 3/2008 | Hodos et al. |
| 2008/0110464 A1 | 5/2008 | Davidson et al. |
| 2008/0110469 A1 | 5/2008 | Weinberg |
| 2008/0149105 A1* | 6/2008 | Matula ............ A61M 16/06 128/206.29 |
| 2008/0178875 A1 | 7/2008 | Henry |
| 2008/0178886 A1 | 7/2008 | Lieberman et al. |
| 2008/0200880 A1 | 8/2008 | Kyvik et al. |
| 2008/0210241 A1 | 9/2008 | Schulz |
| 2008/0230068 A1 | 9/2008 | Rudolph |
| 2008/0257354 A1 | 10/2008 | Davidson et al. |
| 2008/0264413 A1 | 10/2008 | Doherty |
| 2008/0264421 A1 | 10/2008 | Kwok et al. |
| 2008/0302365 A1 | 12/2008 | Cohen et al. |
| 2008/0314389 A1 | 12/2008 | Thomas et al. |
| 2009/0044808 A1 | 2/2009 | Guney et al. |
| 2009/0065729 A1 | 3/2009 | Worboys et al. |
| 2009/0126739 A1 | 5/2009 | Ng et al. |
| 2009/0138527 A1 | 5/2009 | Honda et al. |
| 2009/0139526 A1 | 6/2009 | Melidis et al. |
| 2009/0145429 A1 | 6/2009 | Ging et al. |
| 2009/0151729 A1 | 6/2009 | Judson et al. |
| 2009/0173343 A1 | 7/2009 | Omura et al. |
| 2009/0217929 A1 | 9/2009 | Kwok et al. |
| 2009/0223518 A1 | 9/2009 | Kwok et al. |
| 2009/0223521 A1 | 9/2009 | Howard et al. |
| 2009/0223523 A1 | 9/2009 | Chang |
| 2010/0000534 A1 | 1/2010 | Kooij et al. |
| 2010/0000543 A1 | 1/2010 | Berthon-Jones et al. |
| 2010/0018534 A1 | 1/2010 | Veliss et al. |
| 2010/0043800 A1 | 2/2010 | Omura |
| 2010/0089401 A1 | 4/2010 | Lang et al. |
| 2010/0132717 A1 | 6/2010 | Davidson et al. |
| 2010/0192955 A1 | 8/2010 | Biener et al. |
| 2010/0282265 A1 | 11/2010 | Melidis et al. |
| 2010/0300447 A1 | 12/2010 | Biener et al. |
| 2010/0319700 A1 | 12/2010 | Ng et al. |
| 2011/0030692 A1 | 2/2011 | Jones et al. |
| 2011/0056497 A1 | 3/2011 | Scheiner et al. |
| 2011/0220110 A1 | 9/2011 | Frater et al. |
| 2011/0220114 A1 | 9/2011 | Lithgow et al. |
| 2011/0226254 A1 | 9/2011 | Lang et al. |
| 2011/0259337 A1 | 10/2011 | Hitchcock et al. |
| 2012/0138063 A1 | 6/2012 | Eves et al. |
| 2012/0174928 A1 | 7/2012 | Raje et al. |
| 2012/0266886 A1 | 10/2012 | Davidson et al. |
| 2013/0037033 A1 | 2/2013 | Hitchcock et al. |
| 2013/0081628 A1 | 4/2013 | Davidson et al. |
| 2013/0081629 A1 | 4/2013 | Davidson et al. |
| 2013/0081630 A1 | 4/2013 | Davidson et al. |
| 2013/0081631 A1 | 4/2013 | Davidson et al. |
| 2013/0081632 A1 | 4/2013 | Davidson et al. |
| 2013/0086795 A1 | 4/2013 | Davidson et al. |
| 2013/0086796 A1 | 4/2013 | Davidson et al. |
| 2013/0087147 A1 | 4/2013 | Davidson et al. |
| 2013/0087148 A1 | 4/2013 | Davidson et al. |
| 2013/0087149 A1 | 4/2013 | Davidson et al. |
| 2013/0092168 A1 | 4/2013 | Davidson et al. |
| 2013/0092170 A1 | 4/2013 | Davidson et al. |
| 2013/0133658 A1 | 5/2013 | Ng et al. |
| 2013/0133660 A1 | 5/2013 | Ng et al. |
| 2014/0202466 A1 | 7/2014 | Ho |
| 2014/0338672 A1 | 11/2014 | D'Souza et al. |
| 2014/0373847 A2 | 12/2014 | Ng et al. |
| 2017/0043113 A1 | 2/2017 | Ng et al. |
| 2017/0157352 A1 | 6/2017 | Ng et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 96/51130 | 10/1996 |
| AU | 97/41018 | 4/1998 |
| AU | 98/89312 | 1/1999 |
| AU | 2005100738 | 11/2005 |
| AU | 2006/00031 | 1/2006 |
| CA | 618807 | 4/1961 |
| CA | 623129 | 7/1961 |
| CA | 1039144 | 9/1978 |
| CN | 1219883 | 6/1999 |
| CN | 2464353 | 12/2001 |
| CN | 1901962 A | 12/2004 |
| CN | 1623609 A | 6/2005 |
| CN | 1735439 | 2/2006 |
| CN | 2902337 Y | 5/2007 |
| CN | 101102807 A | 1/2008 |

(56) References Cited

FOREIGN PATENT DOCUMENTS

| | | |
|---|---|---|
| DE | 185 017 | 5/1907 |
| DE | 284 800 | 11/1913 |
| DE | 459 104 | 4/1928 |
| DE | 701 690 | 1/1941 |
| DE | 30 11 900 | 10/1980 |
| DE | 146 688 | 1/1981 |
| DE | 30 15 279 | 10/1981 |
| DE | 31 49 449 | 10/1982 |
| DE | 159 396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 37 19 009 | 12/1988 |
| DE | 39 27 038 | 2/1991 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 23 101 | 7/1998 |
| DE | 197 03 526 | 8/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 44 242 | 3/2001 |
| DE | 199 54 517 | 6/2001 |
| DE | 100 02 571 | 7/2001 |
| DE | 199 62 515 | 7/2001 |
| DE | 100 45 183 | 5/2002 |
| DE | 102 13 905 | 10/2002 |
| DE | 10 2004 055 433 | 11/2004 |
| DE | 103 31 837 | 1/2005 |
| DE | 696 33 023 T2 | 1/2005 |
| DE | 20 2004 018 108 | 2/2005 |
| DE | 103 38 169 | 3/2005 |
| EP | 0 054 154 | 6/1982 |
| EP | 0 252 052 | 1/1988 |
| EP | 0 264 772 | 4/1988 |
| EP | 0 288 937 | 11/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 466 960 | 1/1992 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 658 356 | 6/1995 |
| EP | 0 697 225 | 2/1996 |
| EP | 0 178 925 A2 | 4/1996 |
| EP | 0 747 078 | 12/1996 |
| EP | 0 776 679 | 6/1997 |
| EP | 0 821 978 | 2/1998 |
| EP | 0 853 962 | 7/1998 |
| EP | 1 027 905 | 8/2000 |
| EP | 1 057 494 | 12/2000 |
| EP | 1057494 A2 * | 12/2000 ............ A61M 16/06 |
| EP | 1 099 452 | 5/2001 |
| EP | 1 118 346 | 7/2001 |
| EP | 1 163 923 | 12/2001 |
| EP | 0 830 180 B1 | 3/2002 |
| EP | 1 205 205 | 5/2002 |
| EP | 1 258 266 | 11/2002 |
| EP | 1 356 843 | 10/2003 |
| EP | 1 360 971 | 11/2003 |
| EP | 1 481 702 | 12/2004 |
| EP | 1 982 740 A2 | 10/2008 |
| EP | 2 471 566 | 7/2012 |
| EP | 2 471 567 | 7/2012 |
| FR | 780018 | 4/1935 |
| FR | 2 574 657 | 6/1986 |
| FR | 2 658 725 | 8/1991 |
| FR | 2 720 280 | 12/1995 |
| FR | 2 749 176 | 12/1997 |
| FR | 2 823 122 | 10/2002 |
| GB | 532 214 | 1/1941 |
| GB | 649 689 | 1/1951 |
| GB | 823 887 | 11/1959 |
| GB | 880942 | 10/1961 |
| GB | 1 392 621 | 4/1975 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 176 404 | 12/1986 |
| GB | 2 186 801 | 8/1987 |
| GB | 2 267 648 | 12/1993 |
| GB | 2 368 533 | 5/2002 |
| GB | 2 385 533 | 5/2003 |
| GB | 2 397 244 A | 7/2004 |
| JP | S39-13991 | 7/1964 |
| JP | S51-142793 | 11/1976 |
| JP | H03-007173 | 1/1991 |
| JP | H09-216240 | 8/1997 |
| JP | H11-000397 | 1/1999 |
| JP | H11-104256 | 4/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 4/2002 |
| JP | 2002-543943 | 12/2002 |
| JP | 2003-175106 | 6/2003 |
| JP | 2003-535657 | 12/2003 |
| JP | 2004-000570 | 1/2004 |
| JP | 2005-337371 | 12/2005 |
| JP | 2006-505373 A | 2/2006 |
| JP | 3802872 | 7/2006 |
| JP | 2007-167671 A | 7/2007 |
| JP | 2008/501438 | 1/2008 |
| JP | 2008526391 A | 7/2008 |
| JP | 2008532659 A | 8/2008 |
| JP | 2008541955 A | 11/2008 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20392 | 11/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 96/40370 A1 | 12/1996 |
| WO | WO 97/00092 | 1/1997 |
| WO | WO 97/07847 | 3/1997 |
| WO | WO 97/09090 | 3/1997 |
| WO | WO 97/20597 A1 | 6/1997 |
| WO | WO 97/41911 | 11/1997 |
| WO | WO 98/03145 | 1/1998 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/23305 | 6/1998 |

(56) References Cited

FOREIGN PATENT DOCUMENTS

| | | |
|---|---|---|
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/20072 | 4/2000 |
| WO | WO 00/21600 | 4/2000 |
| WO | WO 00/35525 | 6/2000 |
| WO | WO 00/38772 | 7/2000 |
| WO | WO 00/50121 | 8/2000 |
| WO | WO 00/50122 A1 | 8/2000 |
| WO | WO 00/57942 | 10/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78381 | 12/2000 |
| WO | WO 00/78384 | 12/2000 |
| WO | 2001/62326 | 8/2001 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/11804 | 2/2002 |
| WO | WO 02/32491 | 4/2002 |
| WO | WO 02/38221 | 5/2002 |
| WO | WO 02/45784 | 6/2002 |
| WO | WO 02/47749 A1 | 6/2002 |
| WO | WO 03/005931 | 1/2003 |
| WO | WO 03/059427 | 7/2003 |
| WO | WO 03/082406 | 10/2003 |
| WO | WO 03/090827 | 11/2003 |
| WO | WO 03/105921 | 12/2003 |
| WO | WO 2004/007010 | 1/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | 2004/041341 | 5/2004 |
| WO | WO 2004/041342 | 5/2004 |
| WO | WO 2004/071565 A1 | 8/2004 |
| WO | WO 2004/073778 | 9/2004 |
| WO | WO 2004/078228 | 9/2004 |
| WO | WO 2004/078230 | 9/2004 |
| WO | WO 2004/096332 | 11/2004 |
| WO | WO 2005/002656 | 1/2005 |
| WO | WO 2005/018523 | 3/2005 |
| WO | WO 2005/021075 | 3/2005 |
| WO | WO 2005/028010 | 3/2005 |
| WO | WO 2005/051468 A1 | 6/2005 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/000046 | 1/2006 |
| WO | WO 2006/014630 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO 2006/074515 | 7/2006 |
| WO | WO 2006/074516 | 7/2006 |
| WO | WO 2006/0745514 | 7/2006 |
| WO | WO 2006/096924 | 9/2006 |
| WO | WO 2006/099658 | 9/2006 |
| WO | WO 2006/102707 | 10/2006 |
| WO | WO 2006/130903 | 12/2006 |
| WO | WO 2006/138416 | 12/2006 |
| WO | WO 2007/009182 | 1/2007 |
| WO | 2007/045008 | 4/2007 |
| WO | WO 2007/041751 | 4/2007 |
| WO | WO 2007/041786 | 4/2007 |
| WO | WO 2007041751 A1 * | 4/2007 ........... A61M 16/06 |
| WO | WO 2007045008 A1 * | 4/2007 ........... A61M 16/06 |
| WO | WO 2007/048174 | 5/2007 |
| WO | WO 2007/053878 | 5/2007 |
| WO | WO 2007/143772 | 12/2007 |
| WO | WO 2007/143792 | 12/2007 |
| WO | WO 2007/145534 | 12/2007 |
| WO | WO 2007/147088 A2 | 12/2007 |
| WO | WO 2008/007985 A1 | 1/2008 |
| WO | WO 2008/011682 | 1/2008 |
| WO | WO 2008/011683 | 1/2008 |
| WO | WO 2008/040050 | 4/2008 |
| WO | WO 2008/058330 A1 | 5/2008 |
| WO | WO 2008/070929 | 6/2008 |
| WO | WO 2008/106716 A1 | 9/2008 |
| WO | WO 2009/026627 | 3/2009 |
| WO | WO 2009/052560 | 4/2009 |
| WO | WO 2009/062265 | 5/2009 |
| WO | WO 2009/108994 | 9/2009 |
| WO | WO 2009/108995 | 9/2009 |
| WO | WO 2009/109004 | 9/2009 |
| WO | WO 2010/028425 | 3/2010 |
| WO | WO 2010/066004 | 6/2010 |
| WO | WO 2011/060479 | 5/2011 |
| WO | WO 2013/057647 | 4/2013 |
| WO | WO 2013/061260 | 5/2013 |

OTHER PUBLICATIONS

Statutory Declaration of Jonathan Ellis signed Oct. 27, 2017 and filed in New Zealand Application Nos. NZ 622666, NZ 622670, NZ 607032, NZ 624599, NZ 612787, NZ 701136, and NZ 701183, including Exhibits JE-1 to JE-5 (30 pages).

Statutory Declaration of Brigitte Michelle Jeffs signed Oct. 27, 2017 and filed in New Zealand Application Nos. NZ 622666, NZ 622670, NZ 607032, NZ 624599, NZ 612787, NZ 701136, and NZ 701183 (2 pages).

Sixth Statutory Declaration of Alastair Edwin McAuley signed Oct. 30, 2017 and filed in New Zealand Application No. NZ 607032, including Exhibits AM-24 to AM-31 (333 pages).

Fifth Statutory Declaration of Alastair Edwin McAuley dated Nov. 15, 2017 and filed in related New Zealand Application No. 622666 with Exhibits AM-25 to AM-37 (352 pages).

Statutory Declaration of Jessica Michele Vranjes dated Nov. 10, 2017 and filed in New Zealand Application Nos. 622666, 622670, 607032, 624599, 612787, 701136 and 701183, with Exhibit JV-1 (8 pages).

Brief Communication dated Dec. 6, 2017 in EP Patent No. 2708258 (1 page), including Response filed by Opponent Fisher & Paykel Healthcare Limited on Dec. 1, 2017 (42 pages), with Additional Document D12 (Judgement of the UK High Court of Justice regarding the UK part of the opposed patent dated Nov. 10, 2017) (54 pages), Additional Document D16 (Affidavit by Mr Jason Eaton) (6 pages) and Additional Document D16 (Overview table regarding the auxiliary requests filed by the patentee) (2 pages); (135 total pages).

Non-Final Official Action issued in related U.S. Appl. No. 15/682,117 dated Dec. 18, 2017, 157 pages.

Notification of Third Office Action issued in related Chinese Application No. 201510342347.9 dated Dec. 25, 2017, with English translation, 9 pages.

Decision Denying Institution of Inter Partes Review of U.S. Pat. No. 9,119,931 B2, Case No. IPR2017-01658, dated Jan. 16, 2018 (17 pages).

Decision Denying Institution of Inter Partes Review of U.S. Pat. No. 9,119,931 B2, Case No. IPR2017-01659, dated Jan. 16, 2018 (17 pages).

(56) References Cited

OTHER PUBLICATIONS

Second Office Action issued in related Chinese Application No. 201510341599 dated Aug. 28, 2017, with English translation (21 pages).
Second Office Action issued in related Chinese Application No. 201510341597.0 dated Sep. 11, 2017, with English translation (12 pages).
Fisher & Paykel Healthcare's Reply to ResMed Limited's Patent Owner Response in U.S. Pat. No. 9,119,931, filed in IPR2017-00061 on Sep. 25, 2017 (37 pages).
Transcript of the Deposition of Geoffrey Sleeper taken on Aug. 24, 2017, Ex. 1025, (278 pages).
Sixth Statutory Declaration of Alastair Exhibits Edwin McAuley dated Dec. 7, 2017 and filed in New Zealand Application No. 622670 with Exhibits AM-27 to AM-36 (333 pages).
U.S. Appl. No. 15/682,117, filed Aug. 21, 2017, pending.
U.S. Appl. No. 13/964,280, filed Aug. 12, 2013.
Adam J. Singer MD et al. "The Cyanoacrylate Topical Skin Adhesives," American Journal of Emergency Medicine, vol. 26, 2008, pp. 490-496.
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Australian Appln. No. 2010251884—Examination Report, dated Jul. 27, 2012.
Australian Appln. No. PCT/AU2009/000214—International Search Report, dated May 18, 2009.
Chinese Appln. No. 200480011911.9—Office Action (w/English translation), dated Jun. 24, 2010.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 200910223650.1—Office Action (w/English translation), dated Mar. 29, 2012.
Chinese Appln. No. 201010000226.3—Office Action (w/English translation), dated Apr. 26, 2012.
Chinese Appln. No. 201010517066.X—Office Action (w/English translation), dated Nov. 10, 2011.
ComfortLite™, Respironics, http://comfortlite.respironics.com, before applicants' filing date.
ComfortLite™ 2, Respironics, http://comfortlite2.respironics.com, before applicants' filing date.
"Ear Loop Face Mask", before applicants' filing date.
European Appln. No. EP 01944732.5—Office Action, dated Nov. 27, 2009.
European Appln. No. EP 02714190.2—Search Report, dated Jul. 11, 2006.
European Appln. No. EP 03793493.2—Supplementary Search Report, dated Dec. 2, 2009.
European Appln. No. EP 03793493.2—Office Action, dated Mar. 18, 2011.
European Appln. No. EP 03810331.3—Supplementary Search Report, dated Dec. 18, 2009.

European Appln. No. EP 04730413.4—Supplementary Search Report, dated Sep. 29, 2009.
European Appln. No. EP 05749447.8—Supplementary Search Report, dated Dec. 8, 2009.
European Appln. No. EP 04802114.1—Supplementary Search Report, dated Apr. 27, 2009.
European Appln. No. EP 04802133.1—Supplementary Search Report, dated Sep. 8, 2009.
European Appln. No. EP 04802133.1—Office Action, dated Dec. 22, 2009.
European Appln. No. EP 05746824.1—Supplementary Search Report, dated Dec. 17, 2009.
European Appln. No. EP 06704287.9—Supplementary Search Report, dated Oct. 6, 2009.
European Appln. No. EP 06704287.9—Office Action, dated Jul. 18, 2011.
European Appln. No. EP 07784697.0—Search Report, dated Jul. 27, 2009.
European Appln. No. EP 07845378.4—Search Report, dated Dec. 1, 2009.
European Appln. No. EP 08154854.7—Extended Search Report, dated Nov. 27, 2008.
European Appln. No. EP 08154854.7—Examination Report, dated Jul. 1, 2011.
European Appln. No. EP 08161249.1—Extended Search Report, dated Mar. 19, 2009.
European Appln. No. EP 08161868.8—Search Report, dated Sep. 23, 2008.
European Appln .No. EP 09003544.5—Search Report, dated Jun. 2, 2009.
European Appln. No. EP 09161984.1—Extended Search Report, dated Sep. 3, 2009.
European Appln. No. EP 09178736.6—Search Report, dated Apr. 19, 2010.
European Appln. No. EP 10181516.5—Search Report, dated Jun. 13, 2012.
European Appln. No. EP 10182015.7—Search Report, dated Jun. 15, 2012.
European Appln. No. EP 11174401.7—Search Report, dated Oct. 20, 2011.
European Appln. No. EP 11174407.4—Extended Search Report, dated Oct. 20, 2011.
European Appln. No. EP 12154923.2—Extended Search Report, dated Jun. 1, 2012.
European Appln. No. EP 12154926.5—Extended Search Report, dated Jun. 6, 2012.
European Appln. No. EP 12165749.8—Extended Search Report, dated Oct. 10, 2012.
European Appln. No. EP 12165751.4—Extended Search Report, dated Oct. 8, 2012.
Fisher and Paykel Col.—Product Family—http://www.fphcare.com/osa/products.asp/, before applicants' filing date.
German Patent No. 101 51 984—Decision from Opposition hearing by Weinmann (w/English translation), dated Dec. 6, 2007.
Hans Rudolph, Inc.—Mask Products—http://www.rudolphkc.com/products.php?category=MASKS, before applicants' filing date.
"If You Hate CPAP! You Need CPAP Pro®," www.cpappro.com, before applicants' filing date.
Japanese Appln. No. 2003-537718—Office Action (w/English translation), dated Oct. 7, 2008.
Japanese Appln. No. 2003-559587—Office Action (w/English translation), dated Mar. 17, 2009.
Japanese Appln. No. 2005-004072—Office Action (w/English translation), dated Sep. 24, 2009.
Japanese Appln. No. 2005-337371—Reasons for Rejection (w/English translation), dated Feb. 22, 2011.
Japanese Appln. No. 2007-515732—Office Action (w/English translation), dated Aug. 16, 2011.
Japanese Appln. No. 2005-337371—Final Office Action (w/English translation), dated Jan. 31, 2012.
Japanese Appln. No. 2006-504029—Office A545843ction (w/English translation), dated Nov. 10, 2009.

(56) References Cited

OTHER PUBLICATIONS

Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance, dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2010-268127—Notice of Reasons for Rejection (w/English translation), dated Jul. 10, 2012.
Japanese Appln. No. 2011-038110—Office Action (w/English translation), dated Aug. 14, 2012.
Japanese Appln. No. S52-164619—English translation of Figure 1, Dec. 1977.
Joel W. Beam, "Tissue Adhesives for Simple Traumatic Lacerations," Journal of Athletic Training, 2008, vol. 43, No. 2, pp. 222-224.
JP 11-000397A Machine Translation, provided by the Japanese Patent Office, Jan. 6, 2009, full document.
Laurent Brochard, "Pressure Support Ventilation," Chapter 9, Part IV—Conventional Methods of Ventilator Support, pp. 239-257, 1994.
Mask 1 Photographs, Respironics Inc., Reusable Full Mask (small) Part #452033 Lot #951108, before applicants' filing date.
Mask 2 Photographs, Puritan—Bennett, Adam Curcuit, Shell Part #231700, Swivel Part #616329-00, Pillows (medium) Part #616324, before applicants' filing date.
Mask 3 Photographs, DeVilbiss Healthcare Inc., Devilbiss Seal-Ring and CPAP Mask Kit (medium), Part #73510-669, before applicants' filing date.
Mask 4 Photographs, Respironics Inc., Monarch Mini Mask with Pressure Port, Part #572004, Monarch Headgear, Part #572011, before applicants' filing date.
Mask 5 Photographs, Healthdyne Technologies, Nasal CPAP Mask (medium narrow), Part #702510, before applicants' filing date.
Mask 6 Photographs, Healthdyne Technologies, Soft Series Nasal CPAP Mask, Part #702020, before applicants' filing date.
Mask 7 Photographs, DeVilbiss Healthcare Inc., Small Mask and Seal Rings, Part #73510-668, before applicants' filing date.
Mask 8 Photographs, Respironics Inc., Reusable Contour Mask (medium), Part #302180, before applicants' filing date.
Mask 9 Photographs, Healthdyne Technologies, Healthdyne Large Headgear, before applicants' filing date.
Mask 10 Photographs, Respironics Inc., Soft Cap (medium), Part #302142, before applicants' filing date.
Mask 11 Photographs, Weinmann: Hamburg, Nasalmaskensystem mit Schalldämpfer (medium), Part #WN 23105, before applicants' filing date.
Mask 12 Photographs, Life Care, before applicants' filing date.
Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
McPherson et al., "Respiratory Therapy Equipment," Chapter 8, Third Edition, Introduction to Ventilators, pp. 230-253, 1985.
Merriam-Webster Online Dictionary definition of moveable from the 14$^{th}$ century, before applicants' filing date.
New Zealand Appln. No. 2003275762—Examiner's Report No. 3, dated Nov. 18, 2009.
New Zealand Appln. No. 539836—Examination Report, dated Aug. 25, 2005.
New Zealand Appln. No. 564877—Examination Report, dated Dec. 2, 2009.
Zealand Appln. No. 567375—Examination Report, dated Nov. 17, 2009.
Zealand Appln. No. 587344—Examination Report, dated Jan. 19, 2012.
Zealand Appln. No. 587344—Examination Report, dated Aug. 3, 2012.
Zealand Appln. No. 587820—Examination Report, dated Sep. 13, 2010.
Zealand Appln. No. 597552—Examination Report, dated Jan. 19, 2012.
Zealand Appln. No. 597689—Examination Report, dated Jan. 25, 2012.
PCT/AU2003/001163—International Search Report, dated Nov. 4, 2003.
PCT/AU2003/001471—International Search Report, dated Feb. 12, 2004.
PCT/AU2004/000563—International Search Report, dated Jun. 23, 2004.
PCT/AU2004/001760—International Preliminary Report on Patentability, dated Jul. 3, 2006.
PCT/AU2004/001760—International Search Report, dated Jan. 12, 2005.
PCT/AU2004/001813—International Preliminary Report on Patentability, dated Jul. 3, 2006.
PCT/AU2004/001813—International Search Report, dated Mar. 7, 2005.
PCT/AU2004/001832—International Preliminary Report on Patentability, dated Jul. 3, 2006.
PCT/AU2004/001832—International Search Report, dated Mar. 24, 2005.
PCT/AU2005/000803—International Search Report, dated Jun. 30, 2005.
PCT/AU2005/000850—International Preliminary Report on Patentability, dated Dec. 20, 2006.
PCT/AU2005/000850—International Search Report, dated Aug. 12, 2005.
PCT/AU2006/000032—International Preliminary Report on Patentability, dated Jul. 17, 2007.
PCT/AU2006/000032—International Search Report, dated May 15, 2006.
PCT/AU2006/000770—International Search Report, dated Aug. 3, 2006.
PCT/AU2007/001936—International Search Report, dated Mar. 4, 2008.
PCT/AU2006/001570—International Search Report, dated Jan. 5, 2007.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2009/000240—International Search Report, dated May 21, 2009.
PCT/AU2009/000262—International Search Report, dated Jun. 9, 2009.
PCT/AU2009/001102—International Search Report, dated Dec. 11, 2009.
PCT/AU2009/001144—International Search Report, dated Dec. 8, 2009.
PCT/AU2010/000657—International Search Report, dated Sep. 9, 2010.

(56) References Cited

OTHER PUBLICATIONS

Product Brochure for ResMed "Sullivan® Mirage™—The Mirage is Real. A Perfect Fit-First Time," © 1997 ResMed Limited, 4 pages.
Product Brochure for ResMed "Sullivan® Mirage™—The Mirage is Real. A Perfect Fit-First Time," © 1998 ResMed Limited, 4 pages.
ResMed Co.—Mask Products—http://resmed.com/portal/site/ResMedUS/index.jsp?, before applicants' filing date.
ResMed Ltd., "Improving patient compliance with the ResMed Range of Mask Systems the Ultimate Interface for CPAP treatment," before applicants' filing date, 4 pages.
Respironics Co.—Mask Family—http://masksfamily.respironics.com/, before Applicant's filing date.
SNAPP Nasal Interface, Tiara Medical Systems, Inc.—http://tiaramed.com/asp_shops/shopdisplayproducts.asp?id=109 &cat=SNAPP%2A+Nasal+Interface, before applicants' filing date.
"Somnomask" brochure, 1999 along with various invoices relating to the "Somnomask".
Somnotron CPAP—Great WM 2300 Instruction Manual, Weinmann Hamburg, 1991, 11 pages.
Subbu Venkatraman et al., "Review Skin Adhesives and Skin Adhesion 1. Transdermal Drug Delivery Systems," Biomaterials, vol. 19, 1998, pp. 1119-1136.
The ResMed Range of Mask Systems, product brochure, Nov. 1995, 4 pages.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
Photo of Weinmann Mask (manufactured 1991).
U.S. Appl. No. 12/083,779—Office Action including PTO-892 listings, dated Feb. 17, 2012.
U.S. Appl. No. 12/083,779—Office Action including PTO-892 listings, dated Sep. 28, 2012.
U.S. Appl. No. 60/424,686, filed Nov. 8, 2002 (expired).
U.S. Appl. No. 60/483,622, filed Jul. 1, 2003 (expired).
U.S. Appl. No. 60/533,214, filed Dec. 31, 2003 (expired).
U.S. Appl. No. 60/634,802, filed Dec. 10, 2004 (expired).
U.S. Appl. No. 60/835,442, filed Aug. 4, 2006 (expired).
U.S. Appl. No. 60/643,121, filed Jan. 12, 2005 (expired).
U.S. Appl. No. 60/645,672, filed Jan. 21, 2005 (expired).
U.S. Appl. No. 60/795,615, filed Apr. 28, 2006 (expired).
U.S. Appl. No. 60/833,841, filed Jul. 28, 2006 (expired).
U.S. Appl. No. 60/852,649, filed Oct. 19, 2006 (expired).
U.S. Appl. No. 60/874,968, filed Dec. 15, 2006 (expired).
U.S. Appl. No. 60/907,856, filed Apr. 19, 2007 (expired).
U.S. Appl. No. 60/924,241, filed May 4, 2007 (expired).
U.S. Appl. No. 60/929,393, filed Jun. 25, 2007 (expired).
U.S. Appl. No. 60/935,179, filed Jul. 30, 2007 (expired).
U.S. Appl. No. 60/935,336, filed Aug. 8, 2007 (expired).
U.S. Appl. No. 60/996,160, filed Nov. 5, 2007 (expired).
U.S. Appl. No. 61/006,409, filed Jan. 11, 2008 (expired).
U.S. Appl. No. 61/064,818, filed Mar. 28, 2008 (expired).
U.S. Appl. No. 61/071,512, filed May 2, 2008 (expired).
U.S. Appl. No. 61/213,326, filed May 29, 2009 (expired).
U.S. Appl. No. 61/222,711, filed Jul. 2, 2009 (expired).
U.S. Appl. No. 61/263,175, filed Nov. 20, 2009 (expired).
U.S. Appl. No. 61/272,162, filed Aug. 25, 2009 (expired).
U.S. Appl. No. 61/272,250, filed Sep. 4, 2009 (expired).
U.S. Appl. No. 12/230,120, filed Aug. 8, 2008 (corresponds to JP 2009-0050156, Feb. 2009).
Webster's New World Dictionary, Third College Edition 1988, definition for engaged and flexible, before applicants' filing date.
Webster's Third New International Dictionary, 1993, Dictionary definition for adjustable, bendable, and mild steel, before applicants' filing date.
Notification of the First Office Action and English translation, for corresponding Chinese Application No. 200980116004.3, dated Dec. 24, 2012, 12 pages.

Notice of Reasons for Rejection and English Translation for corresponding JP Application No. 2010-548986, dated Apr. 16, 2003, 5 pages.
First Examination Report for corresponding NZ Application No. 607032, dated Feb. 18, 2013, 2 pages.
Patent Examination Report No. 1 for corresponding AU Application No. 2009221630, dated Mar. 21, 2013, 3 pages.
Office Action dated Apr. 4, 2013 in U.S. Appl. No. 13/747,772.
Office Action dated Apr. 8, 2013 in U.S. Appl. No. 13/747,701.
Notice of Allowance dated Mar. 28, 2013 in U.S. Appl. No. 12/736,024.
Notification of the Second Office Action and English Translation for corresponding Chinese Application No. 200980116004.3, dated Sep. 11, 2013, 14 pages.
European Search Report for corresponding European Application No. 09716457.8, dated Jan. 31, 2014, 5 pages.
Australian Patent Examination Report No. 2 for corresponding Australian Application No. 2009221630, dated Feb. 25, 2014, 3 pages.
European Search Report for corresponding European Application No. 13197251.5, dated Feb. 19, 2014, 6 pages.
Notice of Reasons for Rejection and English Translation for corresponding Japanese Application No. 2010-548986, dated Mar. 3, 2014, 5 pages.
Third Office Action issued in Chinese Application No. 200980116004.3 dated Apr. 8, 2014 (with translation).
New Zealand First Examination Report for Application No. 624599 dated May 13, 2014 (2 pages).
Innovation Patent Examination Report No. 2 dated Aug. 8, 2014 in Australian Application No. 2014100361 (5 pages).
D'Souza et al., U.S. Appl. No. 14/447,673, filed Jul. 31, 2014, entitled "Mask System".
Notice of Opposition to Grant of Patent (Section 21) to New Zealand Patent Application No. 607032, filed Sep. 1, 2014, 7 pages.
Notice of Opposition to Grant of Patent (Section 21) to New Zealand Patent Application No. 622665, filed Sep. 1, 2014, 7 pages.
Notice of Opposition to Grant of Patent (Section 21) to New Zealand Patent Application No. 622666, filed Sep. 1, 2014, 7 pages.
Notice of Opposition to Grant of Patent (Section 21) to New Zealand Patent Application No. 622670, filed Sep. 1, 2014, 7 pages.
Application Under Regulation 168 for Extension of Time in New Zealand Patent Application Nos. 607032, 622666, 622670 and 622665, filed Sep. 1, 2014, 2 pages.
Office Action dated Sep. 17, 2014 in corresponding U.S. Appl. No. 13/747,701 (21 pages).
Amended Notice of Opposition to Grant of Patent filed by Fisher & Paykel Healthcare Limited in New Zealand Patent Application No. 622665 and Statement of Case filed on Oct. 30, 2014 (27 pages).
Amended Notice of Opposition to Grant of Patent filed by Fisher & Paykel Healthcare Limited in New Zealand Patent Application No. 622670 and Statement of Case filed on Oct. 30, 2014 (27 pages).
Amended Notice of Opposition to Grant of Patent filed by Fisher & Paykel Healthcare Limited in New Zealand Patent Application No. 607032 and Statement of Case filed on Oct. 30, 2014 (27 pages).
Amended Notice of Opposition to Grant of Patent filed by Fisher & Paykel Healthcare Limited in New Zealand Patent Application No. 622666 and Statement of Case filed on Oct. 30, 2014 (26 pages).
First Examination Report dated Oct. 24, 2014 in New Zealand Application No. 701183 (2 pages).
First Examination Report dated Oct. 21, 2014 in New Zealand Application No. 701136 (1 page).
Notification of the Fourth Office Action dated Oct. 17, 2014 in Chinese Application No. 200980116004.3, with English Translation (16 pages).
Office Action dated Dec. 8, 2014 in U.S. Appl. No. 14/447,673 (12 pages).
6 photos of ResMed S8 Escape flow generator tub and liner, the tub and liner are joined by a chemical bond resulting from co-moulding.
Japanese Office Action dated Dec. 1, 2014 in Japanese Application No. 2010-548986, with English Translation (8 pages).
Communication dated Jan. 5, 2015 (Extension of Time Granted), with Notice of Opposition filed Dec. 23, 2014, in New Zealand Application No. 624599 (9 pages).

(56) References Cited

OTHER PUBLICATIONS

Extended European Search Report dated Jan. 15, 2015 in European Application No. 14182823.6 (6 pages).
IP Australia Official Receipt dated Jan. 19, 2015, with Statement of Grounds and Particulars, filed in Australian Application No. 2009221630 (21 pages).
Office Action dated Feb. 3, 2015 in U.S. Appl. No. 14/447,673 (19 pages).
Communication Pursuant to Article 94(3) EPC dated Feb. 11, 2015 in European Application No. 13 197 251.5 (4 pages).
Extension of Time Granted (1 page) dated Mar. 2, 2015 in New Zealand Application No. 701136, together with a Notice of Opposition to Grant of Patent (Section 21) (8 pages).
Extension of Time Granted (1 page) dated Mar. 2, 2015 in New Zealand Application No. 701183, together with a Notice of Opposition to Grant of Patent (Section 21) (8 pages).
Deadline for Counterstatement (1 page) dated Mar. 27, 2015 in New Zealand Application No. 624599, together with Amended Notice of Opposition to Grant of Patent (Section 21) (9 pages) and Statement of Case (29 pages).
Statutory Declaration of Christopher Earl Nightingale executed Apr. 17, 2015 for submission in the Opposition of Australian Application No. 2009221630 (1 page).
Statutory Declaration of Alistair Edwin McAuley executed Apr. 9, 2015 for submission in the Opposition of Australian Application No. 2009221630 (39 pages).
Second Statutory Declaration of Alistair Edwin McAuley executed Apr. 14, 2015 for submission in the Opposition of Australian Application No. 2009221630 (6 pages).
Third Statutory Declaration of Alistair Edwin McAuley executed Apr. 17, 2015 for submission in the Opposition of Australian Application No. 2009221630 (11 pages).
Statutory Declaration of Troy Alan Baker executed Apr. 16, 2015 for submission in the Opposition of Australian Application No. 2009221630 (36 pages).
Statutory Declaration of Dr. David Maurice Rapoport executed Apr. 2, 2015 for submission in the Opposition of Australian Application No. 2009221630 (45 pages).
Statement of Case dated Apr. 28, 2015 and filed by Fisher & Paykel Healthcare Limited in New Zealand Opposition No. 701136 (14 pages).
U.S. Appl. No. 13/834,189, filed Mar. 2013, Hitchcock et al.
U.S. Appl. No. 13/870,678, filed Apr. 2013, Kwok et al.
Statement of Case dated Apr. 28, 2015 and filed by Fisher & Paykel Healthcare Limited in New Zealand Opposition No. 701183 (13 pages).
Proceeding Correspondence mailed Jun. 17, 2015 in New Zealand Appln. No. 622670 (2 pages).
Proceeding Correspondence mailed Jun. 17, 2015 in New Zealand Appln. No. 607032 (2 pages).
Affirmation of Chun Cui executed Jun. 12, 2015 for submission in the Opposition of New Zealand Application Nos. 607032 (51 pages).
Statutory Declaration of Troy Alan Baker executed Apr. 16, 2015 for submission in the Opposition of New Zealand Application Nos. 607032, 622666 and 622670 (36 pages).
Statutory Declaration of Dr. David Maurice Rapoport executed Apr. 2, 2015 for submission in the Opposition of New Zealand Application Nos. 607032, 622666 and 622670 (46 pages).
Statutory Declaration of Alistair Edwin McAuley executed Apr. 9, 2015 for submission in the Opposition of New Zealand Application Nos. 607032, 622666 and 622670 (38 pages).
Second Statutory Declaration of Alistair Edwin McAuley executed Apr. 14, 2015 for submission in the Opposition of New Zealand Application Nos. 607032, 622666 and 622670 (3 pages).
Patent Examination Report No. 1 dated May 29, 2015 in Australian Application No. 2014218465 (8 pages).
Notice of Reasons for Rejection dated Jun. 30, 2015 in Japanese Application No. 2014-114555, with English Translation (11 pages).
Proceeding Correspondence mailed Jul. 20, 2015 in New Zealand Application No. 624599 (4 pages).
Extension of Time Granted mailed Oct. 22, 2015 in New Zealand Appln. No. 622666 acknowledging receipt of evidence and amended pleadings filed Oct. 15, 2015 (2 pages).
Extension of Time Granted mailed Oct. 22, 2015 in New Zealand Appln. No. 622670 acknowledging receipt of evidence and amended pleadings filed Oct. 15, 2015 (2 pages).
Extension of Time Granted mailed Oct. 22, 2015 in New Zealand Appln. No. 607032 acknowledging receipt of evidence and amended pleadings filed Oct. 15, 2015 (2 pages).
Declaration of Haydn Llewellyn dated Sep. 23, 2015 (3 pages), with 1 Exhibit (1 page) relating to the sale of HC431 Full Face Mask filed in New Zealand Appln. Nos. 607032, 622666, 622670, 624599, 701136, 701183, 612787 and 599406.
Second Amended Notice of Opposition to Grant of Patent (Section 21) (clean and marked up) filed Oct. 15, 2015 in New Zealand Appln. No. 622666 (20 pages).
First Amended Statement of Case (clean and marked up) filed Oct. 15, 2015 in New Zealand Appln. No. 622666 (32 pages).
Second Amended Notice of Opposition to Grant of Patent (Section 21) (clean and marked up) filed Oct. 15, 2015 in New Zealand Appln. No. 622670 (20 pages).
First Amended Statement of Case (clean and marked up) filed Oct. 15, 2015 in New Zealand Appln. No. 622670 (36 pages).
Third Statutory Declaration of Alastair Edwin McAuley dated Oct. 15, 2015 and filed in New Zealand Appln. No. 622670 (22 pages).
Second Amended Notice of Opposition to Grant of Patent (Section 21) (clean and marked up) filed Oct. 15, 2015 in New Zealand Appln. No. 607032 (22 pages).
First Amended Statement of Case (clean and marked up) filed Oct. 15, 2015 in New Zealand Appln. No. 607032 (43 pages).
Third Statutory Declaration of Alastair Edwin McAuley dated Oct. 15, 2015 and filed in New Zealand Appln. No. 607032 (20 pages).
Communication pursuant to Article 94(3) EPC dated Nov. 27, 2015 in EP Appln. No. 14 182 823.6 (5 pages).
Deadline for Applicant to File Evidence mailed Nov. 17, 2015 in New Zealand Appln. No. 607032 (2 pages).
Deadline for Applicant to File Evidence mailed Nov. 17, 2015 in New Zealand Appln. No. 622666 (2 pages).
Deadline for Applicant to File Evidence mailed Nov. 17, 2015 in New Zealand Appln. No. 622670 (2 pages).
Third Amended Notice of Opposition to Grant of Patent (marked up and clean) filed Nov. 16, 2015 in New Zealand Appln. No. 607032 (20 pages).
Second Amended Statement of Case (marked up and clean) filed Nov. 16, 2015 in New Zealand Appln. No. 607032 (40 pages).
Affirmation of Nicola Jane Kahn with Exhibits NJK-1 to NJK-4 dated Nov. 6, 2015 for New Zealand Appln. No. 607032 (17 pages).
Second Affirmation of Nicola Jane Kahn Exhibits NJK-5 to NJK-7 dated Nov. 13, 2015 for New Zealand Appln. No. 607032 (7 pages).
Statutory Declaration of John Dominic Simpson with Exhibits JDS-1 to JDS-13 dated Nov. 11, 2015 for New Zealand Appln. Nos. 622666, 622670, 607032, 624599, 701136 and 701183 (48 pages).
Statutory Declaration of Christopher Bryn Sparks dated Nov. 11, 2015 for New Zealand Appln. Nos. 622666, 622670, 607032, 624599, 701136 and 701183 (2 pages).
Fourth Statutory Declaration of Alastair Edwin McAuley with Exhibit AM-3 dated Nov. 11, 2015 with Exhibit AM-3 for New Zealand Appln. No. 607032 (23 pages).
Statutory Declaration of Gregory James Olsen with Exhibits GO-1 and GO-2 dated Nov. 16, 2015 for New Zealand Appln. No. 607032 (7 pages).
Third Amended Notice of Opposition to Grant of Patent (marked up and clean) filed Nov. 16, 2015 in New Zealand Appln. No. 622666 (18 pages).
Second Amended Statement of Case (marked up and clean) filed Nov. 16, 2015 in New Zealand Appln. No. 622666 (16 pages).
Affirmation of Nicola Jane Kahn with Exhibits NJK-1 to NJK-4 dated Nov. 6, 2015 for New Zealand Appln. No. 622666 (16 pages).
Second Affirmation of Nicola Jane Kahn Exhibits NJK-5 to NJK-7 dated Nov. 13, 2015 for New Zealand Appln. No. 622666 (7 pages).

(56) References Cited

OTHER PUBLICATIONS

Third Statutory Declaration of Alastair Edwin McAuley dated Nov. 16, 2015 for New Zealand Appln. No. 622666 (28 pages).
Third Amended Notice of Opposition to Grant of Patent (marked up and clean) filed Nov. 16, 2015 in New Zealand Appln. No. 622670 (18 pages).
Second Amended Statement of Case (marked up and clean) filed Nov. 16, 2015 in New Zealand Appln. No. 622670 (34 pages).
Affirmation of Nicola Jane Kahn with Exhibits NJK-1 to NJK-4 dated Nov. 6, 2015 for New Zealand Appln. No. 622670 (16 pages).
Second Affirmation of Nicola Jane Kahn Exhibits NJK-5 to NJK-7 dated Nov. 13, 2015 for New Zealand Appln. No. 622670 (7 pages).
Fourth Statutory Declaration of Alastair Edwin McAuley with Exhibit AM-3 dated Nov. 16, 2015 for New Zealand Appln. No. 622670 (15 pages).
Proceeding Correspondence Mailed Jan. 8, 2016 in New Zealand Application No. 701136 (2 pages).
Extension of Time Granted Mailed Jan. 7, 2016 in New Zealand Application No. 701183 (2 pages).
First Amended Notice of Opposition to Grant of Patent (marked up and clean) filed Dec. 21, 2015 and filed in New Zealand Application No. 701136 (16 pages).
First Amended Statement of Case (marked up and clean) filed Dec. 21, 2015 and filed in New Zealand Application No. 701136 (28 pages).
Affirmation of Nicola Jane Kahn with Exhibits NJK-1 to NJK-22 dated Dec. 14, 2015 filed in New Zealand Appln. Nos. 701136 and 701183 (51 pages).
Statutory Declaration of David Maurice Rapoport with Exhibit DMR-1 dated Dec. 15, 2015 filed in New Zealand Appln. Nos. 701136 and 701183 (47 pages).
Statutory Declaration of Troy Alan Baker with Exhibit TAB-1 dated Dec. 22, 2015 filed in New Zealand Appln. Nos. 701136 and 701183 (38 pages).
Second Statutory Declaration of Alastair Edwin McAuley with Exhibits AM-3 to AM-5 dated Dec. 17, 2015 (103 pages).
Extension of Time Granted mailed Mar. 9, 2016 in NZ Application No. 701136 (2 pages).
Statutory Declaration of Michael George Richardson dated Feb. 18, 2016 filed in New Zealand Appln No. 701136 (11 pages).
Statutory Declaration of Gregory James Olsen dated Feb. 26, 2016 filed in New Zealand Appln Nos. 701136 and 701183 (7 pages).
Statutory Declaration of Arthur Lucian Howden Roberts dated Feb. 26, 2016 filed in New Zealand Appln Nos. 701136 and 701183 (44 pages).
Affirmation of Nicola Jane Kahn dated Feb. 26, 2016 filed in New Zealand Appln No. 701136 (15 pages).
Evidence Correspondence dated Mar. 15, 2016 in New Zealand Application No. 701136 (3 pages).
Second Amended Notice of Opposition dated Mar. 14, 2016 in New Zealand Application No. 701136 (tracked and clean) (19 pages).
Second Amended Statement of Case dated Mar. 14, 2016 in New Zealand Application No. 701136 (tracked and clean) (36 pages).
Fourth Statutory Declaration of Alastair Edwin McAuley dated Mar. 11, 2016 in New Zealand Application No. 701136 (94 pages).
Communication issued in related European Application No. 14 182 823.6 dated Nov. 27, 2015 (5 pages).
Second Statutory Declaration of Arthur Lucian Howden Roberts dated Mar. 10, 2016 in New Zealand Application Nos. 701136 and NZ 701183 (11 pages).
Second Statutory Declaration of Christopher Bryn Sparks dated Mar. 1, 2016 in New Zealand Application Nos. 701136 and NZ 701183 (1 page).
Second Statutory Declaration of Gregory James Olsen dated Mar. 4, 2016 in New Zealand Application Nos. 701136 and NZ 701183 (7 pages).
Opponent's Evidence dated Mar. 14, 2016 for New Zealand Appln No. 701136 (1 page).

Alastair Edwin McAuley Exhibit Note 6, referred to in the Fourth Statutory Declaration of Alastair Edwin McAuley dated Mar. 11, 2016 filed in New Zealand Appln No. 701136 (16 pages).
Alastair Edwin McAuley Exhibit Note 7, referred to in the Fourth Statutory Declaration of Alastair Edwin McAuley dated Mar. 11, 2016 filed in New Zealand Appln No. 701136 (18 pages).
Alastair Edwin McAuley Exhibit Note 8, referred to in the Second Statutory Declaration of Alastair Edwin McAuley dated Mar. 11, 2016 filed in New Zealand Appln No. 701136 (26 pages).
Statutory Declaration of Gregory James Olsen dated Mar. 4, 2016 filed in New Zealand Appln Nos. 701136 and 701183 (7 pages).
Application for Extension of Time to Mar. 29, 2016 in NZ Application No. 701136 (2 pages).
Fifth Statutory Declaration of Alastair Edwin McAuley dated Mar. 22, 2016 in New Zealand Application No. 701136 (1 pages).
Extension of Time Granted dated Apr. 13, 2016 and Application for Extension of Time dated Apr. 12, 2016 in New Zealand Application No. 701183 (4 pages).
Second Affirmation of Nicola Jane Kahn dated Apr. 12, 2016 in New Zealand Application No. 701183 (8 pages).
Second Statutory Declaration of Alastair Edwin McAuley dated Apr. 11, 2016 in New Zealand Application No. 701183 (148 pages).
Deadline for Applicant to File Evidence dated Apr. 27, 2016 in New Zealand Application No. 701136 (2 pages).
Amended Notice of Opposition to Grant of Patent (marked up and clean) filed Apr. 27, 2016 and filed in New Zealand Application No. 701136 (18 pages).
Amended Statement of Case (marked up and clean) filed Apr. 27, 2016 and filed in New Zealand Application No. 701136 (32 pages).
Third Affirmation of Nicola Jane Kahn filed Apr. 26, 2016 and filed in New Zealand Application No. 701136 (5 pages).
Third Statutory Declaration of Alastair Edwin McAuley filed Apr. 26, 2016 and filed in New Zealand Application No. 701136 (117 pages).
Third Statutory Declaration of Arthur Lucian Howden Edwards filed Apr. 21, 2016 and filed in New Zealand Application No. 701136 (24 pages).
Proceeding Correspondence dated Jun. 2, 2016 filed in New Zealand Application No. 701136 (1 page).
Second Amended Notice of Opposition to Grant of Patent (Section 21) in New Zealand Application No. 701136 (9 pages).
Puritan Bennett "Breeze SleepGear User's Guide", Nellcor Puritan Bennett Inc., www.puritanbennett.com, (2007) (16 pages).
Petition for Inter Partes Review of U.S. Pat. No. 9,119,931, *Fisher & Paykel Healthcare v. Resmed Limited*, Case No. IPR2017-00061, dated Oct. 12, 2016 (104 pages).
Affidavit of Christopher Butler, Ultra Mirage Brochure (Ultra Mirage) in Support of Petition for Inter Partes Review of U.S. Pat. No. 9,119,931, *Fisher & Paykel Healthcare v. Resmed Limited*, Case No. IPR2017-00061, dated Sep. 6, 2016 (9 pages).
Affidavit of Christopher Butler, FlexiFit Instructions (FlexiFit) in Support of Petition for Inter Partes Review of U.S. Pat. No. 9,119,931, *Fisher & Paykel Healthcare v. Resmed Limited*, Case No. IPR2017-00061, dated Sep. 6, 2016 (23 pages).
Declaration of Jason Eaton, P.E. in Support of Petition for Inter Partes Review of U.S. Pat. No. 9,119,931, *Fisher & Paykel Healthcare v. Resmed Limited*, Case No. IPR2017-00061, dated Oct. 11, 2016 (136 pages).
Malloy, Robert A., Plastic Part Design for Injection Molding: An Introduction, pp. 336-345 (Hanser Gardner Publications, Inc., 1994) (14 pages).
Declaration of Fiona Cresswell in Support of Petition for Inter Partes Review of U.S. Pat. No. 9,119,931, *Fisher & Paykel Healthcare v. Resmed Limited*, Case No. IPR2017-00061, dated Sep. 21, 2016 (29 pages).
Petition for Inter Partes Review of U.S. Pat. No. 9,119,931, *Fisher & Paykel Healthcare v. Resmed Limited*, Case No. IPR2017-00062, dated Oct. 12, 2016 (106 pages).
Affidavit of Christopher Butler, Ultra Mirage Brochure (Ultra Mirage) in Support of Petition for Inter Partes Review of U.S. Pat. No. 9,119,931, *Fisher & Paykel Healthcare v. Resmed Limited*, Case No. IPR2017-00062, dated Sep. 6, 2016 (9 pages).

(56) References Cited

OTHER PUBLICATIONS

Affidavit of Christopher Butler, FlexiFit Instructions (FlexiFit) dated in Petition for Inter Partes Review of U.S. Pat. No. 9,119,931, *Fisher & Paykel Healthcare* v. *Resmed Limited*, Case No. IPR2017-00062, dated Sep. 6, 2016 (23 pages).
Declaration of Jason Eaton, P.E. in Support of Petition for Inter Partes Review of U.S. Pat. No. 9,119,931, *Fisher & Paykel Healthcare* v. *Resmed Limited*, Case No. IPR2017-00062, dated Oct. 11, 2016 (130 pages).
Declaration of Fiona Cresswell, in Support of Petition for Inter Partes Review of U.S. Pat. No. 9,119,931, *Fisher & Paykel Healthcare* v. *Resmed Limited*, Case No. IPR2017-00062, dated Sep. 21, 2016 (29 pages).
Petition for Inter Partes Review of U.S. Pat. No. 9,119,931, *Fisher & Paykel Healthcare* v. *Resmed Limited*, Case No. IPR2017-00064, dated Oct. 12, 2016 (102 pages).
Declaration of Jason Eaton, P.E. in Support of Petition for Inter Partes Review of U.S. Pat. No. 9,119,931, *Fisher & Paykel Healthcare* v. *Resmed Limited*, Case No. IPR2017-00064, dated Oct. 11, 2016 (133 pages).
Petition for Inter Partes Review of U.S. Pat. No. 9,119,931, *Fisher & Paykel Healthcare* v. *Resmed Limited*, Case No. IPR2017-00065, dated Oct. 12, 2016 (136 pages).
Declaration of Jason Eaton, P.E. in Support of Petition for Inter Partes Review of U.S. Pat. No. 9,119,931, *Fisher & Paykel Healthcare* v. *Resmed Limited*, Case No. IPR2017-00065, dated Oct. 11, 2016 (176 pages).
Affidavit of Christopher Butler, Ultra Mirage Brochure (Ultra Mirage) in Support of Petition for Inter Partes Review of U.S. Pat. No. 9,119,931, *Fisher & Paykel Healthcare* v. *Resmed Limited*, Case No. IPR2017-00065, dated Sep. 6, 2016 (9 pages).
Affidavit of Christopher Butler, FlexiFit Instructions (FlexiFit) dated in Petition for Inter Partes Review of U.S. Pat. No. 9,119,931, *Fisher & Paykel Healthcare* v. *Resmed Limited*, Case No. IPR2017-00065, dated Sep. 6, 2016 (23 pages).
Notification of the First Office Action issued in related Chinese Application No. 2015103415970 with English Translation, dated Dec. 30, 2016 (15 pages).
Notification of the First Office Action issued in related Chinese Application No. 201510341599.X with English Translation, dated Dec. 29, 2016 (7 pages).
Petition for Inter Partes Review of U.S. Pat. No. 9,027,556, *Fisher & Paykel Healthcare* v. *Resmed Limited*, Case No. IPR2017-00501, dated Dec. 16, 2016 (130 pages).
Declaration of Richard Lordo, P.E. in Support of Petition for Inter Partes Review of U.S. Pat. No. 9,027,556, *Fisher & Paykel Healthcare* v. *Resmed Limited*, Case No. IPR2017-00501, dated Dec. 16, 2016 (192 pages).
Petition for Inter Partes Review of U.S. Pat. No. 9,027,556, *Fisher & Paykel Healthcare* v. *Resmed Limited*, Case No. IPR2017-00504, dated Dec. 16, 2016 (133 pages).
Declaration of Richard Lordo, P.E. in Support of Petition for Inter Partes Review of U.S. Pat. No. 9,027,556, *Fisher & Paykel Healthcare* v. *Resmed Limited*, Case No. IPR2017-00504, dated Dec. 16, 2016 (194 pages).
Sixth Statutory Declaration of Alastair Edwin McAuley filed Nov. 2, 2016 and filed in New Zealand Application No. 701136 (9 pages).
Statutory Declaration of Daniel Anthony Hearn filed Sep. 13, 2016 and filed in New Zealand Application No. 701136 (6 pages).
Notification of the First Office Action issued in related Chinese Application No. 201510342347.9, with English Translation, dated Sep. 28, 2016 (24 pages).
Examination Report—Communication Purusant to Article 94(3) EPC issued in corresponding European Application No. 14 182 823.6-1662 dated Dec. 7, 2016, 4 pages.
Fourth Amended Notice of Opposition to Grant of Patent (Section 21) marked-up and clean formats dated Dec. 19 16 in New Zealand Application No. 607032 (16 pages).

Fourth Amended Notice of Opposition to Grant of Patent (Section 21) marked-up and clean formats dated Dec. 23 16 in New Zealand Application No. 701183 (15 pages).
Fourth Amended Notice of Opposition to Grant of Patent (Section 21) marked-up and clean formats dated Dec. 23 16 in New Zealand Application No. 701136 (17 pages).
Sixth Statutory Declaration of Alastair Edwin McAuley filed Nov. 2, 2016 in New Zealand Application No. 701136 (9 pages).
Statutory Declaration of Daniel Anthony Hearn filed Sep. 13, 2016 in New Zealand Application No. 701136 (6 pages).
Fourth Amended Notice of Opposition to Grant of Patent (Section 21) marked-up and clean formats filed Dec. 23, 2016 in New Zealand Application No. 622666 (16 pages).
Third Amended Notice of Opposition to Grant of Patent (Section 21) marked-up and clean formats filed Sep. 1, 2016 in New Zealand Application No. 701136 (18 pages).
Third Amended Statement of Case marked-up and clean formats filed Sep. 1, 2016 in New Zealand Application No. 701136 (32 pages).
Second Amended Notice of Opposition to Grant of Patent (Section 21) marked-up and clean formats filed Jan. 17, 2017 in related New Zealand Application No. 624599 (16 pages).
Third Amended Statement of Case marked-up and clean formats filed Jan. 31, 2017 in related New Zealand Application No. 607032 (45 pages).
Fifth Amended Notice of Opposition to Grant of Patent (Section 21) marked-up and clean formats filed Jan. 31, 2017 in related New Zealand Application No. 607032 (11 pages).
Fourth Amended Statement of Case marked-up and clean formats filed Jan. 31, 2017 in related New Zealand Application No. 701136 (42 pages).
Fifth Amended Notice of Opposition to Grant of Patent (Section 21) marked-up and clean formats filed Jan. 31, 2017 in related New Zealand Application No. 701136 (13 pages).
Second Amended Statement of Case marked-up and clean formats filed Jan. 31, 2017 in related New Zealand Application No. 701183 (36 pages).
Second Amended Notice of Opposition to Grant of Patent (Section 21) marked-up and clean formats filed Jan. 31, 2017 in related New Zealand Application No. 701183 (12 pages).
Decision Instituting Inter Partes Review, 37 C.F.R. § 42.108, *Fisher & Paykel Healthcare* v. *Resmed Limited*, Case No. IPR2017-00061, Patent 9,119,931 B2, dated Mar. 23, 2017 (26 pages).
Scheduling Order, 37 C.F.R. § 42.108, *Fisher & Paykel Healthcare* v. *Resmed Limited*, Case No. IPR2017-00061, Patent 9,119,931 B2, dated Mar. 23, 2017 (8 pages).
Decision Instituting Inter Partes Review, 37 C.F.R. § 42.108, *Fisher & Paykel Healthcare* v. *Resmed Limited*, Case No. IPR2017-00062, Patent 9,119,931 B2, dated Mar. 31, 2017 (37 pages).
Scheduling Order, 37 C.F.R. § 42.108, *Fisher & Paykel Healthcare* v. *Resmed Limited*, Case No. IPR2017-00062, Patent 9,119,931 B2, dated Mar. 31, 2017 (8 pages).
First Office Action issued in related Japanese Application No. 2016-092520 with English translation dated Mar. 27, 2017 (18 pages).
EPO Brief Communication issued in related European Application No. 13197251.5 dated Mar. 28, 2017 (10 pages).
EPO Communication of a Notice of Opposition issued in related European Application No. 13197251.5 dated Sep. 8, 2016 (56 pages).
R.A. Malloy in "Plastic part design for injection molding: An introduction"; Section 6.3 Snap joint assemblies, 1994, Munich, Hanser.
Second Statutory Declaration of Christopher Bryn Sparks in related New Zealand Application Nos. 701136, 701183, 607032, 622666, and 622670, dated Apr. 19, 2017 (6 pages).
Statutory Declaration of Alastair Edwin McAuley in Relation to Simplicity Mask and Sleepnet IQ Mask in related New Zealand Application Nos. 622666, 622670, 607032, 701136, 701183, and 624599, dated Apr. 21, 2017 (5 pages).
Statutory Declaration of Arthur Lucian Howden Roberts in related New Zealand Application Nos. 607032, 622666, 622670, and 624599, dated Apr. 12, 2017 (11 pages).

(56) References Cited

OTHER PUBLICATIONS

Statutory Declaration of Daniel Anthony Hearn in related New Zealand Application Nos. 607032, 622666, 622670, 701136 and 701136, dated Jan. 27, 2017 (41 pages).
Fifth Statutory Declaration of Alastair Edwin McAuley in related New Zealand Application No. 607032, dated Apr. 21, 2017 (153 pages).
EXH-AM4 to AM-23 referred to in Fifth Statutory Declaration of Alastair Edwin McAuley in related New Zealand Application No. 607032, dated Apr. 21, 2017 (188 pages).
Fourth Statutory Declaration of Alastair Edwin McAuley in related New Zealand Application No. 622666, dated Apr. 21, 2017 (220 pages).
EXH-AM3 to AM24 referred to in Fourth Statutory Declaration of Alastair Edwin McAuley in related New Zealand Application No. 622666, dated Apr. 21, 2017 (191 pages).
Fifth Statutory Declaration of Alastair Edwin McAuley in related New Zealand Application No. 607032, dated Apr. 21, 2017 (238 pages).
EXH-AM4 to AM26 referred to in Fifth Statutory Declaration of Alastair Edwin McAuley in related New Zealand Application No. 622670, dated Apr. 21, 2017 (193 pages).
First Examination Report issued in related Australian Application No. 2016222397, dated Feb. 24, 2017, 9 pages.
Decision Denying Institution of Inter Partes Review, 37 C.F.R. § 42.108, *Fisher & Paykel Healthcare* v. *Resmed Limited*, Case No. IPR2017-00064, Patent 9,119,931 B2, dated Apr. 11, 2017 (25 pages).
Decision Denying Institution of Inter Partes Review, 37 C.F.R. § 42.108, *Fisher & Paykel Healthcare* v. *Resmed Limited*, Case No. IPR2017-00065, Patent 9,119,931 B2, dated Apr. 11, 2017 (15 pages).
Notification of Second Office Action issued in related Chinese Application No. 201510342347.9 with English translation dated Apr. 12, 2017 (16 pages).
Third Amended Statement of Case marked-up and clean formats filed Jan. 31, 2017 in related New Zealand Application No. 622670 (47 pages).
Declaration of Jason Eaton, P.E., in Support of Petition for Inter Partes Review of U.S. Pat. No. 9,119,931, Case No. IPR2017-01658, executed Jun. 22, 2017 (352 pages).
Complaint of ResMed Ltd, ResMed Inc., and ResMed Corp. Under Section 337 of the Tariff Act of 1930, as amended, Investigation No. 337-TA-1022, executed Aug. 17, 2016 (30 pages).
Answer of ResMed Corp. to Complaint for Patent Infringement and Counterclaims, *Fisher &Paykel Healthcare Ltd.* v. *ResMed Corp.*, Case No. 3:16-cv-02068-DMS-WVG (S.D. Cal.), filed Sep. 7, 2016 (94 pages).
Declaration of Fiona Cresswell, in Support of Petition for Inter Partes Review of U.S. Pat. No. 9,119,931, Case No. IPR2017-01658, executed Sep. 21, 2016 (5 pages).
Declaration of Jason Eaton, P.E., In Support of Petition for Inter Partes Review of U.S. Pat. No. 9,119,931, Case No. IPR2017-01659, executed Jun. 22, 2017 (333 pages).
Excerpts From the File History of U.S. Pat. No. 9,119,931, D'Souza et al., entitled: Mask System, filed in IPR2017-01658 and IPR2017-01659 on Jun. 22, 2017 (485 pages).
Excerpt from Webster's II New College Dictionary, Third Edition, Houghton Mifflin Company, definition for the term "accommodate", 2005, (3 pages).
Excerpt from The Oxford American College Dictionary, Oxford University Press, Inc., definition for the term "accommodate", 2002, (3 pages).

Second Amended Statement of Case marked-up and clean formats filed May 29, 2017 in related New Zealand Application No. 624599 (80 pages).
Third Amended Notice of Opposition to Grant of Patent (Section 21) marked-up and clean formats filed May 29, 2017 in related New Zealand Application No. 624599 (15 pages).
Fourth Statutory Declaration of Alastair Edwin McAuley in related New Zealand Application No. 701183, dated May 31, 2017 (306 pages).
Statutory Declaration of Daniel Anthony Hearn in related New Zealand Application Nos. 607032, 622666, 622670, and 701136, dated Jan. 27, 2017 (41 pages).
Seventh Statutory Declaration of Alastair Edwin McAuley in related New Zealand Application No. 701136, dated May 31, 2017 (332 pages).
Scheduling Order, 37 C.F.R. § 42.5, *Fisher & Paykel Healthcare* v. *Resmed Limited*, Case No. IPR2017-00501, U.S. Pat. No. 9,027,556 B2, dated Jun. 14, 2017 (10 pages).
Decision, 37 C.F.R. § 42.5, *Fisher & Paykel Healthcare* v. *Resmed Limited*, Case No. IPR2017-00501, U.S. Pat. No. 9,027,556 B2, dated Jun. 14, 2017 (44 pages).
Scheduling Order, 37 C.F.R. § 42.5, *Fisher & Paykel Healthcare* v. *Resmed Limited*, Case No. IPR2017-00504, U.S. Pat. No. 9,027,556 B2, dated Jun. 14, 2017 (10 pages).
Decision, 37 C.F.R. § 42.5, *Fisher & Paykel Healthcare* v. *Resmed Limited*, Case No. IPR2017-00504, U.S. Pat. No. 9,027,556 B2, dated Jun. 14, 2017 (51 pages).
Petition for Inter Partes Review of U.S. Pat. No. 9,119,931, 37 C.F.R. § 42.5, *Fisher & Paykel Healthcare* v. *Resmed Limited*, Case No. IPR2017-01658, dated Jun. 22, 2017, (131 pages).
Petition for Inter Partes Review of U.S. Pat. No. 9,119,931, 37 C.F.R. § 42.5, *Fisher & Paykel Healthcare* v. *Resmed Limited*, Case No. IPR2017-01659, dated Jun. 22, 2017, (125 pages).
Office Action issued in related European Application No. 09 71 6457.8, dated Jun. 19, 2017, (8 pages).
Non-Final Office Action issued in related U.S. Appl. No. 13/964,280, dated May 16, 2017 (77 pages).
Decision of Rejection issued in related Japanese Application No. 2016-92520 dated Feb. 5, 2018, with English Translation, (7 pages).
Letter filed by AJ Park on behalf of Fisher & Paykel Healthcare Limited in New Zealand Application Nos. 701136 and 701183 on Feb. 28, 2018 (2 pages).
Ninth Statutory Declaration of Alastair Edwin McAuley dated Feb. 28, 2018 and filed in New Zealand Application No. 701136, (10 pages).
Fifth Statutory Declaration of Alastair Edwin McAuley dated Feb. 28, 2018 and filed in New Zealand Application No. 701183, (325 pages).
Sixth Statutory Declaration of Alastair Edwin McAuley dated Feb. 28, 2018 and filed in New Zealand Application No. 701183, (4 pages).
Notification of the Third Office Action dated Jan. 17, 2018 in Chinese Application No. 201510341599.X, with English Translation (11 pages).
Statutory Declaration of Yung Chee Kenneth Chong dated Jan. 30, 2018 in connection with New Zealand Application No. 701136, including Exhibit KC-1 (47 pages).
Statutory Declaration of Daniel Anthony Hearn dated Jan. 27, 2017 in connection with New Zealand Application Nos. NZ 607032, NZ 622666, NZ 622670 and NZ 701136, including Exhibits DH-1 to DH-19 (41 pages).
Eighth Statutory Declaration of Alastair Edwin McAuley dated Jan. 30, 2018 in connection with New Zealand Application No. 701136, including Exhibits AM-23 to AM-34 (362 pages).

\* cited by examiner

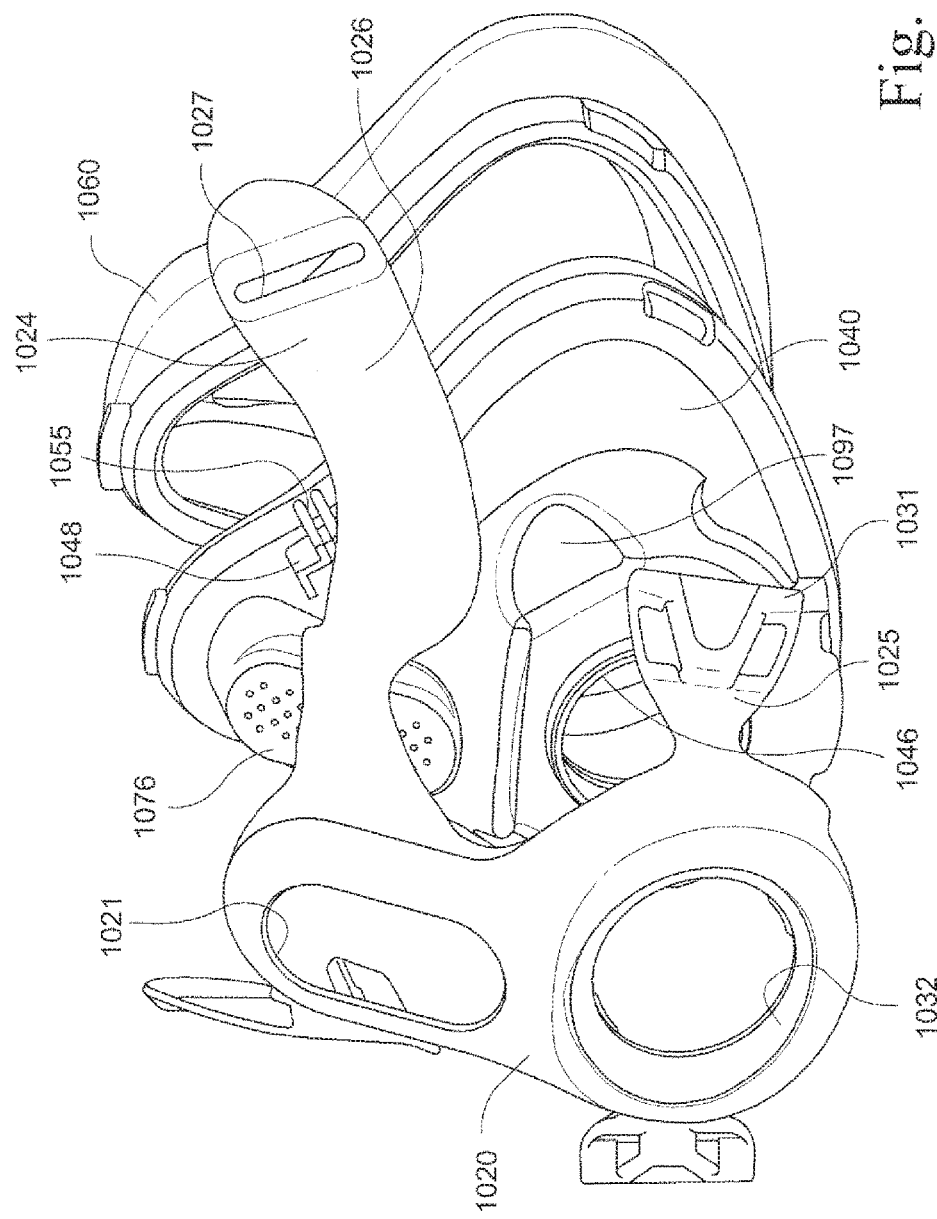

MASK SYSTEM WITH SNAP-FIT SHROUD

CROSS-REFERENCE TO APPLICATION

This application is a continuation of U.S. patent application Ser. No. 15/682,117, filed Aug. 21, 2017, pending, which is a continuation of U.S. patent application Ser. No. 15/440,972, filed Feb. 23, 2017, now U.S. Pat. No. 9,770,568, which is a continuation of U.S. patent application Ser. No. 13/964,280, filed Aug. 12, 2013, now U.S. Pat. No. 9,757,533, which is a continuation of U.S. application Ser. No. 13/745,077, now U.S. Pat. No. 8,528,561, filed on Jan. 18, 2013, which is a continuation of U.S. application Ser. No. 12/736,024, now U.S. Pat. No. 8,550,084, filed on Sep. 2, 2010, which is the U.S. National Stage of PCT/AU2009/000241, filed Feb. 27, 2009, which claims benefit to U.S. Provisional Application Nos. 61/064,406, filed Mar. 4, 2008, 61/071,893, filed May 23, 2008, and 61/136,617, filed Sep. 19, 2008, each of which is incorporated herein by reference in its entirety.

FIELD OF THE INVENTION

The present invention relates to a mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Patient interfaces, such as a full-face or nasal mask systems, for use with blowers and flow generators in the treatment of sleep disordered breathing (SDB), typically include a soft face-contacting portion, such as a cushion, and a rigid or semi-rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present invention provides alternative arrangements of mask systems to enhance the efficacy of therapy and compliance of patients with therapy.

SUMMARY OF THE INVENTION

One aspect of the invention relates to a mask system provided without a forehead support adapted to engage the patient's forehead.

Another aspect of the invention relates to a mask system including a frame and a shroud removably connected to the frame and adapted to attach headgear.

Another aspect of the invention relates to a mask system including a frame defining a breathing chamber, a cushion provided to the frame and adapted to form a seal with the patient's face, and a shroud provided to the frame. The shroud and the frame are co-molded with one another. The frame is constructed of a first, relatively soft, elastomeric material and the shroud is constructed of a second material that is more rigid than the frame. At least a portion of the frame includes a concertina section having a plurality of folds. Each of the folds has a side wall with the side walls of the folds becoming progressively longer away from the patient's face.

Another aspect of the invention relates to a cushion module including a frame defining a breathing chamber and a cushion adapted to form a seal with the patient's face. The frame and the cushion are co-molded with one another. The cushion is constructed of a first, relatively soft, elastomeric material and the frame is constructed of a second material that is more rigid than the cushion. At least a portion of the frame includes a concertina section.

Another aspect of the invention relates to a method for constructing a cushion module. The method includes molding a first part of the cushion module with a first, relatively soft, elastomeric material, co-molding a second part of the cushion module to the first part with a second material that is more rigid than the first material, and molding at least a portion of the second part to include a concertina section.

Another aspect of the invention relates to a shroud for a mask system including a retaining portion structured to retain a frame, a pair of upper headgear connectors each including an elongated arm and a slot at the free end of the arm adapted to receive a headgear strap, and a pair of lower headgear connectors each adapted to attach to a headgear strap, wherein the retaining portion, the upper headgear connectors, and the lower headgear connectors are integrally formed as a one piece structure.

Another aspect of the invention relates to a mask system including a frame defining a breathing chamber, a cushion provided to the frame and adapted to form a seal with the patient's face, a shroud provided to the frame and adapted to attach headgear, and an elbow provided to the frame and adapted to be connected to an air delivery tube that delivers breathable gas to the patient. The shroud includes a retaining mechanism structured to establish a positive connection between the shroud and the frame.

Another aspect of the invention relates to a mask system including a frame defining a breathing chamber and a cushion provided to the frame. The cushion includes a main body and a cushion, wherein the cushion is adapted to engage at least a portion of the patient's face. The cushion includes a base wall connected to an undercushion layer and a membrane, wherein the membrane extends around the perimeter of the cushion and contacts the patient's face. The undercushion layer is positioned underneath the membrane and supports the membrane. The under cushion layer provides differential support to the membrane at predetermined regions of the face.

Another aspect of the invention relates to a mask assembly for use in medical applications having a top and bottom ends defined by its position relative to a patient's face, wherein the mask assembly is connected to a plurality of flexible straps, which are adapted to engage the patient's head. The flexible straps engage at least two elongated rigid arms integrally molded to a portion of the mask assembly, and wherein the elongated arms are molded to the mask assembly proximal to the top end of the mask assembly.

Another aspect of the invention relates to a mask assembly for use in medical applications including a main body connected to a cushion adapted to cover nose and/or mouth and wherein the mask assembly is attached by a force substantially perpendicular towards the face and wherein the force is approximately constant along the length of the mask and is balanced by a portion of the cushion engaging the patient's cheeks.

Another aspect of the invention relates to a cushion for use with a medical mask including an outer membrane layer adapted to sealably engage a face and an undercushion layer adapted to support the membrane layer. The membrane or undercushion layer includes a surface positioned between the two layers adapted to allow the layers to slide against the respective surface.

Another aspect of the invention relates to a mask system including a frame defining a breathing chamber, a cushion provided to the frame and adapted to form a seal with the patient's face, and a releasable shroud adapted to engage a portion of the outer surface of the frame, wherein the shroud is connected to straps to position the mask system.

Another aspect of the invention relates to a mask assembly for use in medical applications including an upper end and a lower end wherein the upper end is adapted to cover the nose and the lower end is adapted to cover the mouth of a patient. The mask assembly includes no forehead support and includes two stiffened members attached to the upper end on opposed sides of the mask assembly, and wherein the stiffened members include a general curved shape and adapted to avoid covering the patient's field of vision.

Another aspect of the invention relates to a cushion for attaching to a medical mask, wherein the cushion is flexible and includes a membrane attached to the circumference of the cushion adapted to seal against the face of a patient, and at least one undercushion adapted to support the membrane and positioned underneath the membrane to prevent collapse of the membrane, in use. The membrane is softer than the undercushion. The undercushion in the regions of nasal bridge or chin is between 0 mm and 30 mm in height as measured between the base and the tip of the undercushion.

Another aspect of the invention relates to a mask assembly for use in medical applications including an upper end and a lower end wherein the upper end is adapted to cover the nose and the lower end is adapted to cover the mouth of a patient. The mask assembly includes no forehead support and includes two stiffened members attached to the upper end on opposed sides of the mask assembly, and wherein the stiffened members include a general curved shape and adapted to avoid covering the patient's field of vision.

In an alternative embodiment, the mask system may include a headgear connector or rigidizer structured to attach to the frame with a snap-fit, mechanical interlock, friction fit, and/or grommet arrangement (e.g., constructed of rubber).

In an alternative embodiment, the mask system may include headgear having an arrangement of straps constructed of silicone and/or Breath-O-Prene™ material.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 4 is another exploded perspective view of the mask system of FIG. 1 showing the frame, cushion, and shroud;

FIGS. 18-1 to 18-2 are cross-sectional views showing in sequential relation attachment of the shroud to the frame of the mask system of FIG. 10;

FIGS. 19-1 to 19-4 are cross-sectional views showing in sequential relation attachment of the shroud to the frame of the mask system of FIG. 10:

FIGS. 31-1 is a rear view of a cushion according to an embodiment of the present invention;

FIG. 31-2 is a front view of the cushion shown in FIG. 31-1 with a partial cut-away:

FIG. 31-3 is a cross-section view through line 31-3-31-3 in FIG. 31-1:

FIG. 31-4 is a cross-section view through line 31-4-31-4 in FIG. 31-1:

FIG. 31-5 is a cross-section view through line 31-5-31-5 in FIG. 31-1;

FIGS. 32-1 to 32-3 illustrate top, front, and side views respectively of a concertina section according to an embodiment of the present invention;

FIGS. 35-1 to 35-3 are front, side, and rear views of a mask system according to another embodiment of the present invention;

FIGS. 37-1 to 37-3 are perspective, front, and side views of a mask system according to another embodiment of the present invention;

FIGS. 38-1 to 38-5 are perspective, front, top, side, and bottom views of a shroud of the mask system shown in FIGS. 37-1 to 37-3:

FIGS. 39-1 to 39-6 are perspective, front, side, bottom, and top views of a mask system according to another embodiment of the present invention:

FIGS. 40-1 and 40-2 are perspective and side views of a mask system according to another embodiment of the present invention:

FIG. 40-3 is a perspective view of the frame of the mask system shown in FIGS. 40-1 and 40-2;

FIGS. 40-4 and 40-5 illustrate a retaining member of the frame shown in FIG. 40-3;

FIGS. 40-6 and 40-7 illustrate a clip-on upper headgear connector of the mask system shown in FIGS. 40-1 and 40-2;

FIGS. 41-1 and 41-2 are rear and front perspective views of a mask system according to another embodiment of the present invention;

FIGS. 41-3 and 41-4 are exploded views of the mask system shown in FIGS. 41-1 and 41-2;

FIGS. 41-5 to 41-12 are various views of a clip-on upper headgear connector of the mask system shown in FIGS. 41-1 and 41-2;

FIG. 42-1 is a rear perspective view of a mask system according to another embodiment of the present invention;

FIG. 42-2 is an exploded view of the mask system shown in FIG. 42-1;

FIGS. 42-3 to 42-7 are various views of a clip-on upper headgear connector of the mask system shown in FIG. 42-1;

FIGS. 43-1 to 43-4 are perspective, side, front, and rear views of a mask system according to another embodiment of the present invention;

DETAILED DESCRIPTION OF ILLUSTRATED EMBODIMENTS

Figure 1:
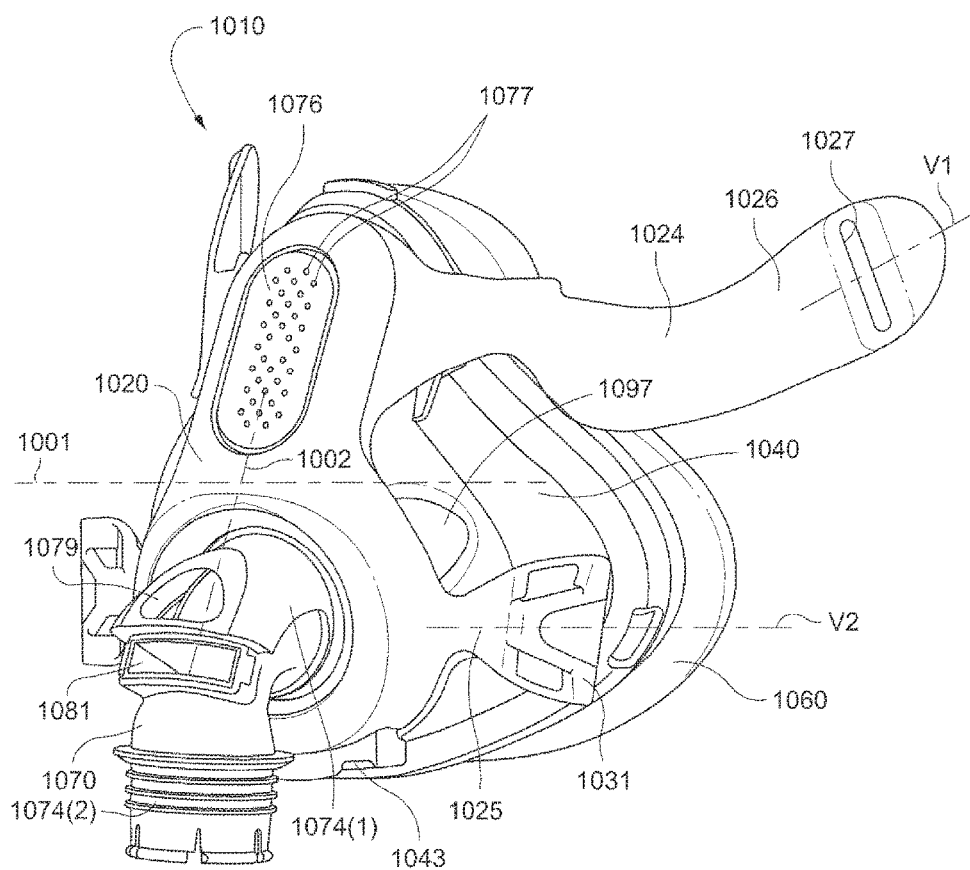
FIG. 1 is a front perspective view of a mask system according to an embodiment of the present invention.

The following description is provided in relation to several embodiments or examples which may share common characteristics and features. It is to be understood that one or more features of any one embodiment or example may be combinable with one or more features of the other embodiments or examples. In addition, any single feature or combination of features in any of the embodiments or examples may constitute additional embodiments or examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The term "shroud" will be taken to include components that partially or fully cover a second component within the illustrated embodiments. In an embodiment, the shroud may include the component that partially covers or is mounted on the frame components of the illustrated embodiments.

The term "positive connection" will be taken to include connections between components of the illustrated embodiments wherein connectors mounted on respective components are adapted to engage each other respectively.

1. Mask System

Embodiments of the invention are directed towards a mask system provided without a forehead support adapted to engage the patient's forehead. Such arrangement provides the mask system with a less obtrusive arrangement which does not significantly affect the patient's field of view. Although the system is designed such that a forehead support is not required, such a forehead support can be added if desired.

As described in greater detail below, the mask system includes a frame, a cushion provided to the frame and adapted to form a seal with the patient's face, a shroud provided to the frame and adapted to attach headgear, and an elbow provided to the frame and adapted to be connected to an air delivery tube that delivers breathable gas to the patient. Headgear may be removably attached to the shroud to maintain the mask system in a desired adjusted position on the patient's face. The mask system is intended for use in positive pressure therapy for users with Obstructive Sleep Apnea (OSA) or another respiratory disorder.

While each embodiment below is described as including a full-face or oro-nasal interface type, each embodiment may be adapted for use with other suitable interface types. That is, the interface type is merely exemplary, and each embodiment may be adapted to include other interface types, e.g., nasal interface, nasal mask, nasal prongs, etc.

2. Stabilizing Mechanisms

The stabilizing mechanisms (e.g., frame, shroud, headgear with associated headgear vectors) of a mask system according to embodiments of the invention are structured to accommodate the elimination of a forehead support from a full-face type interface. For example, a forehead support typically eliminates rotation of the mask system in the sagittal and coronal planes, so the mask system and headgear according to embodiments of the invention are structured to take on these functions since there is no forehead support.

The headgear is connected to the top and bottom of the frame either directly or via the shroud, which shroud provides headgear connection points for headgear positioned and arranged to stably maintain the mask system in position on the patient's face.

2.1 Frame

As shown in FIGS. 1, 1B-1E, and 2-5, the frame 1040 of the mask system 1010 is structured to maintain the cushion 1060, shroud 1020, and elbow 1070 in an operative position with respect to the patient's face. The frame 1040 is constructed (e.g., injection molded) from a more rigid material (e.g., polyurethane) than the cushion 1060 (made of, e.g., silicone), however other materials may function likely as well (e.g., polycarbonate). In an embodiment, the frame has a general wall thickness of about 1-2 mm. e.g., 1.5 mm.

The frame 1040 defines a breathing chamber or cavity adapted to receive the patient's nose and mouth and provide air communication to the patient. One or the lower portion of the frame 1040 includes an opening 1046 adapted to receive or otherwise communicate with the elbow 1070 (e.g., swivel elbow) and another or upper portion of the frame 1040 includes a vent arrangement 1076 for gas washout. In addition, the upper portion of the frame 1040 includes an interfacing structure 1048 adapted to interface or otherwise removably connect to the shroud 1020.

FIGS. 27-30 shows a mask system 10 including a frame 40 with a cushion 44 that provides a sealing portion or sealing ring adapted to form a seal with the patient's nose and/or mouth. Also, the frame 40 includes an opening 46 that is adapted to communicate with the elbow 70.

2.2 Shroud

As shown in FIGS. 1 and 3-6, the shroud 1020 is connected to the frame 1040 and is structured to attach headgear to the mask system. In an embodiment, the shroud 1020 is constructed (e.g., injection molded) of a resilient material including but not limited to plastic or nylon (e.g., Nylon 12). However, the shroud may be constructed of other suitable materials, e.g., polycarbonate, polypropylene, thermoplastic elastomer (TPE), Pocan®, etc. In an embodiment, the shroud has a general wall thickness of about 1-2 mm, e.g., 1.3 mm.

The top end of the shroud 1020 is adapted to be positioned proximal to the nasal bridge region or nose of the patient and the bottom end is adapted to be positioned proximal to the mouth or chin of the patient. The top end includes an opening or vent receiving hole 1021 to accommodate the vent arrangement 1076 that protrudes from the frame 1040, and the bottom end includes an opening or elbow hole 1032 to accommodate the elbow 1070 and elbow opening into the frame 1040 (e.g., shroud provides no contact with elbow when assembled).

Upper headgear connectors 1024 extend from each side of the top end, and lower headgear connectors 1025 extend from each side of the lower end. The headgear connectors 1024, 1025 may be integrally molded or otherwise attached to the shroud.

2.2.1 Upper Headgear Connectors

Each upper headgear connector 1024 includes an elongated arm 1026 and a slot or receiving hole 1027 at the free end of the arm 1026 adapted to receive a respective headgear strap. In use, the arms 1026 extend around the face of the patient in a generally concave angle below the eyes of the patient so as to avoid the patient's field of view, i.e., direct headgear away from the patient's eyes. For example, as shown in FIG. 1E, each arm 1026 may extend at an angle α between about 10-25° (e.g., 170) with respect to horizontal. That is, each arm 1026 is suitably formed, shaped, or contoured to follow the contours of the patient's face and avoid line of sight in use. In an embodiment, the shape of the arms may be generally arcuate and adapted to extend in a direction across the cheek of the patient, % while avoiding the eyes or limiting the field of vision. In an embodiment, the arms may be integrally molded to the shroud of the mask system. One possible advantage of molding the arms onto the shroud is that it greatly increases manufacturability and also the shroud may be easily replaced in the case of accidental breakage of the arms rather than replacing the complete mask system. Additionally, molding of the arms onto the shroud may greatly increase the strength of the connection and reduce or limit the actual likelihood of breakage of the arms.

In an embodiment, the arms 1026 are at least semi-rigid (e.g., relatively rigid) so as to prevent up and down movement or bending of the arms relative to the face of the patient. Thus, the arms 1026 may act as rigidizers to effectively act as a level arrangement and generate a mechanical advantage wherein the pressure or force applied to top end of the mask system is readjusted to a fulcrum point being about the center of balance between the top and bottom ends of the mask system. In an embodiment, the arms are attached to the highest possible point relative to the mask system to additionally stabilize the configuration. In an embodiment, the fulcrum point or moment of pivoting is positioned between the upper and lower connection points of the straps, and wherein the design, angle, length and/or configuration of the arms 1026 may effectively adjust the fulcrum point. In the illustrated embodiment, the fulcrum point is shown to be between the vent arrangement and elbow of the mask system. Additionally, when positioned on the face, the mask system may have a fulcrum point around or about the region between the bottom of the patient's nose and lip area. This feature effectively stabilizes the mask system on the patient's face without the traditional need for a forehead support.

The net result of the arms 1026 mounted in a position extending from the top end of the mask system around the face of the patient is that the mask system is more stable and reduces the net torsional forces experiences about the x-axis 1001 (see FIG. 1) for the mask system in use. Please note that the arms 1026 may be rigidly connected to the mask system in other suitable positions to generate a similar result.

In an embodiment, the arms 1026 may be used to stabilize the mask system by contacting the patient's face at the cheeks. A cheek pad may be provided to the inner surface of the arm to support the arm on the patient's cheek in use. Also, the arms 1026 may be enveloped in a soft fabric sleeve to act as additional padding against the cheeks of the patient. The soft fabric sleeve may be in the configuration of an elastic tube covering a portion of the arms 1026.

2.2.2 Lower Headgear Connectors

Each lower headgear connector 1025 includes an abbreviated arm and a clip receptacle 1031 at the free end of the arm adapted to be removably interlocked with a headgear clip associated with a respective headgear strap. The clips allow for easier positioning or donning/removal of the mask system. In an embodiment, the abbreviated arms and clips are also relatively rigid so as to prevent lateral movement of the arms along the y-axis 1002, relative to the mask system in use.

Figure 28:
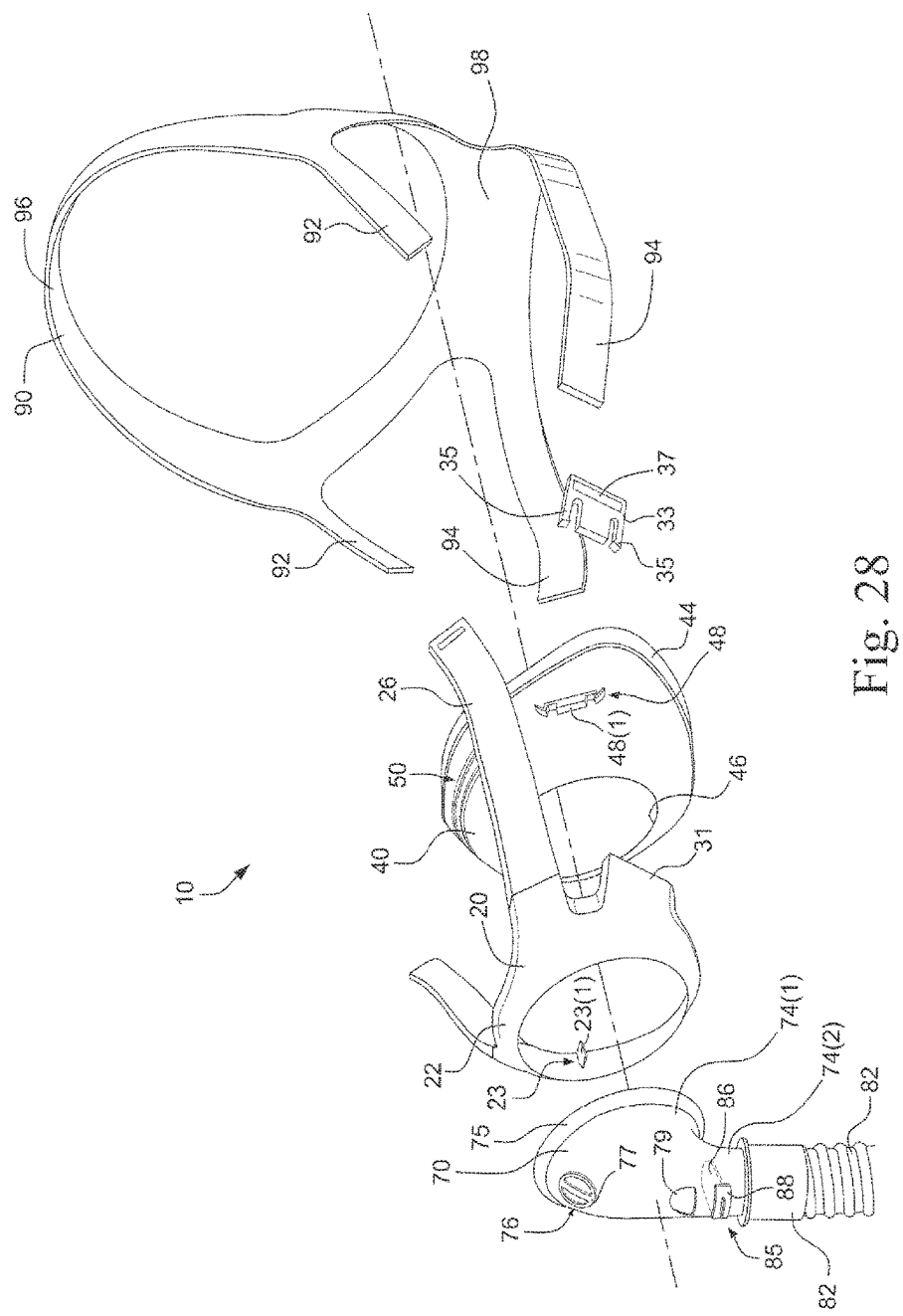
FIG. 28 is an exploded view of the mask system shown in FIG. 27.
Figure 29:
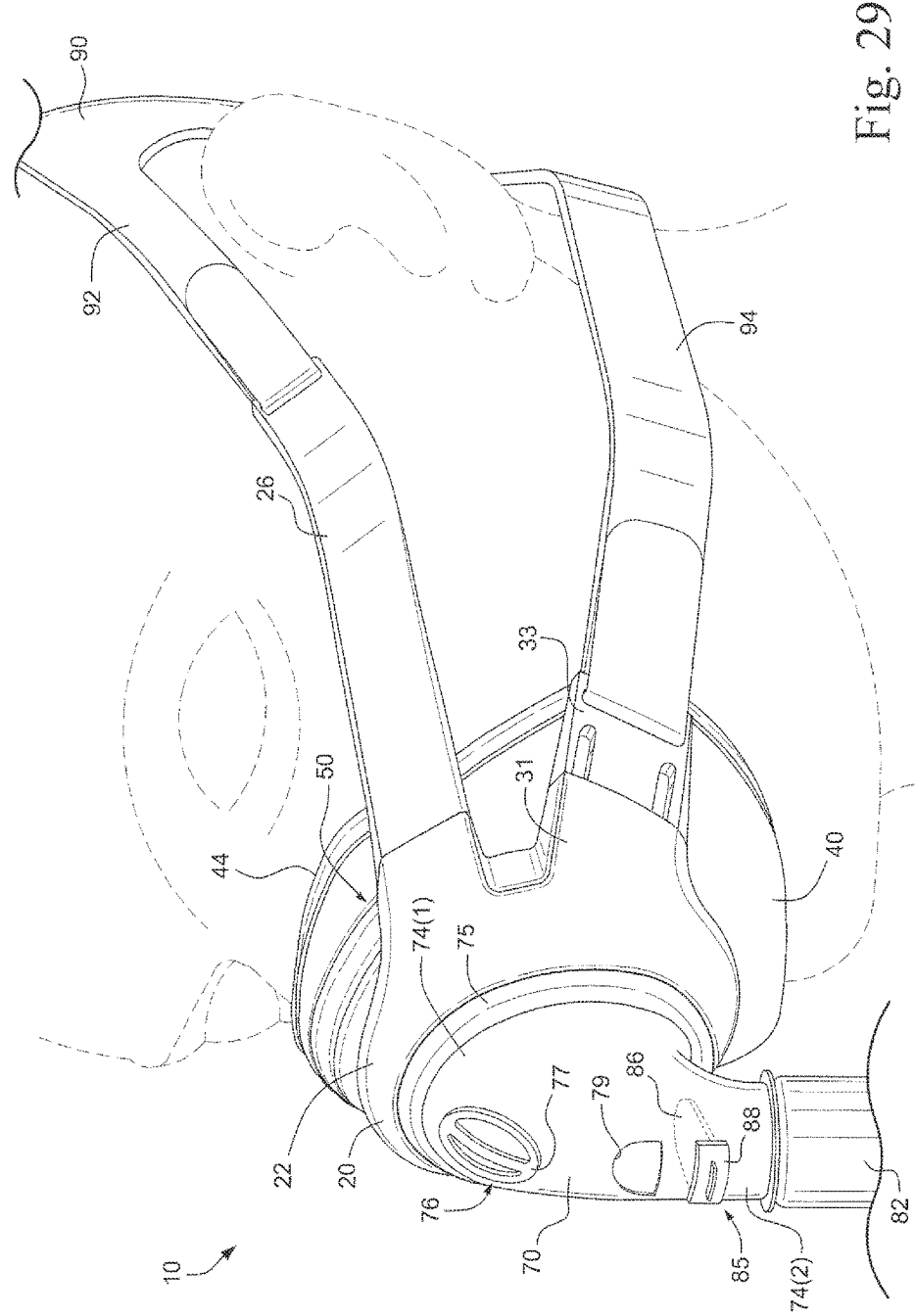
FIG. 29 is an enlarged front perspective view of the mask system shown in FIG. 17.

FIGS. 27-30 illustrate an exemplary headgear clip 33 adapted to be removably interlocked with a clip receptacle 31. As best shown in FIG. 28, each clip 33 includes two spring arms 35 adapted to interlock with the respective clip receptacle 31 with a snap-fit and a slot 37 adapted to receive a respective headgear strap in use.

2.2.3 Alternative Headgear Connectors

As shown in FIGS. 27-30, the arm 26 may be removably coupled to the shroud, e.g., arm 26 includes clip structure adapted to removably interlock with a clip receptacle provided to the shroud. This arrangement allows different styles of upper and lower headgear connectors to be used with the shroud, e.g., arms for both upper and lower headgear connectors, clips for both upper and lower headgear connectors, different length arms for upper and lower headgear connectors, etc.

However, the shroud may provide other suitable arrangements for attaching headgear straps of headgear. Also, the shroud may include one or more additional components, e.g., forehead support.

2.2.4 Headgear Connector Positioning

In the embodiment of FIGS. 1-6, the upper and lower headgear connectors 1024, 1025 provide headgear connection points that are as far from each other as possible (i.e., top and bottom of frame) to allow for greater adjustability (e.g., allows adjustment at the top and bottom of the mask system) and stability (e.g., anchor points spread out around the mask system so more secure on the patient's face). Also, the upper headgear connectors are positioned as close to the top of the mask system as possible without obstructing the patient's eyes in use.

2.2.5 Separate Shroud

In the embodiment of FIGS. 1-6, the shroud 1020 is formed separately (e.g., molded) and attached to the frame 1040. Such arrangement facilitates molding of the shroud, allows different materials to be used for the frame and shroud (e.g., frame can be semi-rigid or rigid for stability and shroud with headgear rigidizers can be flexible for adjustment, allows the shroud to hide elbow retention features around elbow/frame opening for retaining elbow to frame (e.g., provides visual shroud for aesthetics), allows frame to be free of lower clip receptacles, allows shroud to be used with different size frames, and allows the shroud to be designed or stylized to minimize obtrusiveness of the mask system. The separate shroud may also allow the headgear, frame, cushion, and/or elbow to be replaced or washed independently.

2.2.6 Sleeves

In an embodiment, soft fabric sleeves may be mounted on the upper and/or lower headgear connectors. For example, the sleeves may be elastic and adapted to slide over the arms of the headgear connectors to form a tight fit. In an embodiment, the sleeves form elastic tubes. The sleeves may be padded to increase the comfort of the mask system in use. The sleeves may be particularly useful where the arms of the headgear connectors contact the patient's skin, e.g., to protect the patient's skin from irritation.

2.2.7 Arm Extends Over the Patient's Ear

FIGS. 35-1 to 35-3 and 36 illustrate a shroud 220 for mask system 210 according to another embodiment of the present invention. The shroud 220 includes an annular retaining portion 222 structured to retain the frame 240 and upper and lower headgear connectors 224, 225 on each side of the retaining portion 222. In the illustrated embodiment, the shroud 220 is integrally formed in one piece (e.g., see FIG. 36).

In the illustrated embodiment, each upper headgear connector 224 includes an elongated arm 226 and a slot 227 at the free end of the arm 226 adapted to receive a respective rear strap 298 in use. As illustrated, the arm 226 is suitably contoured to extend along the cheeks and over the patient's ear just anterior of the patient's temple and retain the respective rear strap 298 in spaced relation over the patient's ear, e.g., to avoid the strap rubbing or irritating the patient's ear in use.

Also, each arm 226 is structured to extend along and engage an upper strap 292 of the headgear in use. As illustrated, each arm 226 is secured to the upper strap 292 to add rigidity to the strap and stabilize the mask system on the patient's face in use. In addition, the strap 292 provides padding to the arm 226 on the patient's face in use. In an embodiment, the upper strap 292 may be fixed to the arm 226 by gluing or stitching for example. Alternatively, the arms 226 may be encapsulated by or inserted into respective straps 292 so that the arms 226 are substantially not visible.

Each lower headgear connector 225 includes an abbreviated arm 228 with a slot 229 at the free end of the arm 229 adapted to receive a respective lower strap 294 in use. As illustrated, the arm 228 is suitably oriented to retain the respective lower strap 294 in spaced relation under the patient's ear, e.g., to avoid the strap rubbing or irritating the patient's ear in use.

In an embodiment, each arm may be attached to the upper end of the mask system and curves below the patient's field of vision or eyes and curves upwards at an angle between about 10 to 20 degrees away from the horizontal axis.

Figure 36:
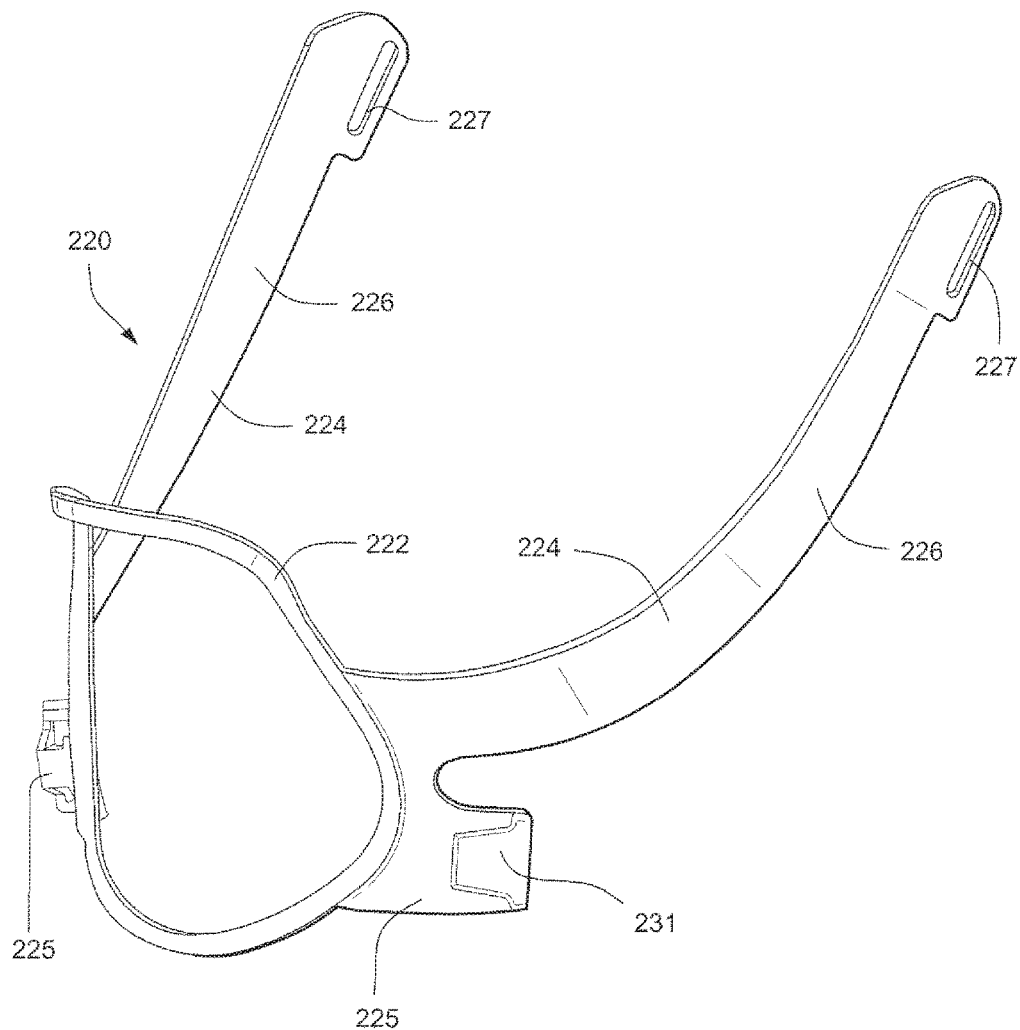
FIG. 36 is a perspective view of a shroud for a mask system according to an embodiment of the present invention.

In an alternative embodiment, as shown in FIG. 36, each lower headgear connector 225 may include a clip receptacle 231 adapted to be removably interlocked with a headgear clip (not shown) associated with a respective lower strap 294. In an embodiment, the headgear clip receptacle and clip may be similar to that on ResMed's Mirage Liberty™ mask. Exemplary clip arrangements are disclosed in U.S. Patent Publication Nos. 2007/0144525 and 2006/0283461, each of which is incorporated herein by reference in its entirety.

2.2.8 Shroud without Upper Headgear Connector

Figure 3:
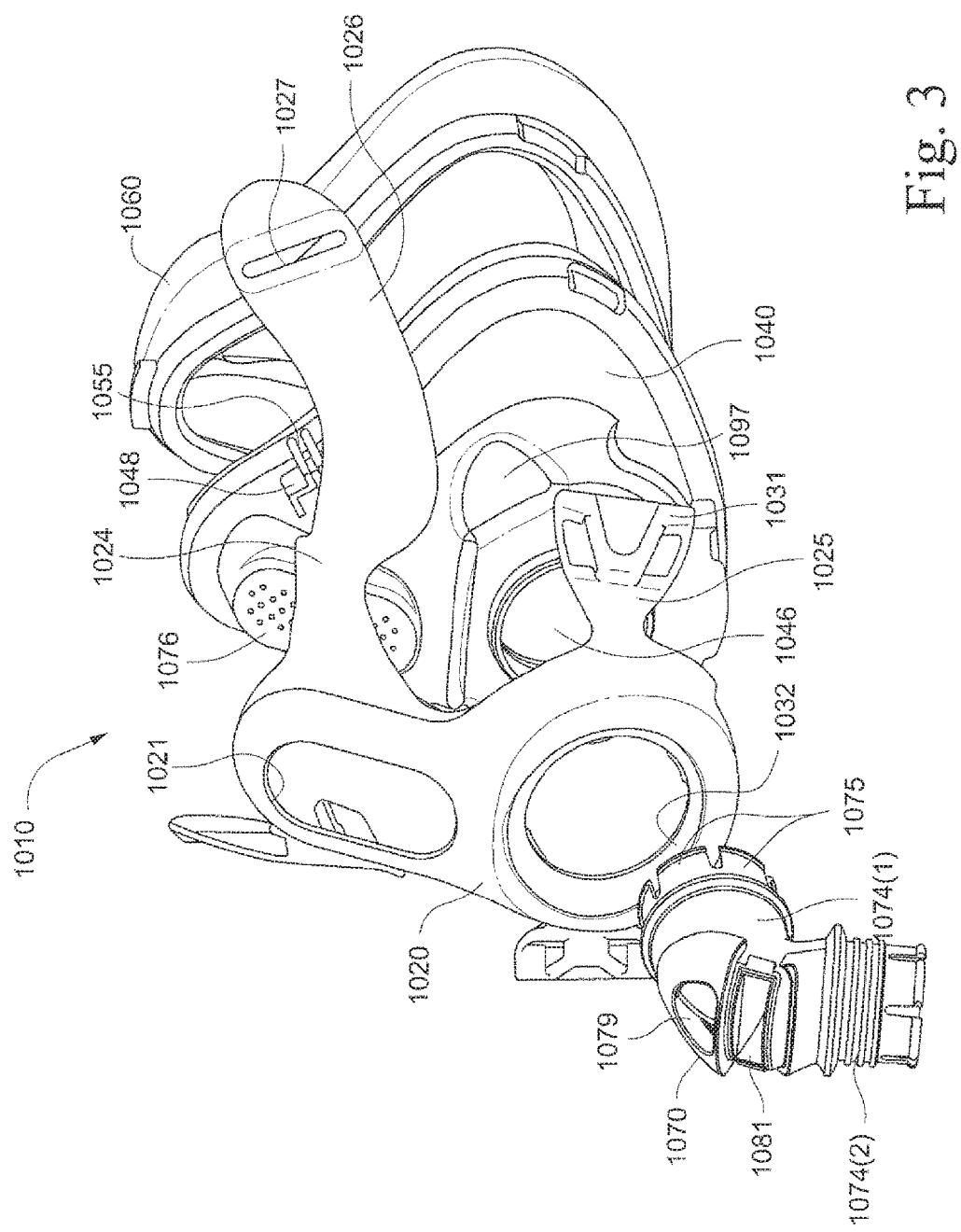
FIG. 3 is an exploded perspective view of the mask system of FIG. 1 showing the frame, cushion, shroud, and elbow.
Figures 1, 37:
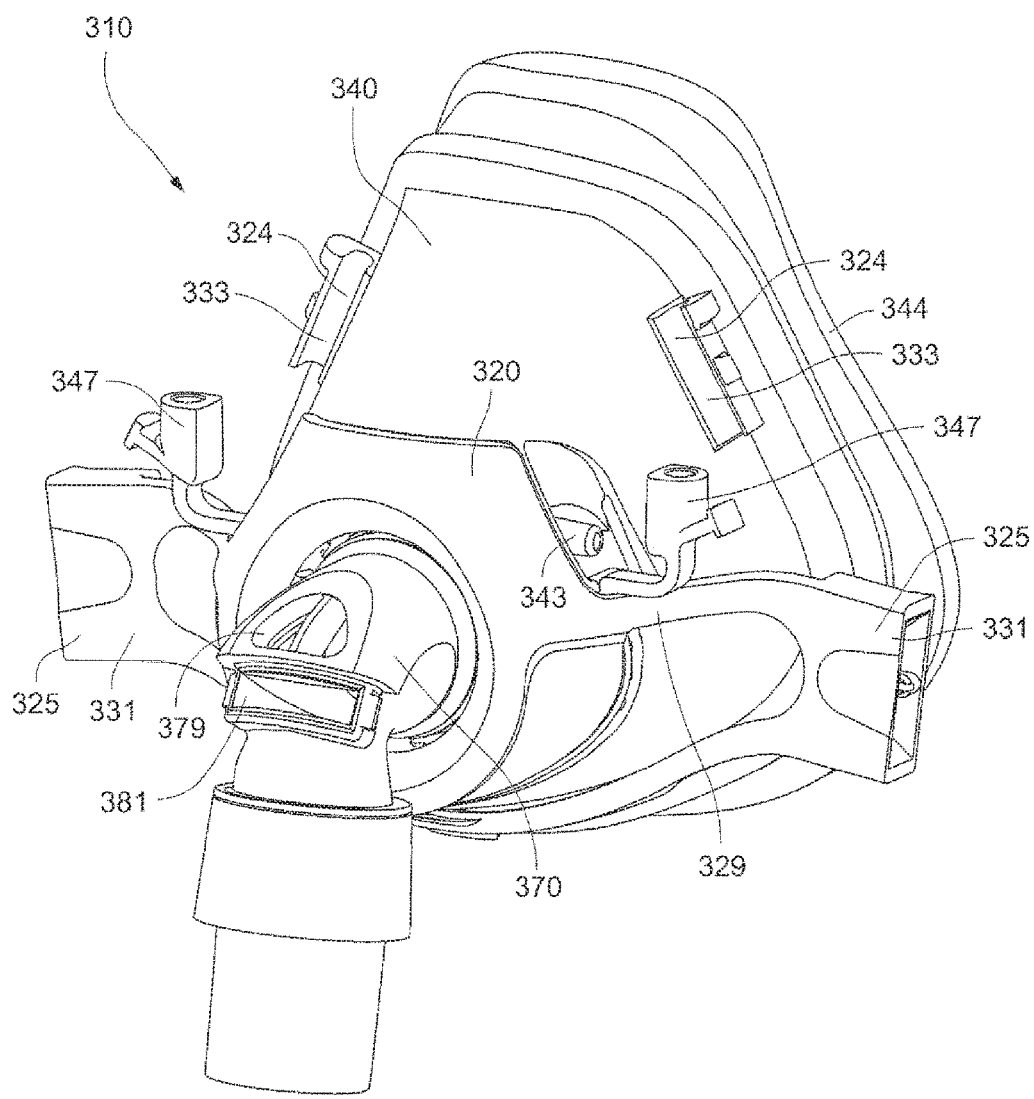
Figures 2, 37:
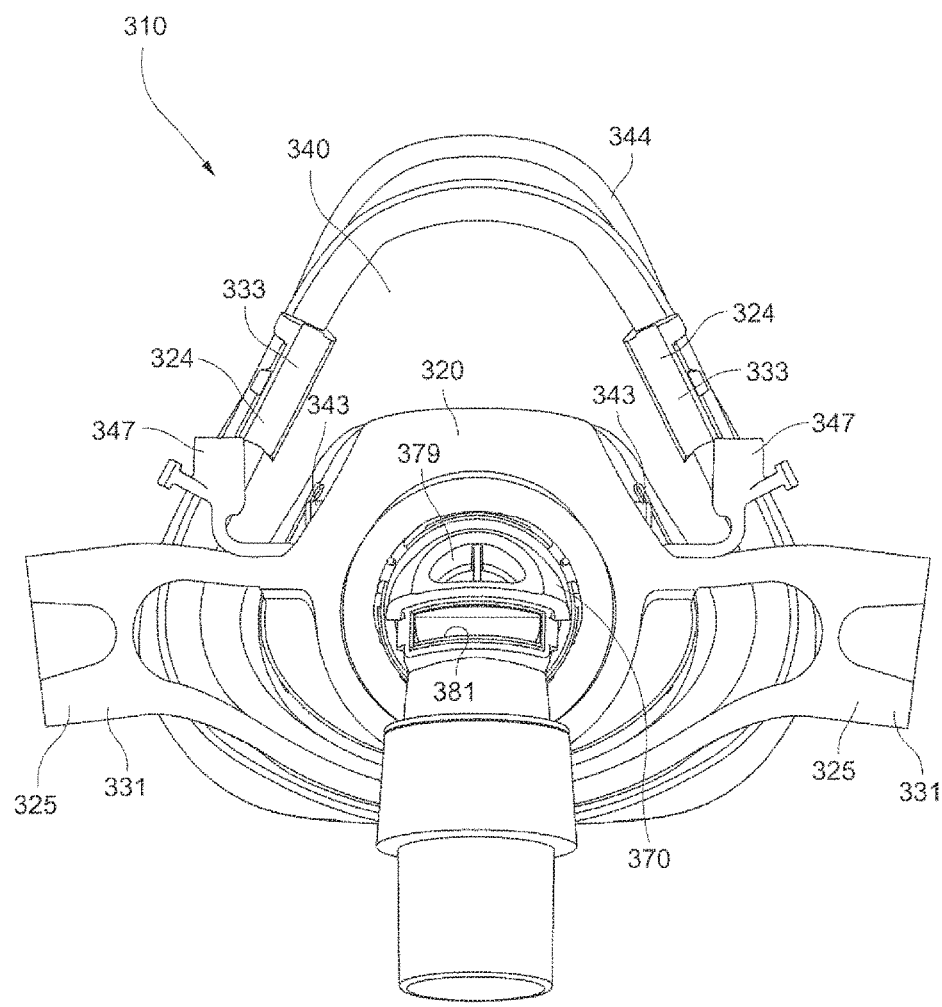
Figures 3, 37:
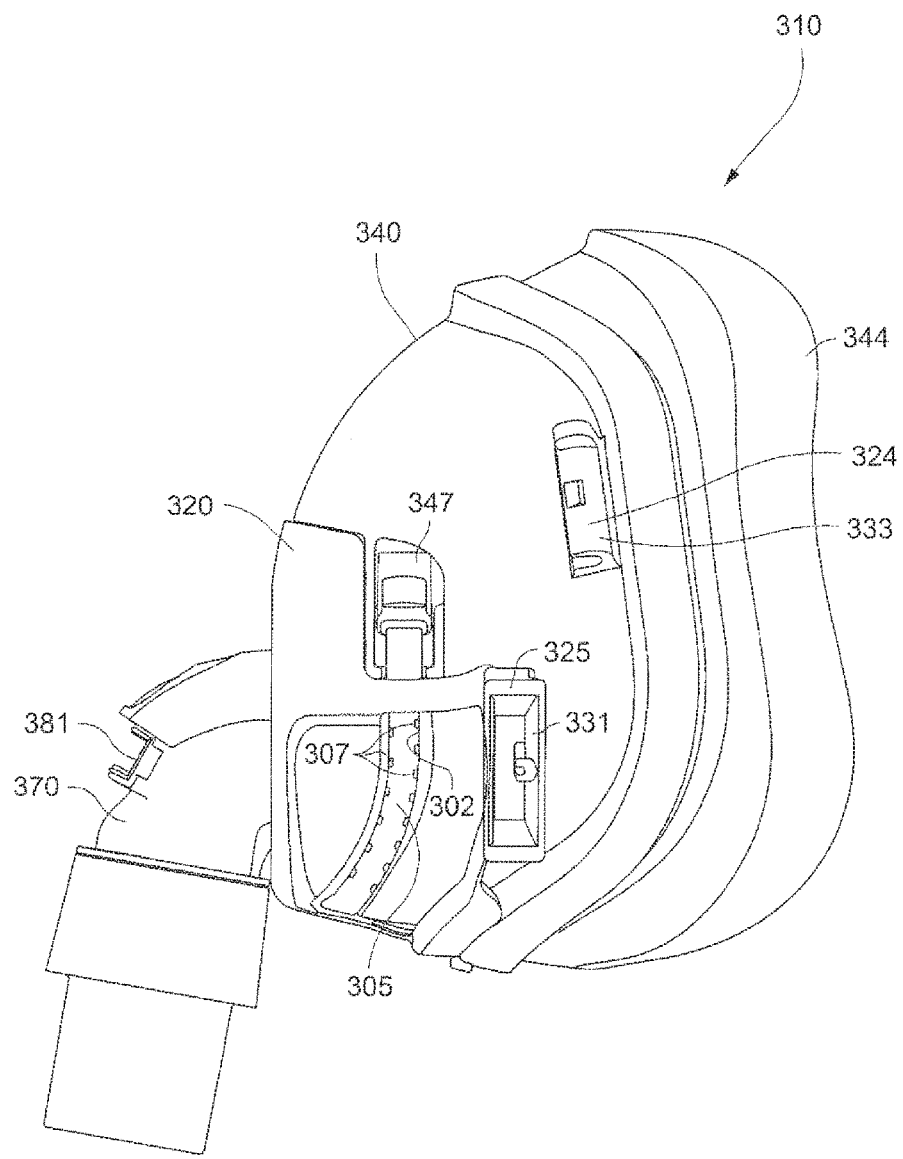

FIGS. 37-1 to 37-3 illustrate a mask system 310 according to another embodiment of the present invention. As illustrated, the mask system 310 includes a shroud 320, a frame 340, a cushion 344, and an elbow 370.

Figure 5:
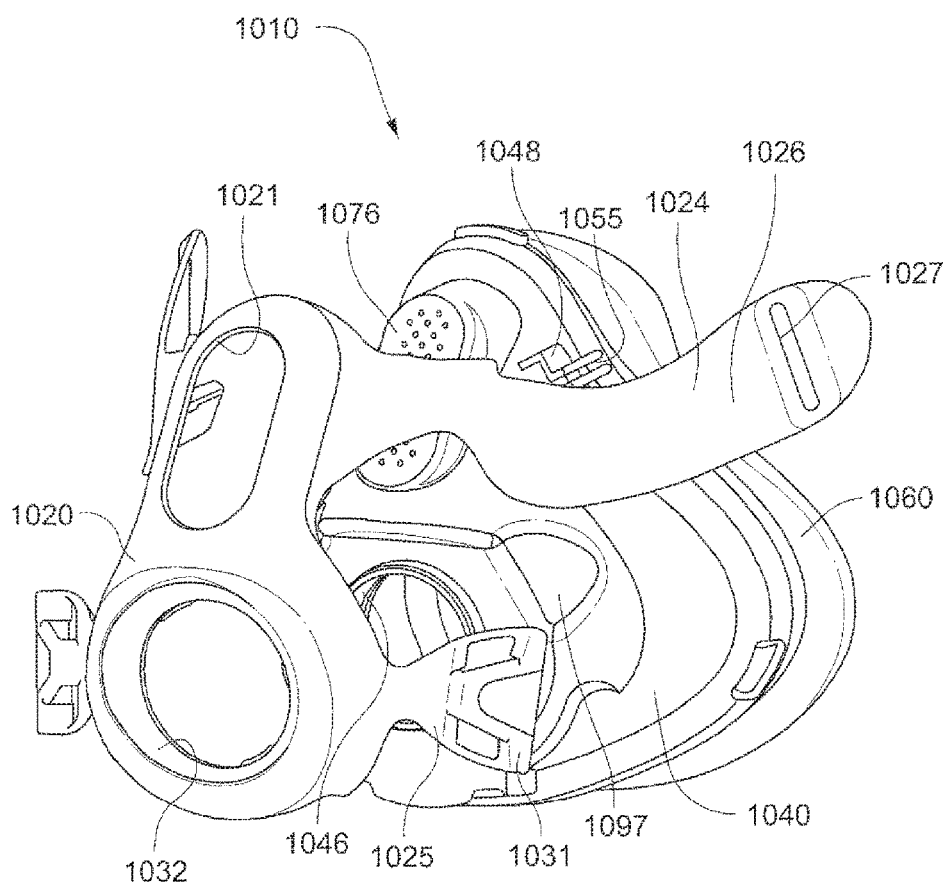
FIG. 5 is an exploded perspective view of the mask system of FIG. 1 showing the shroud and assembled frame/cushion.
Figures 1, 38:
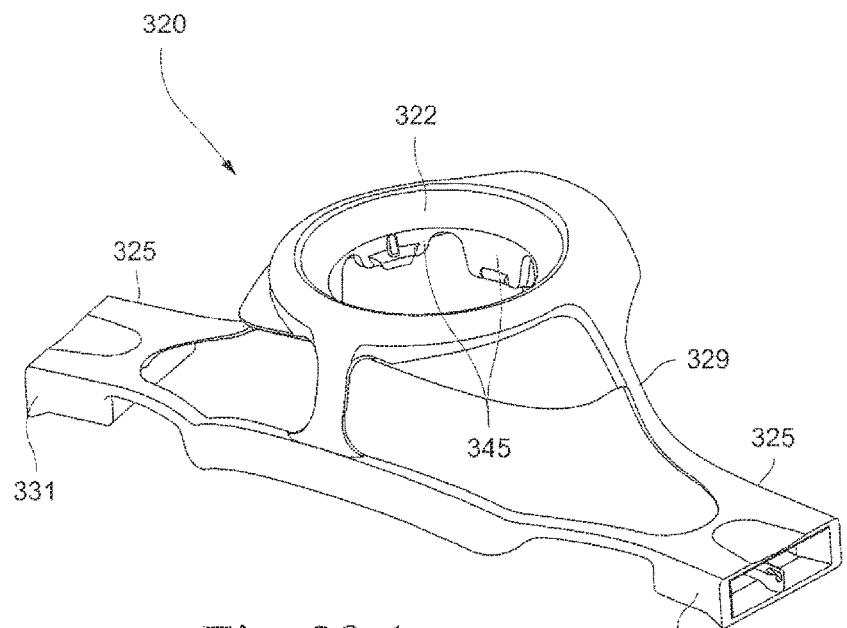
Figures 2, 38:
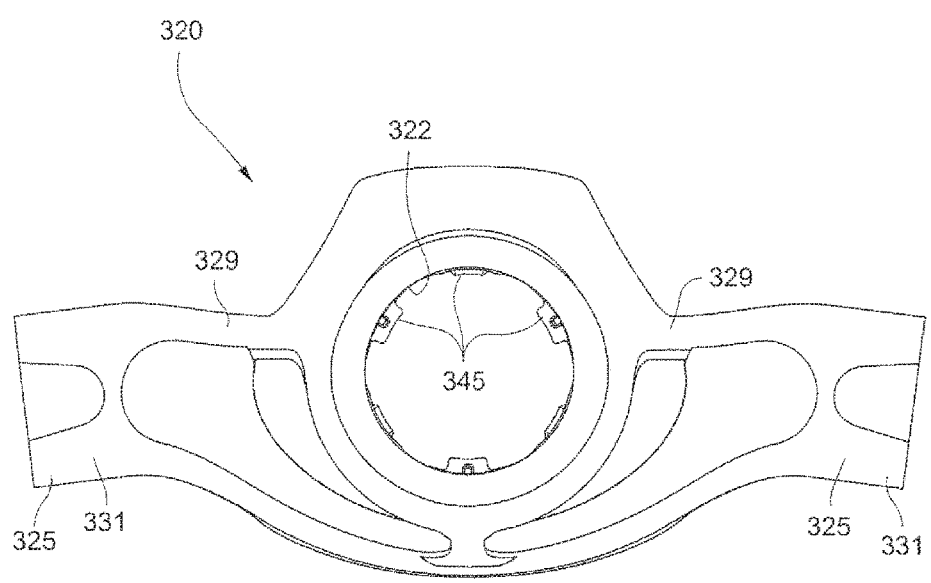
Figures 3, 38:
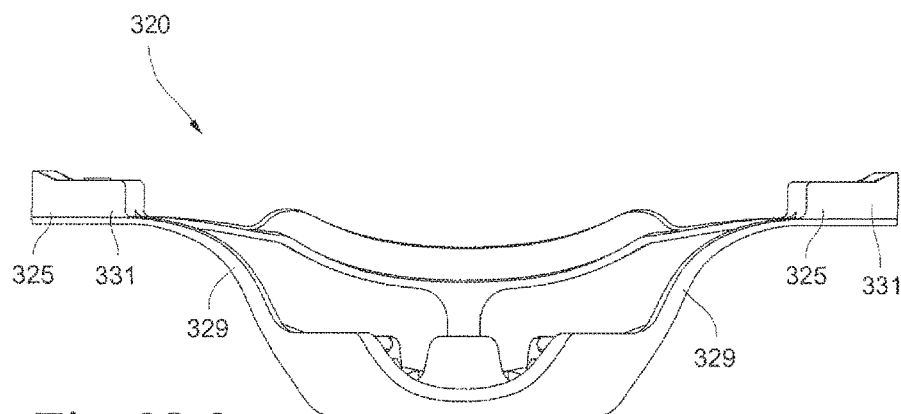
Figures 4, 38:
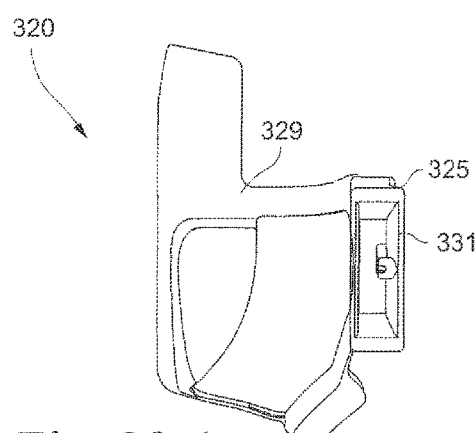
Figures 5, 38:
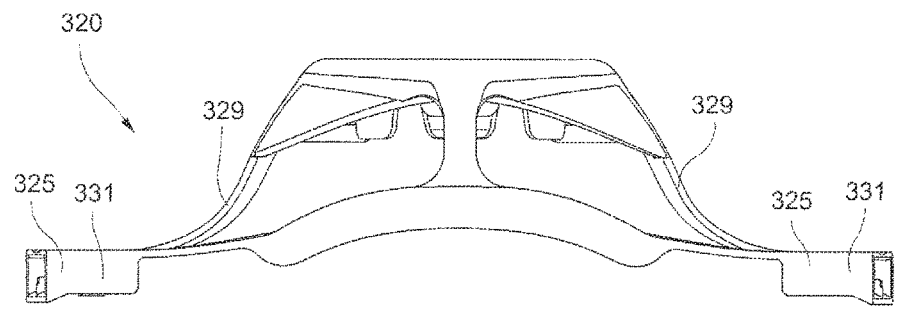

As best shown in FIGS. 38-1 to 38-5, the shroud 320 includes an opening 322 structured to receive the elbow 370 and a headgear connector 325 on each side thereof. In the illustrated embodiment, each headgear connector 325 includes a clip receptacle 331 adapted to be removably interlocked with a headgear clip (not shown) associated with a respective lower headgear strap.

The frame 340 is removably attached to the shroud 320, e.g., fingers and tabs 345 extending from opening 322 adapted to engage collar of frame 340.

The frame 340 includes an upper headgear connector 324 on each upper side thereof. Each headgear connector 324 includes a clip retainer 333 adapted to be removably interlocked with a headgear clip (not shown) associated with a respective upper headgear strap.

Figure 6:
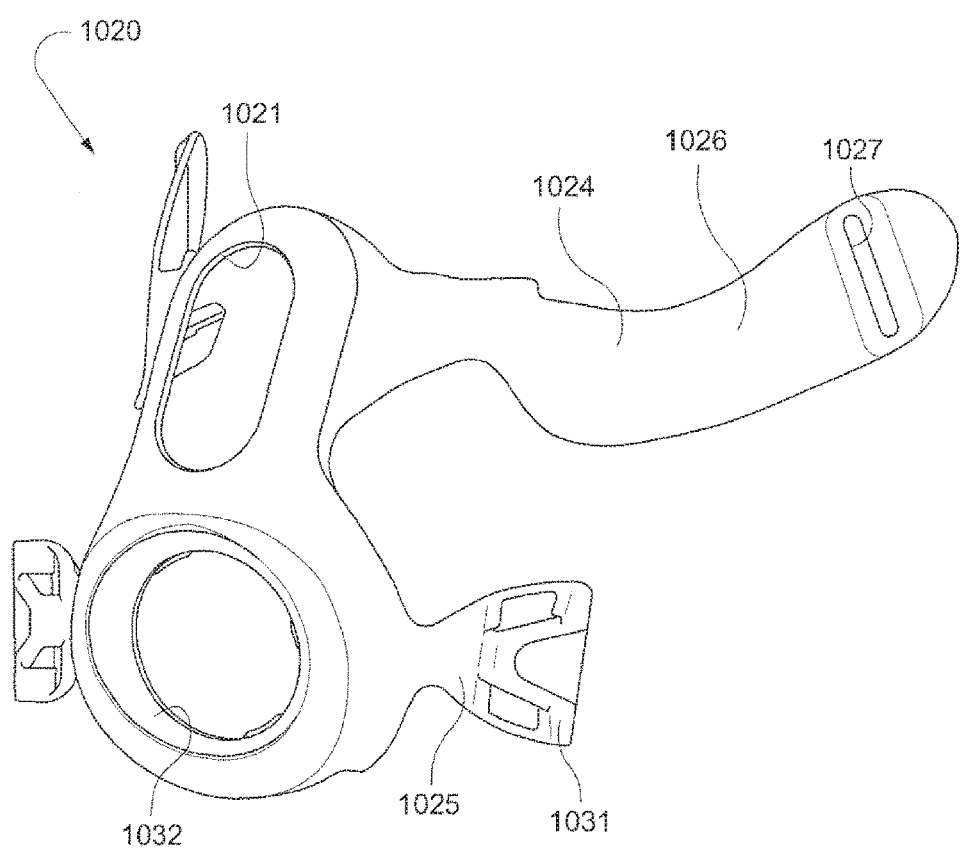
FIG. 6 is a front perspective view showing the shroud of the mask system of FIG. 1.
Figures 1, 39:
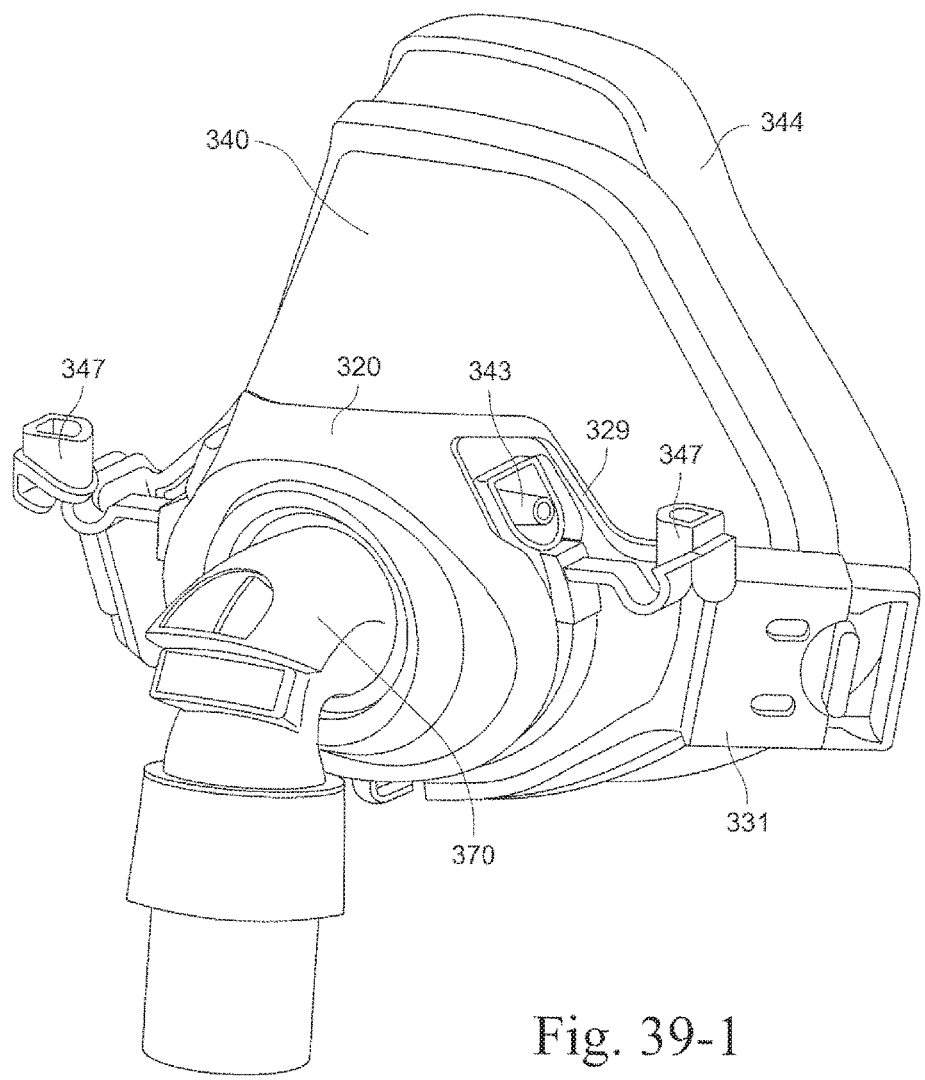
Figures 2, 39:
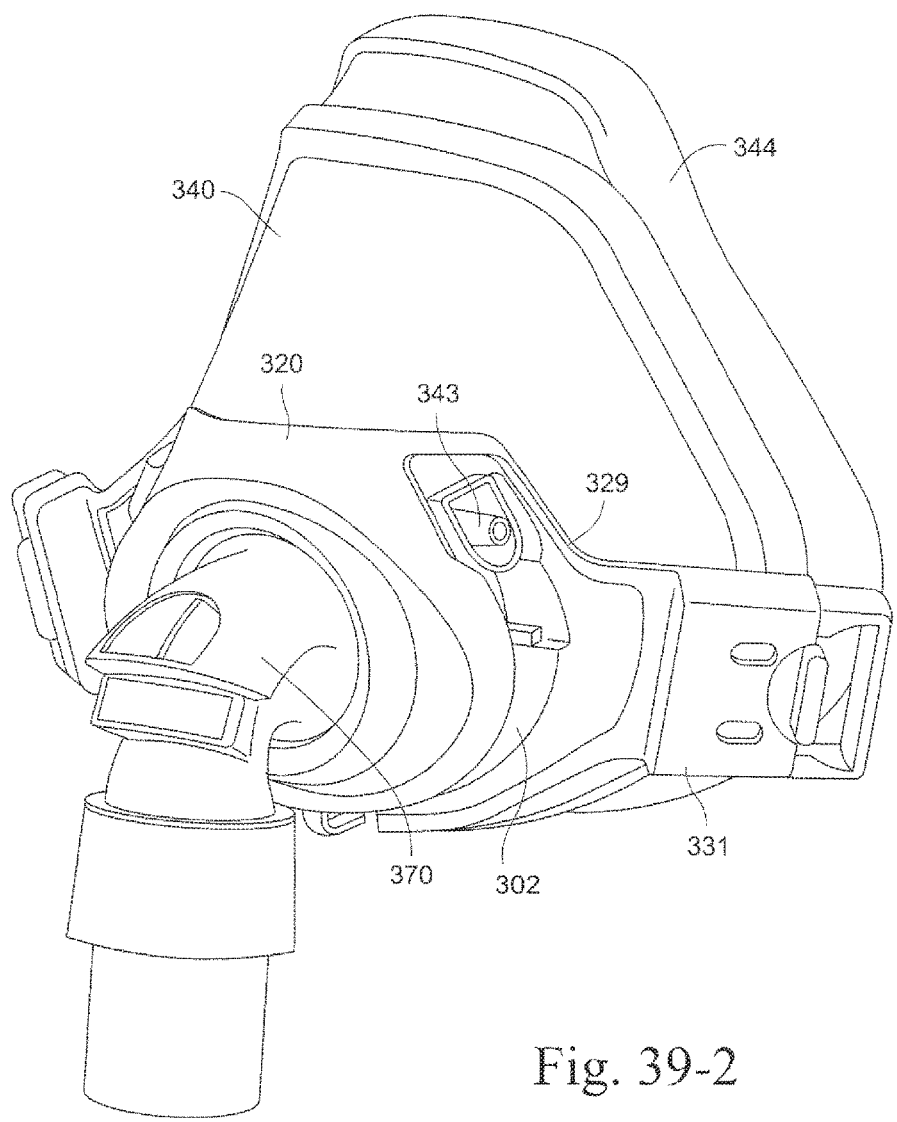
Figures 3, 39:
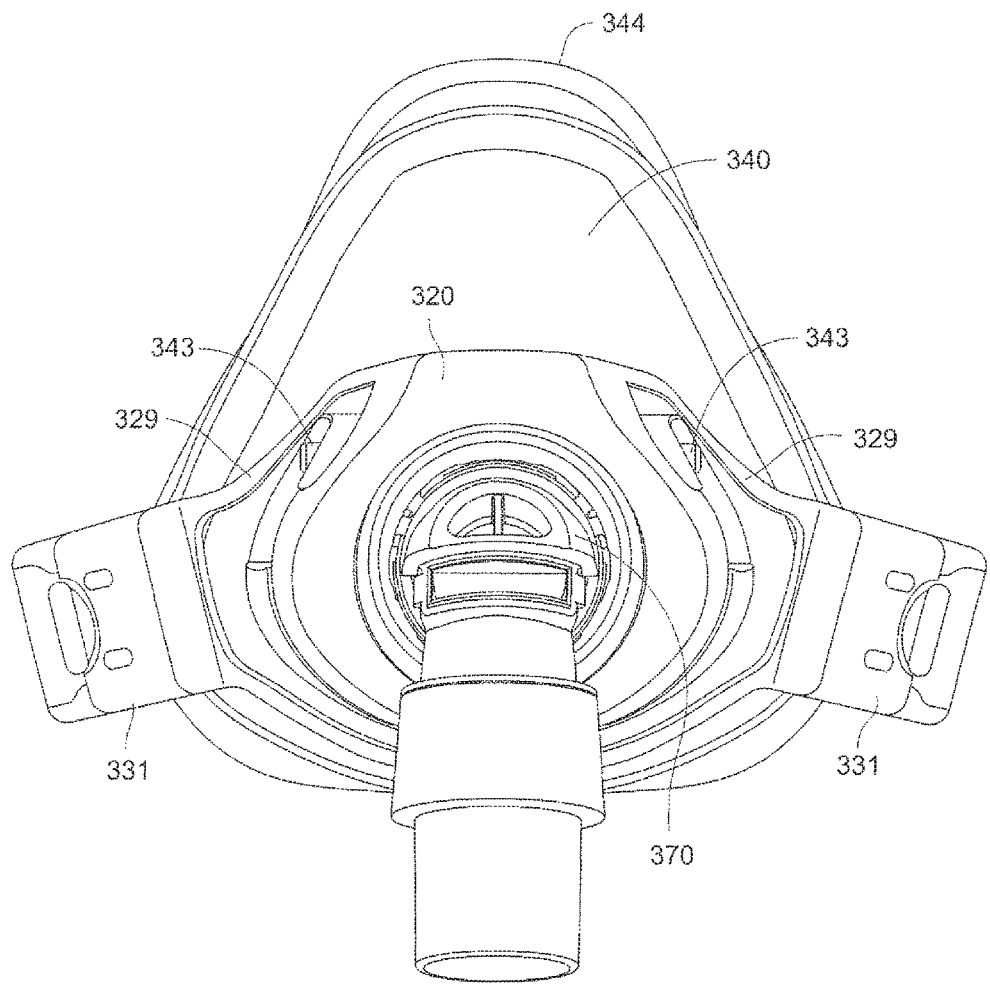
Figures 4, 39:
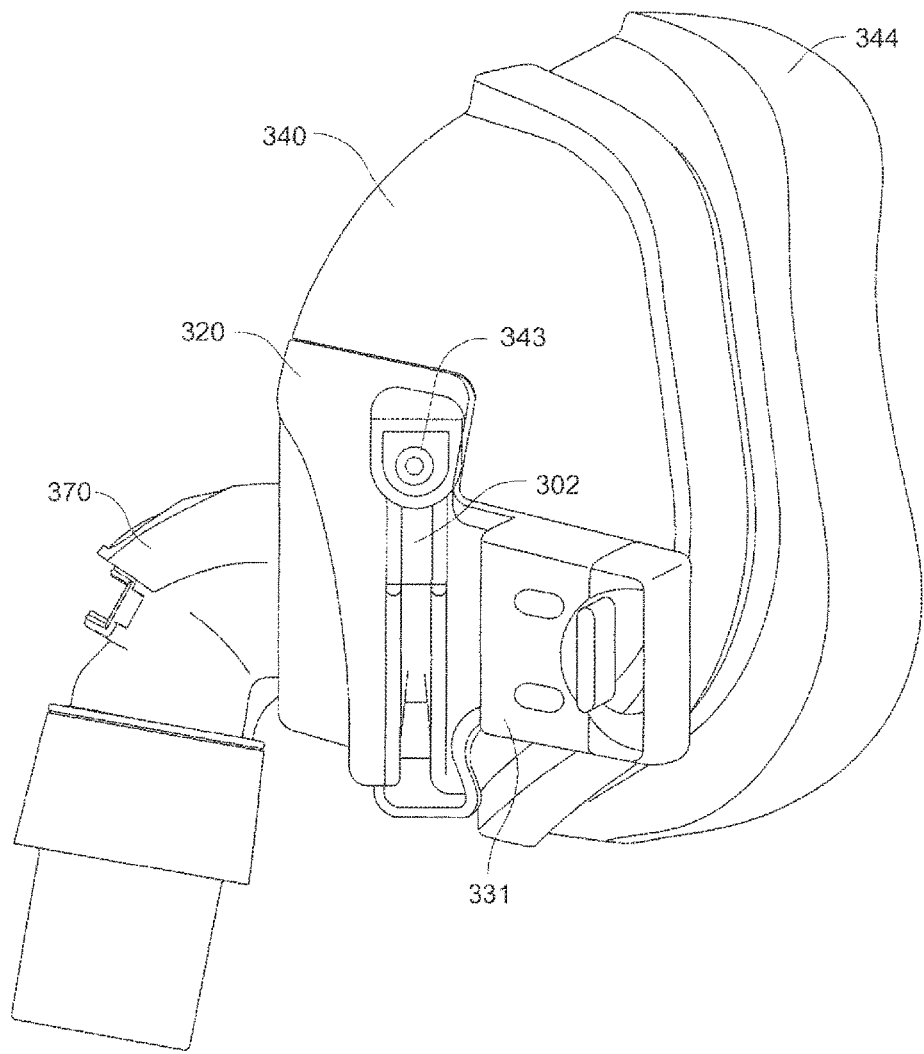
Figures 5, 39:
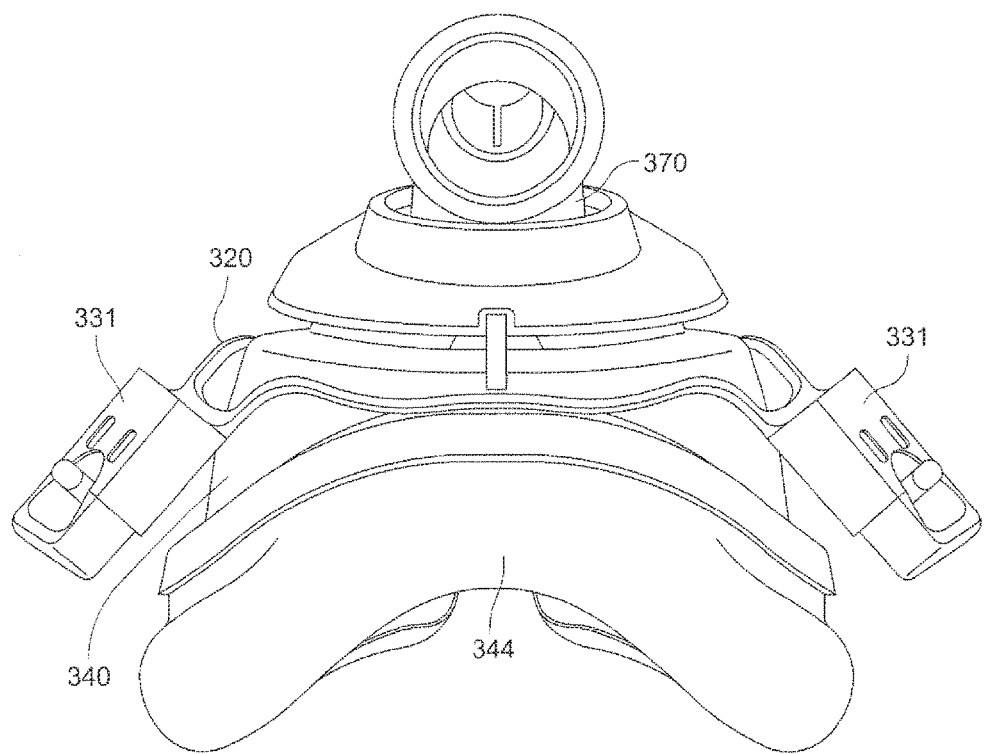
Figures 6, 39:
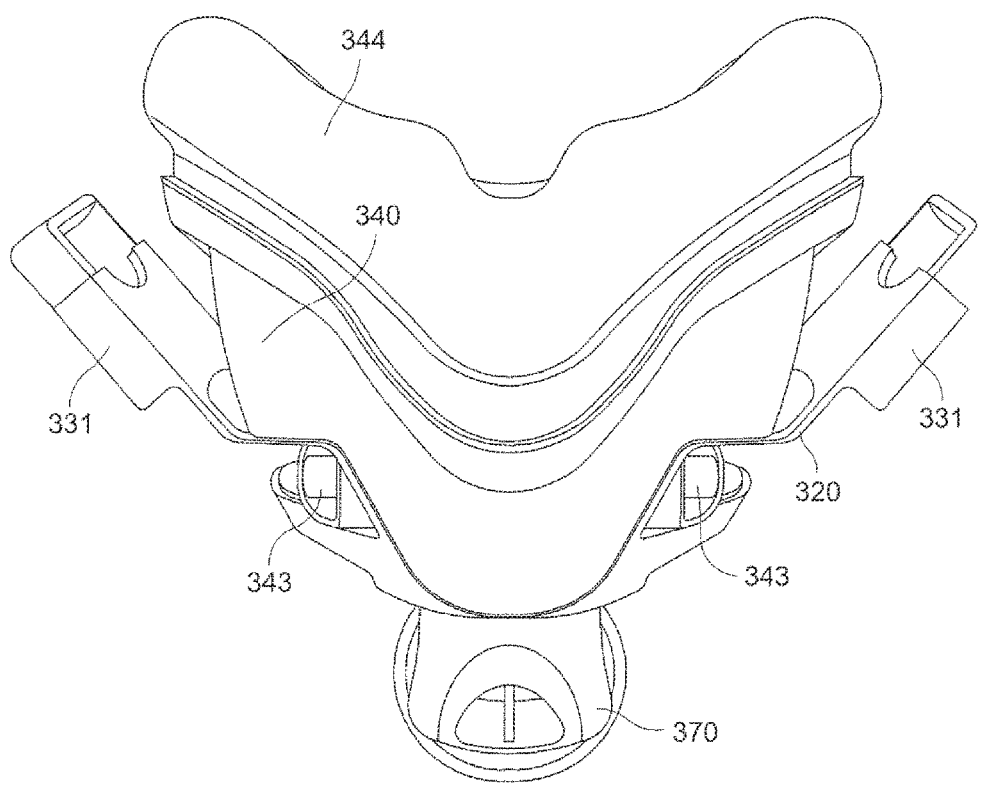

FIGS. 39-1 to 39-6 illustrate an alternative version of the mask system 310, which is indicated with similar reference numerals. As illustrated, the frame 340 is provided without upper headgear connectors, and the each clip receptacle 331 includes an alternative configuration (e.g., holes for snap-fit tabs on the clip). Also, the shroud 320 in FIGS. 39-1 to 39-6 includes support bars 329 structured to wrap around respective auxiliary ports 343, while the shroud 320 in FIGS. 37-1 to 38-5 includes support bars 329 that extend in front of respective auxiliary ports 343.

2.3 Headgear

Figure 1B:
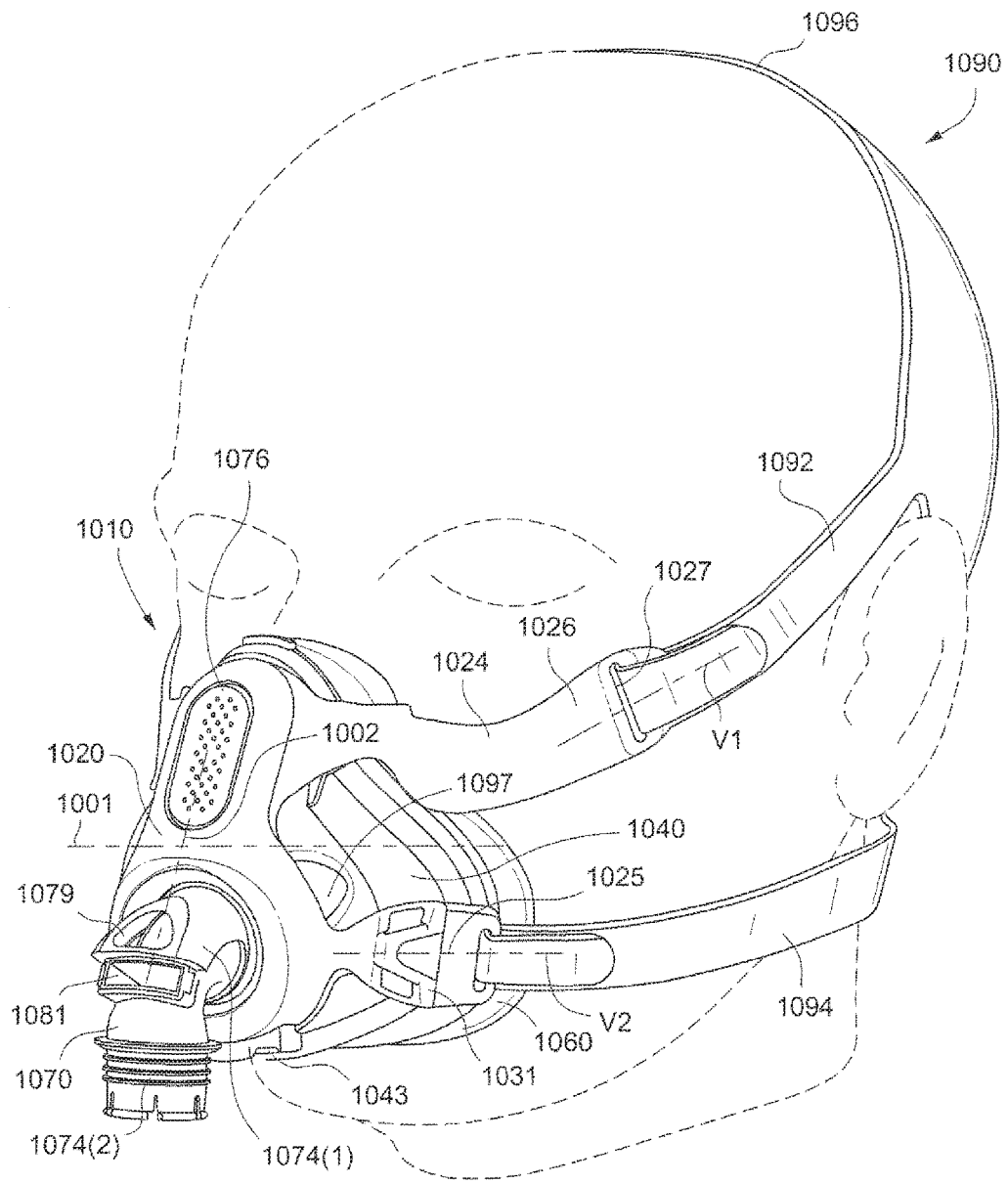
FIG. 1B is a perspective view showing the mask system of FIG. 1 with headgear positioned on a patient's head.

Headgear may be removably attached to the headgear connectors 1024, 1025 of the shroud 1020 to maintain the mask system 1010 in a desired position on the patient's face, e.g., see FIG. 1B.

Figure 9:
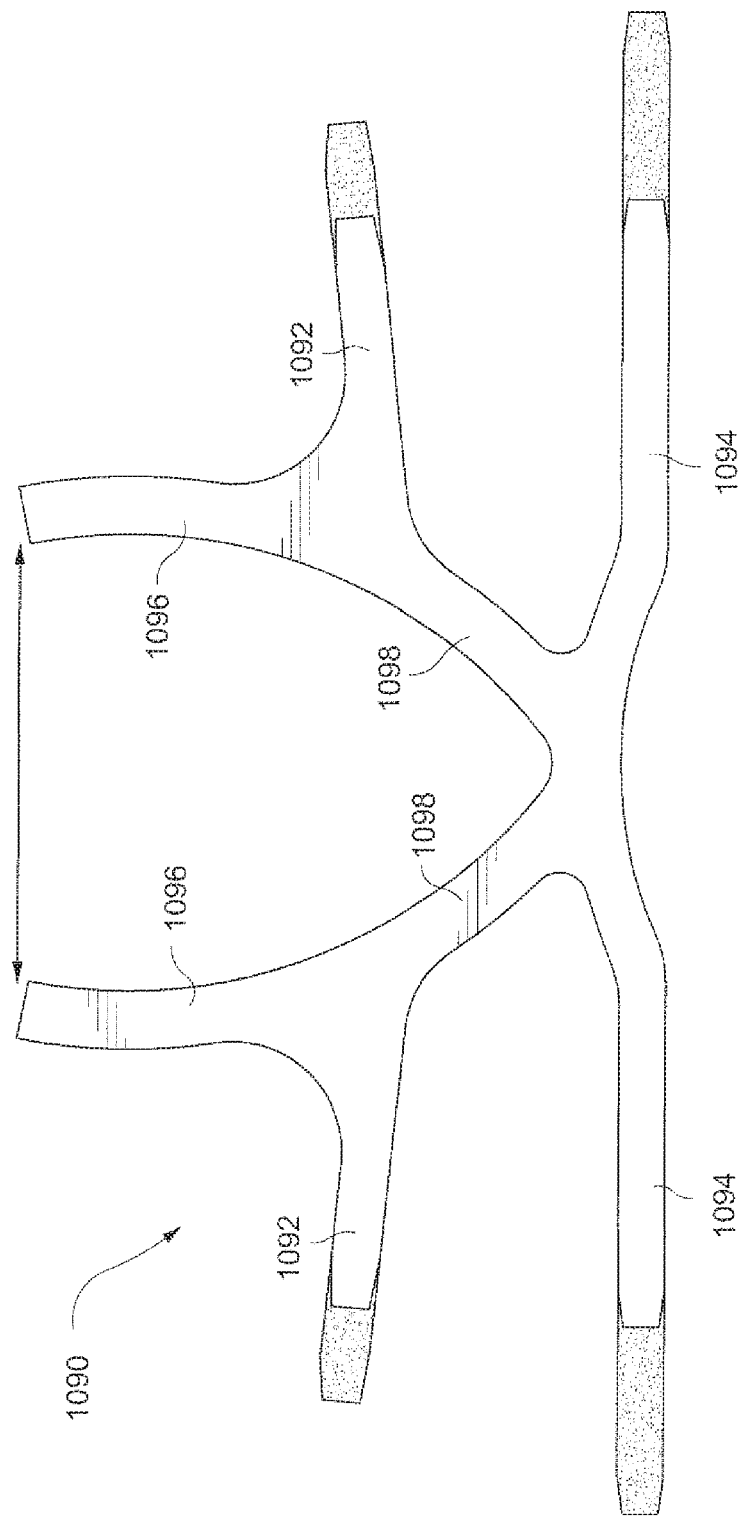
FIG. 9 is a plan view of headgear laid out flat according to an embodiment of the present invention.
Figure 10:
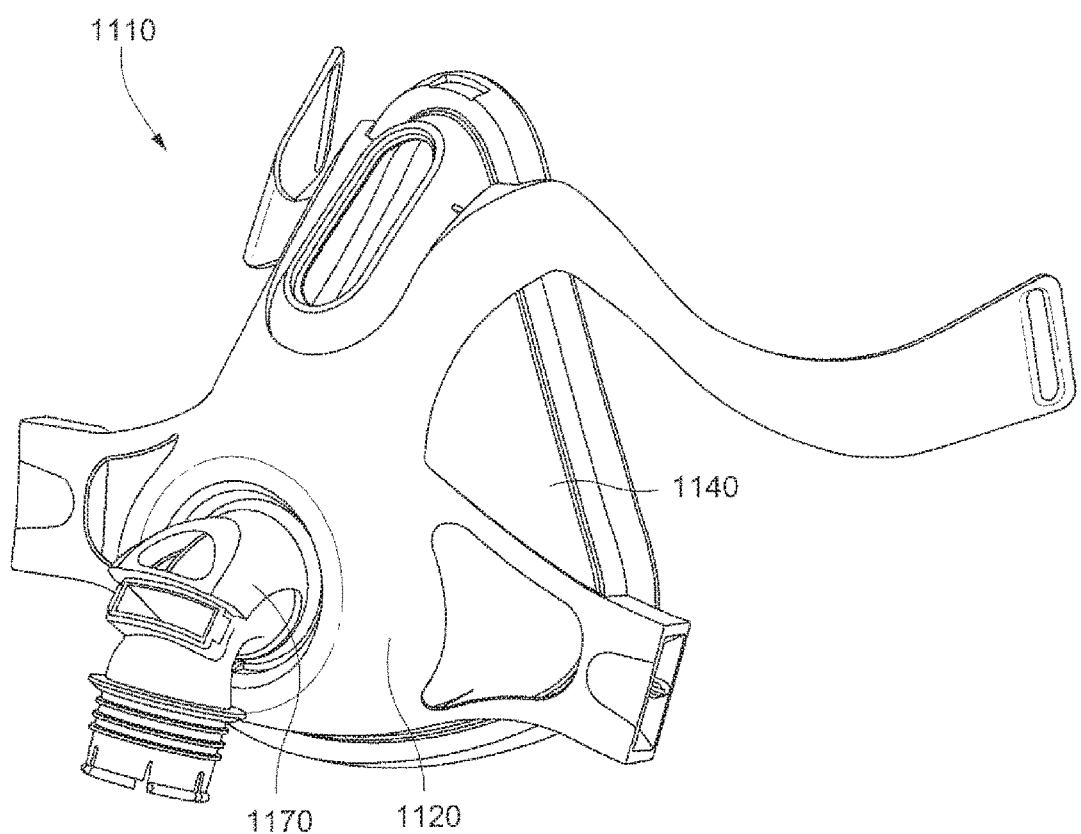
FIG. 10 is a front perspective view of a mask system according to another embodiment of the present invention.

As shown in FIG. 9, the headgear 1090 includes a pair of upper and lower straps 1092, 1094 with the upper straps 1092 removably attached to respective upper headgear connectors 1024 and the lower straps 1094 removably attached to respective lower headgear connectors 1025. The free end of each strap may include a Velcro® tab structured to engage the remainder of the strap to secure the strap in place. Such Velcro® attachment also allows adjustment of the length of the straps. However, the upper and lower headgear straps may be secured to the shroud in any other suitable manners, e.g., adjustable ladder-lock arrangement, etc.

The upper straps 1092 split at the crown of the patient's head to top straps 1096 (e.g., connected to one another by a buckle) adapted to pass over the top of the patient's head in use and rear straps 1098 adapted to pass behind the patient's head in use. In an embodiment, the headgear 1090 is structured to be self-supporting.

In FIG. 9, the top straps 1096 are adapted to be connected to one another by a buckle. In an alternative embodiment, as shown in FIG. 27-30, headgear 90 may include upper and lower straps 92, 94, top strap 96, and rear strap 98, with the top straps 96 integral with one another.

The upper straps 1092 are designed to adjust the position of the mask in a similar way that an adjustable forehead support would alter the position of the mask system, i.e., move the top of the mask system closer or further away from the patient's nasal bridge.

Without the forehead support, the headgear is connected at the top and bottom of the mask frame 1040 via the shroud 1020, and in order to avoid the eyes and ears, the arm 1026 of the upper headgear connector extends at an angle. In doing so, the headgear vectors V1 and V2 (see FIGS. 1 and 1B) are aligned such that the mask system may have a tendency to ride up the patient's face (i.e., upper headgear connectors position upper headgear vectors upwardly from horizontal and lower headgear connectors position lower headgear vectors generally horizontal). By splitting the upper headgear strap 1092 at the crown of the patient's head (i.e., top and rear straps 1096, 1098), the upper headgear vectors are realigned to prevent the mask system from sliding up the patient's face.

2.3.1 Headgear Adjustment

Figures 1, 35:
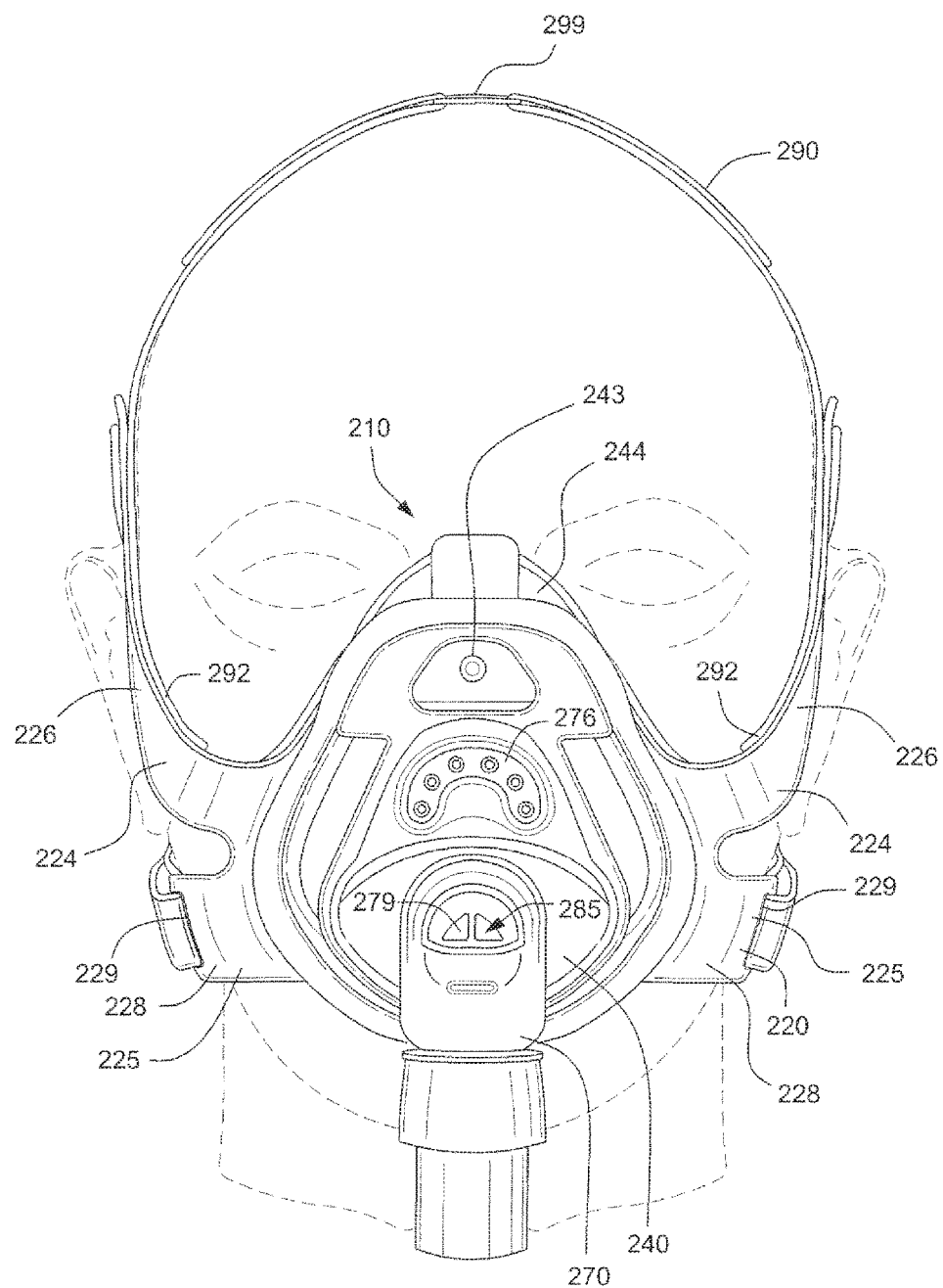
Figures 2, 35:
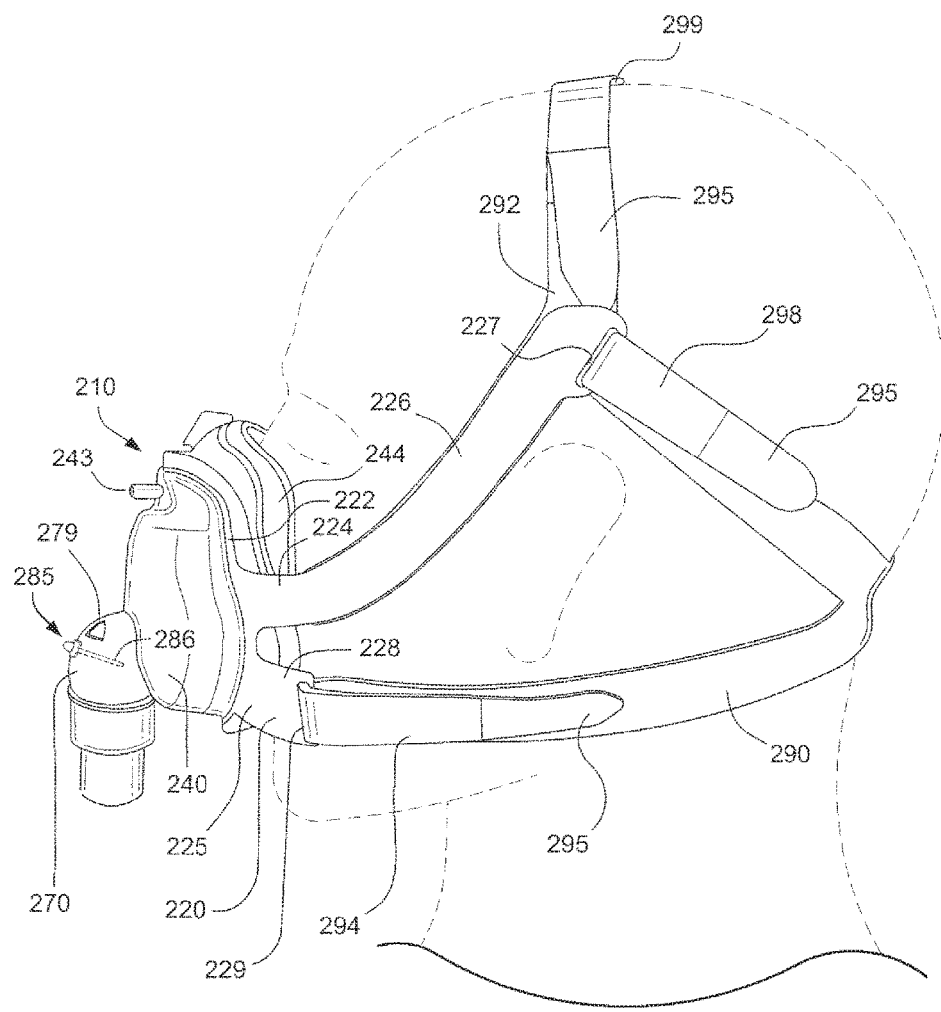
Figures 3, 35:
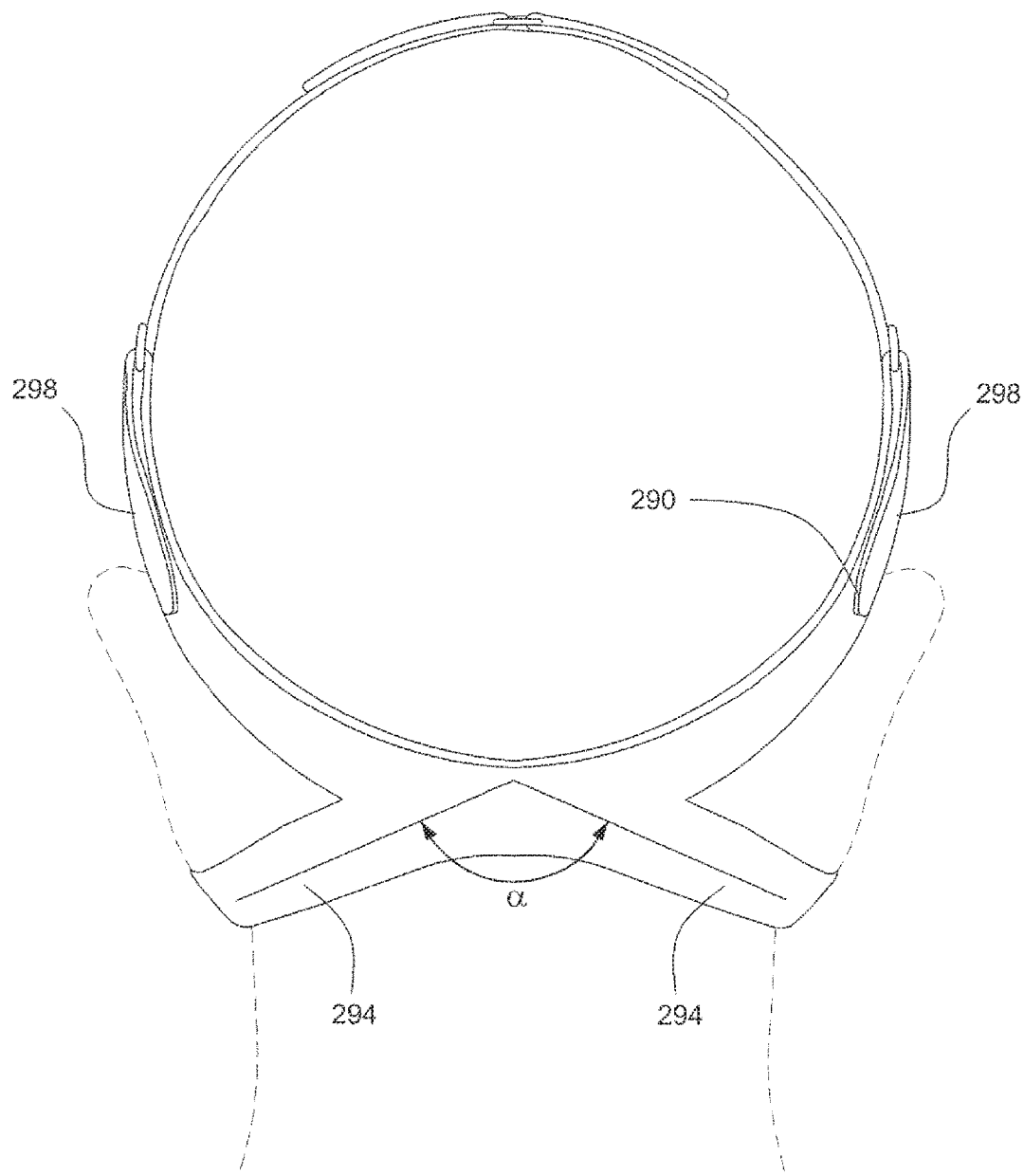

FIGS. 35-1 to 35-3 illustrate headgear 290 attached to the headgear connectors 224, 225 of the shroud 220 to maintain the mask system in a desired position on the patient's face.

In the illustrated embodiment, the headgear 290 includes a pair of upper or top straps 292, a pair of lower or bottom straps 294, and a pair of rear straps 298. In use, the upper straps 292 are secured to respective upper connectors or arms 226, the lower straps 294 are removably attached to respective lower connectors via slots 229/clip arrangement 231, and the rear straps 298 are removably attached to respective upper connectors via slots 227. The upper straps 292 may include upper strap portions adapted to pass over the top of the patient's head and couple to one another, e.g., via a headgear buckle or adjustable ladder-lock arrangement 299. In the illustrated embodiment, the lower straps 294 and rear straps 298 are formed in one piece.

This headgear arrangement allows adjustment to occur at three positions, i.e., upper straps 292 at the headgear buckle 299, lower straps 294 at the slot 229/clip 231 connection, and rear straps 298 at the slot 227 connection.

As illustrated, the free end of each strap may include a hook and loop tab 295 (e.g., Velcro®) structured to engage the remainder of the strap to removably secure the strap in place. Such hook and loop attachment also facilitates adjustment of the length of the straps.

In the illustrated embodiment, the lower straps 294 and rear straps 298 are adapted to join and pass behind the patient's head in use (e.g., see FIG. 35-3). As illustrated, the lower straps 294 join at an angle α (e.g., similar to the bottom strap in ResMed's Mirage Liberty mask) to prevent the strap from irritating the patient's neck and/or prevent movement of the strap due to movement of the patient's neck in use.

In an embodiment, the headgear may be similar to that for ResMed's Mirage Liberty mask, however the top straps have been modified and there is an added rigidizer system. The top straps may be similar to ResMed's Swift style headgear, with the rigidizers extending along the sides.

2.3.2 Alternative Headgear Material

Figures 1, 19:
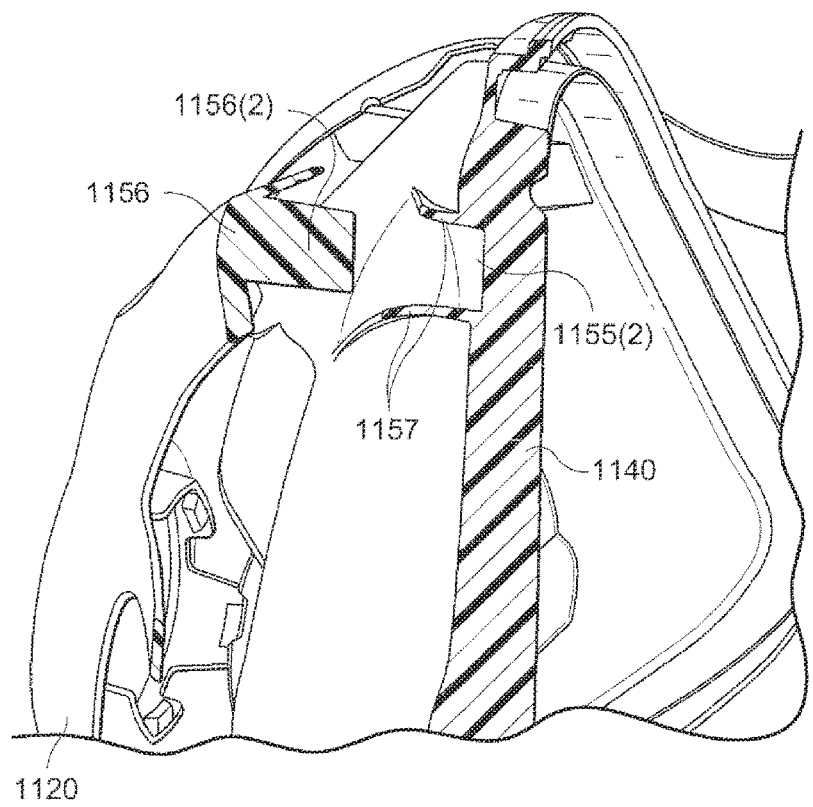
Figures 2, 19:
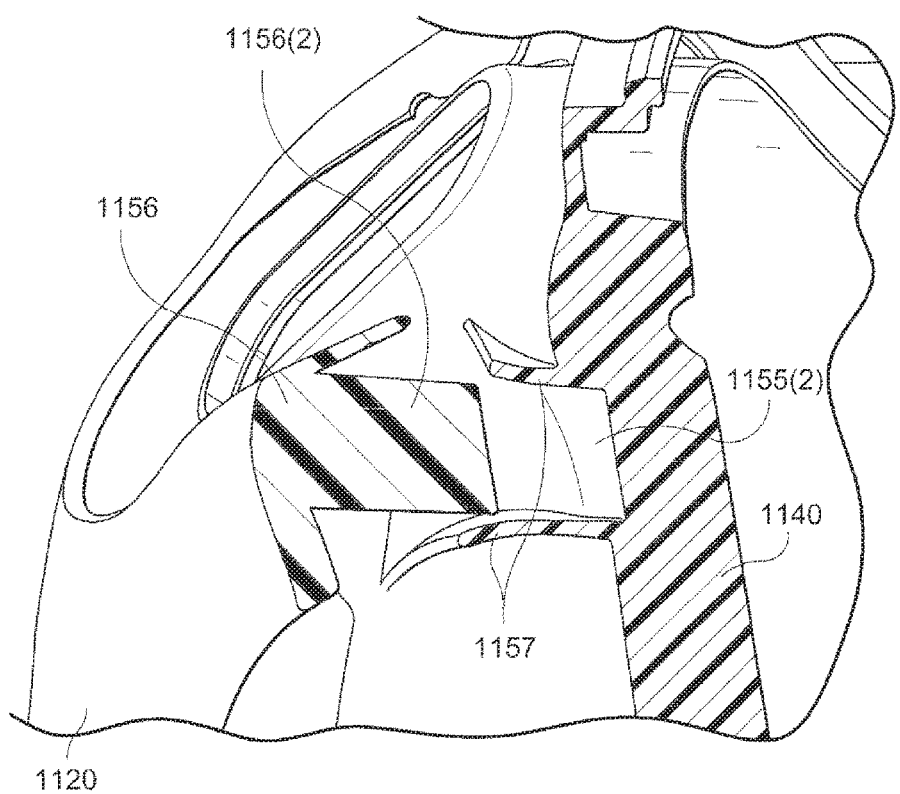
Figures 3, 19:
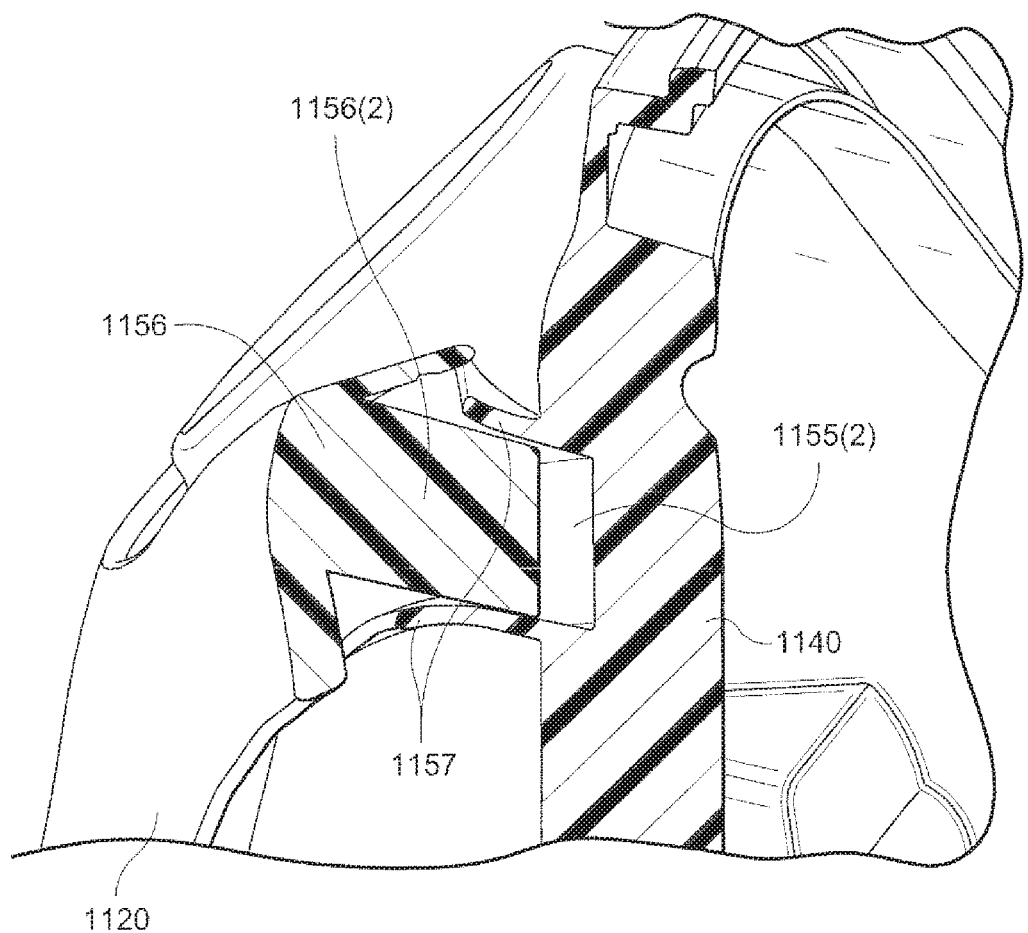
Figures 4, 19:
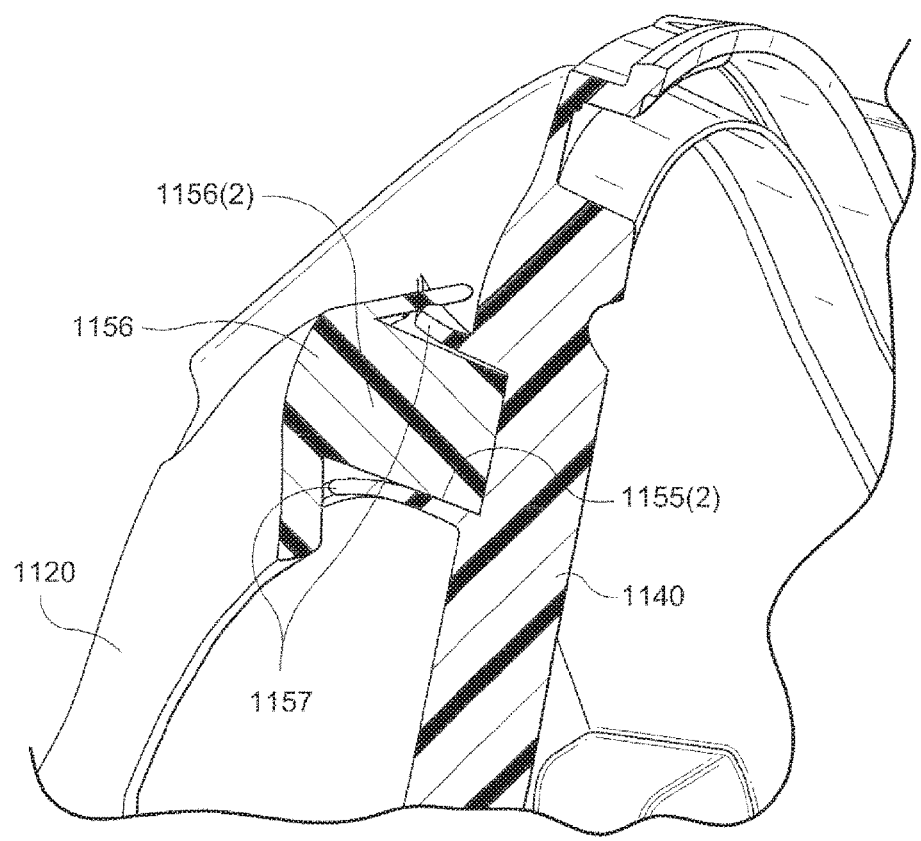
Figures 1, 43:
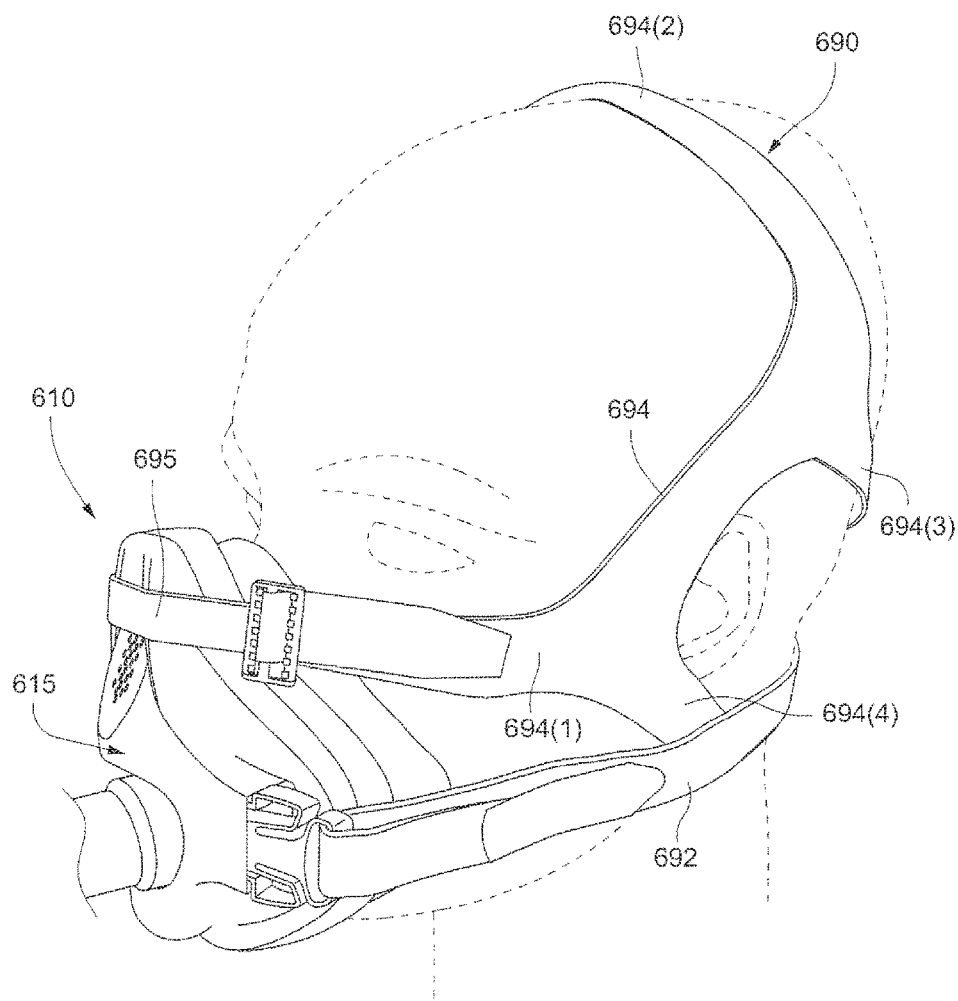
Figures 2, 43:
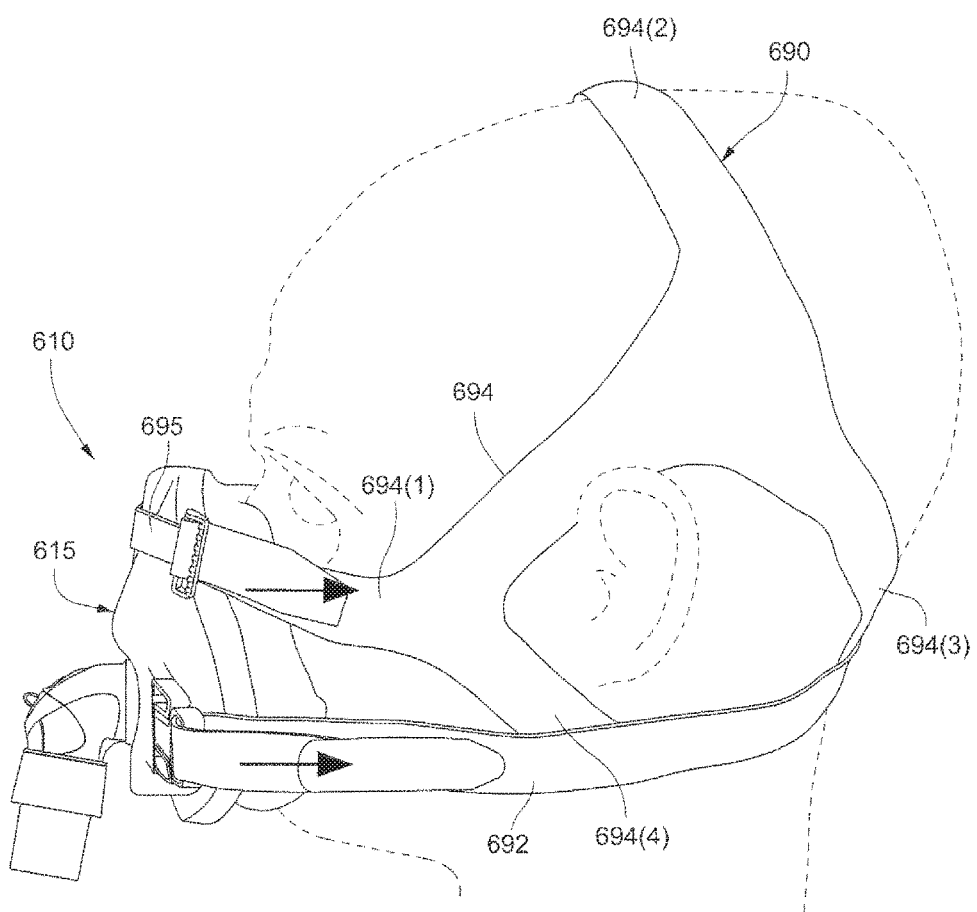
Figures 3, 43:
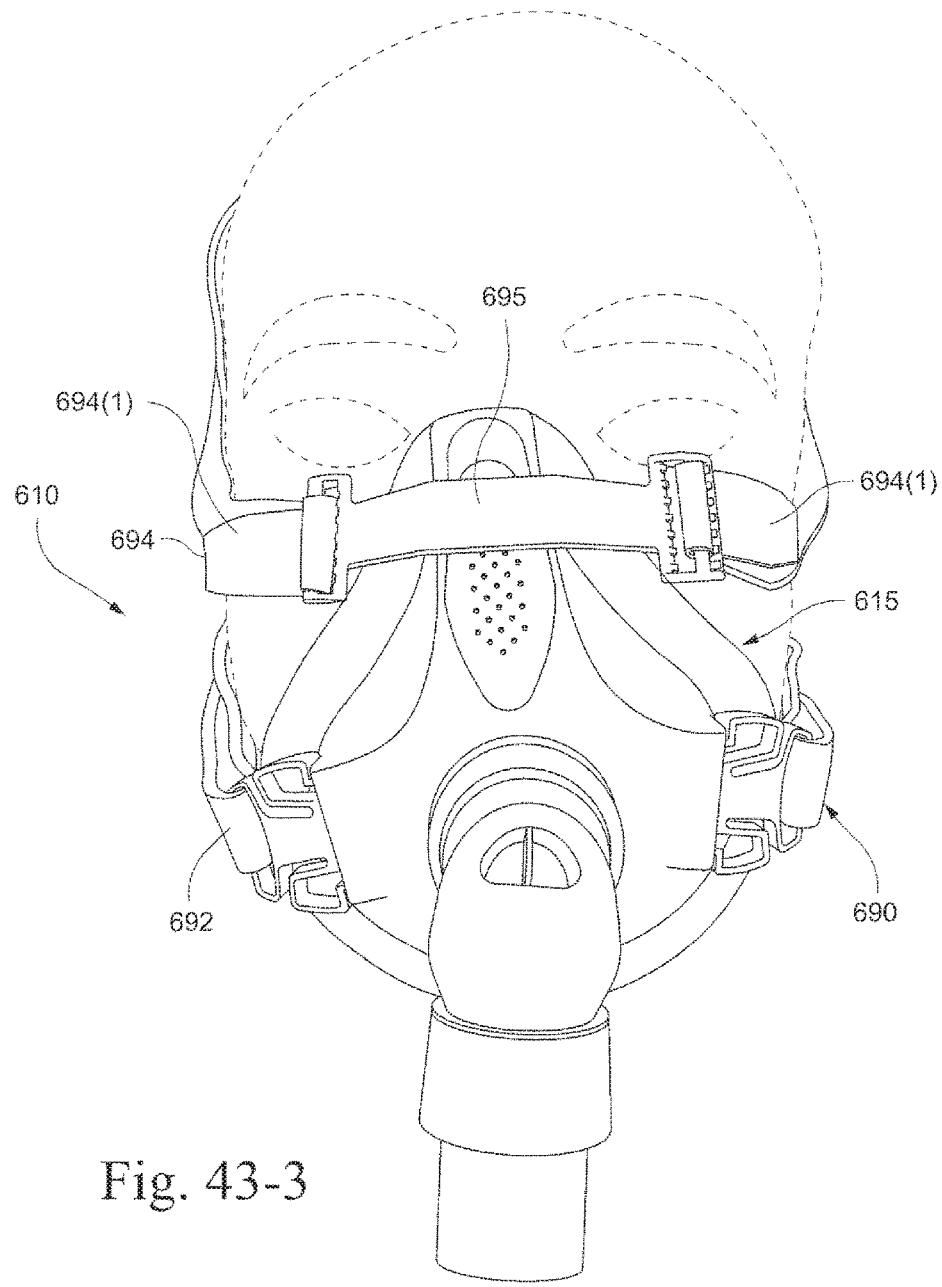
Figures 4, 43:
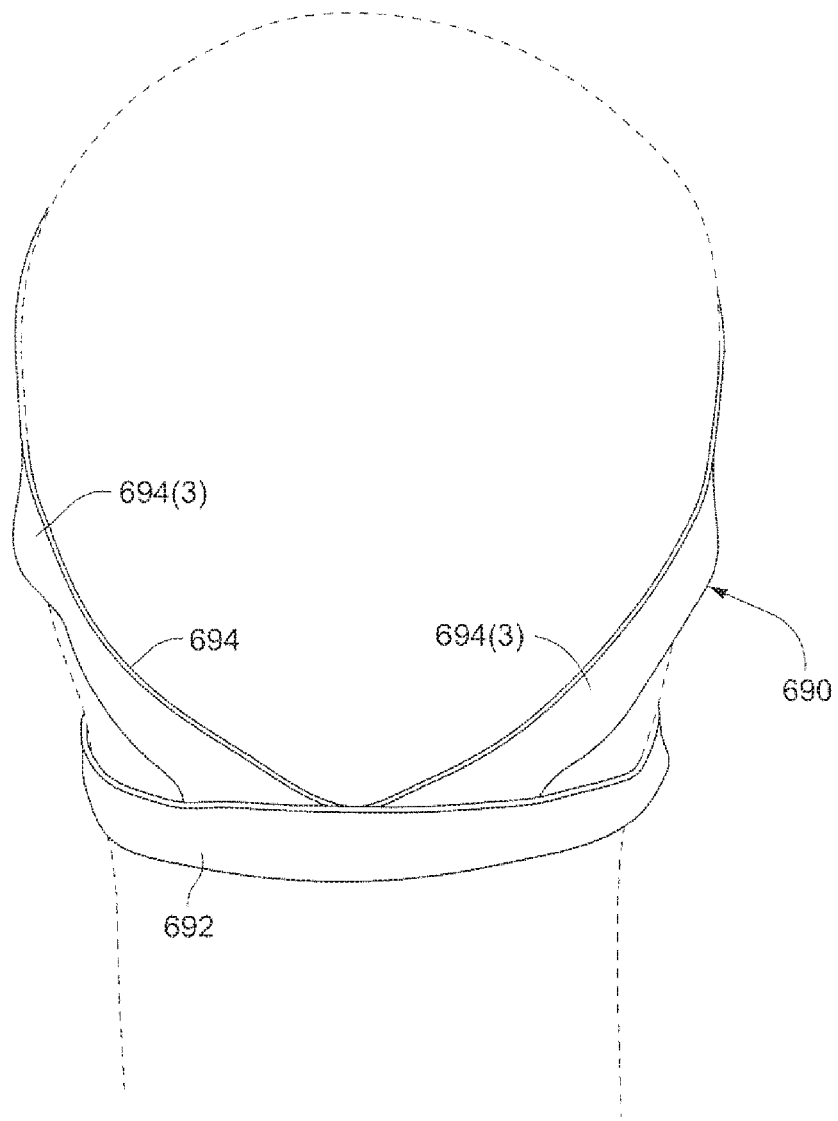

FIGS. 43-1 to 43-4 illustrate a mask system 610 including a mask 615 and headgear 690 according to another embodiment of the present invention. In the illustrated embodiment, the headgear 690 includes an arrangement of straps wherein some of the straps are constructed of silicone and some of the straps are constructed of Breath-O-Prene™ material. However, the headgear may be constructed such that the straps are completely constructed of silicone or completely constructed of Breath-O-Prene™.

As illustrated, the lower strap portion 692 of the headgear is constructed of Breath-O-Prene™ and extends along the cheeks and around the back of the patient's head. The upper strap portion 694 of the headgear is constructed of silicone and includes side straps 694(1) that extend along the upper cheek and over the patient's ear, a top strap 694(2) that extends over the top of the patient's head, rear straps 694(3) that extend behind the patient's head and connects to the lower strap portion 692 (see FIG. 43-4), and connecting portions 694(4) that extend from respective side straps 694(1) in front of the patient's ear and connect to the lower strap portion 692.

The headgear straps may be connected to the mask in any suitable manner. For example, in the illustrated embodiment, the lower strap portion 692 is connected to the mask by a headgear clip arrangement and the upper strap portion 694 is connected to the mask using an elongated buckle 695 with buckle portions on each end thereof.

Figure 2:
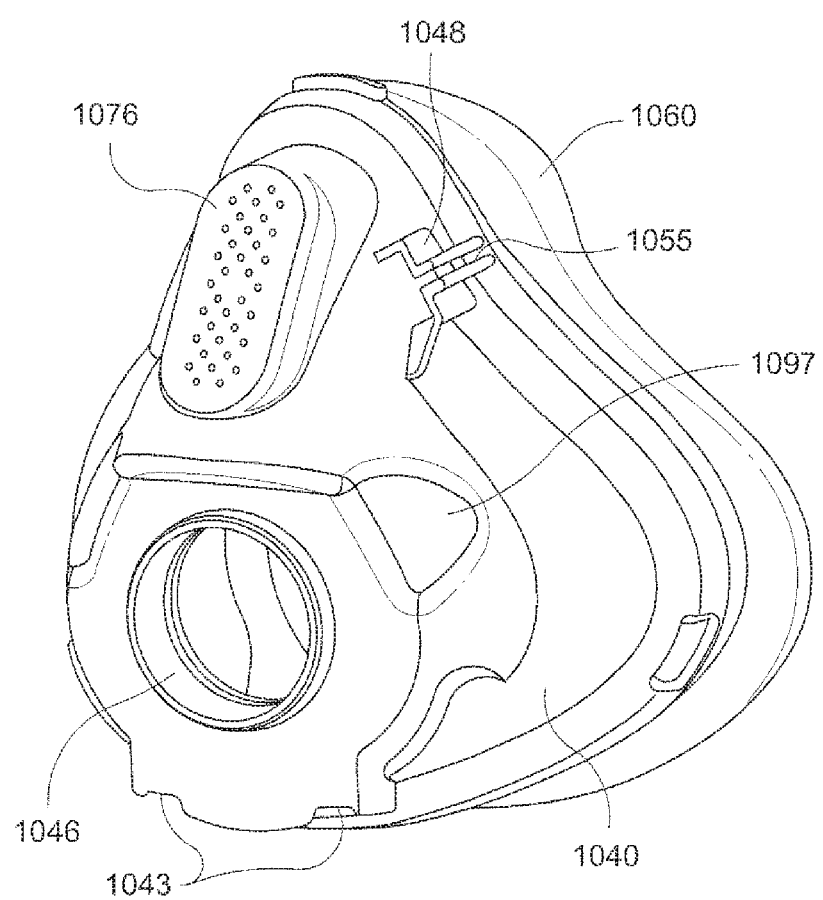
FIG. 2 is a front perspective view showing the frame and cushion of the mask system of FIG. 1.

In an embodiment, the headgear straps are arranged such that the force vectors applied by the headgear to the mask are substantially perpendicular to the mask and substantially parallel to one another (e.g., as shown by the arrows in FIG. 43-2). This arrangement enhances the mask seal as the headgear forces the mask directly into the patient's face.

3. Seal

The seal (i.e., cushion) of the mask system is structured to accommodate the elimination of a forehead support from a full-face type interface.

3.1 Cushion

As shown in FIGS. 1-5 and 7-8, the cushion 1060 is structured to interface with the frame 1040 and form a seal with the patient's nose and mouth in use. In the illustrated embodiment, the cushion is a full-face cushion adapted to engage the patient's face generally along nasal bridge, cheek, and lower lip/chin regions of the patient's face. However, other cushion interfaces are possible, e.g., nasal.

The cushion 1060 is structured be more compliant or flexible (e.g., particularly in the nasal bridge region) to accommodate more movement due to loss of some stability without a forehead support.

Figure 8:
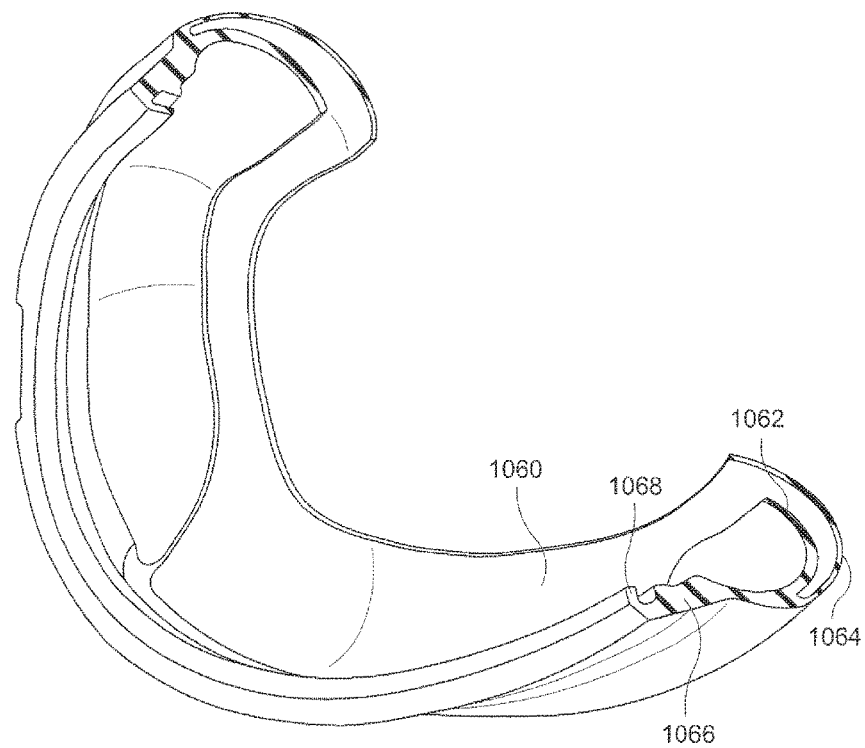
FIG. 8 is a cross-sectional view showing a portion of the cushion of FIG. 7.

The cushion 1060 is constructed of a soft and flexible biocompatible material, e.g., such as silicone. In the illustrated embodiment, the cushion 1060 includes a dual wall configuration wherein the cushion comprises an undercushion or support wall 1062 underneath a membrane 1064 as shown in FIG. 8.

The membrane 1064 is generally softer and less stiff than the undercushion 1062 and provides a seal against the patient's face in use. The membrane may be relatively thin to allow for wider fit range and better conformance to the patient's face in view of less mask stability with a forehead support. The undercushion is structured to generally support the membrane and prevents collapse of the membrane when the mask system is attached and tightened using the headgear.

The membrane 1064 is generally concave and curves inwards towards the breathing chamber. The undercushion 1062 may also curve inwardly but is generally shorter, thicker, and more rigid than the membrane.

Figure 8B:
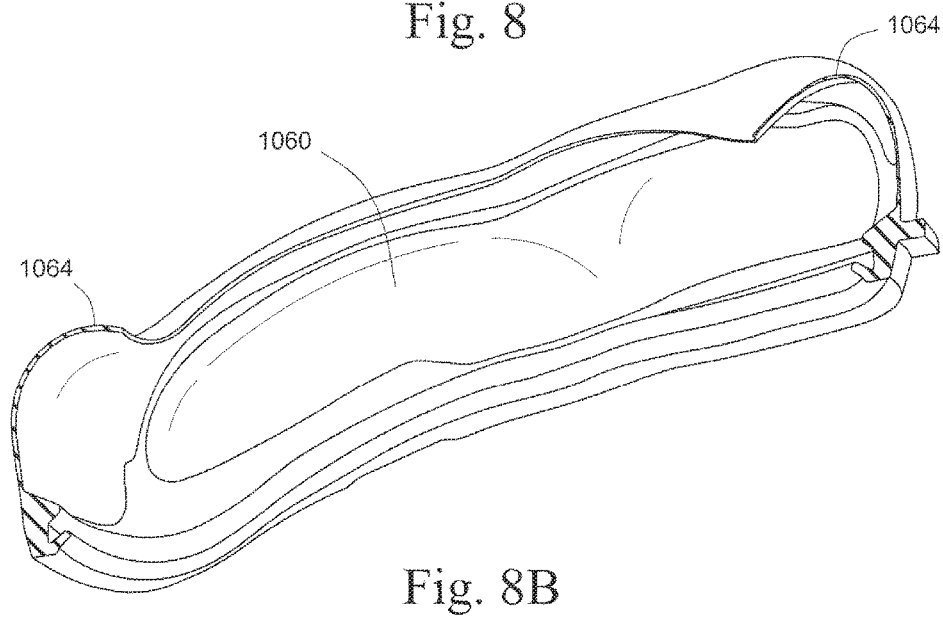
FIG. 8B is a cross-sectional view through nasal bridge and chin regions of the cushion of FIG. 7.

In an embodiment, the undercushion 1062 at the regions of the nasal bridge and/or chin of the patient is shorter in height or completely absent and the height from the tip to base of the undercushion 1062 may be between about 0 mm and 30 mm. The membrane is generally longer than the undercushion 1062 at any given cross-section and may be between about 1 mm and 40 mm. For example, FIG. 8B illustrates a cross-section through nasal bridge and chin regions of the cushion to illustrate the membrane 1064 without an undercushion in these regions.

In an embodiment, the undercushion 1062 may only be provided in selected regions of the mask system, e.g., where the mask system is to be pushed away from the patient's face. Certain pre-determined regions of the patient's face may be preferably avoided for applying pressure by the tightening of the headgear. In the illustrated embodiment, the nasal bridge and chin regions of the patient do not include an undercushion 1062. In these regions, the undercushion is only provided along lateral sides of the cushion (e.g., see FIG. 7) which press against the cheeks of a patient so as to more evenly distribute the force vectors applied by the mask system in use. In an embodiment, the undercushion may be relatively stiff along the cheek regions because these points of contact are acting as anchor points, i.e., holds mask system in position to provide effective seal.

This configuration of avoiding the nasal bridge and chin of the patient may increase the comfort of the mask system for patients by reducing the pressure or force applied to sensitive areas or to protruding regions of the patient's face that experience relatively higher contact pressures. Additionally, this arrangement avoids the cushion pinching the nasal bridge of the patient when the mask system is adjusted. Additionally, the cushion of this embodiment may be noticeably softer in the regions of the nasal bridge and chin because of the absence of the undercushion.

In an embodiment, the undercushion may include a variable height, stiffness, and/or thickness to generate a variable softness in the aforementioned predetermined regions of the face that require lighter support.

In the illustrated embodiment, the cushion may be structured to seal lower down on the patient's nasal bridge and the eye sockets so that the cushion is less obtrusive.

In an embodiment, the cushion may be generally frosted except at patient contacting surfaces where it is polished. In an embodiment, the frosting of the cushion may reduce restriction between the face and membrane and/or the membrane and undercushion. The frosting allows the surface of the membrane and undercushion to slide against each other's respective surface without the same restriction of unfrosted silicone. This feature may also prevent or limit sticking of the membrane to the undercushion components and also may generally improve the overall comfort and sealing properties of the cushion. Additionally, the frosting of the cushion may be easier to manufacture and may lead to a reduction of costs of manufacturing. The cushion may be constructed of frosted silicone or other suitable materials.

3.2 Cushion Lower on Nasal Bridge

Figures 1, 31:
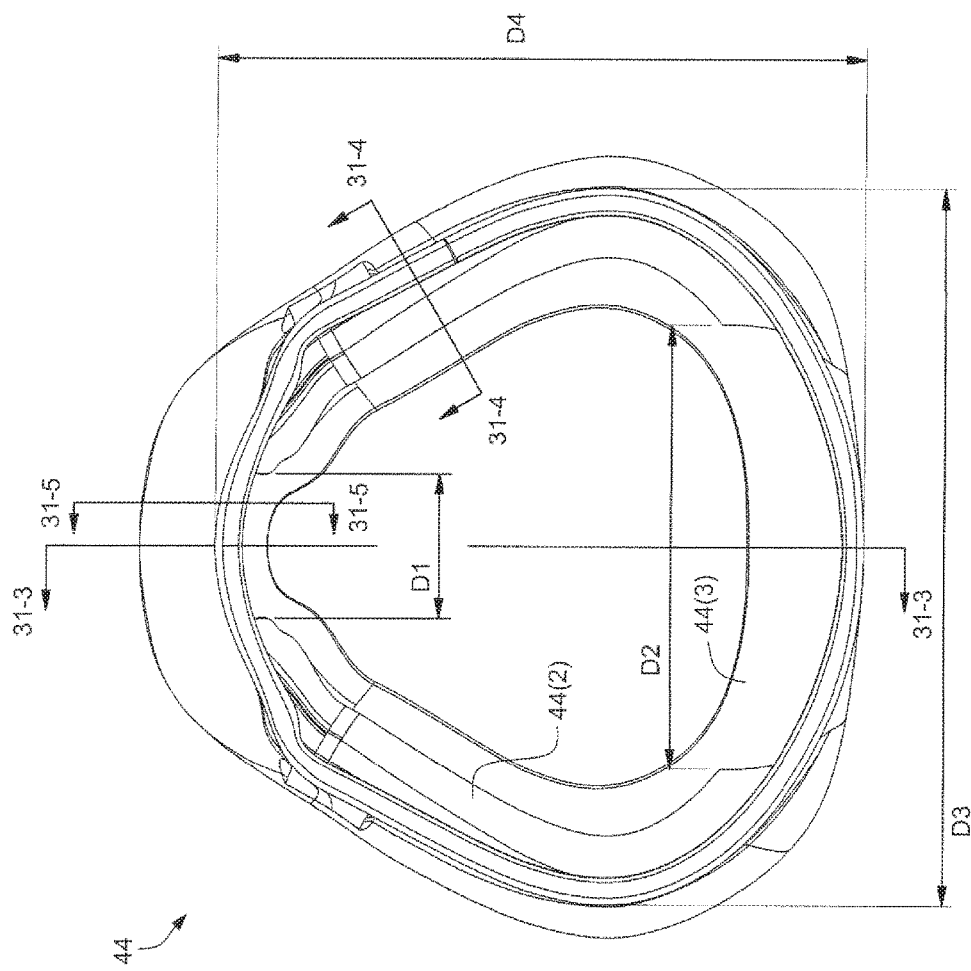
Figures 2, 31:
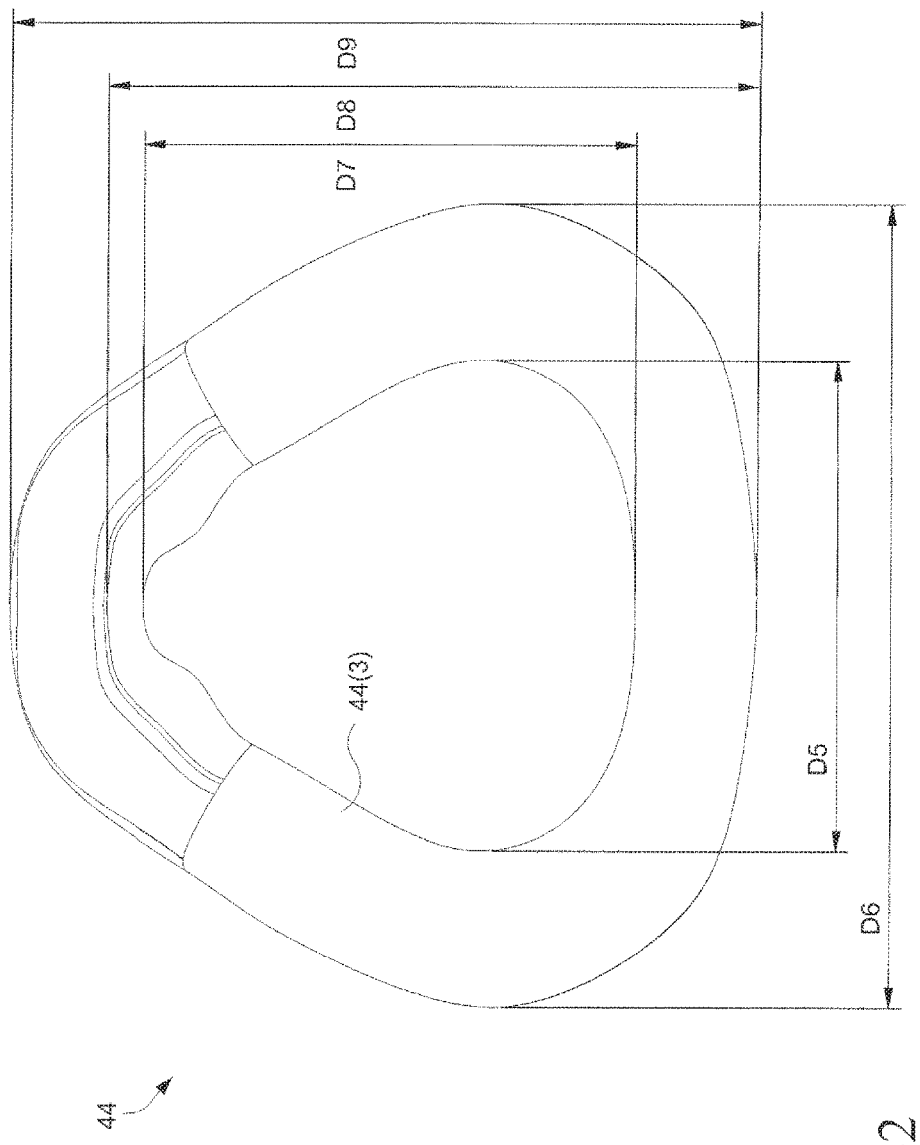
Figures 3, 31:
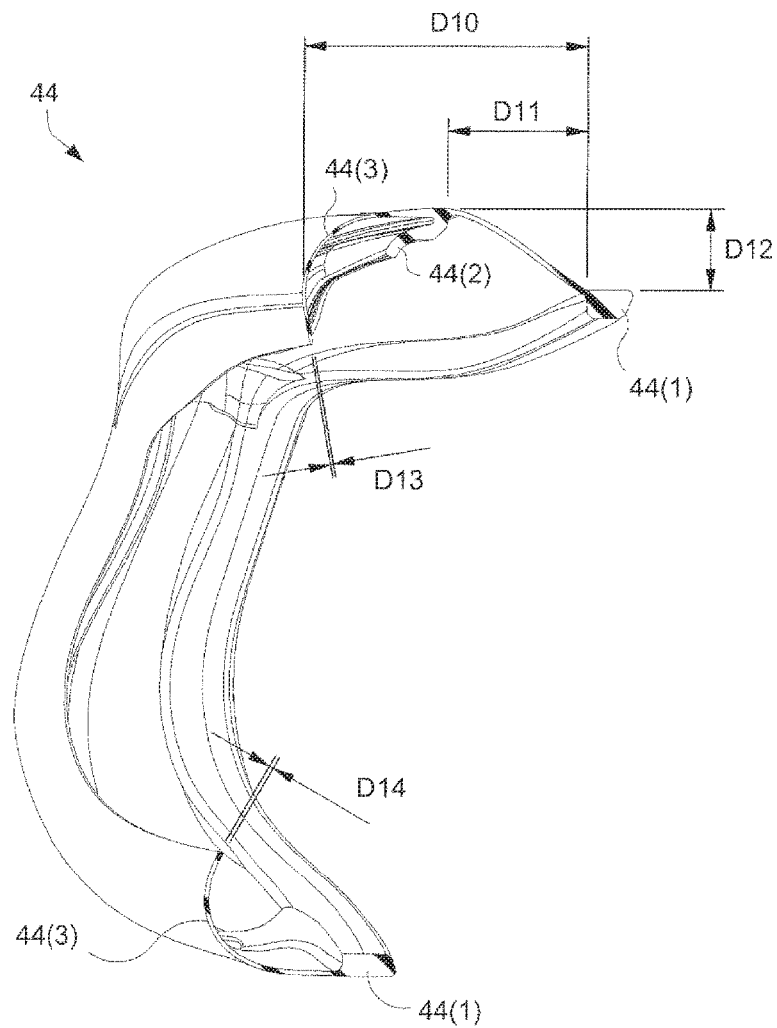
Figures 5, 31:
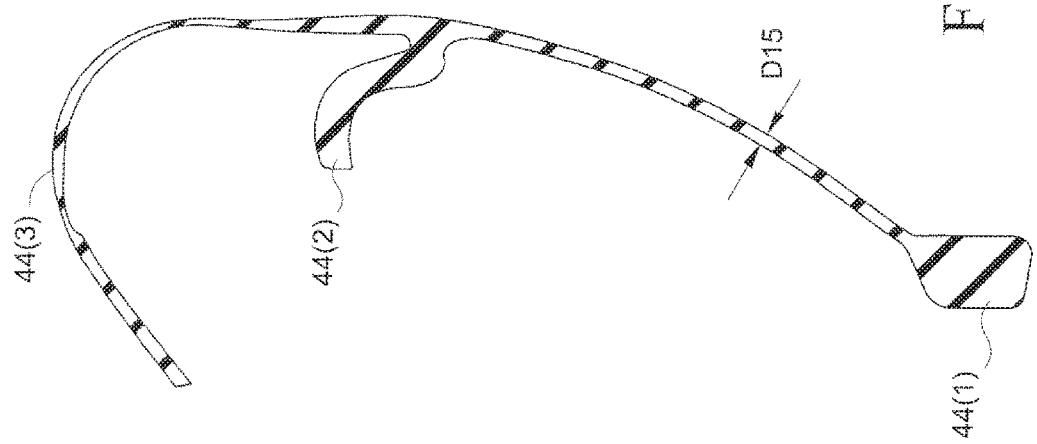
Figures 4, 31:
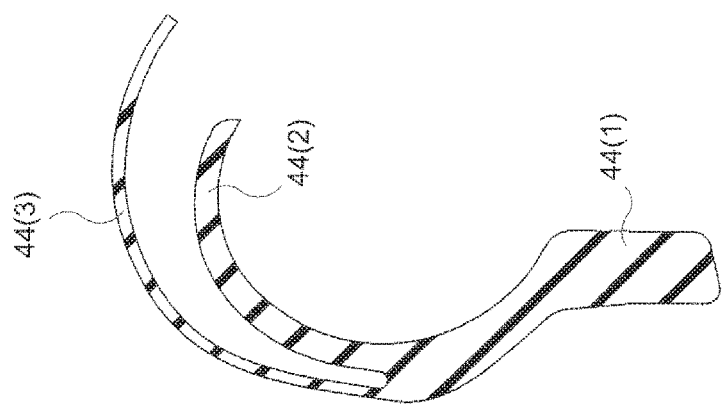

FIGS. 31-1 to 31-5 illustrate various views of a cushion 44 (e.g., constructed of silicone) according to an embodiment of the present invention. As illustrated, the cushion 44 includes a base wall 44(1) provided to the frame, an undercushion layer (UCL) 44(2) extending away from the base wall 44(1), and a membrane 44(3) provided to substantially cover the UCL 44(2) and provide a sealing structure. In the illustrated embodiment, the cushion 44 is structured to sit lower on the nasal bridge to reduce mask obtrusiveness and improve "line of sight" in use.

Also, as best shown in FIGS. 31-3 and 31-5, the UCL 44(2) design in the nasal bridge region is structured to provide improved stability across the nasal bridge in use. As shown in FIGS. 31-1 and 31-3, the UCL is not provided in the lower lip/chin region. However, other arrangements of the UCL are possible, e.g., UCL around entire perimeter.

In an embodiment of the cushion shown in FIGS. 31-1 to 31-5, D1 may be about 15-20 mm, e.g., 18.2 mm, D2 may be about 53-59 mm, e.g., 55.8 mm, D3 may be about 88-93 mm, e.g., 90 mm, D4 may be about 78-83 mm, e.g., 81.1, D5 may be about 58-63 mm, e.g., 60 mm, D6 may be about 95-100 mm, e.g., 98.1 mm, D7 may be about 57-62 mm. e.g., 59.7 mm, D8 may be about 77-82 mm, e.g., 79 mm, D9 may be about 88-93 mm, e.g., 90.7 mm, D10 may be about 30-35 mm, e.g., 33.1 mm, D11 may be about 14-19 mm. e.g., 16.4 mm, D12 may be about 8-13 mm, e.g., 9.6 mm. D13 may be about 0.3-0.5 mm, e.g., 0.35 mm, D14 may be about 0.4-0.6 mm, e.g., 0.5 mm, and D15 may be about 0.3-0.5 mm. e.g., 0.4 mm. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

3.3 Cushion Higher on Nasal Bridge

FIGS. 35-1 and 35-2 illustrate a full-face cushion 244 adapted to engage the patient's face generally along nasal bridge, cheek, and lower lip/chin regions of the patient's face. In this embodiment, the cushion 244 is structured such that it is positioned higher on the bridge of the nose for sealing and comfort (e.g., with respect to the cushion 44 described above). The cushion 244 may also be better for anthropometrics, i.e., the cushion will fit more people.

In an embodiment, the cushion 244 may include a concertina section as described below (e.g., in the nasal bridge region) to enhance the flexibility of the cushion in use.

3.4 Concertina Section

Figure 30:
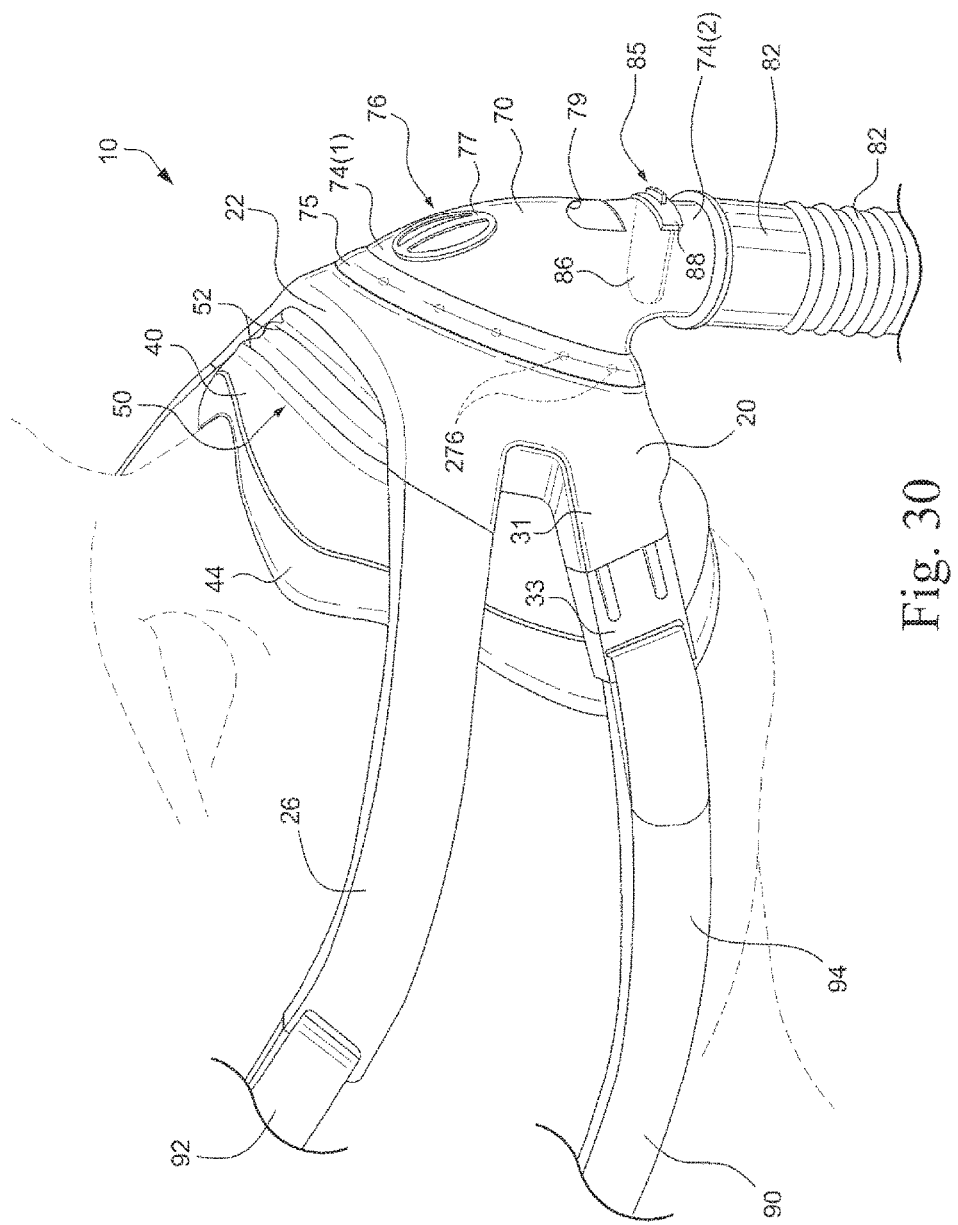
FIG. 30 is a side view of the mask system shown in FIG. 27.
Figure 33:
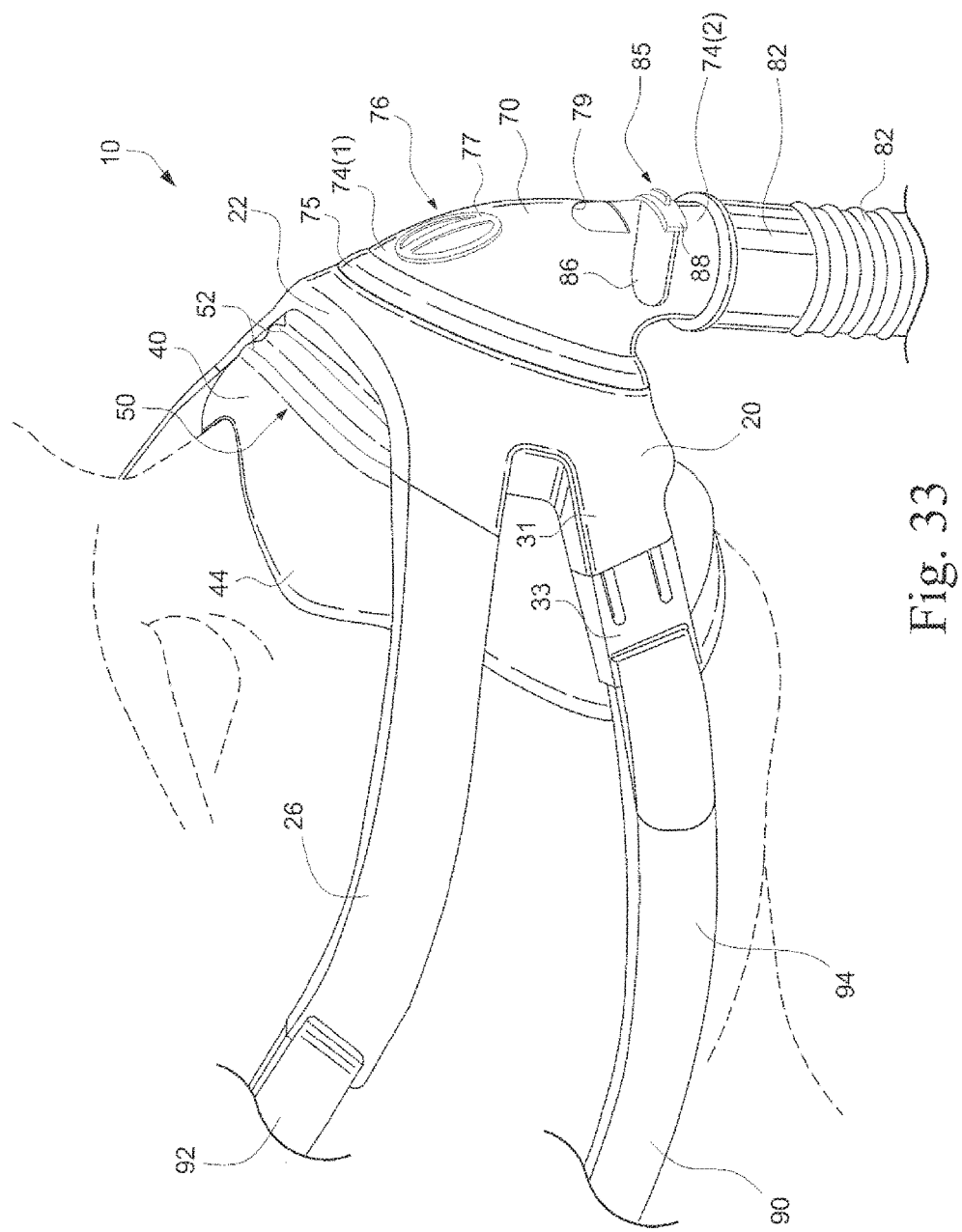
FIG. 33 is a side view of a mask system according to a variation of the present invention.

As best shown in FIGS. 30 and 33, a concertina section 50 may be provided in a nasal bridge region of the cushion and/or frame. As illustrated, the concertina section 50 includes a bellows structure with one or more folds 52 that provide a higher degree of flexibility or increased movement. That is, the concertina section 50 provides a higher level of adaptability or flexibility to the nasal bridge region of the cushion/frame which is a more sensitive region of the patient's face in use. Moreover, the concertina section 50 provides increased movement without compromising seal.

Figures 1, 32:
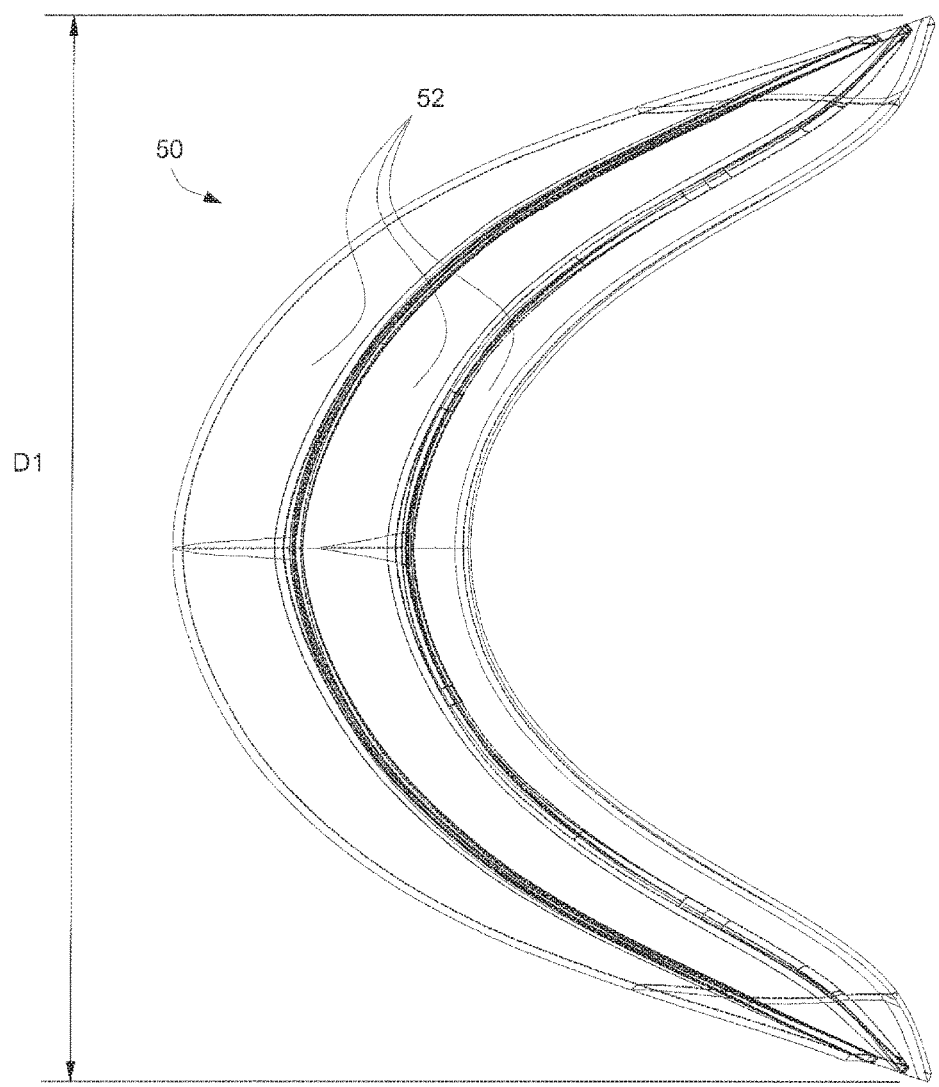
Figures 2, 32:
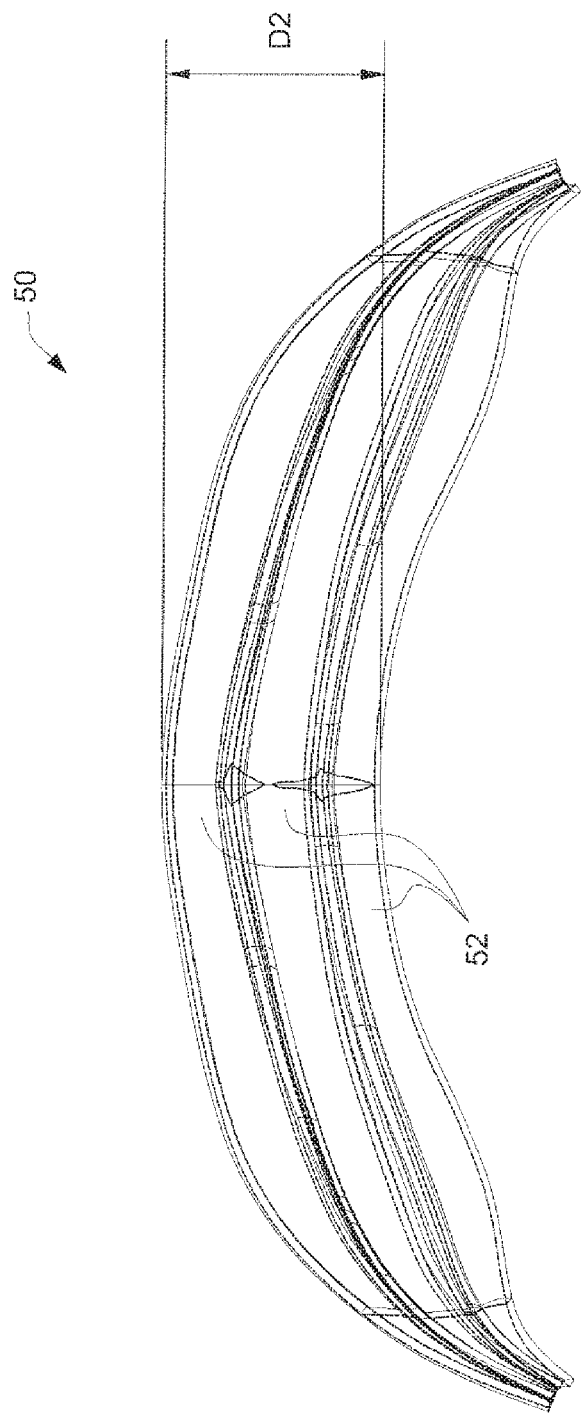
Figures 3, 32:
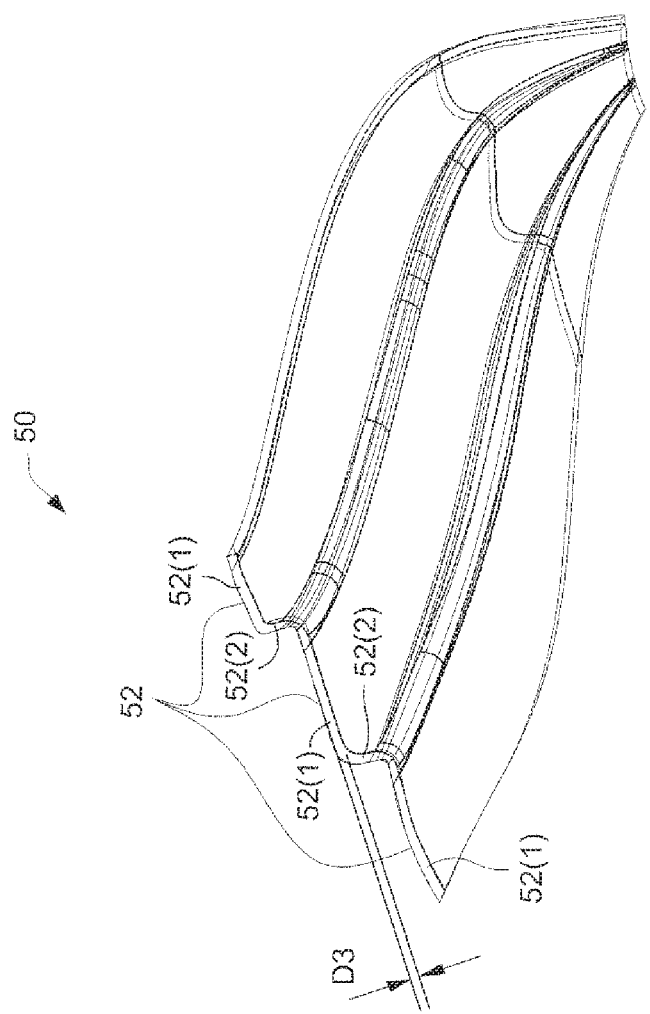

FIGS. 32-1 to 32-3 illustrate various views of a concertina section 50 (isolated from the remainder of the cushion/frame) with one or more folds 52 according to an embodiment of the present invention. As best shown in FIG. 32-3, the folds may have different lengths, depths, and/or contours with respect to one another to optimize the concertina effect, e.g., provide sufficient degree of movement without compromising seal. For example, as shown in FIG. 32-3, each fold 52 includes a first side wall 52(1) and a second side wall 52(2) that interconnects adjacent side walls 52(1).

In the illustrated embodiment, the first side walls 52(1) and/or the second side walls 52(2) may become progressively longer away from the patient's face. For example, the first side wall 52(1) and/or the second side wall 52(2) adjacent patient's face, or the combination of side walls 52(1) and 52(2), may have a length that is longer than and in some cases significantly longer than the adjacent side wall 52(1) and/or 52(2) (e.g., one side wall at least 25% greater than and up to 5× as long as the other side wall, e.g., 1×, 2×, 3×, or 4×).

The folds may be constructed and arranged to provide a predetermined order of movement or folding, e.g., folds structured to fold in a sequential or progressive manner wherein one fold collapses before an adjacent fold collapses. For example, upon application of force, the folds closest to the patient's face may fold or collapse before the folds furthest from the patient's face. Also, the folds may be constructed and arranged to provide various degrees of fold or collapse, e.g., folds may fold or collapse more than others.

In an embodiment of the concertina section shown in FIGS. 32-1 to 32-3, D1 may be about 50-60 mm, e.g., 55.7 mm, D2 may be about 5-15 mm, e.g., 9.7 mm, and D3 may be about 0.3-0.5 mm, e.g., 0.4 mm. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

It should be appreciated that a concertina section 50 may be provided in other regions of the cushion and/or frame, e.g., depending on patient comfort. For example, the concertina section 50 may be provided around the entire perimeter of the cushion and/or frame or may be provided in selected regions of the cushion and/or frame.

Also, the flexibility of the concertina section 50 may be varied and may be varied in different regions of the cushion and/or frame, e.g., depending on patient comfort. For example, the cushion and/or frame may include a concertina section in the nasal bridge region with a relatively high degree of flexibility and a concertina section in the lower lip/chin region with a relatively low degree of flexibility. The flexibility of the concertina section 50 may be varied by varying the number of folds 52 (e.g., 1-5 folds), the wall lengths, the wall thickness of the folds 52, the depth of the folds 52, etc.

As noted above, the cushion and frame may be co-molded of two parts with different materials/rigidities or may be integrally formed of the same material. In both embodiments, the concertina section may be provided in the frame and/or the cushion.

In FIGS. 27-30, the cushion 44 and frame 40 are co-molded of two parts with the concertina section 50 provided in the frame 40. The frame 40 and cushion 44 include different rigidities in order to optimize the function of each part. For example, one part (i.e., cushion 44) may be constructed of a relatively soft, supple material to optimize the sealing effect and the other part (i.e., frame 40) may be constructed of a more rigid material to provide adequate support for the cushion while at the same time allowing a sufficient degree of movement to optimize the concertina effect. While the frame is more rigid than the cushion, the frame may be constructed of a flexible material to allow the concertina effect.

In FIG. 33, the frame 40 and cushion 44 are integrally formed in one piece with the concertina section 50 provided in the frame 40. The material properties and/or dimensions may be selectively modified to optimize sealing and concertina effects.

Figure 34:
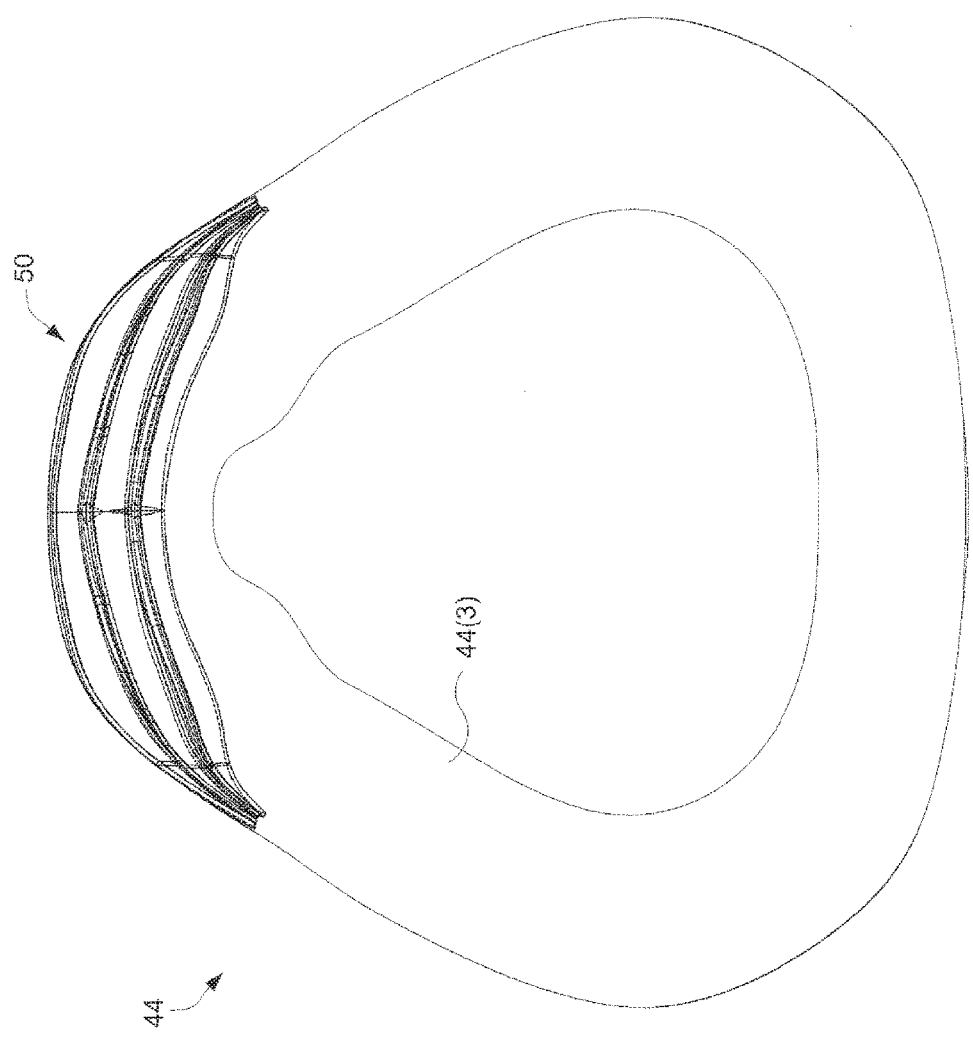
FIG. 34 illustrates a cushion including a concertina section according to an embodiment of the present invention.

For both embodiments of FIGS. 27-30 and 33, it should be appreciated that the concertina section may be alternatively provided in the cushion 44 or in both the frame 40 and cushion 44. For example, FIG. 34 illustrates a concertina section 50 integrally formed with the cushion 44 in the nasal bridge region.

4. Elbow

As shown in FIG. 3, the elbow 1070 (e.g., constructed of a relatively hard material such as polycarbonate or polypropylene) includes a first end portion 1074(1) and a second end portion 1074(2). The first end portion 1074(1) provides an interfacing structure structured to interface or otherwise attach to the frame 1040. The second end portion 1074(2) is adapted to be connected to an air delivery tube.

4.1 Elbow Connection to Frame

The frame 1040 is structured to maintain the elbow 1070 in an operative position with respect to the patient's face. That is, the frame acts as a carrier and bearing surface for the elbow. The frame and elbow may connect with a friction fit, snap-fit, mechanical interlock, or other suitable attachment mechanism. However, other suitable arrangements for attaching the elbow to the frame are possible.

In the illustrated embodiment, the elbow 1070 includes a series of tangs 1075 adapted to releasably engage within the opening 1032 of the frame 1040, e.g., with a snap-fit. The tangs 1075 hold the elbow in place (e.g., preferably a relatively airtight connection) and permit rotation or swiveling of the elbow with respect to the frame.

That is, the elbow is rotatably attached to the frame so that the elbow may be rotated relative to the frame in use, e.g., 360° rotation. This arrangement allows the elbow to assume different orientations in use, e.g., depending on patient preference. For example, the elbow may assume a first orientation so that the elbow extends generally downwardly from the mask to direct the air delivery tube under the patient's head in use. Alternatively, the elbow may be rotated and assume a second orientation so that the elbow extends upwardly from the mask to direct the air delivery tube over the patient's head in use. In an embodiment, the frame and elbow may be constructed of dissimilar materials to prevent or at least reduce squeak between the components in use.

The second end portion of the elbow may be provided to a swivel joint adapted to be connected to the air delivery tube. For example, FIGS. 27-30 illustrate a swivel joint 80 provided to the second end portion 74(2) of elbow 70. In the illustrated embodiment, the swivel joint 80 is provided to a short tube 82 (e.g., extendable and retractable tube) that interconnects the elbow with the air delivery tube. In an embodiment, the swivel joint 80 may be integrally formed in one piece with the short tube 82.

4.2 AAV

The elbow 1070 includes a slot 1081 to receive an anti-asphyxia valve (AAV), a port 1079 that is selectively closed by a flap portion of the AAV (depending on the presence of pressurized gas), and structure for attaching the AAV, e.g., with a snap-fit.

FIGS. 27-30 illustrate an exemplary AAV 85 including a flap portion 86 to selectively close port 79 in elbow 70. In this embodiment, a clip portion 88 is provided to the flap portion 86 for attaching the AAV 85 to the elbow 70. In the illustrated embodiment, the flap portion 86 and the clip portion 88 are co-molded with one another to form a one-piece, integrated component. However, the flap portion 86 and clip portion 88 may be secured to one another in other suitable manners, e.g., mechanical interlock.

In an embodiment, the flap portion 86 may be constructed of a relatively soft elastomeric material (e.g., silicone) and the clip portion 88 may be constructed of a more rigid material (e.g., rigid plastic) for interfacing with the elbow 70.

The clip portion 88 of the AAV 85 includes structure for removably interlocking with the elbow 70, e.g., with a snap-fit. For example, the clip portion 88 may include tabs structured to interlock with respective recesses/protrusions provided to the elbow.

FIGS. 35-1 and 35-2 illustrate an elbow 270 including a port 279 that is selectively closed by a flap portion 286 of the AAV 285 (depending on the presence of pressurized gas). Also, FIGS. 37-1 to 37-3 illustrate elbow 370 including a port 379 and a slot 381 to retain the AAV.

Alternative embodiments of the AAV are disclosed in PCT Application No. PCT/AU2006/000031, which is incorporated herein by reference in its entirety.

4.3 Large Diameter End Portion

As shown in FIGS. 27-30, the first end portion 74(1) of the elbow 70 may provide a relatively large diameter which allows the potential for cleaner/smoother lines thereby contributing to the overall mask aesthetic and reduced obtrusiveness. In addition, the relatively large diameter elbow offers the potential for the patient's nose to protrude into the elbow cavity thereby permitting the mask to be brought closer to the patient's face (i.e., reduced obtrusiveness), less moment since center of gravity of mask is closer to the patient's face, and/or improved line of sight.

5. Modular Design

The mask system provides a modular design that allows different styles and/or sizes of the frame (also referred to as a frame module), shroud (also referred to as a shroud module), cushion (also referred to as a cushion module), and/or elbow (also referred to as an elbow module) to be interchanged or mixed and matched with one another to provide a more customized mask system for the patient. In addition, such design allows selected modules to be easily replaced, e.g., treatment requirements change, worn out or damaged, etc.

In an embodiment, the mask system may be provided with a number of different cushions, e.g., each having cushions of different styles and/or sizes (e.g., depending on patient preference and/or fit). For example, the non-face contacting side of each cushion may include a common or universal configuration for interfacing with the frame, and the face-contacting side of the cushion may include different styles and/or sizes. This provides a modular arrangement that allows the frame to be selectively (e.g., and removably) coupled to one of multiple cushion. For example, the different cushions may include different size cushions (e.g., small, medium, and large) and may include a different cushion structures.

In an embodiment, the mask system may be provided with different shrouds, e.g., each shroud having a different style and/or size (e.g., shroud with different arrangement/style of headgear connectors, shroud with forehead support, different headgear vectors, etc).

In an embodiment, the mask system may be provided with different frames, e.g., each frame having a different style and/or size (e.g., frame with different vent arrangement, small, medium, and large size frame, etc).

In an embodiment, the mask system may be provided with a number of different elbows, e.g., each having a vent arrangement, AAV (in the case of an oro-nasal mask), and/or elbow of different styles and/or sizes. In the illustrated embodiment of FIGS. 27-30, the vent arrangement 76 and AAV 85 are structured to be removably attachable to the elbow 70. This provides a modular arrangement that allows the elbow to be selectively and removably coupled to one of multiple vent arrangements and/or AAVs. This also allows the vent arrangement and AAV to be easily replaced, e.g., if damaged.

5.1 Shroud to Frame Connection

The shroud is mounted on the outer surface of the frame, e.g., preferably with a tight, conforming fit on the frame.

5.1.1 Upper Retaining Mechanism

In the illustrated embodiment of FIGS. 1-5, the shroud 1020 is connected to the frame 1040 by an upper retaining mechanism or interfacing structure 1048 located on the top end of the frame and shroud.

As shown in FIGS. 2 to 5, the upper retaining mechanism 1048 is in the form of two taper locks structured to secure the shroud 1020 on the frame 1040 and prevent unintentional disassembly particularly due to headgear forces. In this embodiment, opposing sides of the frame include a female slot 1055 adapted to receive a respective tang protrusion (which tapers along its length) on the underside of the shroud 1020. The tapered protrusion engages within a respective female slot, e.g., with a friction fit.

FIGS. 10 to 19-4 show another embodiment of a mask system 1110 which more clearly illustrates an embodiment of the taper lock. FIGS. 10 to 17 show various views of the frame 1140, shroud 1120, and elbow 1170 of the mask system 1110.

Figure 11:
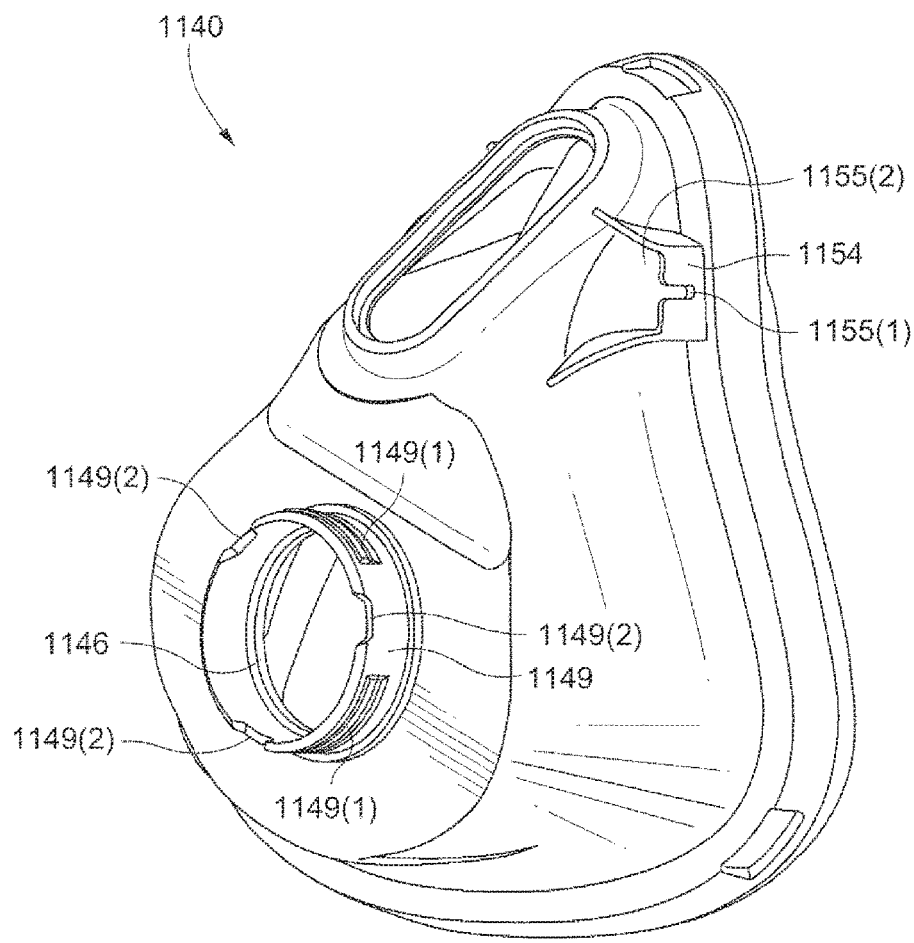
FIG. 11 is a front perspective view showing the frame of the mask system of FIG. 10.
Figure 12:
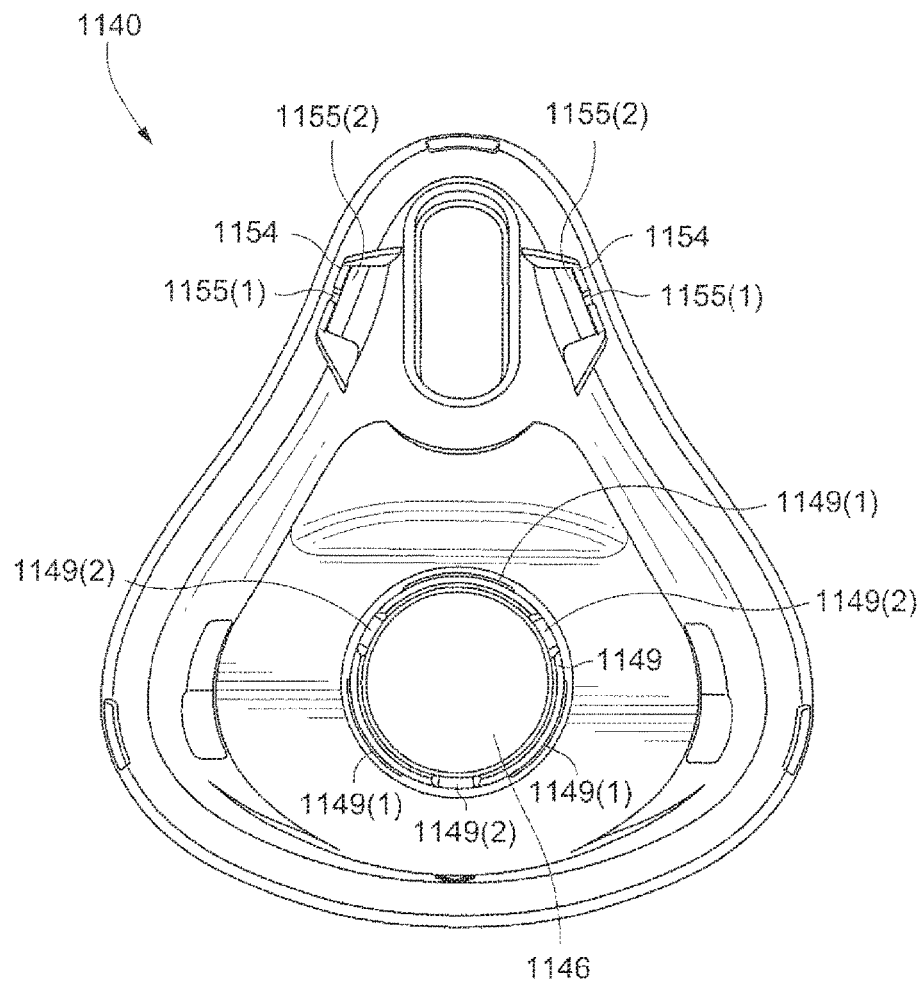
FIG. 12 is a front view showing the frame of the mask system of FIG. 10.
Figure 13:
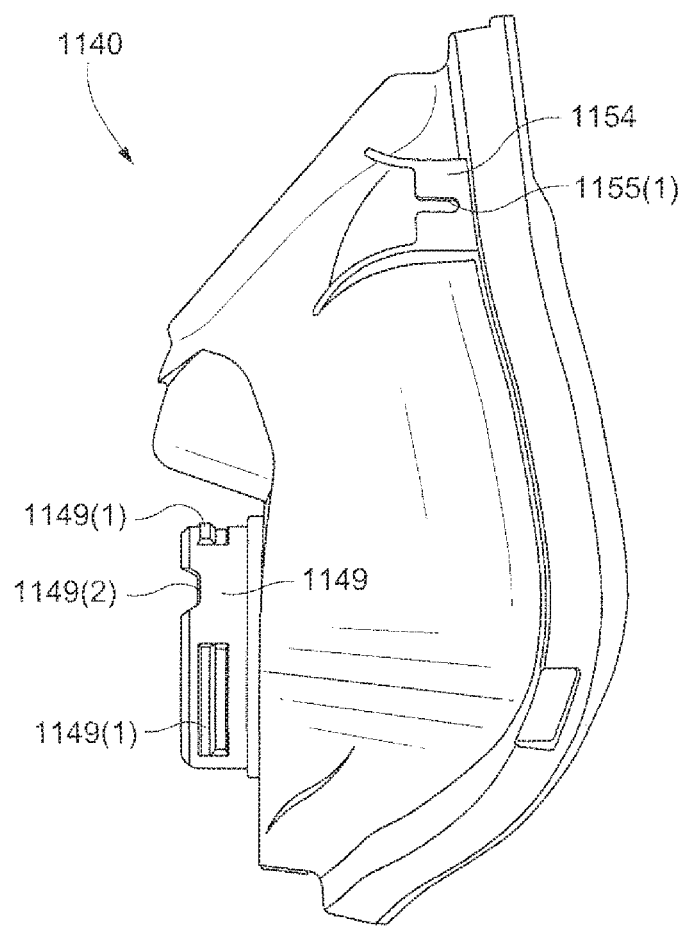
FIG. 13 is a side view showing the frame of the mask system of FIG. 10.
Figure 14:
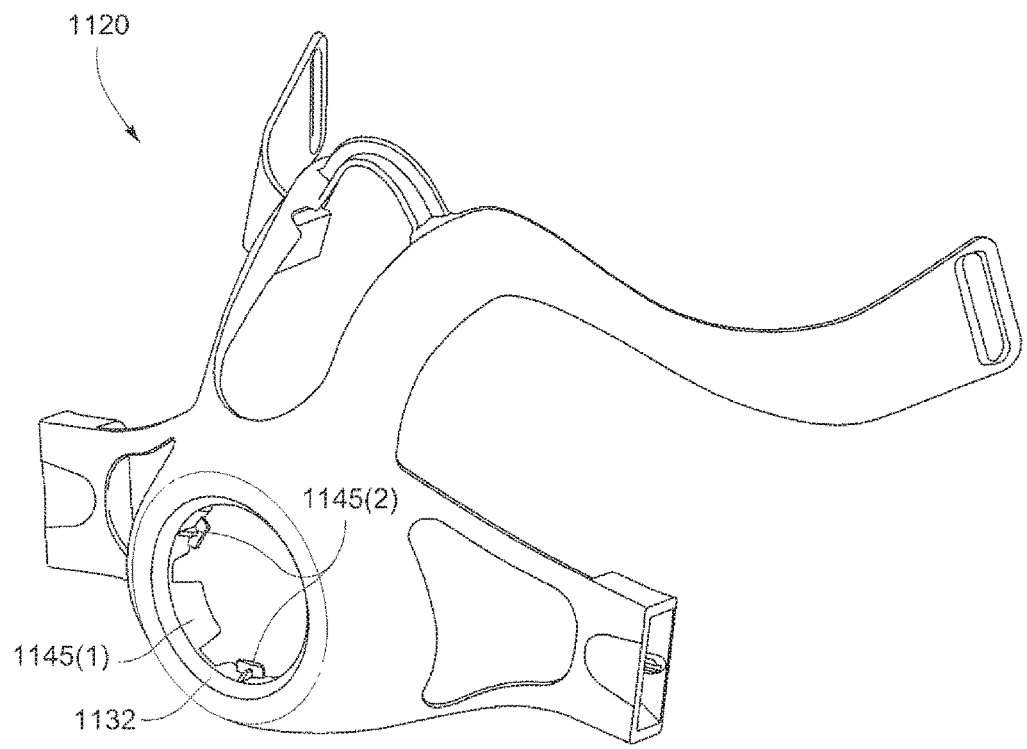
FIG. 14 is a front perspective view showing the shroud of the mask system of FIG. 10.
Figure 15:
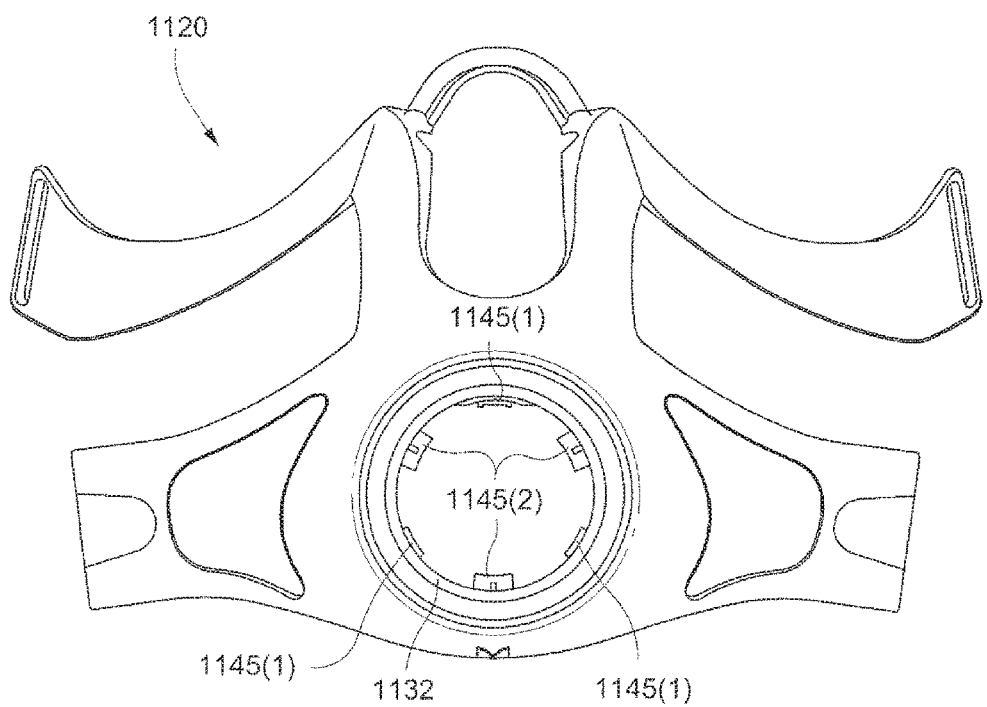
FIG. 15 is a front view showing the shroud of the mask system of FIG. 10.
Figure 16:
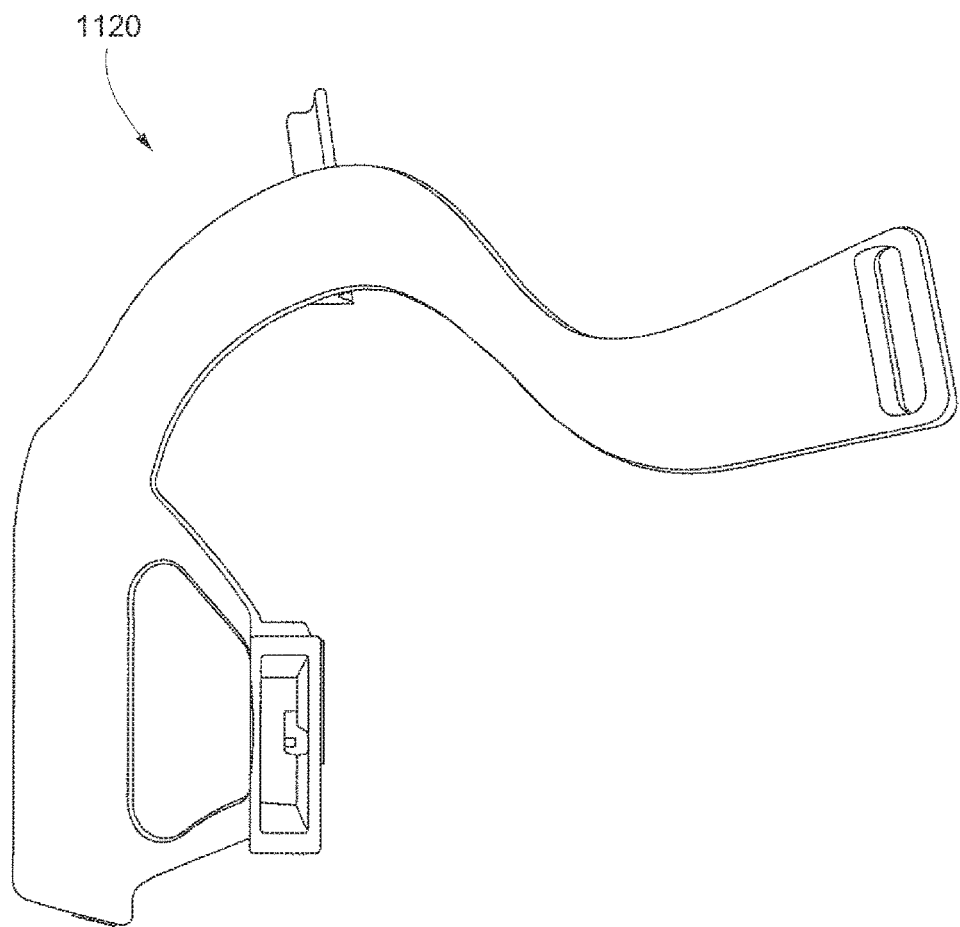
FIG. 16 is a side view showing the shroud of the mask system of FIG. 10.
Figure 17:
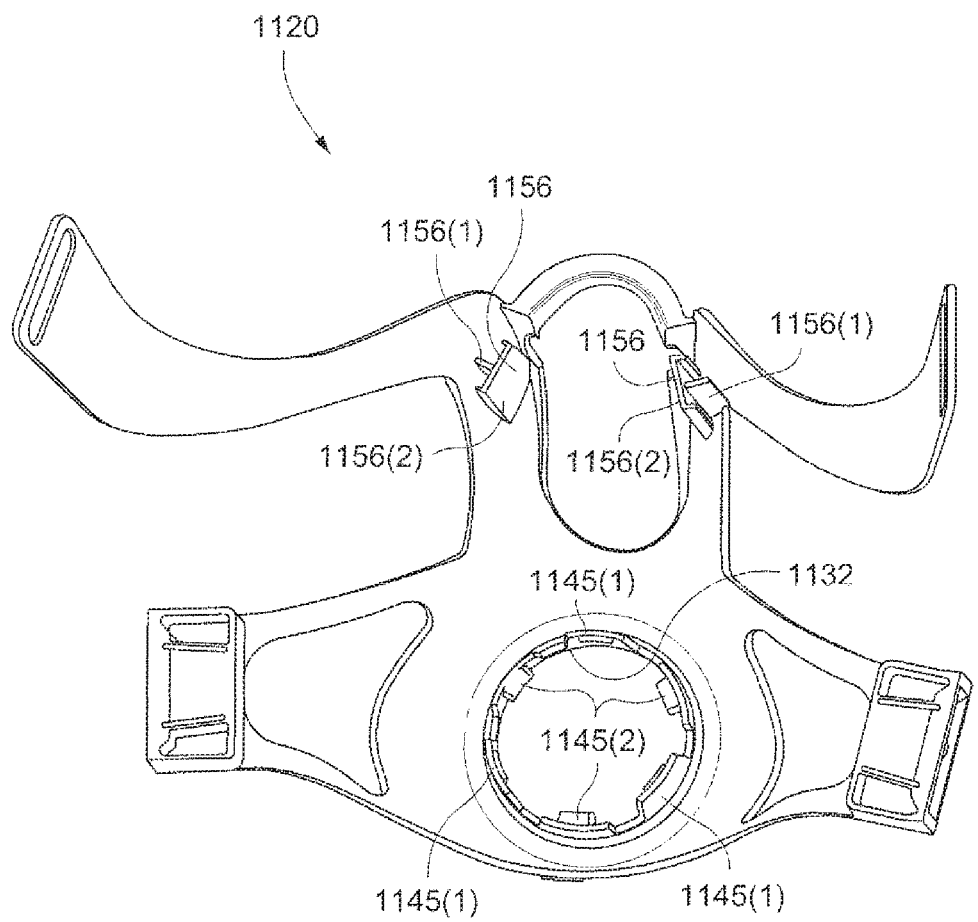
FIG. 17 is a rear perspective view showing the shroud of the mask system of FIG. 10.
Figures 1, 18:
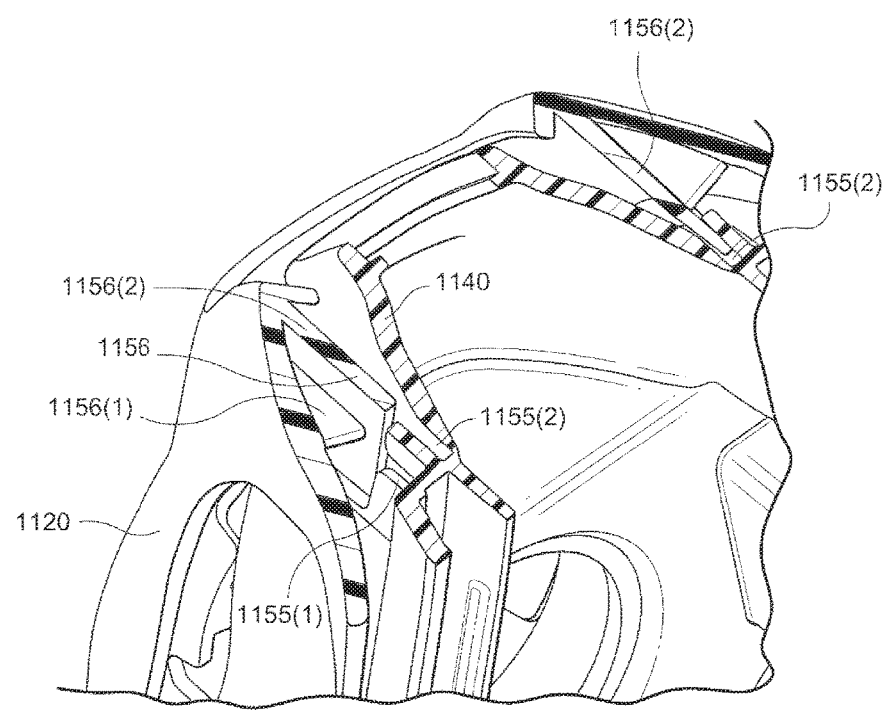
Figures 2, 18:
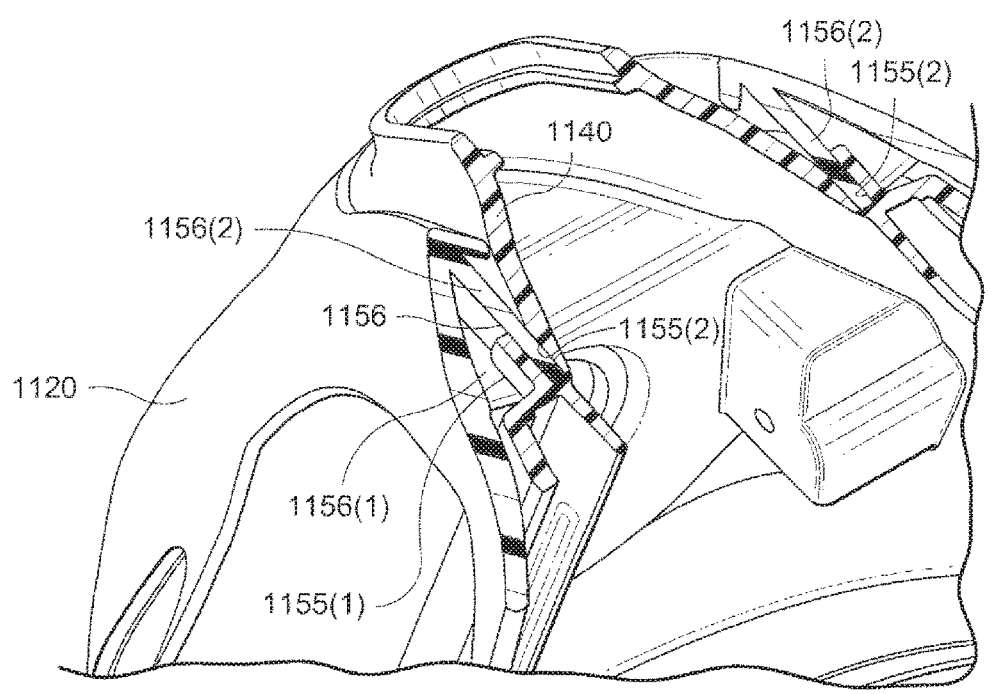

As best shown in FIGS. 11 to 13, opposing sides of the top end of the frame 1140 include a platform 1154 which provides a first female slot 1155(1). In addition, the space between the platform 1154 and the outer surface of the frame 1140 defines a second female slot 1155(2). As best shown in FIG. 17, opposing sides of the top end of the shroud 1120 include a tang protrusion 1156 on the underside of the shroud 1120. The tang protrusion 1156 includes a first tang 1156(1) and a second tang 1156(2) that extends generally transverse to the first tang 1156(1). As shown in FIGS. 18-1 and 18-2, each tang may taper along its length, i.e., thinner towards its free end.

FIGS. 18-1 and 18-2 and 19-1 to 19-4 sequentially illustrate attachment of the shroud 1120 to the frame 1140. As illustrated, the tangs 115((1), 1156(2) of each tang protrusion 1156 are structured to engage with respective slots 1155(1). 1155(2), e.g., with a friction fit. As best shown in FIGS. 19-1 to 19-4, each slot 1155(2) includes lead-ins or guides 1157 that curve along their length (i.e., extend in vertical and horizontal direction) so as to guide the tang 1156(2) into the slot 1155(2) and aid assembly. FIGS. 18-2 and 19-4 show the tangs 1156(1), 1156(2) when fully inserted with respective slots 1155(1), 1155(2).

Figure 20:
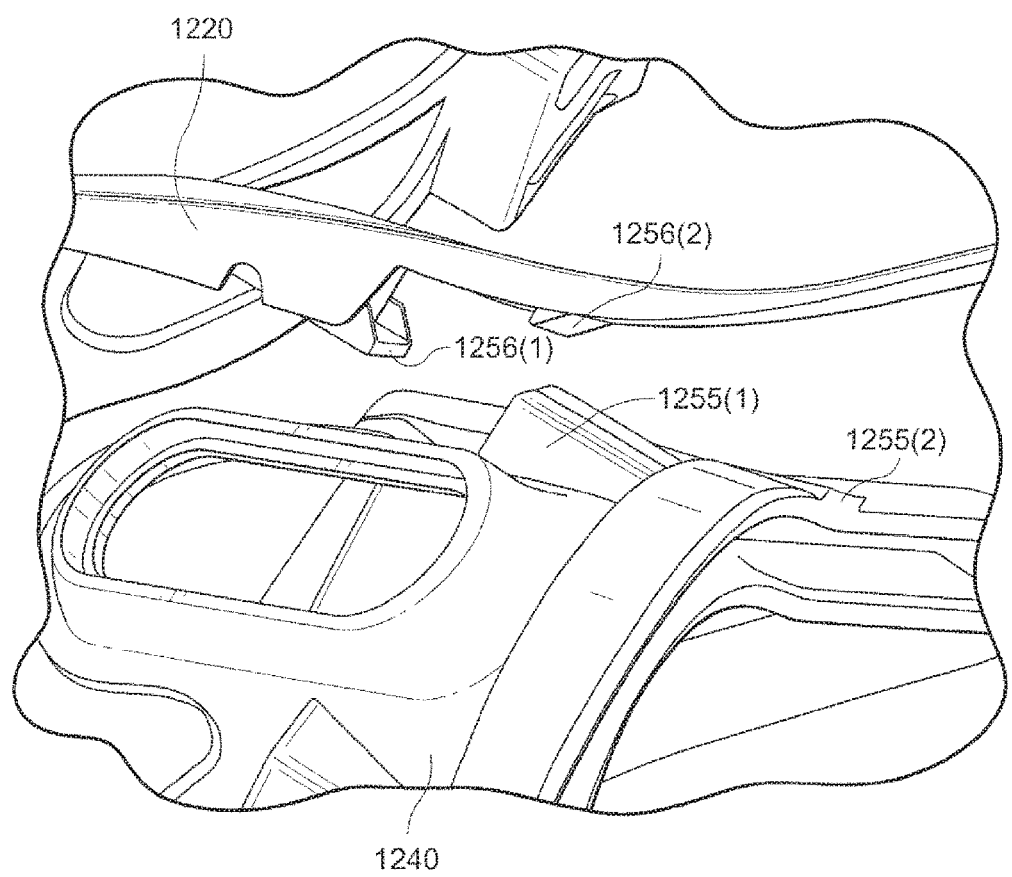
FIG. 20 is a perspective view showing an alternative arrangement for attaching the shroud to the frame.
Figure 21:
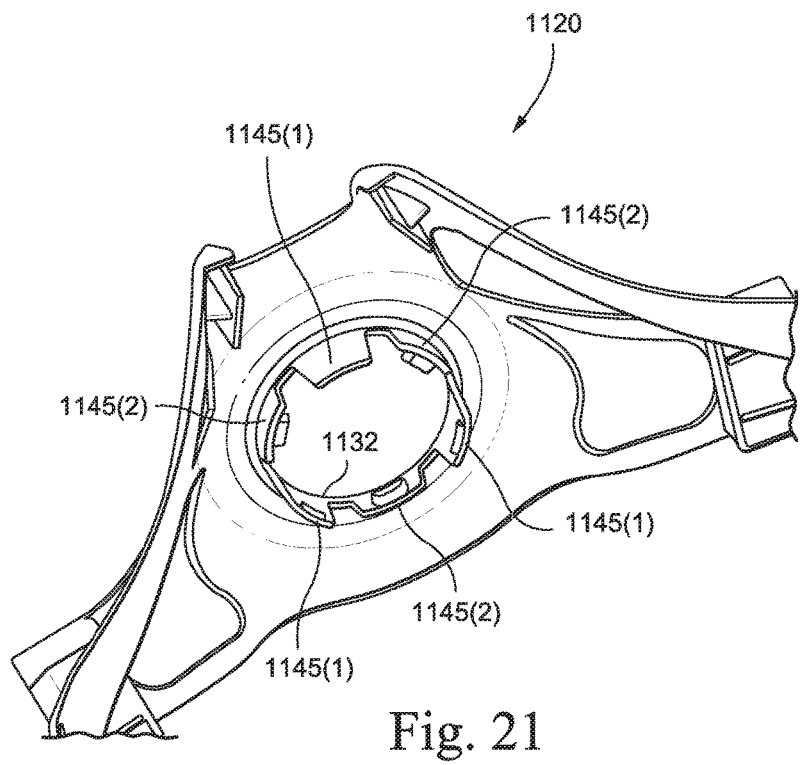
FIG. 21 is a rear perspective view showing the shroud of the mask system of FIG. 10.

In an alternative embodiment, as shown in FIG. 20, the upper retaining mechanism may include a clip-type arrangement. As illustrated, opposing sides of the top end of the frame 1240 provide a shoulder 1255(1) and a tapered protrusion 1255(2). Opposing sides of the top end of the shroud 1220 include a first tang 1256(1) and a second tang 1256(2) on the underside of the shroud 1220. In use, each first tang 1256(1) is engaged with the respective shoulder 1255(1) and the second tang 1256(2) is engaged or clipped onto the tapered protrusion 1255(2), e.g., with a snap-fit.

5.1.2 Lower Retaining Mechanism

In an embodiment, the shroud may also be connected to the frame by a lower retaining mechanism located on the bottom end of the frame and shroud. For example, a retaining mechanism may be provided to the opening of the shroud which is structured to interlock or otherwise engage with the opening of the frame.

For example, as shown in FIGS. 14, 15, 17, and 21, the opening 1132 of the shroud 1120 may include structure adapted to engage the collar 1149 surrounding the frame opening 1146 with a snap-fit. As illustrated, the shroud 1120 includes snap fingers 1145(1) (e.g., three snap fingers) and sandwich tabs 1145(2) (e.g., three sandwich tabs) that extend from the opening 1132. The snap fingers and sandwich tabs are alternatively spaced about the opening.

Figure 22:
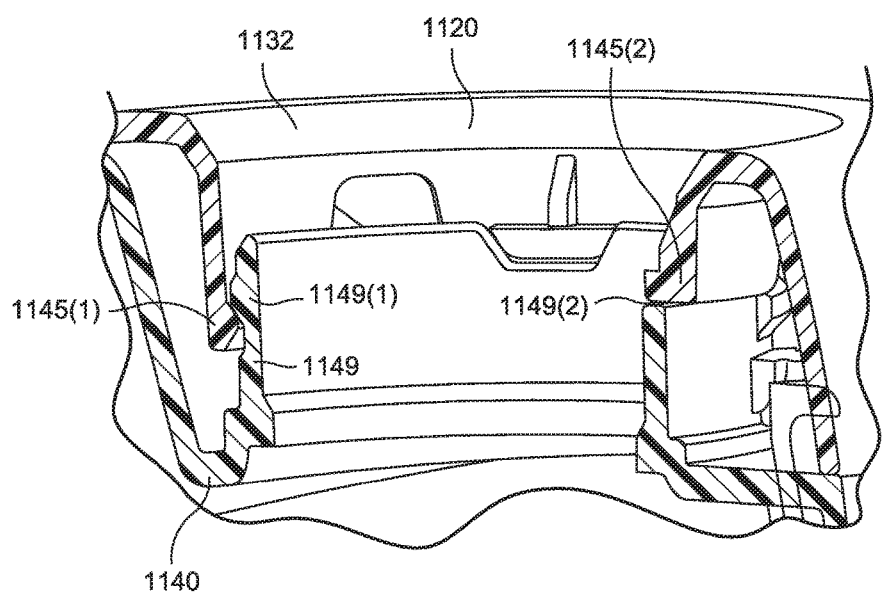
FIG. 22 is a cross-sectional view showing attachment of the shroud to the frame of the mask system of FIG. 10.
Figure 23:
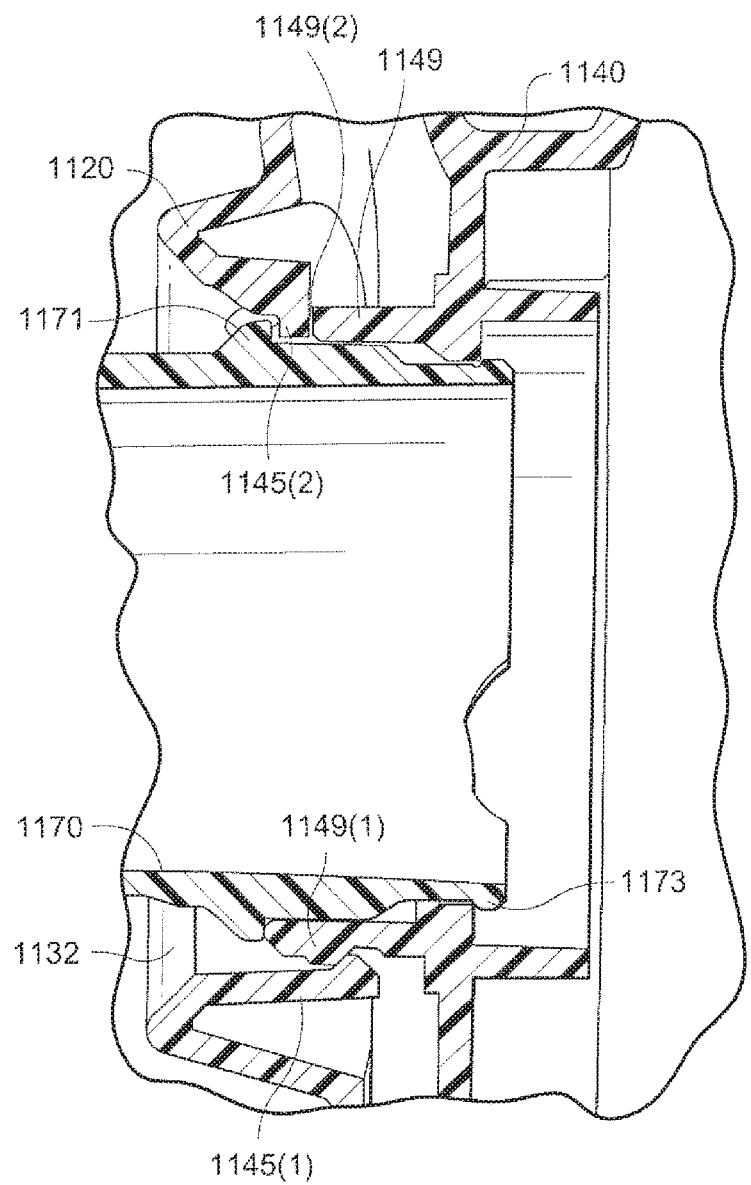
FIG. 23 is a cross-sectional view showing attachment of the shroud, frame, and elbow of the mask system of FIG. 10.

In use, the snap fingers 1145(1) resiliently deflect (e.g., 0.5 mm deflection) and engage respective part-annular protrusions 1149(1) provided to the collar 1149 (e.g., see FIGS. 22 and 23) to provide an initial retention of the shroud 1120 to the frame 1140 (e.g., with allowable stresses), e.g., to facilitate assembly and disassembly. In addition, as the snap fingers 1145(1) engage respective protrusions 1149(1), the sandwich tabs 1145(2) are received in respective recesses 1149(2) provided to the end of the collar 1149 (e.g., see FIGS. 22 and 23). When the elbow 1170 is engaged with the frame 1140 (e.g., see FIG. 23), an annular protrusion 1171 on the elbow 1170 is positioned on an opposing side of the sandwich tabs 1145(2) so that the sandwich tabs 1145(2) are sandwiched between the collar 1149 and the elbow 1170. Thus, the sandwich tabs utilize elbow retention forces to retain the shroud on the frame during use. The elbow 1170 has a distal shoulder 1173 adapted to extend under the edge of the frame 1140 to retain the elbow to the frame. The snap fingers 1145(1) allow the shroud to connect to the frame independent of the elbow.

Figure 24:
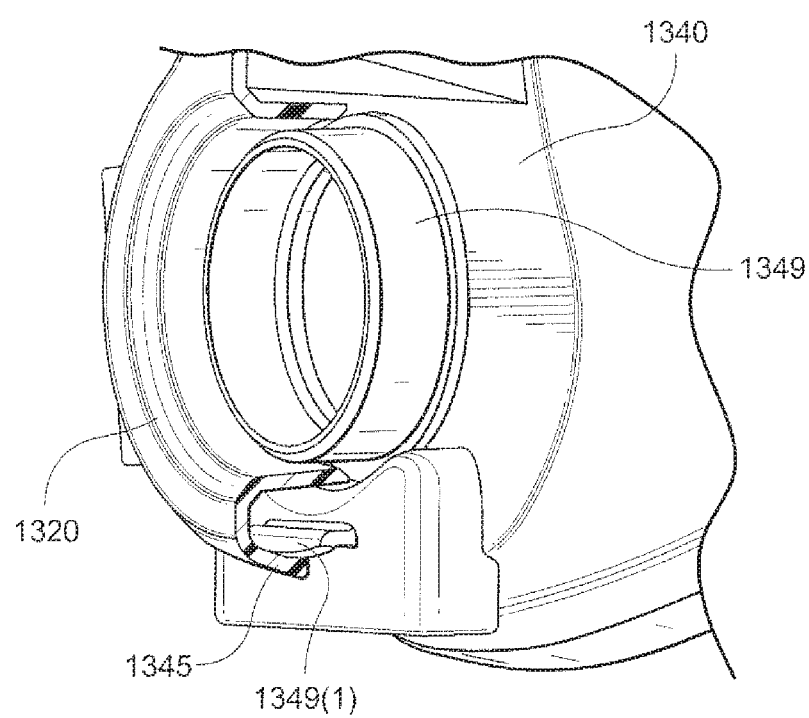
FIG. 24 is a cross-sectional view showing an alternative arrangement for attaching the shroud to the frame.

In an alternative embodiment, as shown in FIG. 24, the shroud's lower section may be structured to clip to a single point below the collar. As illustrated, the lower end of the shroud 1320 includes a snap finger 1345 that is engaged or clipped onto a protrusion 1349(1) spaced below the collar 1349 of the frame 1340, e.g., with a snap-fit. In this embodiment, the protrusion 1349 extends from the cover enclosing auxiliary ports. This arrangement may facilitate molding of the collar on the frame, e.g., uniform thickness of the collar prevents molding distortions. In addition, removal of the protrusions 1149(1)/recesses 1449(2) from the collar may reduce the risk of leak.

5.1.3 Finger Grip

In an embodiment, the outer surface of the frame 1040 may include finger grips or recessed portions 1097, which are positioned to be exposed under the shroud 1020. The finger grips are adapted to allow the patient an improved ability to grip the frame and/or shroud which is particularly useful when disengaging the shroud from the frame.

5.1.4 Alternative Interfacing Structure

In an alternative embodiment, as shown in FIG. 27-30, the shroud 20 includes an open construction that provides an annular or part annular retaining portion 22 structured to retain the frame 40 and the elbow 70. As illustrated, the annular retaining portion 22 includes an interfacing structure 23 along an inner edge that is adapted to interface with or otherwise removably connect to an interfacing structure 48 along the outer perimeter of the frame 40 (e.g., see FIG. 28). In the illustrated embodiment, the interfacing structure 23 is in the form of opposed flanges 23(1) that are adapted to interlock with respective locking structures 48(1) provided on opposing sides of the frame 40. However, other suitable arrangements for attaching the frame 40 to the shroud 20 are possible, e.g., friction fit, snap-fit, mechanical interlock, or other suitable attachment mechanism.

For example, the frame 40 may be coupled to the shroud 20 in a manner that allows the frame 40 to be locked in different angular positions with respect to the shroud 20, e.g., pivotally mounted.

5.1.5 Alternative Upper Headgear Connector

Figure 7:
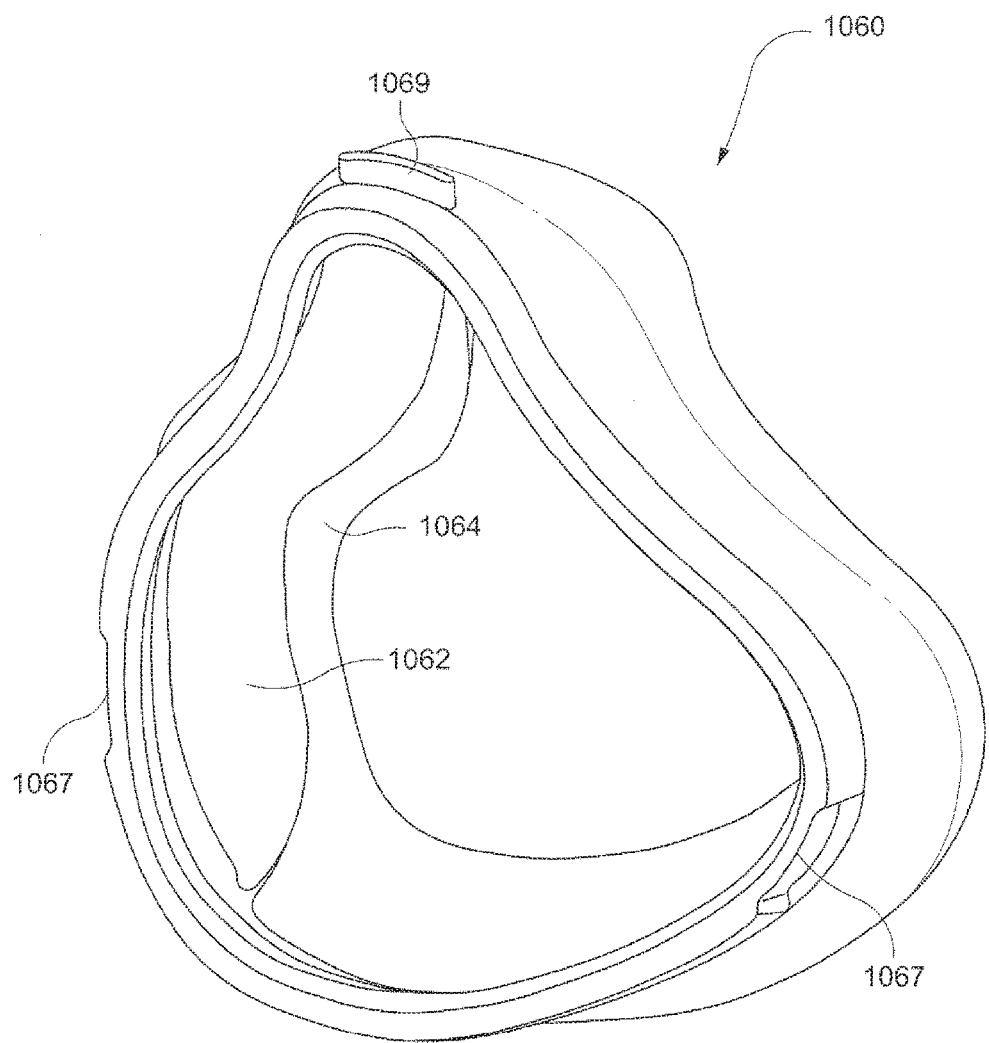
FIG. 7 is a front perspective view showing the cushion of the mask system of FIG. 1.
Figures 1, 40:
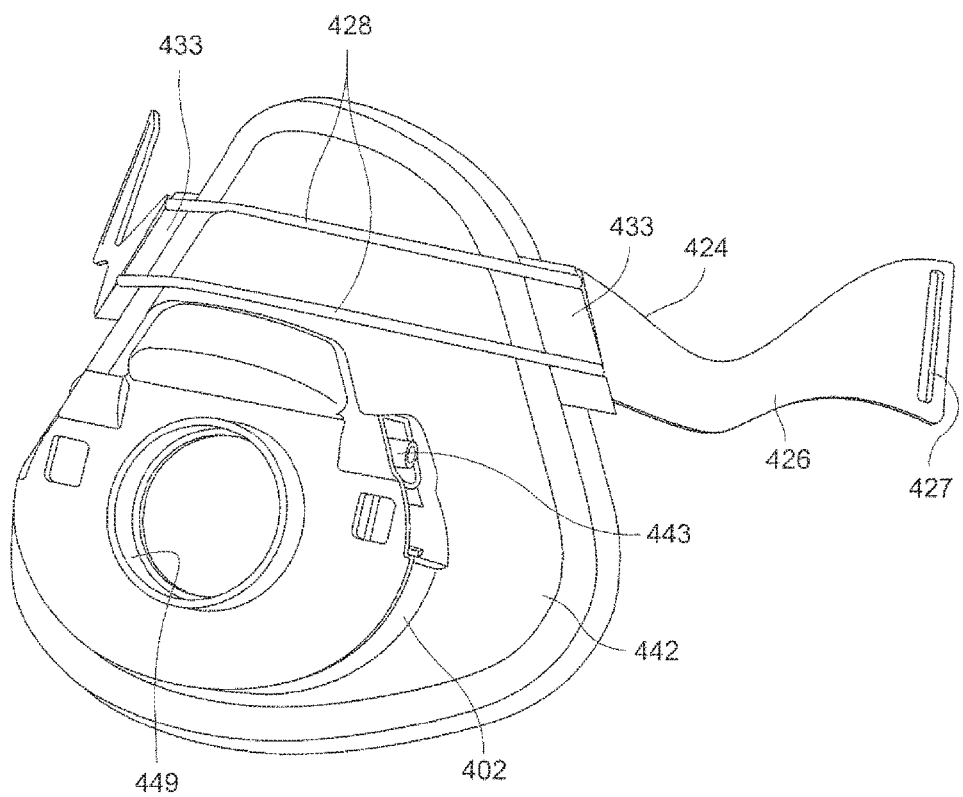
Figures 2, 40:
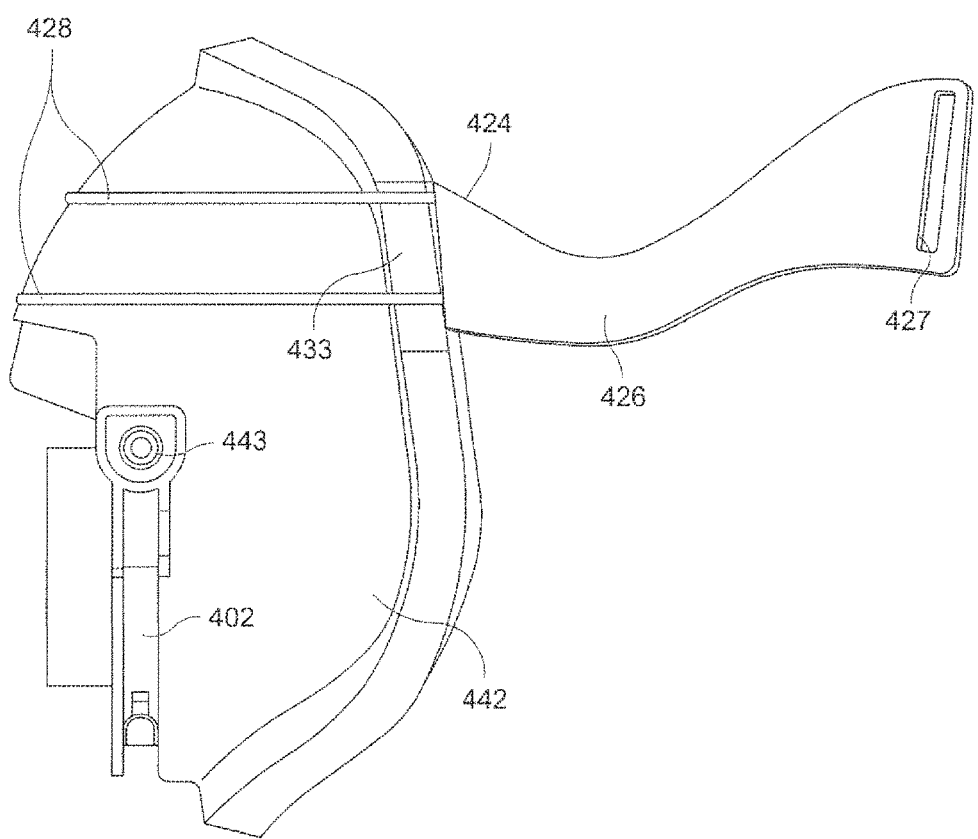
Figures 3, 40:
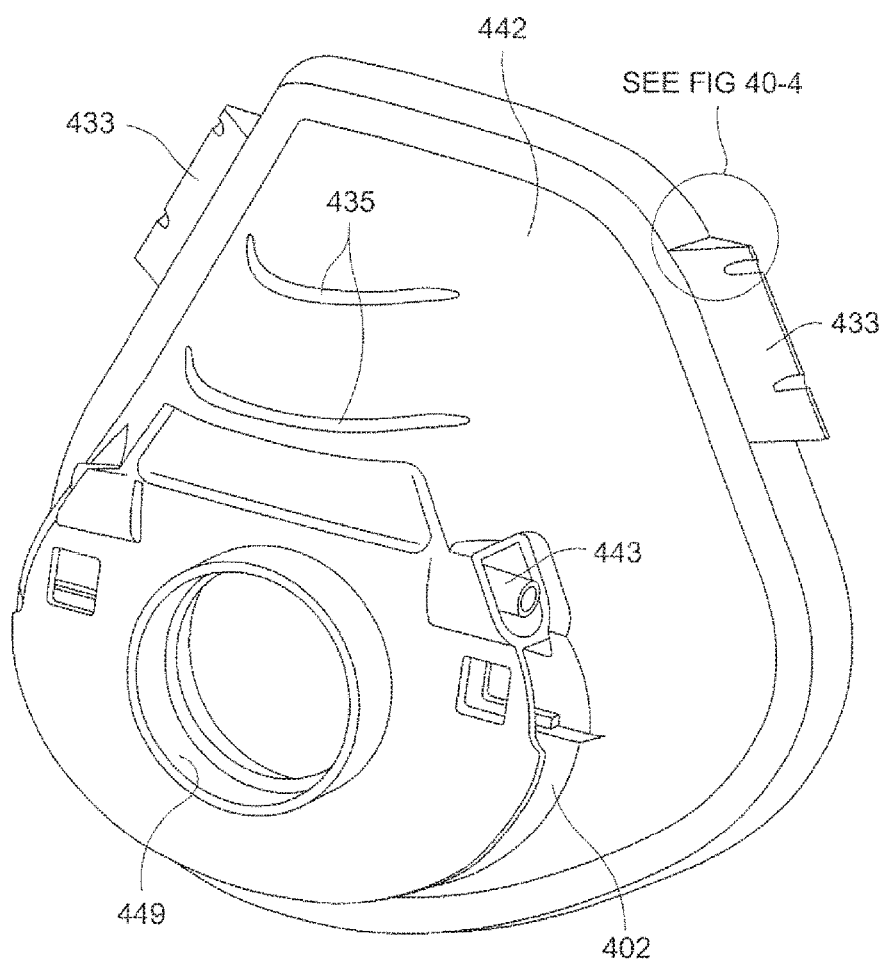
Figures 4, 40:
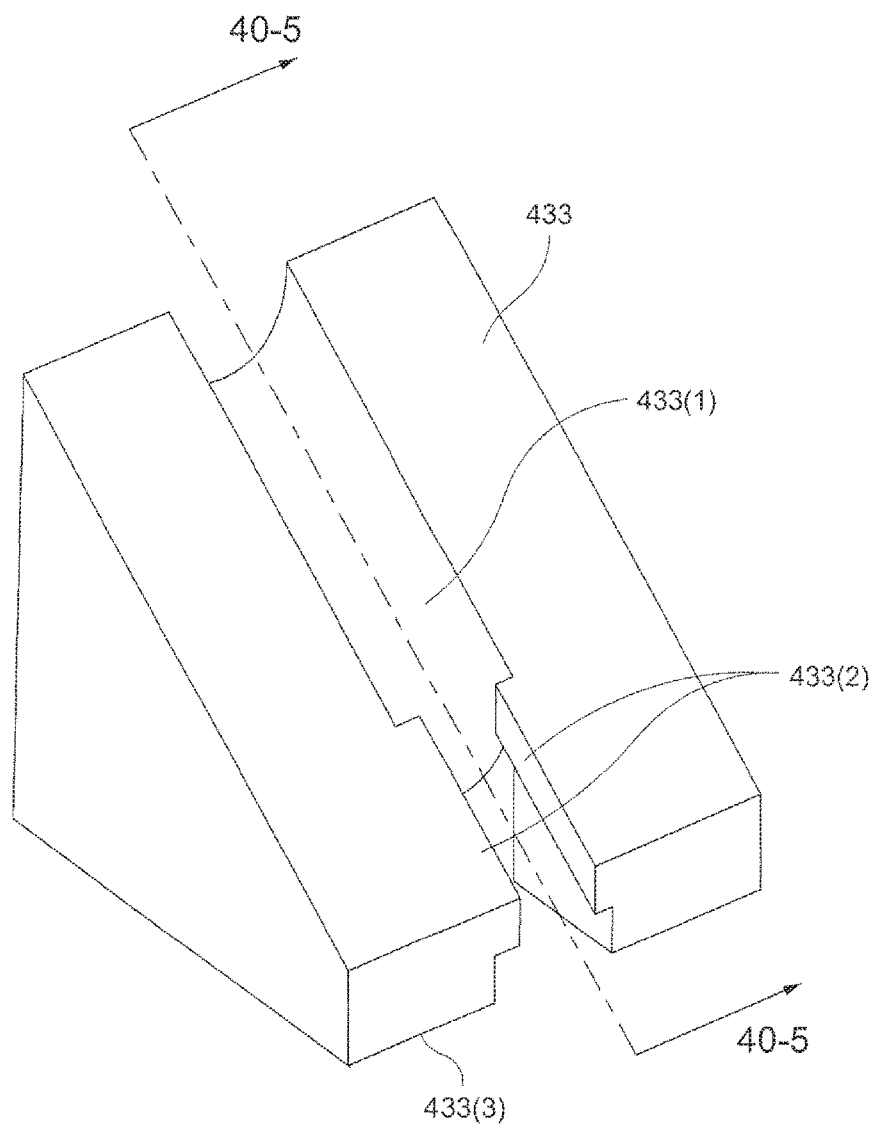
Figures 5, 40:
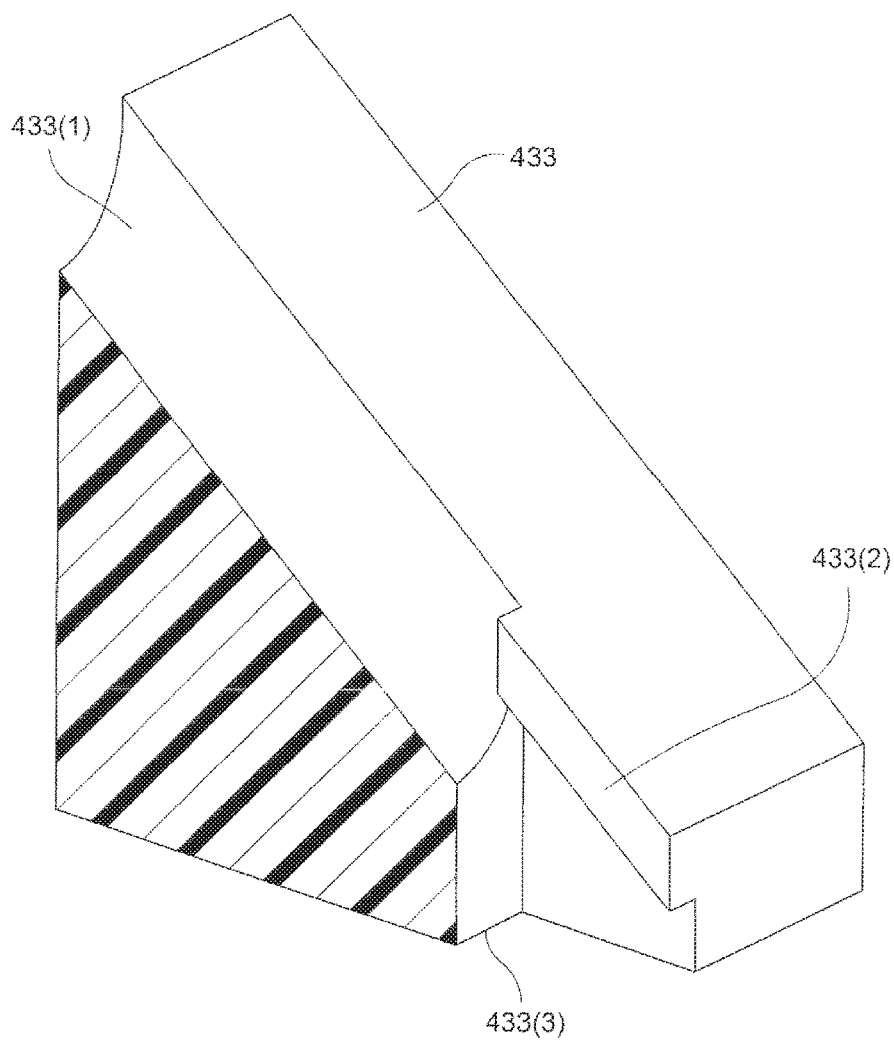
Figures 6, 40:
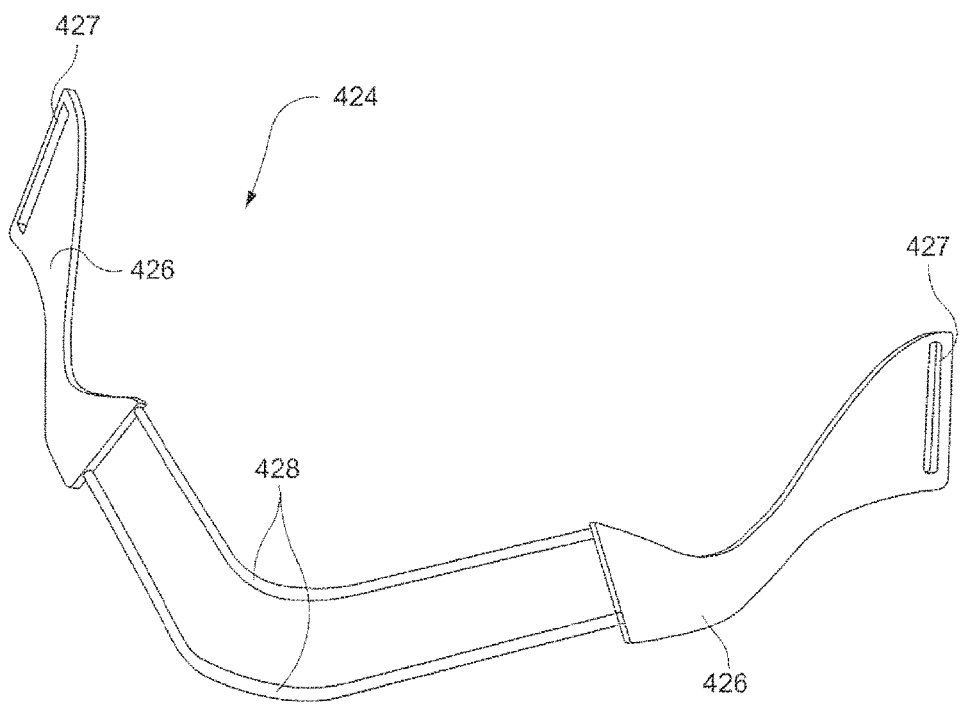
Figures 7, 40:
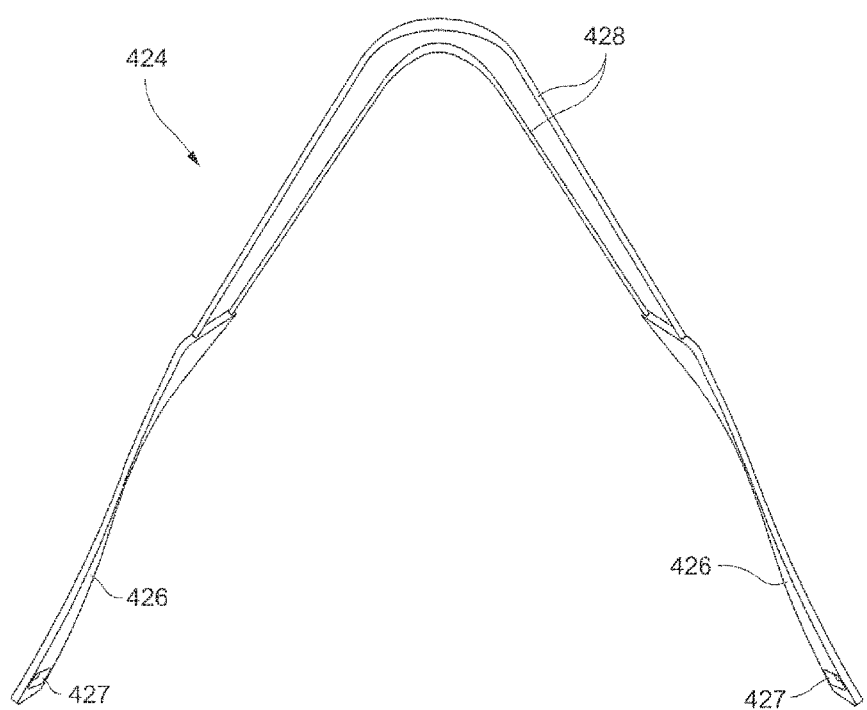

FIGS. 40-1 to 40-7 illustrate a frame and a clip-on upper headgear connector or rigidizer according to another embodiment of the present invention.

The frame 442 includes an opening 449 adapted to engage a frame shroud and/or elbow. Around and under the opening 449 is the u-shaped slot 402 for gas washout and auxiliary ports 443 on each side thereof.

In this embodiment, each upper side of the frame 442 includes a retaining member 433 and an upper intermediate portion of the frame 442 includes retaining grooves 435, which are structured and arranged to retain an upper headgear connector or rigidizer 424.

As best shown in FIGS. 40-6 and 40-7, the upper headgear connector 424 includes a pair of elongated arms or rigidizers 426 coupled by a pair of wire members 428. Each rigidizer 426 includes a slot 427 at its free end adapted to receive a respective headgear strap in use.

In use, the upper headgear connector 424 is adapted to clip onto the frame 442 (e.g., see FIGS. 40-1 and 40-2). Specifically, intermediate portions of the wire members 428 are received in respective grooves 435 of the frame 442, and end portions of the wire members 428 extend through respective retaining members 433 with the rigidizers 426 providing a shoulder to interlock with respective retaining members 433. FIGS. 40-4 and 40-5 show an upper portion of a retaining member 433 to illustrate the groove 433(1) adapted to receive a respective wire. As illustrated, the end of the groove 433(1) includes tapered side walls 433(2) and drops off towards a rear side 433(3) to position the rigidizers 426 into interlocking engagement with the retaining member 433.

Figures 1, 41:
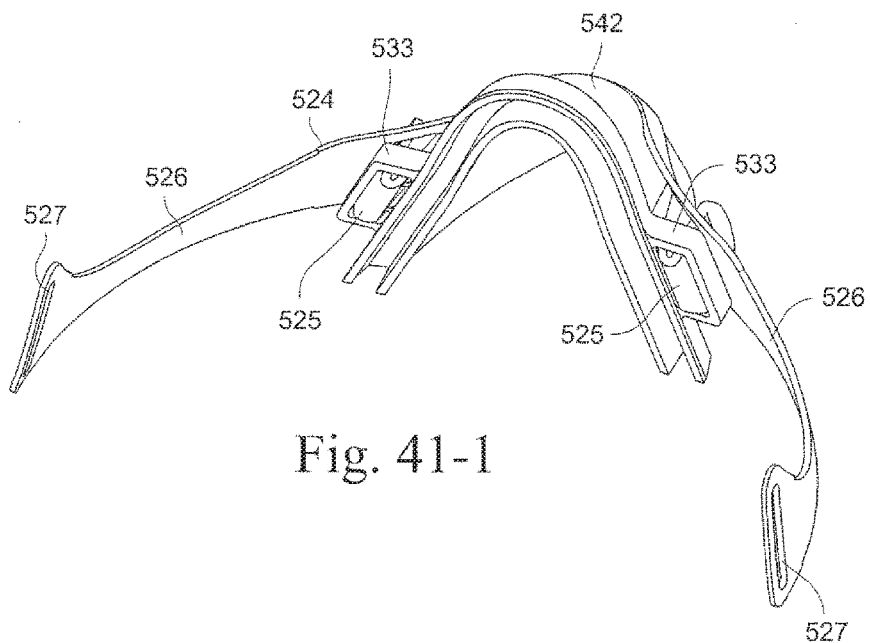
Figures 2, 41:
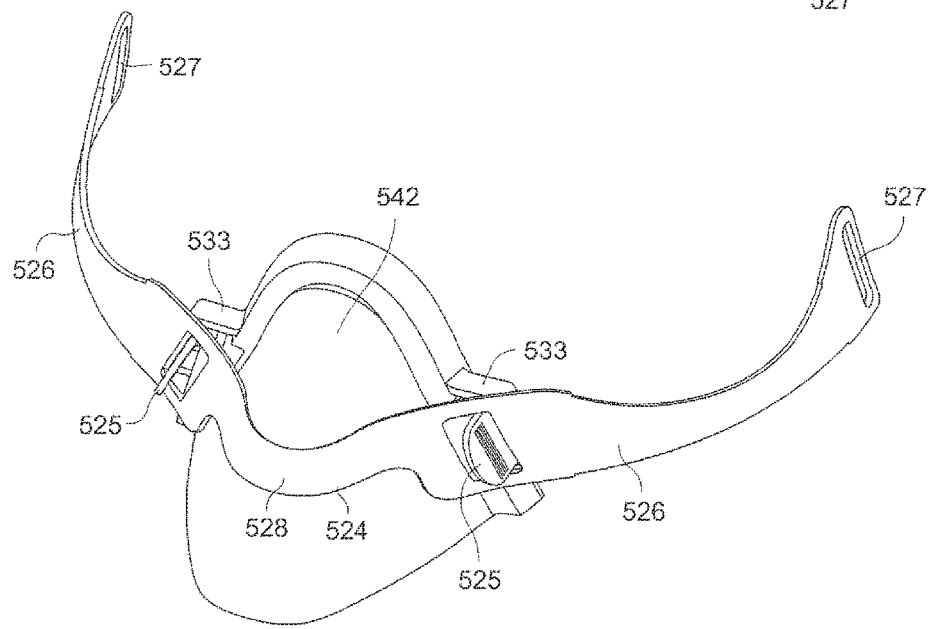
Figures 3, 41:
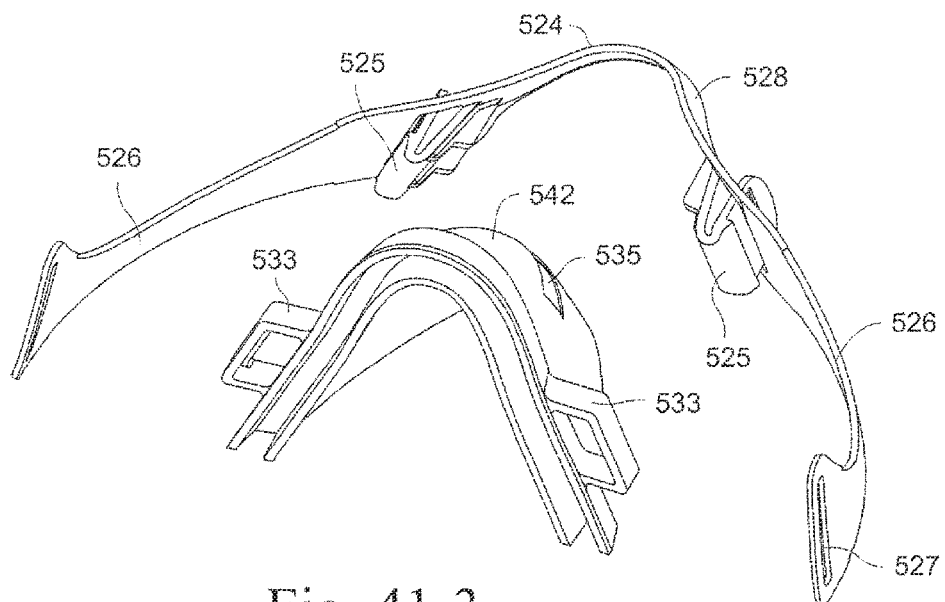
Figures 4, 41:
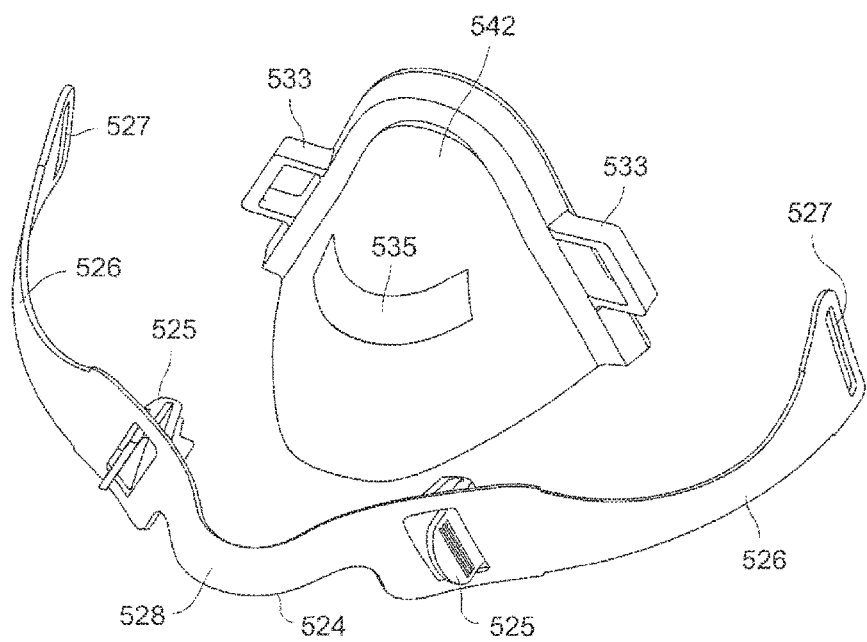
Figures 5, 41:
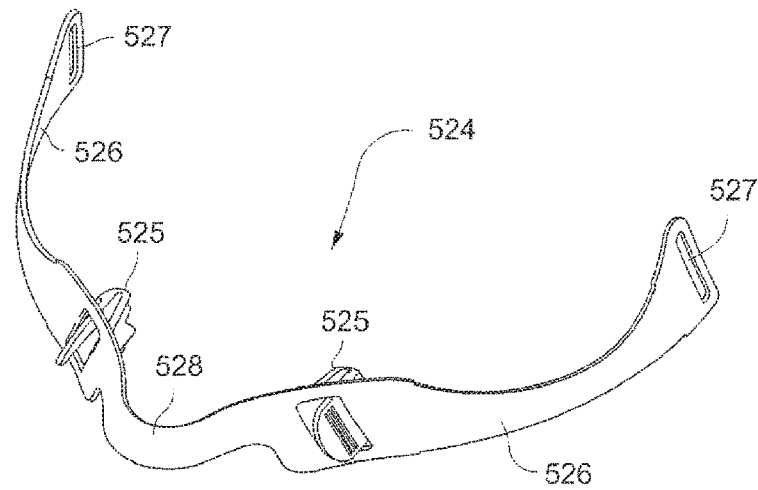
Figures 6, 41:
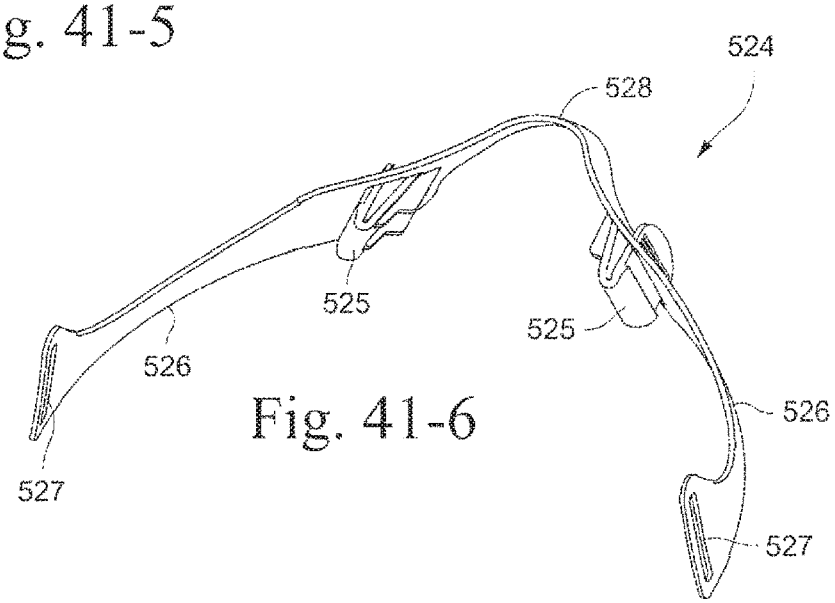
Figures 7, 41:
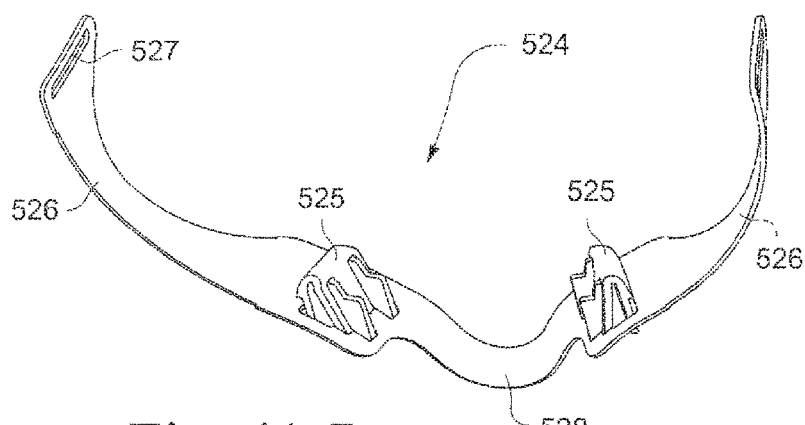
Figures 8, 41:
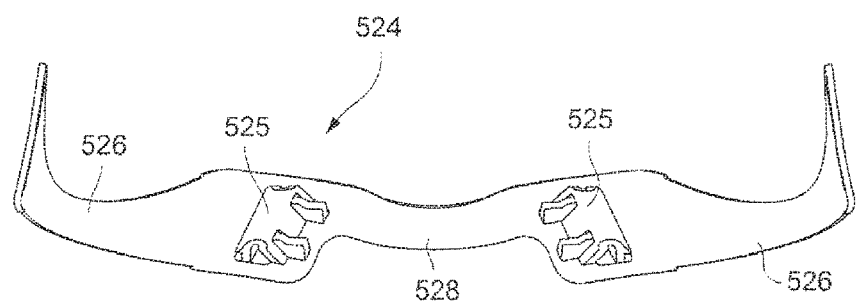
Figures 9, 41:
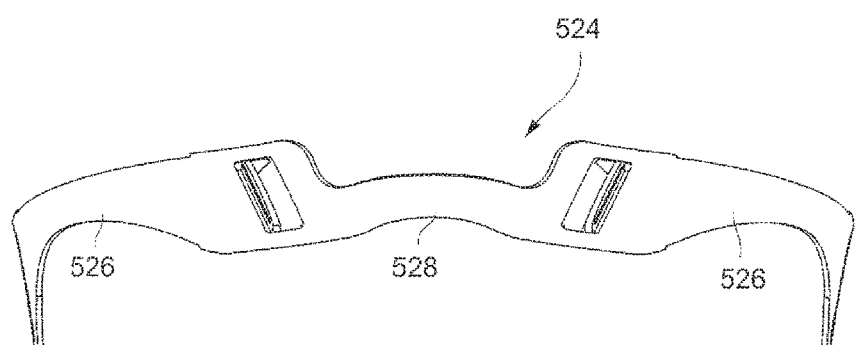
Figures 10, 41:
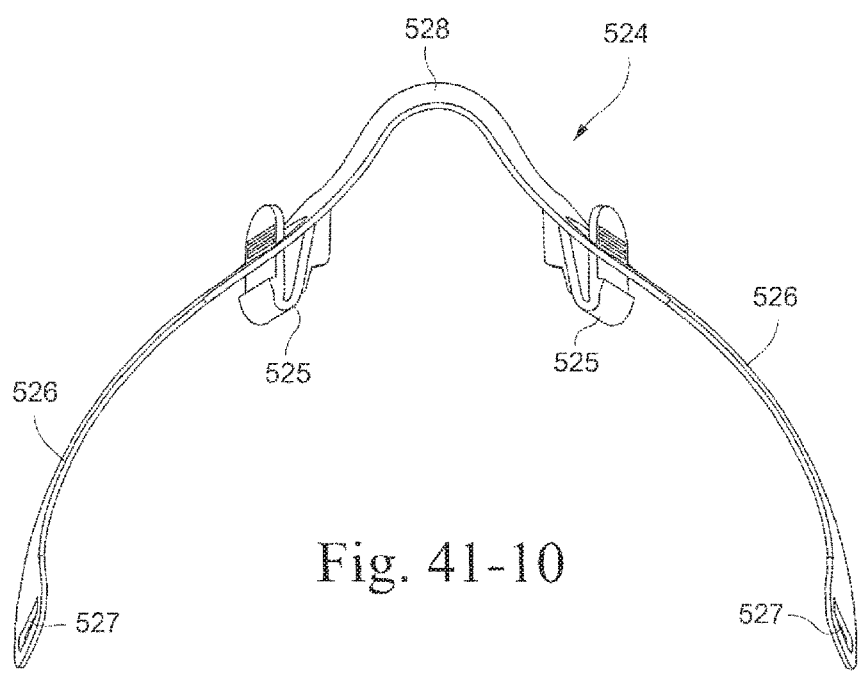
Figures 11, 41:
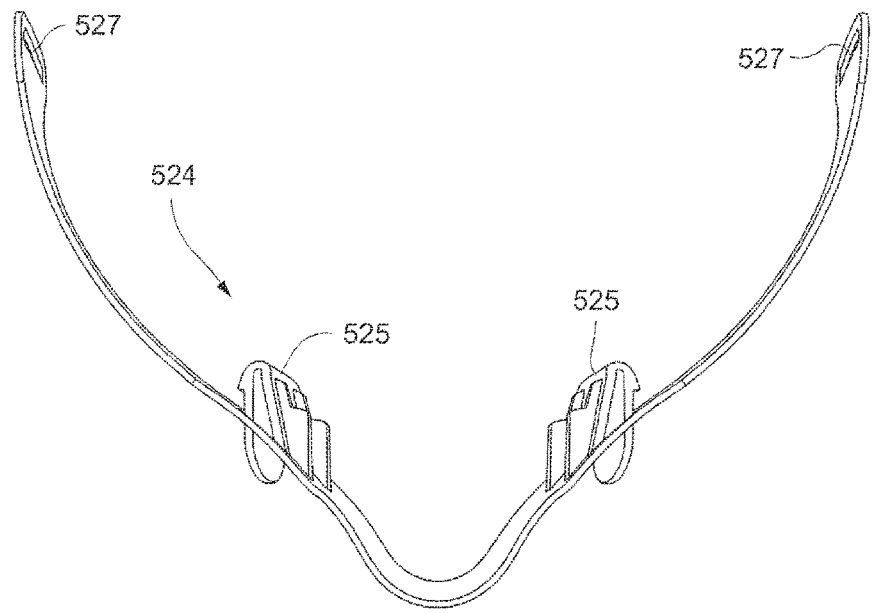
Figures 12, 41:
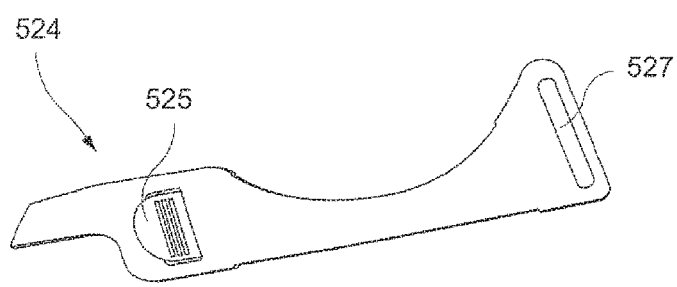

FIGS. 41-1 to 41-12 illustrate an upper portion of a frame and a clip-on upper headgear connector or rigidizer according to another embodiment of the present invention.

As illustrated, the upper portion of the frame 542 includes a retaining member 533 on each side thereof and a retaining groove 535 along an intermediate portion thereof, which are structured and arranged to retain an upper headgear connector or rigidizer 524.

As best shown in FIGS. 41-5 and 41-12, the upper headgear connector 524 includes a pair of elongated arms or rigidizers 526 coupled by a connecting portion 528. Each rigidizer 526 includes a slot 527 at its free end adapted to receive a respective headgear strap in use. In addition, the upper headgear connector 524 includes a clip structure 525 on each side of the connecting portion 528.

In use, the upper headgear connector 524 is adapted to clip onto the frame 542 (e.g., see FIGS. 41-1 and 41-2). Specifically, the connecting portion 528 is received in the groove 535 of the frame 542, and the clip structures 525 releasably interlock with respective retaining members 533. As best shown in FIGS. 41-3 and 41-4, each retaining member 533 provides a cross-bar, and each clip structure 525 provides a v-shaped configuration that is adapted to resiliently deflect through the cross-bar and provide a shoulder to releasably interlock with the cross-bar.

Figures 1, 42:
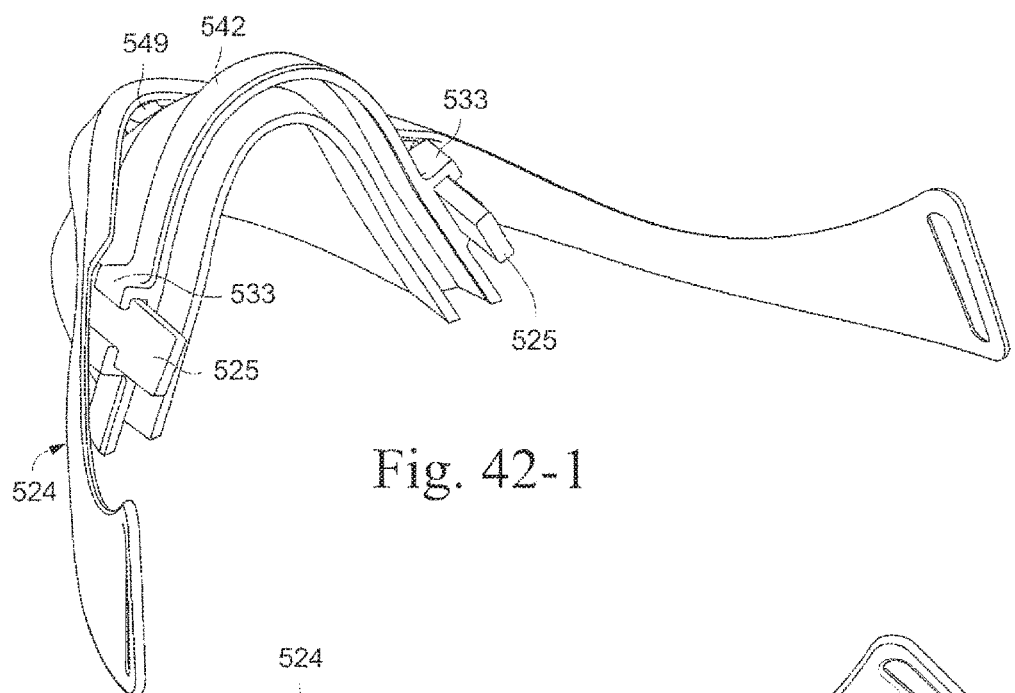
Figures 2, 42:
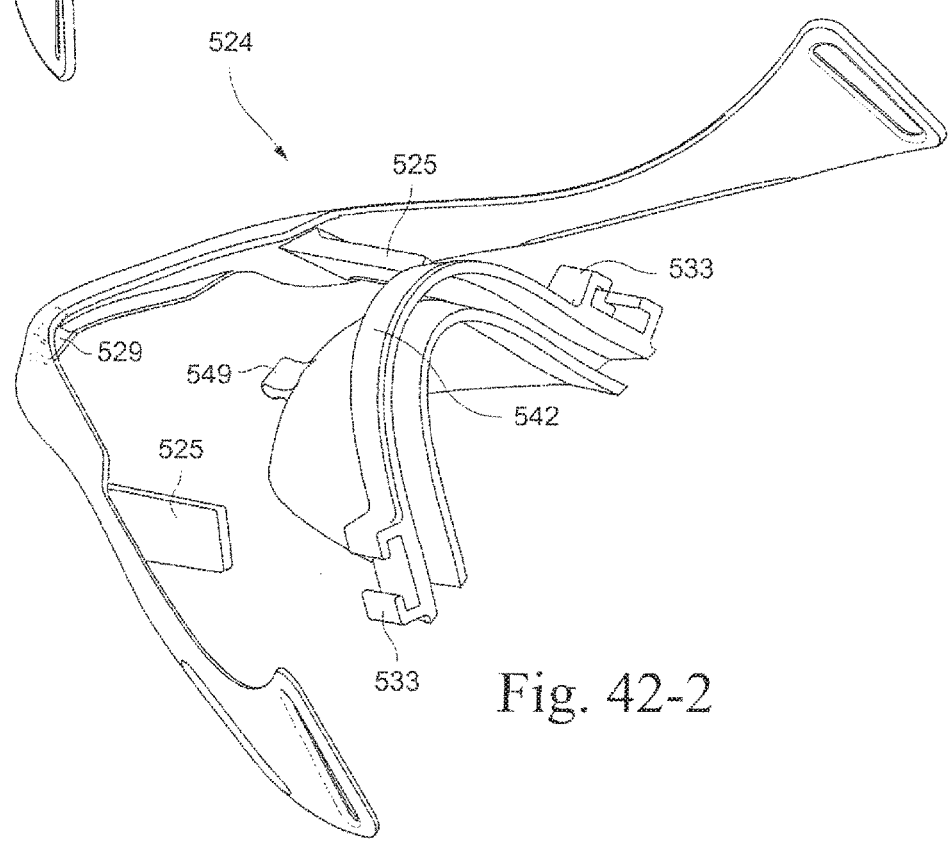
Figures 3, 42:
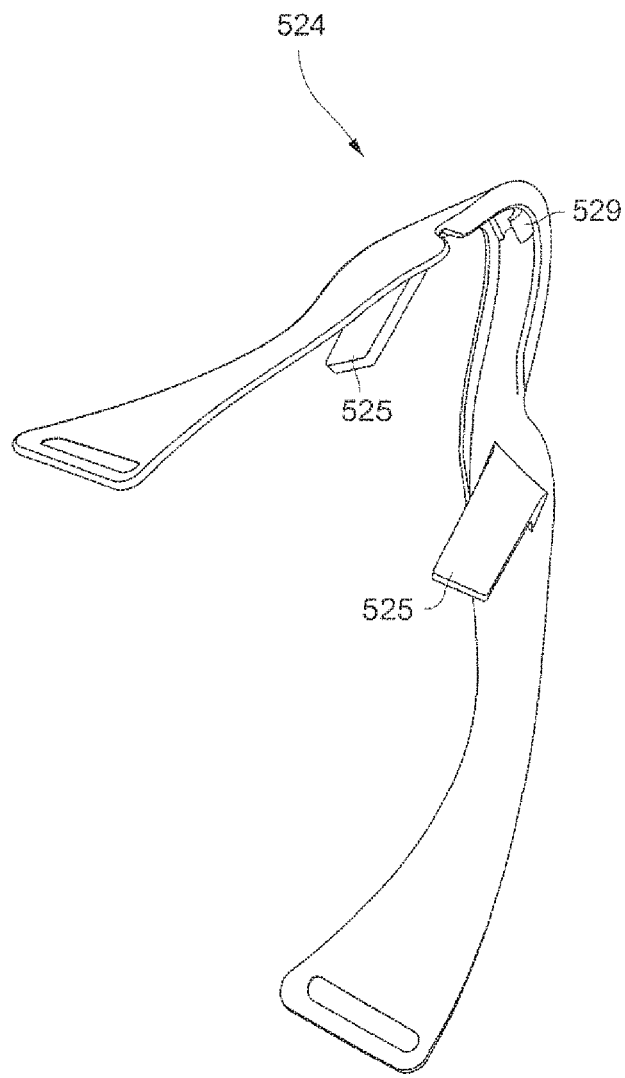
Figures 4, 42:
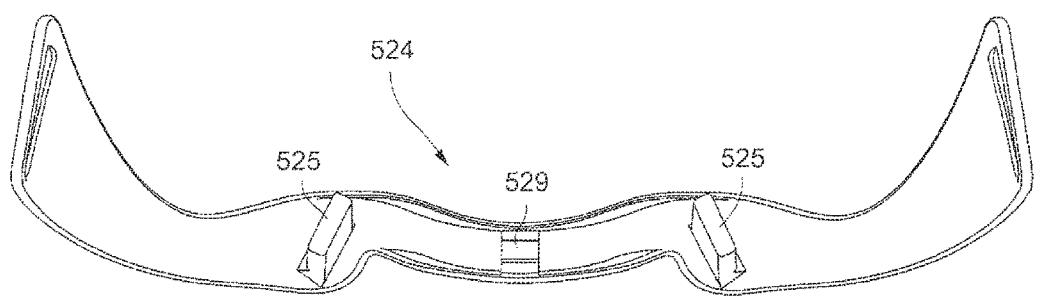
Figures 5, 42:
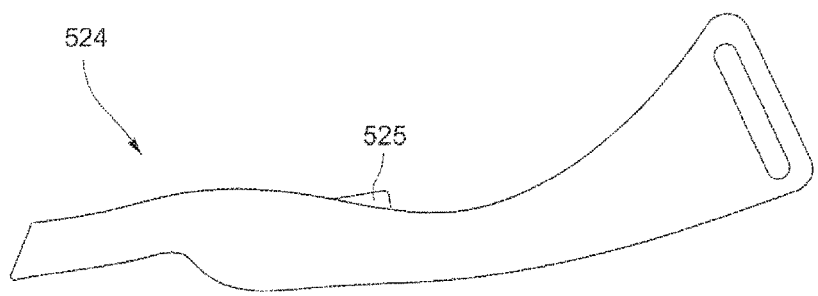
Figures 6, 42:
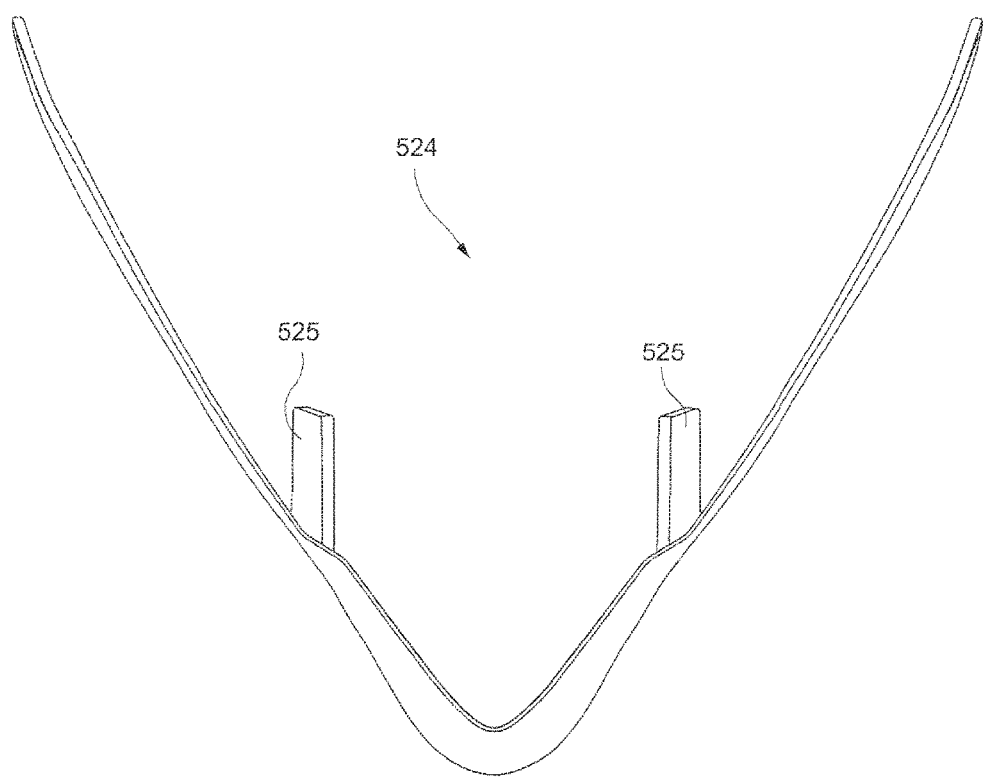
Figures 7, 42:
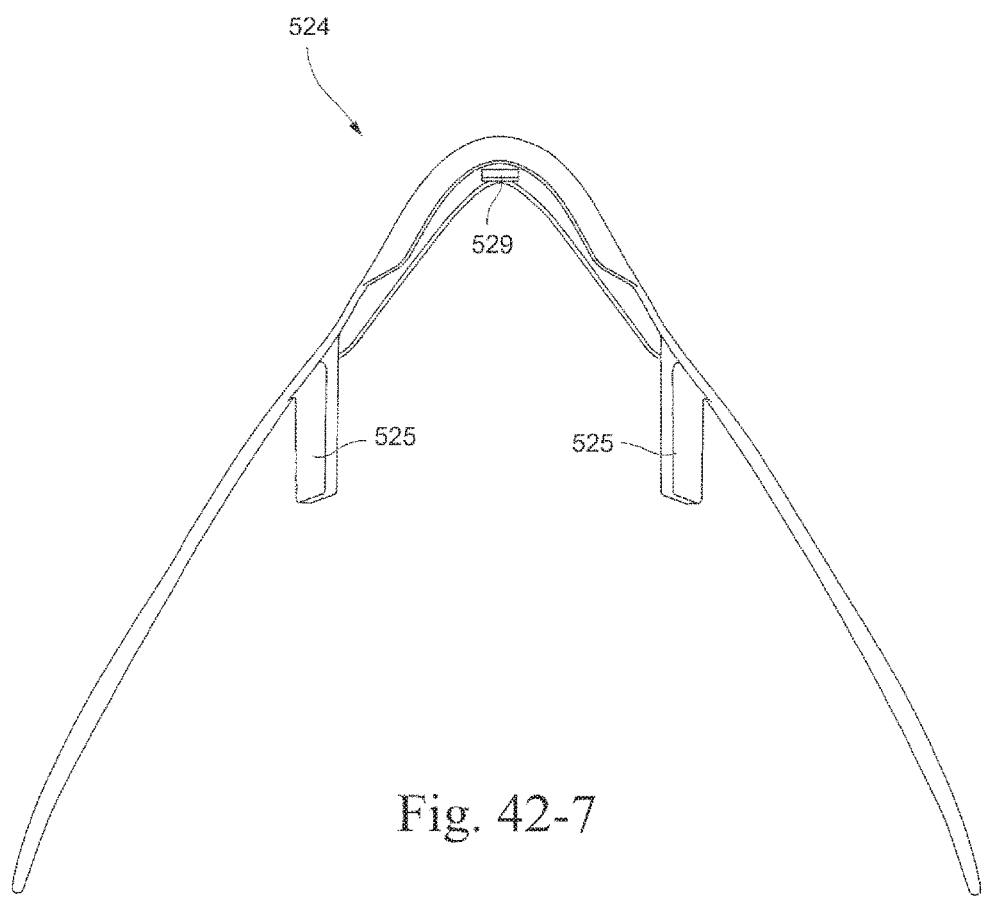

FIGS. 42-1 to 42-7 illustrate an alternative embodiment for engaging the upper headgear connector with the frame. As illustrated, each retaining member 533 provides an open-ended cross-bar, and each clip structure 525 provides an elongated arm. In this embodiment, the cross-bar is structured to resiliently deflect to allow the clip structure 525 to extend through the cross-bar and releasably engage the cross-bar, e.g., with a friction fit. In addition, the upper headgear connector 524 of FIGS. 42-1 to 42-7 includes a c-shaped clip structure 529 adapted to interlock with a tab 549 provided to the frame 542 (see FIGS. 42-1 and 42-2).

5.1.6 Grommet Attachment

Figure 44:
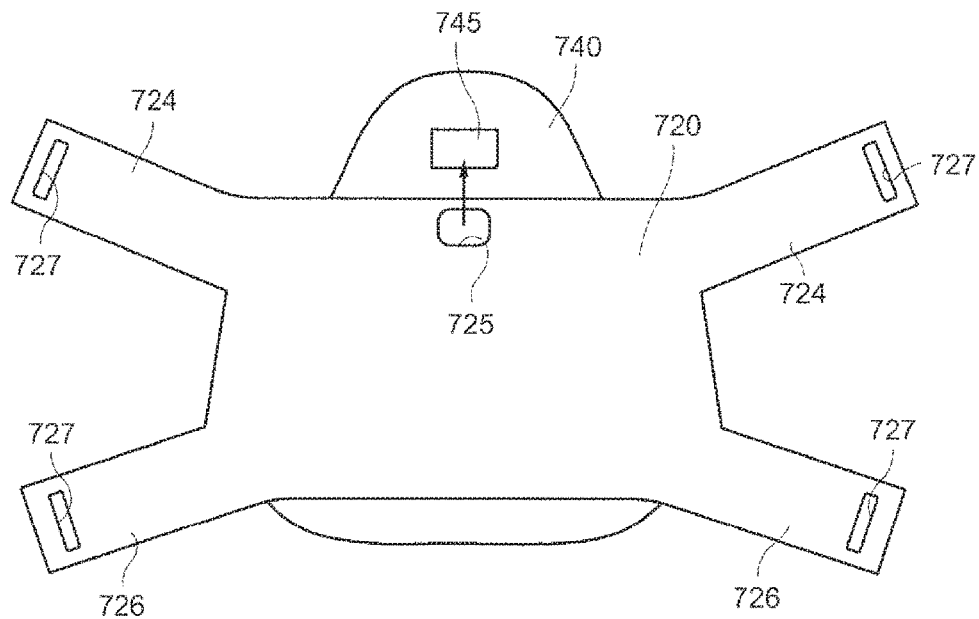
FIG. 44 illustrates a mask system according to another embodiment of the present invention.
Figure 45:
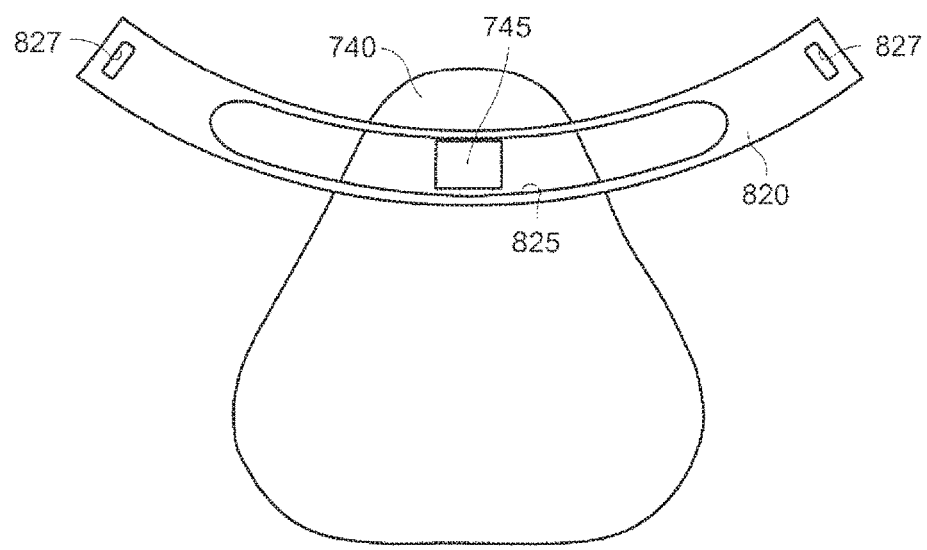
FIG. 45 illustrates a mask system according to another embodiment of the present invention.

FIGS. 44 and 45 illustrate an alternative mask arrangement in which the shroud is attached to the frame via a grommet.

For example, as shown in FIG. 44, the frame 740 includes a grommet 745 (e.g., constructed of a rubber) and the shroud 720 includes an opening 725 adapted to receive the grommet 745 to secure the shroud 720 to the frame 740. As illustrated, the shroud 720 includes elongated upper and lower arms 724, 726 each with a slot 727 at its free end adapted to receive a respective headgear strap in use.

FIG. 45 illustrates an alternative shroud 820 which includes a single arm with a slot 827 at each end adapted to receive a respective headgear strap in use. In addition, the shroud 820 provides an elongated inner slot 825 adapted to receive the grommet 745 of the frame 740. The elongated slot 825 allows the grommet 745 to be fixed in one of multiple positions along the length of the slot 825, in contrast to the shroud 720 which provides a single fixed position. In an embodiment, the shroud 820 may be slidable with respect to the grommet 745 to allow an infinite number of positions with respect to the frame 740.

In each embodiment, the grommet 745 (e.g., constructed of a rubber) fixes the shroud in position but the inherent flexibility of the grommet provides a flexible connection to decouple the shroud from the frame and allow a range of movement between the two components, e.g., like a ball joint or gimbal. Such arrangement helps with fitting and sealing of the mask to the patient's face. That is, the flexible connection allows the mask to selectively adjust and/or self-fit with the patient's face.

5.2 Cushion to Frame Connection

In FIGS. 1-8, the non-face contacting side of the cushion 1060 is connected to frame 1040 in a tongue and groove relationship. The tongue 1066 (see FIGS. 1C, 1D, and 8) of the cushion 1060 is inserted within a groove 1041 (see FIGS. 1C and 1D) provided along the perimeter of the frame 1040. The tongue and groove relationship may also include a locking lip or sealing lip 1068 (see FIGS. 1C, 1D, and 8) on the cushion that is adapted to interlock with an undercut bead 1042 (see FIGS. 1C and 1D) within the frame groove to fixably retain the cushion to the frame.

In the illustrated embodiment, the cushion 1060 also includes one or more positioning features located around its circumference to assist with proper alignment of the cushion with the frame 1040. As shown in FIG. 7, the cushion 1060 includes notches and/or protrusions (e.g., two notches 1067 and one protrusion 1069) adapted to engage with complementary features in the frame, e.g., interlocking relationship.

5.2.1 Co-Molding Frame and Cushion

In an embodiment, as shown in FIGS. 27-30, the frame 40 and cushion 44 may be co-molded with one another to form a one-piece, integrated component. For example, the frame 40 may be molded of a first material adapted to interface with the shroud 20 and the cushion 44 may be co-molded onto the frame 40 of a second material adapted to interface with patient's face.

In such embodiment, the cushion 44 may be constructed of a relatively soft elastomeric material (e.g., silicone) for sealing and the frame 40 may be constructed of a more rigid material than the cushion 44 (e.g., polycarbonate, polypropylene) for interfacing with the frame.

Co-molding the frame 40 to the cushion 44 provides a chemical bond without necessarily forming a mechanical interlock. As a result, the connection includes no cracks, a gas tight seal, and clean interface. Moreover, such co-molded connection relaxes tolerances as the mold materials are sufficiently flexible to fill in any gaps at the interface between the frame 40 and the cushion 44. Also, the co-molded frame/cushion provides a reduced part count (reduced cost) and facilitates assembly/disassembly to the shroud 20.

In an alternative embodiment, as shown in FIG. 33, the frame 40 and cushion 44 may be integrally formed in one piece, e.g., of a silicone material. That is, the frame 40 may have the same shape and structure as described above, but be integrally molded of the same material, e.g., silicone.

In an embodiment, the integrally formed frame 40/cushion 44 may be co-molded to the shroud 20, e.g., constructed of polycarbonate or polypropylene. For example, the shroud 20 may be constructed of a relatively rigid material (e.g., polycarbonate or polypropylene) and the frame 40/cushion 44 may be co-molded onto the shroud 20 of a relatively soft elastomeric material (e.g., silicone).

5.3 Vent Arrangement

Figure 1C:
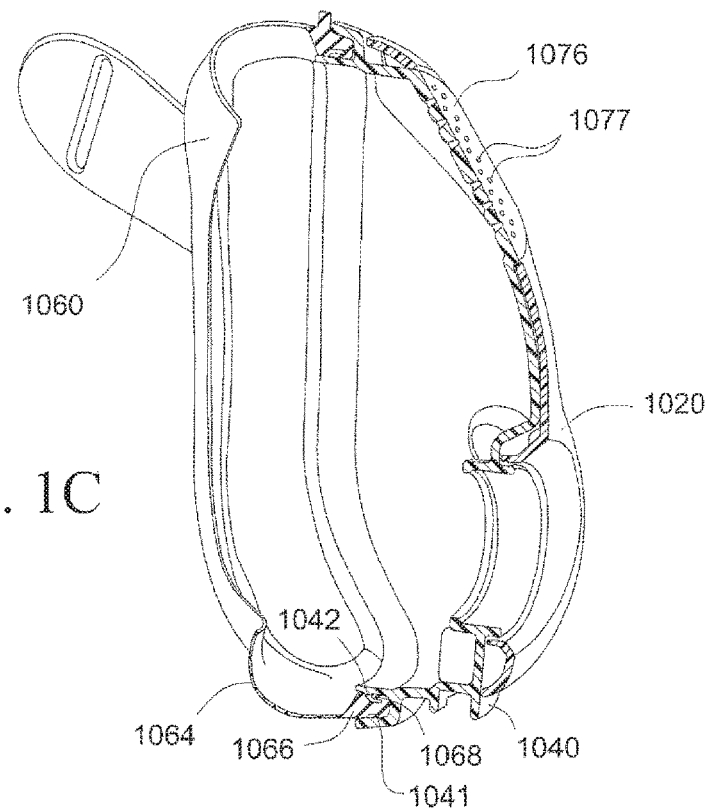
FIG. 1C is a cross-sectional view through the mask system of FIG. 1.
Figure 1D:
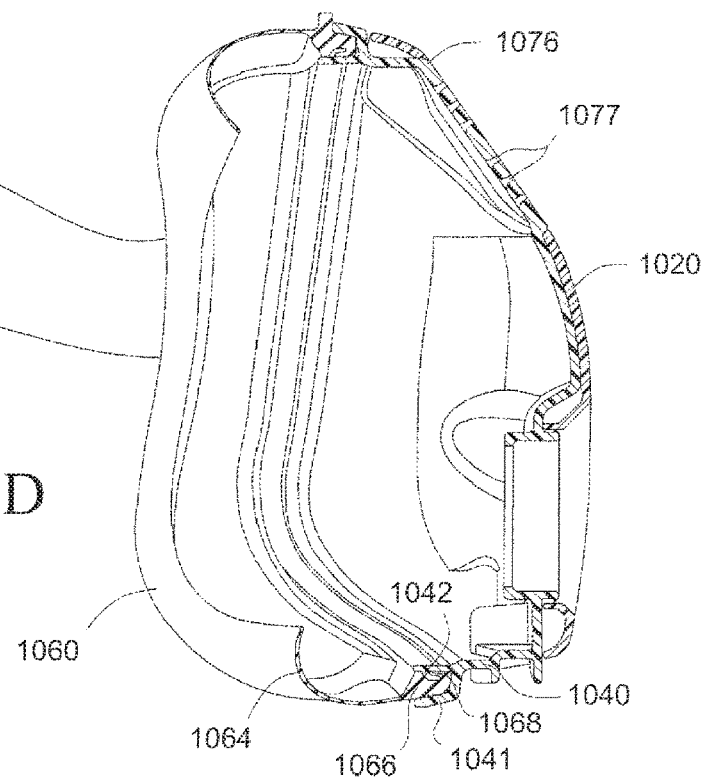
FIG. 1D is another cross-sectional view through the mask system of FIG. 1.
Figure 1E:
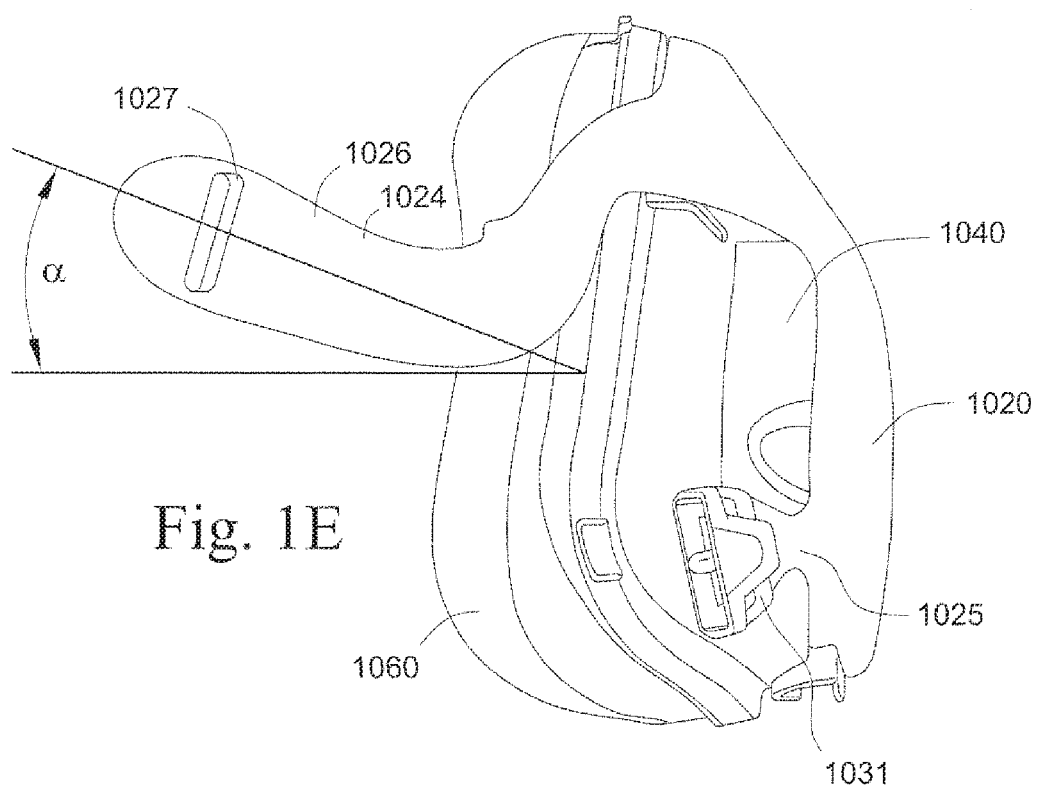
FIG. 1E is a side view of the mask system of FIG. 1.

In FIGS. 1, 1B, IC, 1D, and 2-5, the vent arrangement 1076 is provided to the frame and includes a plurality of holes 1077 (e.g., 5-100 holes, e.g., 20-50 holes, or about 35 holes) oriented at an angle (e.g., 45°) on the outer surface of the frame so as ensure the exhausted air is directed away from the patient and preferably their bed partner when the patient is sleeping. As shown in FIGS. 1C and 1D, each hole 1077 may include a contour or taper along its length. However, it should be appreciated that the vent arrangement may include other suitable arrangements, e.g., different number of holes, hole arrangement, positioning on frame, vent provides part pf interlocking structure with shroud, etc.

FIG. 35-1 illustrates a vent arrangement 276 provided to the frame 240 for gas washout. In the illustrated embodiment, the vent arrangement 276 is in the form of a vent insert (e.g., elastomeric vent insert) that is adapted to be removably supported within an outlet opening in the frame 240. The vent insert may be similar those described in U.S. Pat. Nos. 6,561,190, 6,561,191, and 7,207,335, each of which is incorporated herein by reference in its entirety. However, it should be appreciated that the vent arrangement may have other suitable forms (e.g., vent holes in main body, etc.).

FIGS. 37-3, 39-2, and 39-4 illustrate a frame 340 that includes a u-shaped slot 302 that receives a u-shaped plug-type vent 305 for gas washout. As illustrated, the plug-type vent 305 wraps around and under the opening in the frame 340 for the elbow 370. The plug-type vent 305 includes a plurality of tracks or grooves 307 on each side thereof. In use, the grooved plug-type vent 305 forms a seal with the slot 302 so that exhausted air can exit between the slot walls and the grooves 307 on the plug-type vent 305. In an embodiment, the port caps 347 may be integrated or incorporated into the plug-type vent 305 (e.g., integrally formed in one piece). Further details of such a plug-type vent arrangement are provided in U.S. patent application Ser. No. 12/230,120, filed Aug. 22, 2008, which is incorporated herein by reference in its entirety. FIGS. 39-2 to 39-6 show the frame 340 with the grooved plug-type vent 305 removed so as to more clearly illustrate the u-shaped slot 302 and auxiliary ports 343 on each side thereof.

Also, it should be appreciated that the vent arrangement may be provided to the elbow. For example, a shown in FIGS. 27-30, the vent arrangement 76 is in the form of a vent insert that is adapted to be removably supported within an outlet opening in the elbow 70. In an embodiment, the vent arrangement 76 includes a base adapted to be supported within the outlet opening, one or more grill components or media (e.g., filter, membrane, or other porous material) provided to the base and structured to diffuse vent flow, and a cover to maintain the grill components/media within the base. Only the cover 77 of the vent arrangement 76 is visible in FIGS. 27-30.

Exemplary embodiments of such a vent arrangement are disclosed in U.S. patent application Ser. No. 12/230,120, filed Aug. 22, 2008, which is incorporated herein by reference in its entirety.

However, it should be appreciated that the vent arrangement may include other suitable arrangements, e.g., vent insert with one or more vent holes.

Also, the elbow may provide an alternative venting arrangement to the vent insert. For example, as indicated in dashed lines in FIG. 30, the first end portion 74(1) of the elbow 70 (e.g., along the interfacing structure 75) may include one or more vent holes 276 for gas washout. The one or more holes 276 may be provided to a soft part (e.g., silicone seal as described below) and/or a hard part (e.g., polycarbonate, polypropylene) of the elbow. The holes 276 may extend around the entire perimeter of the first end portion 74(1) or may extend along one or more portions of the first end portion 74(1). It is noted that providing vent holes along the entire perimeter of the elbow may help to disperse the vent flow in use. However, other suitable hole arrangements, hole numbers, and/or hole shapes along the first end portion 74(1) and/or other portions of the elbow are possible.

5.4 Ports

In FIGS. 1-5, the base of the frame 1040 includes two ports 1043 positioned so that in use, oxygen or other breathable gas can be delivered close to the patient's nares or pressure monitoring equipment can be attached. The ports 1043 may also be used to attach additional medical equipment such as pressure or flow sensors. The ports may be selectively closable or sealable by a ports cap.

Figure 25:
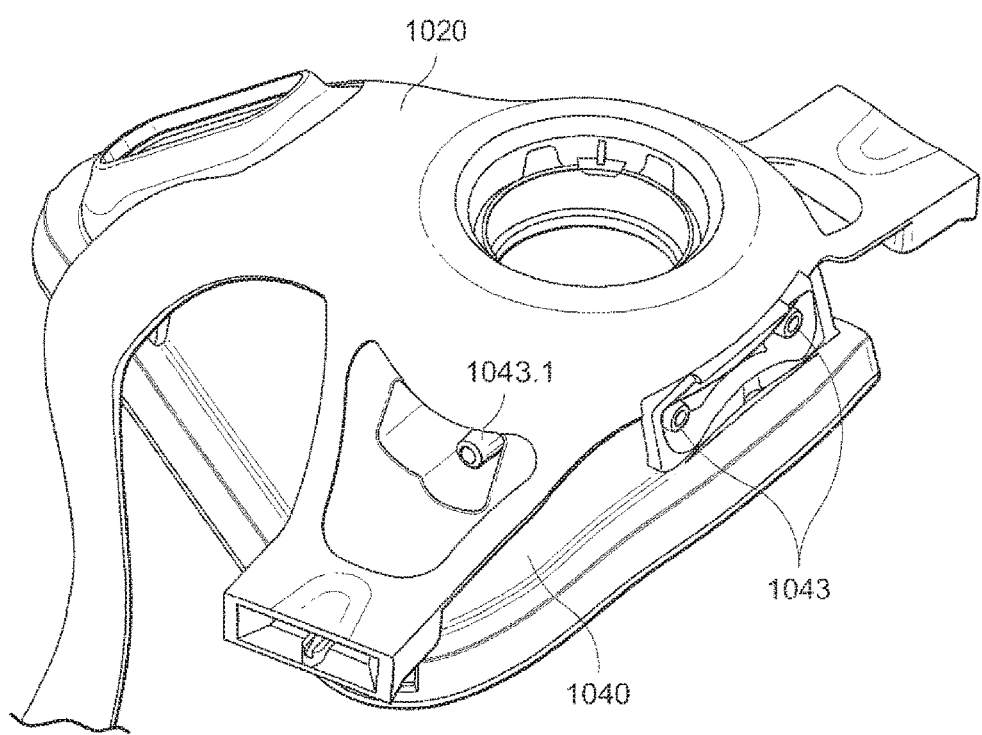
FIG. 25 is a front perspective view of a mask system according to another embodiment of the present invention.
Figure 26:
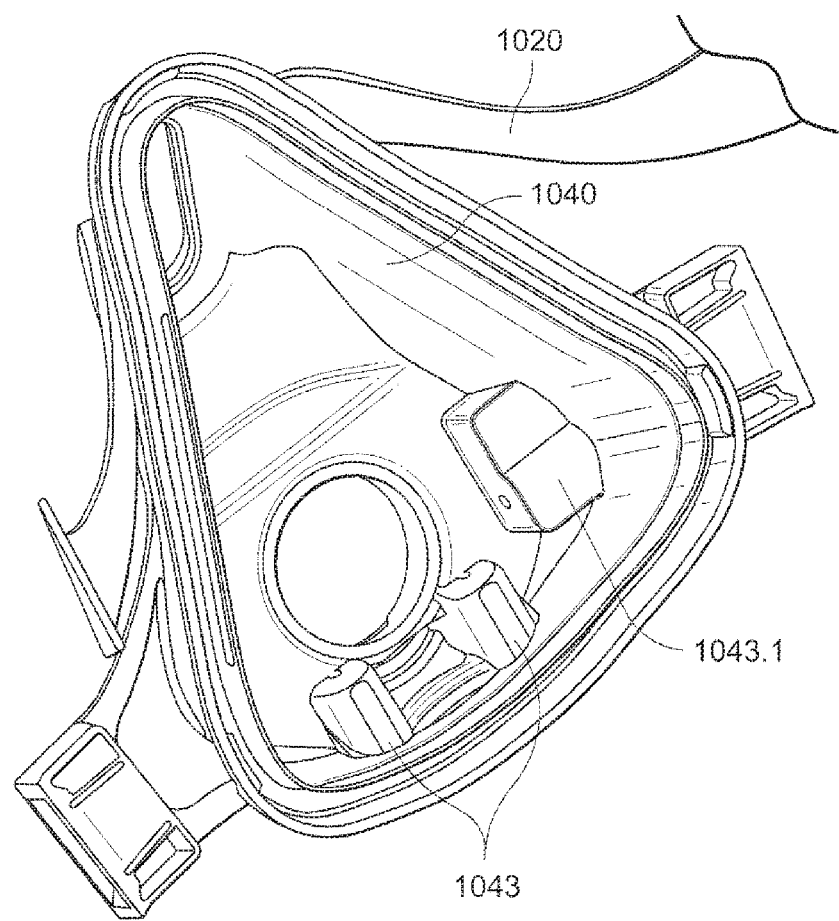
FIG. 26 is a rear perspective view of the mask system of FIG. 25.
Figure 27:
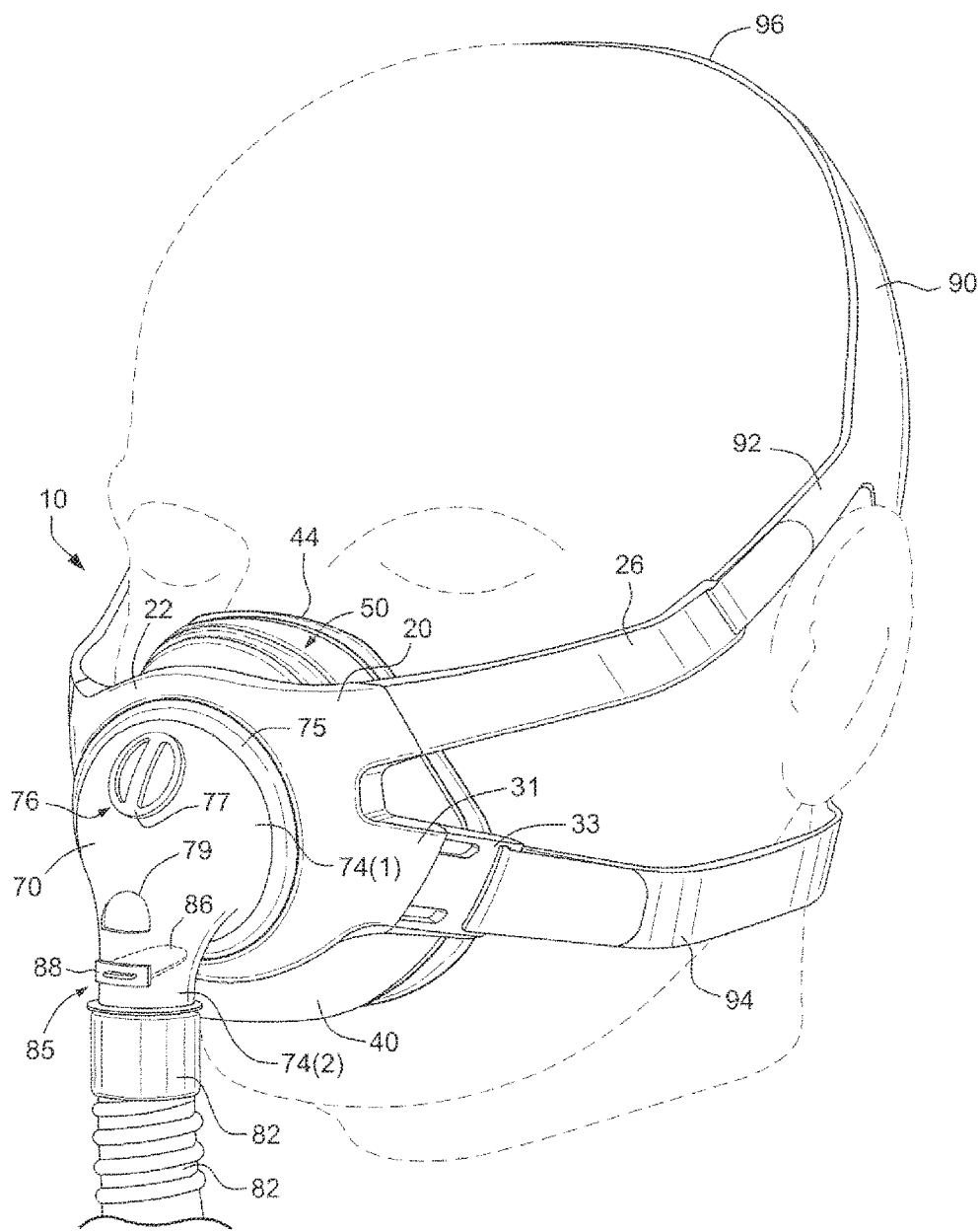
FIG. 27 is a front perspective view of a mask system according to another embodiment of the present invention.

In an alternative embodiment, as shown in FIGS. 25 and 26, the frame 1040 may include a side port 1043.1, e.g., in addition to or as an alternative to the ports 1043.

FIGS. 35-1 and 35-2 show a frame 240 that includes an auxiliary port or spigot 243 on an upper portion of the frame, e.g., for supplemental oxygen, measurement device, etc.

In FIGS. 37-1 to 37-3 and 39-1 to 39-6, the frame 340 includes an auxiliary port or spigot 343 on each side thereof, e.g., for supplemental oxygen, measurement device, etc. Port caps 347 are provided to seal respective ports 343.

6. Interface Seal

In an embodiment, a seal may be provided at the interface between the elbow and the shroud, at the interface between the frame and the shroud, and/or at the interface between the elbow and the frame. For example, a seal (e.g., elastomeric, ring-shaped seal) may be formed separately from the modules and attached at the interface (e.g., sandwiched between modules, adhesive, etc.). Alternatively, a seal may be co-molded with one or more of the modules. In an embodiment, a silicone lip seal may be provided to the frame to seal against the elbow, thereby reducing leak.

In another embodiment, as shown in FIG. 27-30, the interfacing structure 75 of the elbow 70 may be constructed of a relatively soft, sealing material (e.g., silicone, which may be co-molded to the harder material of the elbow) that is structured to provide a seal at the interface between the elbow 70 and the shroud 20. Also, the relatively soft interfacing structure 75 (e.g., silicone) provides a "soft" attachment to the relatively hard shroud 20 (e.g., polycarbonate, polypropylene) which may allow an interference type fit. As noted above, one or more vent holes may be provided to the softer interfacing structure and/or the harder elbow.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system to provide positive air pressure therapy to a patient, the mask system comprising:
    a cushion module forming a breathing chamber, the cushion module comprising:
        a frame having an interior surface exposed to the breathing chamber, the frame including a frame opening positioned to receive a supply of air at positive pressure, wherein the frame includes a collar surrounding the frame opening and extending away from an exterior surface of the frame, the collar having a longitudinal axis, and the collar having a cylindrical surface with an axis that is coincident with the longitudinal axis of the collar, wherein the collar includes a first radial protrusion and a second radial protrusion extending from the cylindrical surface, each of the first radial protrusion and the second radial protrusion having a part-annular shape and having a curvature centered about the longitudinal axis of the collar, wherein the frame, including the collar and each of the first radial protrusion and the second radial protrusion, is constructed from a first material, and
        a cushion constructed of an elastomeric material that is a different material from the first material, the first material of the frame being harder than the elastomeric material of the cushion, the frame being more rigid than the cushion, the cushion configured to seal against the patient's face in use to enable the supply of air at positive pressure to be delivered to at least the patient's nose,
        wherein the cushion and the frame are joined to form an integrated component;
    an elbow configured to receive the supply of air at positive pressure and deliver the supply of air at positive pressure to the breathing chamber;
    a shroud configured to removably connect to the frame of the cushion module, wherein the shroud includes an elbow opening that accommodates the elbow, wherein the shroud includes a rear surface at least partly covering the exterior surface of the frame, the shroud having a first part-annular snap connection portion and a second part-annular snap connection portion circumferentially spaced from one another and centered about a longitudinal axis of the elbow opening, the first part-annular snap connection portion and the second part-annular snap connection portion being positioned rearward of the elbow opening of the shroud, wherein the shroud, including the first part-annular snap connection portion and the second part-annular snap connection portion, is constructed from a second material, the second material of the shroud being harder than the elastomeric material of the cushion, and the shroud being more rigid than the cushion;

headgear configured to connect to the shroud to maintain the cushion module in position on the patient's head in use; and a vent arrangement having a plurality of holes for gas washout from the breathing chamber to atmosphere, wherein the shroud includes headgear connectors structured to connect to said headgear, wherein, to releasably connect the shroud to the cushion module, each of the first radial protrusion and the second radial protrusion and a corresponding one of the first part-annular snap connection portion and the second part-annular snap connection portion are structured to form a removable snap-fit connection by moving the cushion module and the shroud towards one another along the longitudinal axis of the collar, and wherein when the first radial protrusion and the second radial protrusion and the first part-annular snap connection portion and the second part-annular snap connection portion are joined to form the removable snap-fit connection, the cushion module and the shroud are stabilized against rotation relative to one another.

2. The mask system of claim 1, wherein the collar and the snap-fit connection are arranged to remain stationary relative to one another as the elbow is rotated relative to the shroud.

3. A system for treating a patient with sleep disordered breathing, comprising:
the mask system of claim 1;
a flow generator to generate a supply of air at positive pressure to be delivered to the mask system; and
an air delivery tube configured to deliver the supply of air from the flow generator to the mask system.

4. The mask system of claim 1, wherein:
the elbow opening of the shroud is circular,
the collar of the frame is cylindrical,
the cylindrical surface is on an exterior of the collar,
the first radial protrusion and the second radial protrusion are spaced circumferentially about the cylindrical surface,
the first radial protrusion and the second radial protrusion and the first part-annular snap connection portion and the second part-annular snap connection portion are configured to form the removable snap-fit connection between a front end of the cylindrical surface and a rear end of the cylindrical surface,
the cushion is constructed to engage the patient's face along a nasal bridge region, a cheek region, and an upper lip region of the patient's face when in use,
the elastomeric material of the cushion is silicone,
the shroud does not include a forehead support,
the first material is polycarbonate,
the second material is polycarbonate,
the cushion and the frame are joined by a chemical bond,
the elbow is directly attached to the shroud at the elbow opening,
the elbow is rotatable 360° relative to the shroud,
the first part-annular snap connection portion and the second part-annular snap connection portion are arranged to remain stationary relative to the first radial protrusion and the second radial protrusion as the elbow is rotated,
the headgear connectors comprise a pair of upper headgear connectors and a pair of lower headgear connectors,
the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use,
each of the pair of upper headgear connectors comprises an elongated arm to direct a corresponding one of the pair of upper straps away from the patient's corresponding eye, each elongated arm being shaped to follow contours of the patient's face and avoid the patient's line of sight in use,
each elongated arm has an inner surface including a cheek pad,
each elongated arm is constructed of a flexible material, each elongated arm is configured to be positioned inferior to the patient's corresponding eye in use and is configured to direct a corresponding one of the pair of upper straps superior to the patient's corresponding ear in use,
each of the pair of lower headgear connectors is configured to direct a corresponding one of the pair of lower straps inferior to the patient's corresponding ear in use, and
the mask system further includes a seal at an interface between the elbow and the frame.

5. A system for treating a patient with sleep disordered breathing, comprising:
the mask system of claim 4;
a flow generator to generate a supply of air at positive pressure to be delivered to the mask system; and
an air delivery tube configured to deliver the supply of air from the flow generator to the mask system.

6. The mask system of claim 1, wherein:
the frame opening of the frame is circular,
the elbow opening of the shroud is circular,
the collar of the frame is cylindrical,
the cushion is constructed to engage the patient's face along a nasal bridge region, a cheek region, and a lower lip/chin region of the patient's face when in use,
the elastomeric material of the cushion is silicone,
the cushion and the frame are constructed and arranged to be in an interlocking relationship with one another,
the first material is polycarbonate,
the second material is polycarbonate,
said headgear comprises hook and loop material,
the shroud further comprises a forehead support,
the elbow is directly attached to the shroud at the elbow opening,
the elbow includes an anti-asphyxia valve,
the elbow is rotatable 360° relative to the shroud,
the collar and the snap-fit connection are arranged to remain stationary relative to one another as the elbow is rotated relative to the shroud,
the vent arrangement comprises a protruding vent arrangement that protrudes from the frame, the protruding vent arrangement including a vent-wall having the plurality of holes, the vent-wall being spaced from the frame by a lower wall and two lateral side walls of the protruding vent arrangement, and the protruding vent arrangement positioned above the frame opening, the first radial protrusion and the second radial protrusion are spaced circumferentially about the frame opening, the first radial protrusion and the second radial protrusion positioned between and spaced away from both a front end and a rear end of the cylindrical surface, the first part-annular snap connection portion is a first part-annular snap finger and the second part-annular snap connection portion is a second part-annular snap finger, the first part-annular snap finger and the second part-annular snap finger extend from the elbow opening of the shroud and rearward from the rear surface of the shroud, the headgear connectors comprise a pair of upper headgear connectors and a pair of lower headgear connectors, the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use, each of the pair of upper headgear connectors is configured to direct a corresponding one of the pair of upper straps superior to the patient's corresponding ear in use, each of the pair of lower headgear connectors is configured to direct a corresponding one of the pair of lower straps inferior to the patient's corresponding ear in use, said pair of lower headgear connectors structured to connect to said headgear via clips, the part-annular shape of each of the first part-annular snap finger and the second part-annular snap finger has a curvature that is centered on the longitudinal axis of the collar, a region of the cushion positioned to engage the nasal bridge region of the patient is configured to allow increased movement compared to another region of the cushion that is adapted to seal with another region of the patient's face, and the mask system being constructed so that the snap-fit connection is established when a force is applied to move the shroud and cushion module toward one another along the longitudinal axis until a rear end of each of the first part-annular snap finger and the second part-annular snap finger initially contacts a front end of a corresponding one of the first radial protrusion and the second radial protrusion on the collar, whereupon further application of the force causes each of the first part-annular snap finger and the second part-annular snap finger to ride over a corresponding one of the first radial protrusion and the second radial protrusion and therefore resiliently deflect in a first radial direction relative to the longitudinal axis of the collar, and upon further movement towards one another, each of the first part-annular snap finger and the second part-annular snap finger resiliently moves in a second radial direction, opposite the first radial direction, and engages a rear end of a corresponding one of the first radial protrusion and the second radial protrusion to snap each of the first part-annular snap finger and the second part-annular snap finger into place, thereby removably connecting the shroud and the cushion module.

7. A system for treating a patient with sleep disordered breathing, comprising:
the mask system of claim 6;
a flow generator to generate a supply of air at positive pressure to be delivered to the mask system; and
an air delivery tube configured to deliver the supply of air from the flow generator to the mask system.

8. The mask system of claim 1, wherein:
the frame opening of the frame is circular,
the elbow opening of the shroud is circular,
the first radial protrusion and the second radial protrusion are spaced circumferentially about the cylindrical surface,
the cushion is constructed to engage the patient's face along a nasal bridge region, a cheek region, and an upper lip region of the patient's face when in use,
the cushion and the frame are constructed and arranged to be in an interlocking relationship with one another,
the elastomeric material of the cushion is silicone,
said headgear comprises hook and loop material,
the shroud includes a forehead support,
the first material is polycarbonate,
the second material is polycarbonate,
the elbow is directly attached to the shroud at the elbow opening,
the elbow is rotatable 360° relative to the shroud,
the collar and the snap-fit connection are arranged to remain stationary relative to one another as the elbow is rotated,
the headgear connectors comprise a pair of upper headgear connectors and a pair of lower headgear connectors,
the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use,
each of the pair of upper headgear connectors is configured to direct a corresponding one of the pair of upper straps superior to the patient's corresponding ear in use,
each of the pair of lower headgear connectors is configured to direct a corresponding one of the pair of lower straps inferior to the patient's corresponding ear in use,
said pair of lower headgear connectors are structured to connect to said headgear via clips,
the part-annular shape of each of the first part-annular snap connection portion and the second part-annular snap connection portion has a curvature that is centered on the longitudinal axis of the collar,
a region of the cushion positioned to engage the nasal bridge region of the patient is configured to allow increased movement compared to another region of the cushion that is adapted to seal with another region of the patient's face, and
the mask system being constructed so that the snap-fit connection is established when a force is applied to move the shroud and cushion module toward one another along the longitudinal axis until a rear end of each of the first part-annular snap connection portion and the second part-annular snap connection portion initially contacts a front end of a corresponding one of the first radial protrusion and the second radial protrusion on the collar, whereupon further application of the force causes each of the first part-annular snap connection portion and the second part-annular snap connection portion to ride over a corresponding one of the first radial protrusion and the second radial protrusion and therefore resiliently deflect in a first radial direction relative to the longitudinal axis of the collar, and upon further movement towards one another, each of the first part-annular snap connection portion and the second part-annular snap connection portion resiliently moves in a second radial direction, opposite the first radial direction, and engages a rear end of a corresponding one of the first radial protrusion and the second radial protrusion to snap each of the first part-annular snap connection portion and the second part-annular snap connection portion into place, thereby removably connecting the shroud and the cushion module.

9. The mask system of claim 8, further comprising at least one tab and recess arrangement positioned circumferentially between mating ones of the first part-annular snap connection portion and the second part-annular snap connection portion and the first radial protrusion and the second radial protrusion, the tab and recess arrangement resisting rotation of the collar relative to the shroud upon establishing the snap-fit connection between the shroud and the cushion module.

10. A system for treating a patient with sleep disordered breathing, comprising:
the mask system of claim 8;
a flow generator to generate a supply of air at positive pressure to be delivered to the mask system; and
an air delivery tube configured to deliver the supply of air from the flow generator to the mask system.

11. The mask system of claim 1, wherein:
the frame opening of the frame is circular,
the elbow opening of the shroud is circular,
the first radial protrusion and the second radial protrusion are spaced circumferentially about the cylindrical surface,
the cushion and the frame are constructed and arranged to be in an interlocking relationship with one another,
the elastomeric material of the cushion is silicone,
said headgear comprises hook and loop material,
the shroud does not include a forehead support,
the first material is polycarbonate,
the second material is polycarbonate,
the elbow is directly attached to the shroud at the elbow opening,
the elbow is rotatable 360° relative to the shroud,
the collar and the snap-fit connection are arranged to remain stationary relative to one another as the elbow is rotated,
the headgear comprises a pair of straps, each of the pair of straps configured to be positioned on a corresponding lateral side of the patient's head in use,
each of the headgear connectors is configured to direct a corresponding one of the pair of straps superior to the patient's corresponding ear in use,
said headgear connectors are structured to connect to said headgear via clips,
the part-annular shape of each of the first part-annular snap connection portion and the second part-annular snap connection portion has a curvature that is centered on the longitudinal axis of the collar, and
the mask system being constructed so that the snap-fit connection is established when a force is applied to move the shroud and cushion module toward one another along the longitudinal axis until a rear end of each of the first part-annular snap connection portion and the second part-annular snap connection portion initially contacts a front end of a corresponding one of the first radial protrusion and the second radial protrusion on the collar, whereupon further application of the force causes each of the first part-annular snap connection portion and the second part-annular snap connection portion to ride over a corresponding one of the first radial protrusion and the second radial protrusion and therefore resiliently deflect in a first radial direction relative to the longitudinal axis of the collar, and upon further movement towards one another, each of the first part-annular snap connection portion and the second part-annular snap connection portion resiliently moves in a second radial direction, opposite the first radial direction, and engages a rear end of a corresponding one of the first radial protrusion and the second radial protrusion to snap each of the first part-annular snap connection portion and the second part-annular snap connection portion into place, thereby removably connecting the shroud and the cushion module.

12. The mask system of claim 11, further comprising at least one tab and recess arrangement positioned circumferentially between mating ones of the first part-annular snap connection portion and the second part-annular snap connection portion and the first radial protrusion and the second radial protrusion, the tab and recess arrangement resisting rotation of the collar relative to the shroud upon establishing the snap-fit connection between the shroud and the cushion module.

13. A system for treating a patient with sleep disordered breathing, comprising:
the mask system of claim 11;
a flow generator to generate a supply of air at positive pressure to be delivered to the mask system; and
an air delivery tube configured to deliver the supply of air from the flow generator to the mask system.

14. A mask system to provide positive air pressure therapy to a patient, the mask system comprising:
a cushion module comprising:
a frame constructed of a first material, the frame having an interior surface at least partly forming a breathing chamber, the frame including a protruding vent arrangement for gas washout from the breathing chamber to atmosphere, the protruding vent arrangement having a plurality of vent holes, the frame including a circular frame opening configured to, in use, receive a supply of air at positive pressure, and
a cushion constructed of an elastomeric material that is a different material from the first material of the frame, the first material of the frame being harder than the elastomeric material of the cushion, the frame being more rigid than the cushion, the cushion configured to seal against the patient's face in use to enable the supply of air at positive pressure to be delivered to the patient's airways, and wherein the cushion is connected to the frame;
a shroud structured to removably retain the frame of the cushion module, the shroud having a rear wall that at least partly covers an exterior surface of the frame, the shroud constructed of a second material, the second material of the shroud being harder than the elastomeric material of the cushion, the shroud being more rigid than the cushion, wherein the shroud includes a vent-receiving opening that receives said protruding vent arrangement; and
headgear configured to maintain the mask system in position on the patient's head in use, the headgear connected to the shroud, wherein the frame includes a cylindrical collar extending from the exterior surface of the frame in a direction away from the breathing chamber, the collar having a longitudinal axis, and wherein the shroud includes a plurality of part-annular snap fingers positioned rearward from the rear wall towards the breathing chamber, and the collar further comprises protrusions to engage corresponding ones of the plurality of part-annular snap fingers with a removable snap-fit connection by moving the cushion module and the shroud towards one another along the longitudinal axis of the collar.

15. The mask system of claim 14, further comprising an elbow configured to receive the supply of air at positive pressure and deliver the supply of air at positive pressure to the frame opening, wherein:

the plurality of part-annular snap fingers project rearward from the rear wall towards the breathing chamber, the cushion is constructed to engage the patient's face along a nasal bridge region, a cheek region, and a lower lip/chin region of the patient's face when in use, the elastomeric material of the cushion is silicone, the cushion and the frame are constructed and arranged to be in an interlocking relationship with one another, the first material is polycarbonate, the second material is polycarbonate, said headgear comprises hook and loop material, the shroud further comprises a forehead support, the elbow and the shroud are configured to be directly connected to one another, a region of the cushion positioned to engage the nasal bridge region of the patient is configured to allow increased movement compared to another region of the cushion that is adapted to seal with another region of the patient's face, the protrusions are part-annular and spaced circumferentially around the frame opening, the elbow includes an anti-asphyxia valve, and the protrusions are positioned between and spaced away from both a front end and a rear end of the collar.

16. The mask system of claim 14, further comprising an elbow configured to receive the supply of air at positive pressure and deliver the supply of air at positive pressure to the frame opening, wherein:

the cushion is constructed to engage the patient's face along a nasal bridge region, a cheek region, and a lower lip/chin region of the patient's face when in use, the elastomeric material of the cushion is silicone, the cushion and the frame are constructed and arranged to be in an interlocking relationship with one another, the first material is polycarbonate, said headgear comprises hook and loop material, the protrusions are spaced circumferentially around the frame opening, and the elbow includes an anti-asphyxia valve, the cushion and the frame are connected via a tongue and groove arrangement including a tongue of the cushion that fits within a groove along a perimeter of the frame, the cushion and the frame include positioning features to assist with proper alignment of the cushion with the frame, the cushion having a pair of lower corners and a top apex, each of the lower corners including a corner notch to mate with a corner protrusion of the frame, and the top apex including a top protrusion to mate with a complementary feature in the frame, when the cushion and the frame are attached to one another by inserting the tongue into the groove, each said corner notch of the cushion being positioned on the tongue and each said corner protrusion of the frame being positioned within the groove, the mask system further includes a vent arrangement including a vent-wall and two lateral side walls, the vent-wall having 20-50 holes for gas washout from the breathing chamber to atmosphere, the vent-wall projecting from the exterior surface of the frame by the two lateral side walls, and the vent arrangement positioned on the frame such that the vent arrangement is superior to the frame opening in use, the vent-receiving opening is bounded by a rim of closed shape that is similar to a shape of the vent arrangement, lateral portions of the rim being adjacent to corresponding ones of the two lateral side walls when the shroud is connected to the cushion module the vent-wall is oriented at an angle relative to the frame opening such that a longitudinal axis of each of the plurality of vent holes and the longitudinal axis of the cylindrical collar are not parallel, the elbow is attached to the frame and is rotatable 360° relative to the frame, and the mask system includes an upper retaining mechanism to help retain the shroud and the cushion module, the upper retaining mechanism including a pair of platforms provided on opposing sides of an upper part of the frame, each platform including a first slot, each platform being spaced from the exterior surface of the frame to at least partly define a second slot, the upper retaining mechanism including a pair of tang protrusions provided on opposing sides of an upper part of the rear wall of the shroud, each tang protrusion including a first tang to be received in the first slot and a second tang to be received in the second slot when the shroud and the cushion module are attached to one another.

17. A system for treating a patient with sleep disordered breathing, comprising:

the mask system of claim 14;

a flow generator to generate a supply of air at positive pressure to be delivered to the mask system; and an air delivery tube configured to deliver the supply of air from the flow generator to the mask system.

18. A mask system to provide positive air pressure therapy to a patient, the mask system comprising:

a cushion module comprising:

a frame having an interior surface at least partly forming a breathing chamber, the frame including a frame opening positioned to receive a supply of air at positive pressure, wherein the frame includes a collar surrounding the frame opening and extending away from an exterior surface of the frame, the collar having a longitudinal axis, and the collar having a cylindrical surface with an axis that is coincident with the longitudinal axis of the collar, wherein the collar includes at least one radial protrusion extending from the cylindrical surface, the at least one radial protrusion having a curvature centered about the longitudinal axis of the collar, wherein the frame, including the collar and the at least one radial protrusion, is constructed from a first material, and a cushion constructed of an elastomeric material that is a different material from the first material, the first material of the frame being harder than the elastomeric material of the cushion, the frame being more rigid than the cushion, the cushion configured to seal against the patient's face in use to enable the supply of air at positive pressure to be delivered to at least the patient's nose,
wherein the cushion and the frame are joined to form an integrated component;
an elbow configured to receive the supply of air at positive pressure and deliver the supply of air at positive pressure to the breathing chamber;
a shroud configured to removably connect to the frame of the cushion module, wherein the shroud includes an elbow opening that accommodates the elbow, wherein the shroud includes a rear surface at least partly covering the exterior surface of the frame, the shroud having a plurality of part-annular snap connection portions circumferentially spaced from one another and centered about a longitudinal axis of the elbow opening, the snap connection portions being positioned rearward of the elbow opening of the shroud, wherein the shroud, including the snap connection portions, is constructed from a second material, the second material of the shroud being harder than the elastomeric material of the cushion, and the shroud being more rigid than the cushion,
headgear configured to connect to the shroud to maintain the cushion module in position on the patient's head in use; and
a vent arrangement having a plurality of holes for gas washout from the breathing chamber to atmosphere,
wherein:
the shroud includes a pair of upper headgear connectors and a pair of lower headgear connectors, said pair of upper headgear connectors structured to connect to said headgear, and said pair of lower headgear connectors structured to connect to said headgear,
to releasably connect the shroud to the cushion module, the at least one radial protrusion and the snap connection portions are structured to form a removable snap-fit connection by moving the cushion module and the shroud towards one another along the longitudinal axis of the collar,
when the collar and the snap connection portions are joined to form the removable snap-fit connection, the cushion module and the shroud are stabilized against rotation relative to one another,
the frame opening of the frame is circular,
the elbow opening of the shroud is circular,
the collar of the frame is cylindrical,
the cushion is constructed to engage the patient's face along a nasal bridge region, a cheek region, and a lower lip/chin region of the patient's face when in use,
the elastomeric material of the cushion is silicone,
the shroud does not include a forehead support,
the elbow includes an anti-asphyxia valve,
the first material is polycarbonate,
the second material is polycarbonate,
the elbow is directly attached to the shroud at the elbow opening,
the elbow is rotatable 360° relative to the shroud,
the at least one radial protrusion further comprising a single radial protrusion having an annular shape,
the single radial protrusion and the snap connection portions are arranged to remain stationary relative to one another as the elbow is rotated,
the cushion and the frame are joined by a chemical bond,
the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use,
each of the pair of upper headgear connectors comprises an elongated arm to direct a corresponding one of the pair of upper straps away from the patient's corresponding eye, each elongated arm being shaped to follow contours of the patient's face and avoid the patient's line of sight in use,
a portion of each elongated arm is enveloped by a fabric sleeve,
each elongated arm is constructed of a flexible material,
each elongated arm is connected to the shroud,
each elongated arm is configured to be positioned inferior to the patient's corresponding eye in use and is configured to direct a corresponding one of the pair of upper straps superior to the patient's corresponding ear in use, and
each of the pair of lower headgear connectors is configured to direct a corresponding one of the pair of lower straps inferior to the patient's corresponding ear in use.

19. A system for treating a patient with sleep disordered breathing, comprising:
the mask system of claim 18;
a flow generator to generate a supply of air at positive pressure to be delivered to the mask system; and
an air delivery tube configured to deliver the supply of air from the flow generator to the mask system.

20. A mask system to provide positive air pressure therapy to a patient, the mask system comprising:
a cushion module comprising:
a frame having an interior surface at least partly forming a breathing chamber, the frame including a frame opening positioned to receive a supply of air at positive pressure, wherein the frame includes a collar surrounding the frame opening and extending away from an exterior surface of the frame, the collar having a longitudinal axis, and the collar having a cylindrical surface with an axis that is coincident with the longitudinal axis of the collar, wherein the collar includes at least one radial protrusion extending from the cylindrical surface, the at least one radial protrusion having a curvature centered about the longitudinal axis of the collar, wherein the frame, including the collar and the at least one radial protrusion, is constructed from a first material, and
a cushion constructed of an elastomeric material that is a different material from the first material, the first material of the frame being harder than the elastomeric material of the cushion, the frame being more rigid than the cushion, the cushion configured to seal against the patient's face in use to enable the supply of air at positive pressure to be delivered to at least the patient's nose,
wherein the cushion and the frame are joined to form an integrated component;
an elbow configured to receive the supply of air at positive pressure and deliver the supply of air at positive pressure to the breathing chamber;
a shroud configured to removably connect to the frame of the cushion module, wherein the shroud includes an elbow opening that accommodates the elbow, wherein the shroud includes a rear surface at least partly covering the exterior surface of the frame, the shroud having a plurality of part-annular snap connection portions circumferentially spaced from one another and centered about a longitudinal axis of the elbow opening, the snap connection portions being positioned rearward of the elbow opening of the shroud, wherein the shroud, including the snap connection portions, is constructed from a second material, the second material of the shroud being harder than the elastomeric material of the cushion, and the shroud being more rigid than the cushion, headgear configured to connect to the shroud to maintain the cushion module in position on the patient's head in use; and a vent arrangement having a plurality of holes for gas washout from the breathing chamber to atmosphere, wherein:

the shroud includes a pair of upper headgear connectors and a pair of lower headgear connectors, said pair of upper headgear connectors structured to connect to said headgear, and said pair of lower headgear connectors structured to connect to said headgear, to releasably connect the shroud to the cushion module, the at least one radial protrusion and the snap connection portions are structured to form a removable snap-fit connection by moving the cushion module and the shroud towards one another along the longitudinal axis of the collar, when the collar and the snap connection portions are joined to form the removable snap-fit connection, the cushion module and the shroud are stabilized against rotation relative to one another, the elbow opening of the shroud is circular, the collar of the frame is cylindrical, the cylindrical surface is on an exterior of the collar, the at least one radial protrusion comprises a plurality of protrusions spaced circumferentially about the cylindrical surface, each of the plurality of protrusions having a part-annular shape, the protrusions and the snap connection portions are configured to form the removable snap-fit connection between a front end of the cylindrical surface and a rear end of the cylindrical surface, the cushion is constructed to engage the patient's face along a nasal bridge region, a cheek region, and an upper lip region of the patient's face when in use, the elastomeric material of the cushion is silicone, the shroud does not include a forehead support, the first material is polycarbonate, the second material is polycarbonate, the cushion and the frame are joined by a chemical bond, the elbow is directly attached to the shroud at the elbow opening, the elbow is rotatable 360° relative to the shroud, the collar and the snap-fit connection are arranged to remain stationary relative to one another as the elbow is rotated, the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use, each of the pair of upper headgear connectors comprises an elongated arm to direct a corresponding one of the pair of upper straps away from the patient's corresponding eye, each elongated arm being shaped to follow contours of the patient's face and avoid the patient's line of sight in use, each elongated arm has an inner surface including a cheek pad, each elongated arm is constructed of a flexible material, each elongated arm is configured to be positioned inferior to the patient's corresponding eye in use and is configured to direct a corresponding one of the pair of upper straps superior to the patient's corresponding ear in use, each of the pair of lower headgear connectors is configured to direct a corresponding one of the pair of lower straps inferior to the patient's corresponding ear in use, and the mask system further includes a seal at an interface between the elbow and the frame.

21. A system for treating a patient with sleep disordered breathing, comprising:

the mask system of claim 20;

a flow generator to generate a supply of air at positive pressure to be delivered to the mask system; and an air delivery tube configured to deliver the supply of air from the flow generator to the mask system.

22. A mask system to provide positive air pressure therapy to a patient, the mask system comprising:

a cushion module comprising:

a frame having an interior surface at least partly forming a breathing chamber, the frame including a frame opening positioned to receive a supply of air at positive pressure, wherein the frame includes a collar surrounding the frame opening and extending away from an exterior surface of the frame, the collar having a longitudinal axis, and the collar having a cylindrical surface with an axis that is coincident with the longitudinal axis of the collar, wherein the collar includes at least one radial protrusion extending from the cylindrical surface, the at least one radial protrusion having a curvature centered about the longitudinal axis of the collar, wherein the frame, including the collar and the at least one radial protrusion, is constructed from a first material, and a cushion constructed of an elastomeric material that is a different material from the first material, the first material of the frame being harder than the elastomeric material of the cushion, the frame being more rigid than the cushion, the cushion configured to seal against the patient's face in use to enable the supply of air at positive pressure to be delivered to at least the patient's nose, wherein the cushion and the frame are joined to form an integrated component;

an elbow configured to receive the supply of air at positive pressure and deliver the supply of air at positive pressure to the breathing chamber;

a shroud configured to removably connect to the frame of the cushion module, wherein the shroud includes an elbow opening that accommodates the elbow, wherein the shroud includes a rear surface at least partly covering the exterior surface of the frame, the shroud having a plurality of part-annular snap connection portions circumferentially spaced from one another and centered about a longitudinal axis of the elbow opening, the snap connection portions being positioned rearward of the elbow opening of the shroud, wherein the shroud, including the snap connection portions, is constructed from a second material, the second material of the shroud being harder than the elastomeric material of the cushion, and the shroud being more rigid than the cushion, headgear configured to connect to the shroud to maintain the cushion module in position on the patient's head in use; and
a vent arrangement having a plurality of holes for gas washout from the breathing chamber to atmosphere,
wherein:
the shroud includes a pair of upper headgear connectors and a pair of lower headgear connectors, said pair of upper headgear connectors structured to connect to said headgear, and said pair of lower headgear connectors structured to connect to said headgear,
to releasably connect the shroud to the cushion module, the at least one radial protrusion and the snap connection portions are structured to form a removable snap-fit connection by moving the cushion module and the shroud towards one another along the longitudinal axis of the collar,
when the collar and the snap connection portions are joined to form the removable snap-fit connection, the cushion module and the shroud are stabilized against rotation relative to one another,
the frame opening of the frame is circular,
the elbow opening of the shroud is circular,
the collar of the frame is cylindrical,
the cushion is constructed to engage the patient's face along a nasal bridge region, a cheek region, and a lower lip/chin region of the patient's face when in use,
the elastomeric material of the cushion is silicone,
the cushion and the frame are constructed and arranged to be in an interlocking relationship with one another,
the first material is polycarbonate,
the second material is polycarbonate,
said headgear comprises hook and loop material,
the shroud further comprises a forehead support,
the elbow is directly attached to the shroud at the elbow opening,
the elbow includes an anti-asphyxia valve,
the collar and the snap-fit connection are arranged to remain stationary relative to one another as the elbow is rotated,
the vent arrangement comprises a protruding vent arrangement that protrudes from the frame, the protruding vent arrangement including a vent-wall having the plurality of holes, the vent-wall being spaced from the frame by a lower wall and two lateral side walls of the protruding vent arrangement, and the protruding vent arrangement positioned above the frame opening,
the at least one radial protrusion further comprises a plurality of part-annular protrusions spaced circumferentially about the frame opening,
the snap connection portions comprise part-annular snap fingers that extend from the rear surface and are spaced circumferentially about the elbow opening,
the part-annular protrusions and the part-annular snap fingers are configured to form the removable snap-fit connection between a front end of the cylindrical surface and a rear end of the cylindrical surface relative to the patient in use,
each of the part-annular snap fingers has a curvature that is centered on the longitudinal axis of the collar,
a region of the cushion positioned to engage the nasal bridge region of the patient is configured to allow increased movement compared to another region of the cushion that is adapted to seal with another region of the patient's face, and
the mask system being constructed so that the snap-fit connection is established when a force is applied to move the shroud and cushion module toward one another along the longitudinal axis until a rear end of each of the part-annular snap fingers initially contacts a front end of the corresponding protrusion on the collar, whereupon further application of the force causes each of the part-annular snap fingers to ride over the corresponding part-annular protrusion and therefore resiliently deflect in a first radial direction relative to the longitudinal axis of the collar, and upon further movement towards one another, each of the part-annular snap fingers resiliently moves in a second radial direction, opposite the first radial direction, and engages a rear end of the corresponding part-annular protrusion to snap each of the part-annular snap fingers into place, thereby removably connecting the shroud and the cushion module.

23. A system for treating a patient with sleep disordered breathing, comprising:
the mask system of claim 22;
a flow generator to generate a supply of air at positive pressure to be delivered to the mask system; and
an air delivery tube configured to deliver the supply of air from the flow generator to the mask system.

24. A mask system to provide positive air pressure therapy to a patient, the mask system comprising:
a cushion module comprising:
a frame having an interior surface at least partly forming a breathing chamber, the frame including a frame opening positioned to receive a supply of air at positive pressure, wherein the frame includes a collar surrounding the frame opening and extending away from an exterior surface of the frame, the collar having a longitudinal axis, and the collar having a cylindrical surface with an axis that is coincident with the longitudinal axis of the collar, wherein the collar includes at least one radial protrusion extending from the cylindrical surface, the at least one radial protrusion having a curvature centered about the longitudinal axis of the collar, wherein the frame, including the collar and the at least one radial protrusion, is constructed from a first material, and
a cushion constructed of an elastomeric material that is a different material from the first material, the first material of the frame being harder than the elastomeric material of the cushion, the frame being more rigid than the cushion, the cushion configured to seal against the patient's face in use to enable the supply of air at positive pressure to be delivered to at least the patient's nose,
wherein the cushion and the frame are joined to form an integrated component;
an elbow configured to receive the supply of air at positive pressure and deliver the supply of air at positive pressure to the breathing chamber;
a shroud configured to removably connect to the frame of the cushion module, wherein the shroud includes an elbow opening that accommodates the elbow, wherein the shroud includes a rear surface at least partly covering the exterior surface of the frame, the shroud having a plurality of part-annular snap connection portions circumferentially spaced from one another and centered about a longitudinal axis of the elbow opening, the snap connection portions being positioned rearward of the elbow opening of the shroud, wherein the shroud, including the snap connection portions, is constructed from a second material, the second material of the shroud being harder than the elastomeric material of the cushion, and the shroud being more rigid than the cushion, headgear configured to connect to the shroud to maintain the cushion module in position on the patient's head in use; and a vent arrangement having a plurality of holes for gas washout from the breathing chamber to atmosphere, wherein:

the shroud includes a pair of upper headgear connectors and a pair of lower headgear connectors, said pair of upper headgear connectors structured to connect to said headgear, and said pair of lower headgear connectors structured to connect to said headgear, to releasably connect the shroud to the cushion module, the at least one radial protrusion and the snap connection portions are structured to form a removable snap-fit connection by moving the cushion module and the shroud towards one another along the longitudinal axis of the collar, when the collar and the snap connection portions are joined to form the removable snap-fit connection, the cushion module and the shroud are stabilized against rotation relative to one another, the elbow opening of the shroud is circular, the collar of the frame is cylindrical, the at least one radial protrusion further comprises two part-annular protrusions spaced circumferentially about the cylindrical surface, the cushion is constructed to engage the patient's face along a nasal bridge region, a cheek region, and an upper lip region of the patient's face when in use, the elastomeric material of the cushion is silicone, the shroud includes a forehead support, the first material is polycarbonate, the second material is polycarbonate, the elbow is directly attached to the shroud at the elbow opening, the elbow is rotatable 360° relative to the shroud, the collar and the snap-fit connection are arranged to remain stationary relative to one another as the elbow is rotated, the snap connection portions are structured to resiliently deflect relative to corresponding ones of the two part-annular protrusions in a radial direction relative to the longitudinal axis of the collar to form the removable snap-fit connection, the headgear comprises a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use, each of the pair of upper headgear connectors is configured to direct a corresponding one of the pair of upper straps superior to the patient's corresponding ear in use, and each of the pair of lower headgear connectors is configured to direct a corresponding one of the pair of lower straps inferior to the patient's corresponding ear in use.

25. The mask system of claim 24, further comprising at least one tab and recess arrangement positioned circumferentially between mating ones of the snap connection portions and protrusions, the tab and recess arrangement resisting rotation of the collar relative to the shroud upon establishing the snap-fit connection between the shroud and the cushion module.

26. A system for treating a patient with sleep disordered breathing, comprising:

the mask system of claim 24;

a flow generator to generate a supply of air at positive pressure to be delivered to the mask system; and an air delivery tube configured to deliver the supply of air from the flow generator to the mask system.

27. A mask system to provide positive air pressure therapy to a patient, the mask system comprising:

a cushion module comprising:

a frame having an interior surface at least partly forming a breathing chamber, the frame including a circular frame opening positioned to receive a supply of air at positive pressure, wherein the frame includes a cylindrical collar surrounding the frame opening and extending away from an exterior surface of the frame, the collar having a longitudinal axis, and the collar having a cylindrical surface with an axis that is coincident with the longitudinal axis of the collar, wherein the collar includes at least one radial protrusion extending from the cylindrical surface, the at least one radial protrusion having a curvature centered about the longitudinal axis of the collar, wherein the frame, including the collar and the at least one radial protrusion, is constructed from polycarbonate, and a cushion constructed of silicone, the polycarbonate of the frame being harder than the silicone of the cushion, the frame being more rigid than the cushion, the cushion configured to seal against the patient's face in use to enable the supply of air at positive pressure to be delivered to the patient, the cushion is constructed to engage the patient's face along a nasal bridge region, a cheek region, and a lower lip/chin region of the patient's face when in use, wherein the cushion and the frame are joined to form an integrated component;

an elbow configured to receive the supply of air at positive pressure and deliver the supply of air at positive pressure to the breathing chamber, the elbow having an anti-asphyxia valve;

a shroud without a forehead support, the shroud configured to removably connect to the frame of the cushion module, wherein the shroud includes a circular elbow opening that accommodates the elbow, wherein the shroud includes a rear surface at least partly covering the exterior surface of the frame, the shroud having a plurality of part-annular snap connection portions circumferentially spaced from one another and centered about a longitudinal axis of the elbow opening, the snap connection portions extending rearward from the rear surface of the shroud, wherein the shroud, including the snap connection portions, is constructed from polycarbonate, the polycarbonate of the shroud being harder than the silicone of the cushion, and the shroud being more rigid than the cushion;

headgear configured to connect to the shroud to maintain the cushion module in position on the patient's head in use, the headgear comprising a pair of upper straps, each of the pair of upper straps configured to be positioned on a corresponding lateral side of the patient's head in use, and a pair of lower straps, each of the pair of lower straps configured to be positioned on a corresponding lateral side of the patient's head in use; and a vent arrangement having a plurality of holes for gas washout from the breathing chamber to atmosphere, wherein:
the shroud includes a pair of upper headgear connectors and a pair of lower headgear connectors, said pair of upper headgear connectors structured to connect to said headgear, and said pair of lower headgear connectors structured to connect to said headgear,
each of the pair of upper headgear connectors comprises an elongated arm to direct a corresponding one of the pair of upper straps away from the patient's corresponding eye, each elongated arm being shaped to follow contours of the patient's face and avoid the patient's line of sight in use,
a portion of each elongated arm is enveloped by a fabric sleeve,
each elongated arm is constructed of a flexible material,
each elongated arm is configured to be positioned inferior to the patient's corresponding eye in use and is configured to direct a corresponding one of the pair of upper straps superior to the patient's corresponding ear in use,
each of the pair of lower headgear connectors is configured to direct a corresponding one of the pair of lower straps inferior to the patient's corresponding ear in use to releasably connect the shroud to the cushion module,
the at least one radial protrusion and the snap connection portions are structured to form a removable snap-fit connection by moving the cushion module and the shroud towards one another along the longitudinal axis of the collar,
when the collar and the snap connection portions are joined to form the removable snap-fit connection, the cushion module and the shroud are stabilized against rotation relative to one another,
the elbow is directly attached to the shroud at the elbow opening, and
the elbow is rotatable 360° relative to the shroud.

28. A system for treating a patient with sleep disordered breathing, comprising:
the mask system of claim 27;
a flow generator to generate a supply of air at positive pressure to be delivered to the mask system; and
an air delivery tube configured to deliver the supply of air from the flow generator to the mask system.

29. The mask system of claim 27, wherein:
the frame includes a rearwardly extending portion that is constructed of the polycarbonate of the frame, the rearwardly extending portion extending rearward from the collar and terminating in an edge having a substantially triangular shape,
the cushion is joined to the frame about the edge,
the rearwardly extending portion includes the interior surface of the frame that forms the breathing chamber,
the collar, the shroud, and the elbow are structured such that a plane perpendicular to the longitudinal axis of the collar intersects each of the shroud, the elbow, and the collar when the frame, the shroud, and the elbow are assembled,
the collar comprises a front end positioned to face away from the patient in use,
the collar and the snap-fit connection are arranged to remain stationary relative to one another as the elbow is rotated, and
when the frame and the shroud are assembled together, the front end of the collar is positioned rearward of the rear surface of the shroud.

30. A system for treating a patient with sleep disordered breathing, comprising:
the mask system of claim 29;
a flow generator to generate a supply of air at positive pressure to be delivered to the mask system; and
an air delivery tube configured to deliver the supply of air from the flow generator to the mask system.

* * * * *